United States Patent
Bachmann et al.

(10) Patent No.: US 12,084,454 B2
(45) Date of Patent: Sep. 10, 2024

(54) PROCESS FOR PREPARING BTK INHIBITORS

(71) Applicant: Hoffmann-La Roche Inc., Little Falls, NJ (US)

(72) Inventors: Stephan Bachmann, Allschwil (CH); Lukas Chytil, Grellingen (CH); Serena Maria Fantasia, Saint-Louis (FR); Alec Fettes, Hagendorn (CH); Ursula Hoffmann, Muttenz (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 18/501,647

(22) Filed: Nov. 3, 2023

(65) Prior Publication Data
US 2024/0132508 A1    Apr. 25, 2024

Related U.S. Application Data

(63) Continuation of application No. PCT/EP2022/061741, filed on May 3, 2022.

(30) Foreign Application Priority Data

May 5, 2021 (EP) ..................................... 21172180
Jun. 23, 2021 (EP) ..................................... 21181156

(51) Int. Cl.
*C07D 487/04* (2006.01)
*B01J 21/18* (2006.01)
*B01J 23/648* (2006.01)
*B01J 31/22* (2006.01)
*B01J 31/24* (2006.01)
*C07D 401/04* (2006.01)

(52) U.S. Cl.
CPC ............ *C07D 487/04* (2013.01); *B01J 21/18* (2013.01); *B01J 23/6482* (2013.01); *B01J 31/2256* (2013.01); *B01J 31/2265* (2013.01); *B01J 31/2404* (2013.01); *C07D 401/04* (2013.01); *B01J 2231/4211* (2013.01); *B01J 2531/824* (2013.01)

(58) Field of Classification Search
None
See application file for complete search history.

(56) References Cited

U.S. PATENT DOCUMENTS

| | | |
|---|---|---|
| 10,385,058 B2 | 8/2019 | Beaudry et al. |
| 10,882,864 B2 | 1/2021 | Beaudry et al. |
| 11,661,424 B2 | 5/2023 | Beaudry et al. |
| 2013/0116235 A1 | 5/2013 | Crawford et al. |
| 2017/0120231 A1* | 5/2017 | Colacot ................. C07C 67/343 |
| 2018/0230155 A1 | 8/2018 | Beaudry et al. |
| 2023/0250103 A1 | 8/2023 | Beaudry et al. |
| 2023/0348471 A1 | 11/2023 | Xu et al. |

FOREIGN PATENT DOCUMENTS

| | | |
|---|---|---|
| WO | 2013/067274 A1 | 5/2013 |
| WO | 2015/189555 A1 | 12/2015 |
| WO | 2018/109050 A1 | 6/2018 |

OTHER PUBLICATIONS

Avril, A., et al., "Continuous flow hydrogenations using novel catalytic static mixers inside a tubular reactor" React Chem Eng-Uk 2:180-188 (Dec. 20, 2016).
Espinosa, M., et al., "Differences in the Performance of Allyl Based Palladium Precatalysts for Suzuki-Miyaura Reactions" Adv Synth Catal 362(22):5062-5078 (Nov. 18, 2020).
Hornung, C., et al., "Additive Layer Manufacturing of Catalytic Static Mixers for Continuous Flow Reactors" Johnson Matthey Tech RVW 62(3):350-360 (Jul. 1, 2018).
Hornung, C., et al., "Use of Catalytic Static Mixers for Continuous Flow Gas-Liquid and Transfer Hydrogenations in Organic Synthesis" ACS Org Process Res Dev 21(9):1311-1319 (Jun. 28, 2017).
"International Search Report—PCT/EP2022/061741" (w/Written Opinion),:pp. 1-25 (Oct. 18, 2022).
Lebl, R., et al., "Scalable continuous flow hydrogenations using Pd/Al2O3-coated rectangular cross-section 3D-printed static mixers" Catalysis Today 383:55-63 (Jan. 1, 2022).
Melvin, P., et al., "Design of a Versatile and Improved Precatalyst Scaffold for Palladium-Catalyzed Cross-Coupling: (η3-1-tBu-indenyl)2(μ-Cl)2Pd2" ACS Catalysis 5(6):3680-3688 (May 19, 2015).
Trost, B., et al., "Palladium-Catalyzed Asymmetric Benzylation of 3-Aryl Oxindoles" ACS J Am Chem Soc 132(44):15534-15536 (Oct. 20, 2010).
Ueno, M., et al., "Catalytic Flow Hydrogenation of Aromatic Nitro Compounds Using Polysilane-Supported Palladium" J Flow Chem 4(4):160-163 (Dec. 10, 2014).
Zhang H., et al., "Development of an Efficient Manufacturing Process for Reversible Bruton's Tyrosine Kinase Inhibitor GDC-0853" ACS Org Process Res Dev 22(8):978-990 (Jul. 2, 2018).
"International Preliminary Report on Patentability—PCT/EP2022/061741" :pp. 1-16 (Nov. 16, 2023).

* cited by examiner

*Primary Examiner* — Joseph R Kosack
(74) *Attorney, Agent, or Firm* — Katherine J. Mackenzie

(57) ABSTRACT

Methods for preparing the Bruton's Tyrosine Kinase ("BTK") inhibitor compound 2-{3'-hydroxymethyl-1-methyl-5-[((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one are provided.

23 Claims, 13 Drawing Sheets

A: Compound 140   B: Dimer impurity   C: Combined azo+azoxy impurities

PROCESS FOR PREPARING BTK INHIBITORS

CROSS-REFERENCE TO RELATED APPLICATIONS

This application is a continuation of International Application No. PCT/EP2022/061741, filed May 3, 2022, which claims the benefit of priority to European Application No. 21181156.7, filed Jun. 23, 2021; and European Application No. 21172180.8, filed May 5, 2021, the contents of which are incorporated by reference in their entireties.

BACKGROUND

The present disclosure relates generally to methods of preparing the Bruton's Tyrosine Kinase ("BTK") inhibitor compound 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one. The disclosure further relates generally to methods of preparing intermediates in the synthesis of aforementioned BTK inhibitor compound, such as tricyclic lactam compounds.

The BTK inhibitor compound 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one of the following structure:

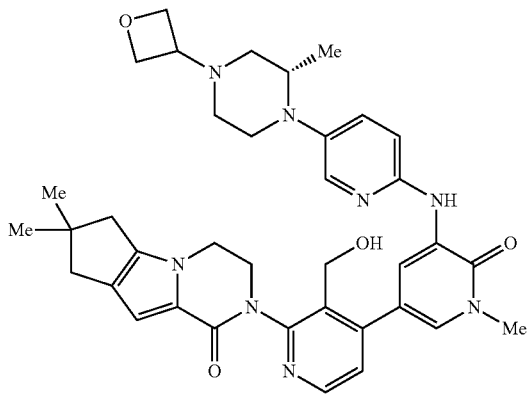 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

is known from U.S. publication US 2013/0116235 A1 as a BTK inhibitor that is useful for the treatment of diseases or disorders, such as those selected from immune disorders, cancer, cardiovascular disease, viral infection, inflammation, metabolism/endocrine function disorders, and neurological disorders. US 2013/0116235 is incorporated herein by reference in its entirety. Alternative names for 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one can be used, but the shown chemical structure controls. One such alternative name is (S)-2-(3'-(hydroxymethyl)-1-methyl-5-((5-(2-methyl-4-(oxetan-3-yl)piperazin-1-yl)pyridin-2-yl)amino)-6-oxo-1,6-dihydro-[3,4'-bipyridin]-2' yl)-7,7-dimethyl-2,3,4,6,7,8-hexahydro-1H-cyclopenta[4,5]pyrrolo[1,2-a]pyrazin-1-one. The US 2013/0116235 publication discloses a useful method for preparing 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one, but the method requires chromatographic purification and a low yield was achieved.

A useful process for preparing 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one is further known from US 2018/0230155 and from Zhang, H., et al., "Development of an Efficient Manufacturing Process for Reversible Bruton's Tyrosine Kinase Inhibitor GDC-0853", Org. Process Res. Dev. 2018, 22, 8, 978-990. US 2018/0230155 and the Zhang publication are incorporated herein by reference in its entirety.

A need exists for improved methods for preparing 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one and intermediate compounds therefore. For example, there is a need for improved methods with higher yield, lower presence of byproduct, or combinations thereof.

BRIEF DESCRIPTION

One aspect of the disclosure is directed to a method of preparing compound 190, or a stereoisomer, geometric isomer, tautomer, or salt thereof. The method comprises forming a reaction mixture comprising compound 170, compound 181, a palladium catalyst, a solvent system comprising water and a base, wherein the equivalent ratio of the palladium catalyst to compound 170 is from about 0.001:1 to less than 0.005:1. The reaction mixture is reacted to form a reaction product mixture comprising compound 190 (or a stereoisomer, geometric isomer, tautomer, or salt thereof) according to the following scheme:

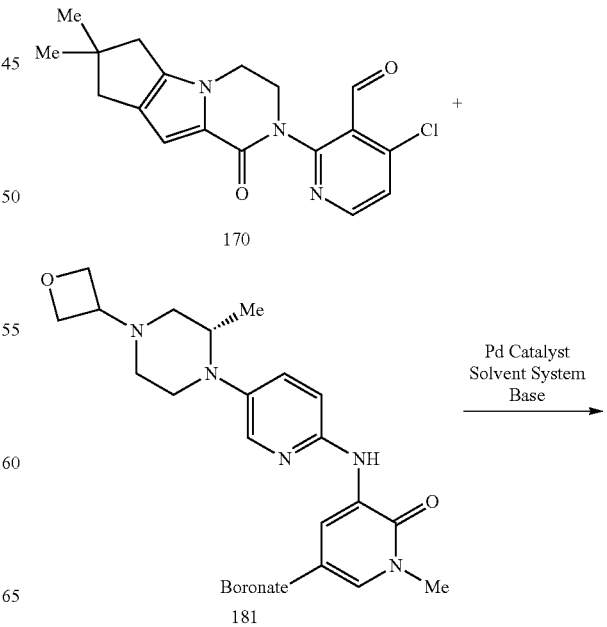

-continued

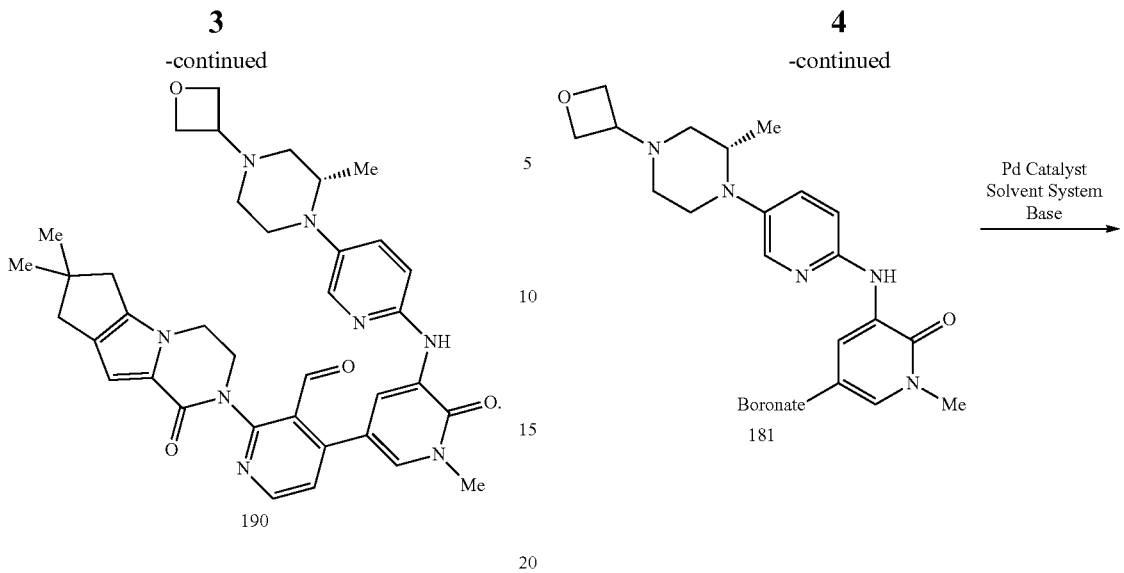
190

In some aspects, the Pd catalyst comprises a palladium(II) species containing a phosphine ligand and at least one palladium-carbon bond. In some aspects, the fragment giving rise to the palladium-carbon bond is an allyl derivative of the formula:

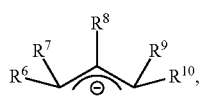

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring. In some aspects, the yield of compound 190 (or a stereoisomer, geometric isomer, tautomer, or salt thereof) is at least 50% based on compound 170.

One aspect of the disclosure is directed to a method of reducing byproduct formation in a Suzuki coupling reaction. The method comprises forming a reaction mixture comprising compound 170, compound 181, a palladium catalyst, a solvent system comprising water, and a base, wherein the equivalent ratio of the palladium catalyst to compound 170 is from about 0.001:1 to less than 0.005:1, and reacting the reaction mixture to form a reaction product mixture comprising compound 190 (or a stereoisomer, geometric isomer, tautomer, or salt thereof) according to the following scheme:

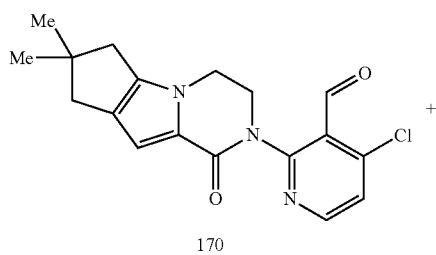
170

-continued

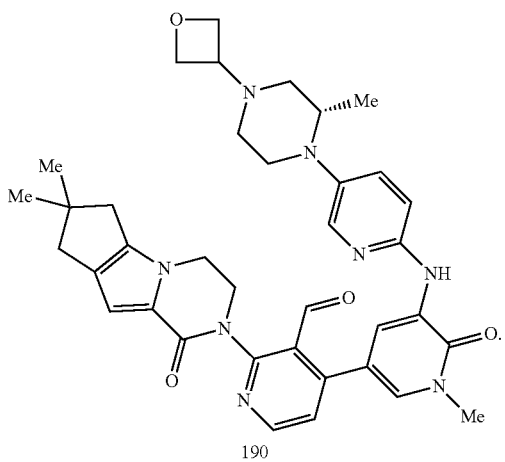
181

190

In some aspects, the Pd catalyst comprises a palladium(II) species containing a phosphine ligand and at least one palladium-carbon bond. In some aspects, the fragment giving rise to the palladium-carbon bond is an allyl derivative of the formula:

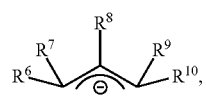

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring. In some aspects, the content of dimer impurity in the resulting reaction product mixture is less than 0.3 area % based on compound 190 (or a stereoisomer, geometric isomer, tautomer, or salt thereof), wherein the dimer impurity is of the structure:

In some aspects, the combined content of ketone and alcohol impurities in the resulting reaction product mixture is less than 0.25 area % based on compound 190 (or a stereoisomer, geometric isomer, tautomer, or salt thereof), wherein the ketone and alcohol impurities are of the structures:

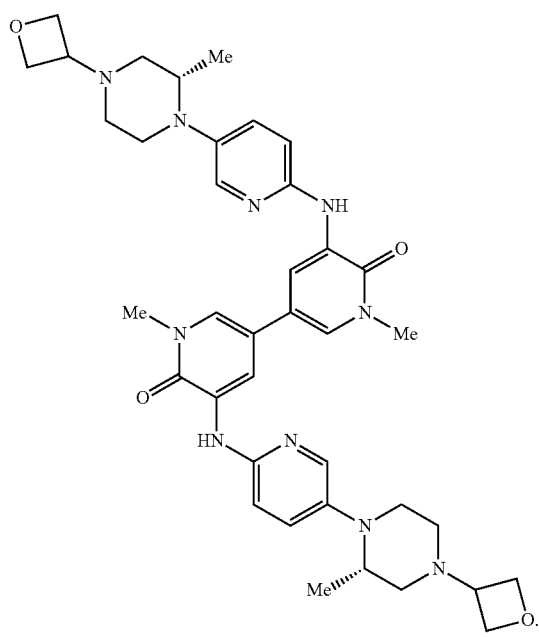 [SMILES: C[C@H]1CN(C2COC2)CCN1c1ccc(Nc2cc(-c3cc(Nc4ccc(N5CCN(C6COC6)C[C@@H]5C)cn4)c(=O)n(C)c3)cn(C)c2=O)nc1]

Alcohol

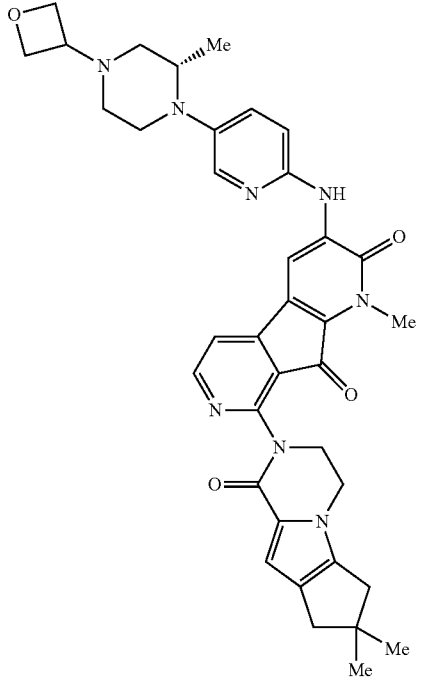

Ketone

One aspect of the disclosure is directed to a method of improving yield in a Suzuki coupling reaction. The method comprises forming a reaction mixture comprising compound 170, compound 181, a palladium catalyst, a solvent system comprising water, and a base, wherein the equivalent ratio of the palladium catalyst to compound 170 is from about 0.001:1 to less than 0.005:1, and reacting the reaction mixture to form a reaction product mixture comprising compound 190 (or a stereoisomer, geometric isomer, tautomer, or salt thereof) according to the following scheme:

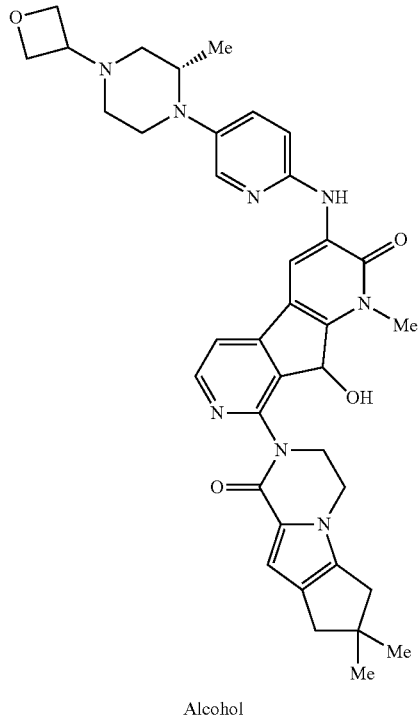

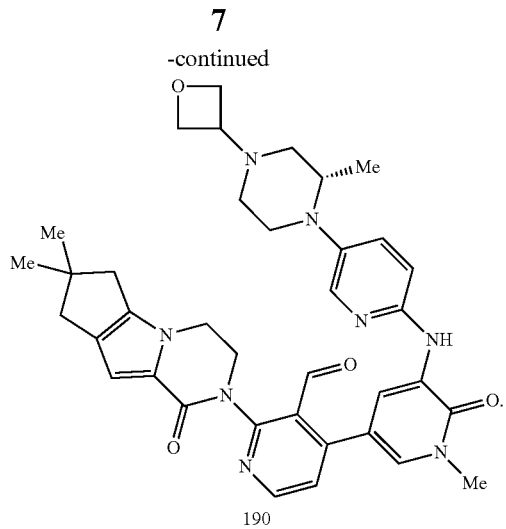

190

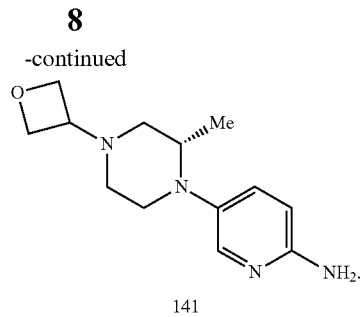

141

Said method further comprises forming a second reaction mixture comprising compound 141, compound 90, a palladium catalyst, a catalyst ligand, a base, and a solvent, and reacting the second reaction mixture to form a second reaction product mixture comprising compound 180 according to the following scheme:

In some aspects, the Pd catalyst comprises a palladium(II) species containing a phosphine ligand and at least one palladium-carbon bond. In some aspects, the fragment giving rise to the palladium-carbon bond is an allyl derivative of the formula:

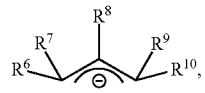

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring. In some aspects, the yield of compound 190 (or a stereoisomer, geometric isomer, tautomer, or salt thereof) based on compound 170 is at least 80% or at least 85%.

One aspect of the disclosure is directed to a method of preparing compound 180, stereoisomers thereof, geometric isomers thereof, tautomers thereof, or salts thereof. The method comprises forming a first reaction mixture comprising compound 140, a platinum/vanadium on carbon catalyst, a solvent, and hydrogen, and reacting the first reaction mixture to form a first reaction product mixture comprising compound 141 according to the following scheme:

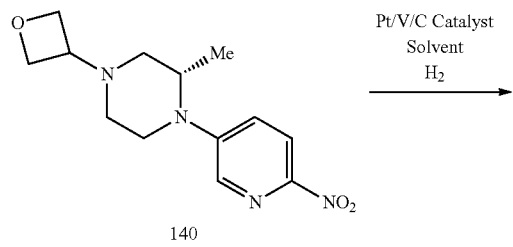

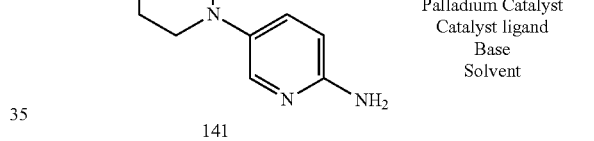

141

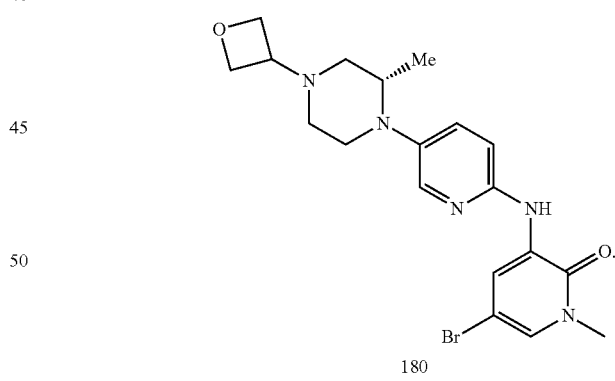

180

In some aspects, the yield of compound 141 based on compound 140 is at least 90% or at least 95%, and the yield of compound 180 based on compound 141 is at least 60%, at least 70%, at least 80%, and the purity of compound 180 is at least 95%, at least 98%, or at least 99%.

Another aspect of the disclosure is directed to a composition comprising at least 98.5 w/w % compound 190, or stereoisomer, geometric isomer, tautomer, or salt thereof,

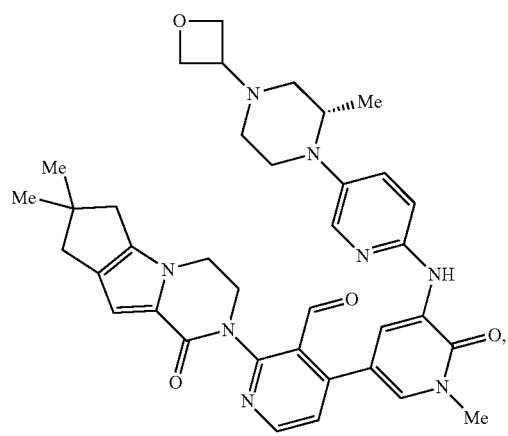

190 and wherein (a) the content of a dimer impurity is less than 0.15 area % based on compound 190 (or a stereoisomer, geometric isomer, tautomer, or salt thereof), wherein the dimer impurity is of the structure

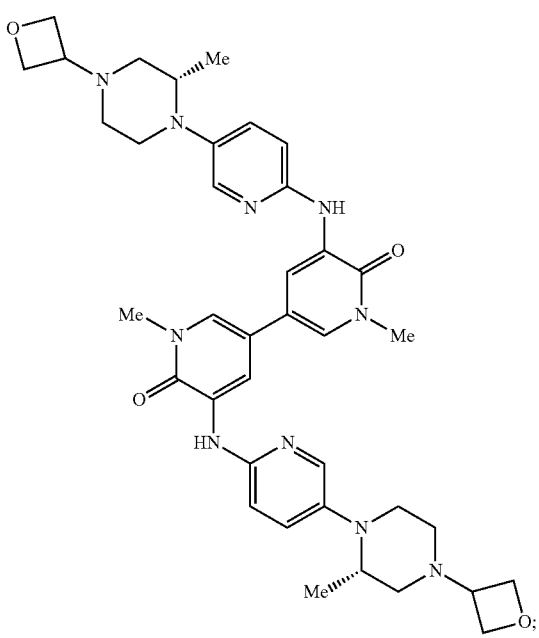 [SMILES: C[C@H]1CN(C2COC2)CCN1c1ccc(Nc2cc(-c3cc(Nc4ccc(N5CCN(C6COC6)C[C@@H]5C)cn4)c(=O)n(C)c3)cn(C)c2=O)nc1]

and (b) the combined content of an alcohol and a ketone impurity is less than 0.35 area % based on compound 190 (or a stereoisomer, geometric isomer, tautomer, or salt thereof), wherein the alcohol and ketone impurities are of the structure

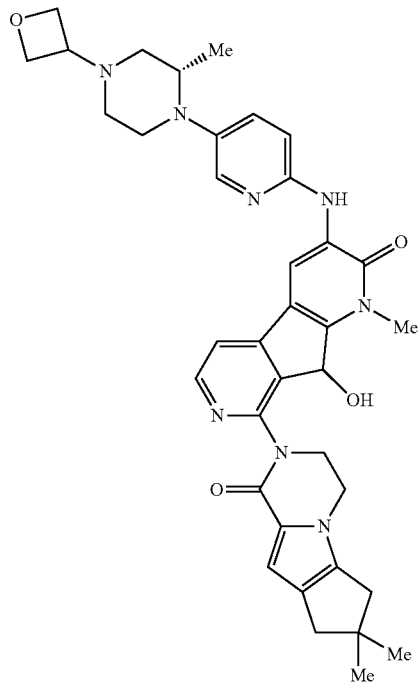

Alcohol

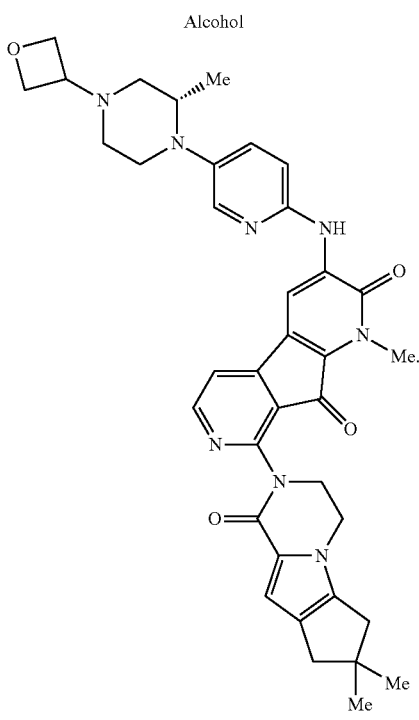

Ketone

DETAILED DESCRIPTION

Figure 1:
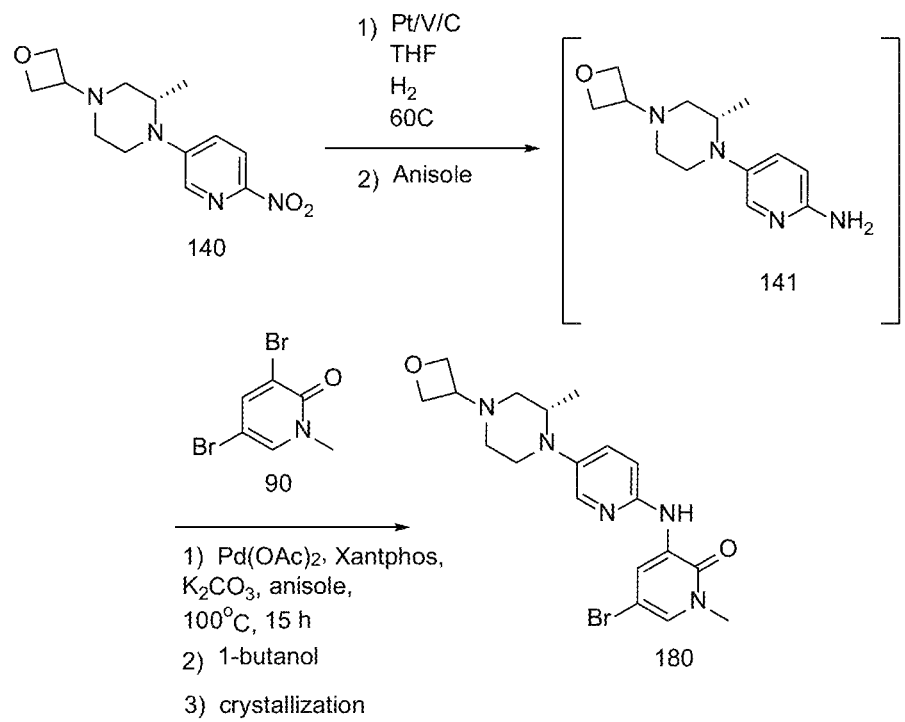
FIG. 1 shows a method for the preparation of compounds 141 and 180.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application. including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety.

Definitions

When indicating the number of substituents, the term "one or more" refers to the range from one substituent to the highest possible number of substitution, i.e., replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e., replacement of one hydrogen up to replacement of all hydrogens by substituents.

As used herein, "alkyl" refers to a monovalent linear or branched saturated hydrocarbon moiety, consisting solely of carbon and hydrogen atoms, having from one to twenty carbon atoms. "Lower alkyl" refers to an alkyl group of one to six carbon atoms, i.e., $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like. Alkyl groups may be optionally substituted, such as with one or more halogens.

As used herein, "cycloalkyl" refers to a carbocyclic moiety consisting of monocyclic or polycyclic rings. Cycloalkyl can optionally be substituted as defined herein. Examples of cycloalkyl moieties include, but are not limited to, cyclopropyl, cyclobutyl, cyclopentyl, cyclohexyl (i.e., "Cy"), cycloheptyl, and the like. Polycyclic ring structures include fused and bridged bicyclic, fused and bridged polycyclic and spirocyclic hydrocarbon ring system such as, for example, bicyclo[2.2.1]heptane, pinane, bicyclo[2.2.2]octane, adamantane, and norborene. Cycloalkyls may be saturated or partially unsaturated (e.g., cycloalkenyl).

As used herein, "aryl" refers to a monovalent aromatic hydrocarbon radical of 6-20 carbon atoms ($C_6$-$C_{20}$). Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein. In some aspects, aryl may be substituted with alkyl, cycloalkyl, halogen, or haloalkyl.

As used herein, "alkoxy" refers to a moiety of the structure —OR, wherein R is an alkyl moiety as defined herein. Examples of alkoxy moieties include, but are not limited to, methoxy, ethoxy, isopropoxy, and the like.

As used herein, "haloalkyl" refers to an alkyl as defined herein in which one or more hydrogen atoms have been replaced with the same or a different halogen. Exemplary haloalkyls include —$CH_2Cl$, —$CH_2CF_3$, —$CH_2CCl_3$, —$CF_3$, $CHF_2$, and the like.

As used herein, "halogen" refers to chlorine, fluorine, bromine and iodine.

As used herein, "amino" refers to a moiety of the structure —NRR' wherein R and R' each hydrogen, "monoalkylamino" refers to such a structure where one of R and R' is hydrogen and the other of R and R' is alkyl, and "dialkylamino" refers to such a structure where each of R and R' is alkyl.

As used herein, "optionally substituted" as used herein refers to a moiety that may be unsubstituted or substituted with specific groups. Examples of substituents include, but are not limited to hydroxy, alkyl, alkoxy, halo, haloalkyl, oxo, amino, monoalkylamino, or dialkylamino.

As used herein, "chiral" refers to molecules which have the property of non-superimposability of the mirror image partner, while the term "achiral" refers to molecules which are superimposable on their mirror image partner.

As used herein, "stereoisomers" refers to compounds which have identical chemical constitution, but differ with regard to the arrangement of the atoms or groups in space.

As used herein, "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

As used herein, "enantiomers" refer to two stereoisomers of a compound which are non-superimposable mirror images of one another.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or Rand S, are used to denote the absolute configuration of the molecule about its chiral center (s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, while stereochemical determination awaits, such as x-ray crystallographic data.

As used herein, the terms "tautomer" and "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "salt" refers to both acid addition salts and base addition salts. "Acid addition salt" refers to salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as fomlic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid mesylate, ethanesulfonic acid, p-toluenesulfonic acid, and salicyclic acid. "Base addition salt" refers to salts formed with an organic or inorganic base.

As used herein an "inorganic base" generally includes sodium, potassium, ammonium, calcium, magnesium, iron, zinc, copper, manganese, and aluminum salts. Non-limiting examples include phosphates such as dipotassium monohydrogen phosphate, potassium dihydrogen phosphate, tripotassium phosphate, disodium monohydrogen phosphate, sodium dihydrogen phosphate, trisodium phosphate, diammonium monohydrogen phosphate, ammonium dihydrogen phosphate and triammonium phosphate; acetates such as potassium acetate, sodium acetate and ammonium acetate; formates such as potassium formate and sodium formate; carbonates such as potassium carbonate, sodium carbonate, potassium hydrogen carbonate and sodium hydrogen carbonate; and alkali metal hydroxides such as lithium hydroxide, sodium hydroxide and potassium hydroxide. The inorganic bases may be used singly, or in combination of two or more kinds thereof.

As used herein, an "organic base" generally includes primary, secondary, and tertiary amines, substituted amines including naturally occurring substituted amines, cyclic amines and basic ion exchange resins, such as pyridine, isopropylamine, trimethylamine, diethylamine, triethylamine, triethanolamine, diisopropylamine, ethanolamine, 2-diethylaminoethanol, trimethylamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

As used herein, "non-polar solvent" refers to a solvent without significant partial charges on any atoms or a solvent where polar bonds are arranged in such a way that the effect of their partial charges cancel out. Non-limiting examples of non-polar solvents include pentane, hexane, heptane, cyclocpentane, cyclohexane, benzene, toluene, 1,4-dioxane, dichloromethane ("DCM"), methyl tert-butyl ether ("MTBE"), chloroform, carbon tetrachloride, and diethyl ether.

As used herein, an "aprotic solvent" refers to a solvent that does not donate hydrogen. As used herein, "polar aprotic solvent" refers to a solvent having high dielectric constants and high dipole movements and that lack an acidic hydrogen. Non-limiting examples of polar aprotic solvents include tetrahydrofuran ("THF"), methyl tetrahydrofuran ("Me-THF"), ethyl acetate ("EA"), acetone, dimethylformamide ("DMF"), acetonitrile ("ACN"), cyclopropylmethyl ether ("CPME"), petroleum ether, N-methyl-2-pyrrolidone ("NMP"), trifluorotoluene, chlorobenzene, anisole, and dimethyl sulfoxide. In some aspects, the aprotic solvent is a low molecular weight ester. Non-limiting examples of aprotic low molecular weight ester solvents include methyl acetate, ethyl acetate, n-propyl acetate, i-propyl acetate, i-butyl acetate, propylene glycol methyl ether acetate, monoethyl ether acetate, and combinations thereof.

As used herein, "polar protic solvent" refers to a solvent having a labile hydrogen bound to an oxygen atom or a nitrogen atom. Non-limiting examples of polar protic solvents include formic acid, n-butanol, i-propanol, n-propanol, ethanol, methanol, acetic acid and water.

As used herein, "solvent" refers to a non-polar solvent, an aprotic solvent, a polar protic solvent, and combinations thereof.

As used herein, a "palladium catalyst" refers to any palladium catalyst that affects the rate and conversion of a chemical substrate compound to a product compound at a commercially acceptable yield and conversion. In some aspects, the palladium catalyzed reactions described herein require a zero valent palladium species (Pd(O)). Exemplary catalytically active (Pd(O)) species may be applied directly (e.g., as commercial Pd(O) complexes such as Pd(PPh$_3$)$_4$, Pd(PCy$_3$)$_2$, Pd(PtBu$_3$)$_2$ or similar Pd(O) complexes), or may be formed from a palladium source in combination either with a ligand and/or a base (e.g., KOtBu, KOH, NaOAc, K$_3$PO$_4$, K$_2$CO$_3$, Hunig's base, NEt$_3$, NPr$_3$). In some aspects, the palladium catalyst comprises a palladium(II) species. In some embodiments, the catalyst further comprises a ligand. In some embodiments, the ligand is a phosphine ligand. In some aspects, the palladium source is selected from the following non-exclusive listing: [PdCl(X)]$_2$ (X=e.g., allyl, cinnamyl, or crotyl), [PdCl(X)PR$_3$] (R=alkyl or aryl), [Pd(X)(Y)] (Y=e.g., cyclopentadienyl or p-cymyl), Pd(dba)$_2$, Pd$_2$(dba)$_3$, Pd(OAc)$_2$, PdZ$_2$ (Z=Cl, Br, I), Pd$_2$Z$_2$(PR$_3$)$_2$, or Pd(TFA)$_2$. In some aspects, the catalytic palladium species is a palladium source selected from the following non-exclusive listing: [Pd(allyl)Cl]$_2$, Pd(MeCN)$_2$Cl$_2$, Pd(benzonitrile)$_2$Cl$_2$, Pd(dba)$_2$, Pd(OAc)$_2$, PdCl$_2$, PdBr$_2$, Pd(TFA)$_2$, Pd(MeCN)$_4$(BF$_4$)$_2$, Pd$_2$(dba)$_3$, Pd(PCy$_3$)$_2$Cl$_2$, Pd(acac)$_2$, and Pd(PPh$_3$)$_4$. In some such aspects, the palladium source is Pd$_2$(dba)$_3$ or Pd(OAc)$_2$. In some embodiments, the palladium source is Pd(PCy$_3$)$_2$. In some other aspects, the catalytic palladium species can be formed in situ from a palladium source, such as described above, and one or more ligands. Non-limiting examples of ligands include DPPF, DTPBF, BINAP, DPPE, DPPP, DCPE, RuPhos, SPhos, APhos (amphos), CPhos, XPhos, t-BuXPhos, Me$_4$t-BuXPhos, neopentyl(t-Bu)$_2$P, (t-Bu)$_2$PMe, (t-Bu)$_2$PPh, PCy$_3$, PPh$_3$, XantPhos, and N-XantPhos, DPEPhos. In some aspects, the ligand is an aryl phosphate. In some aspects, the ligand is XPhos, XantPhos, or DPEPhos In particular aspects, the ligand is XPhos (2-dicyclohexylphosphino-2', 4',6'-triisopropylbiphenyl), Xantphos (4,5-bis(diphenylphosphino)-9,9-dimethylxanthene) or DPEPhos (Oxydi-2,1-phenylene)bis(diphenylphosphine) of the following structures:

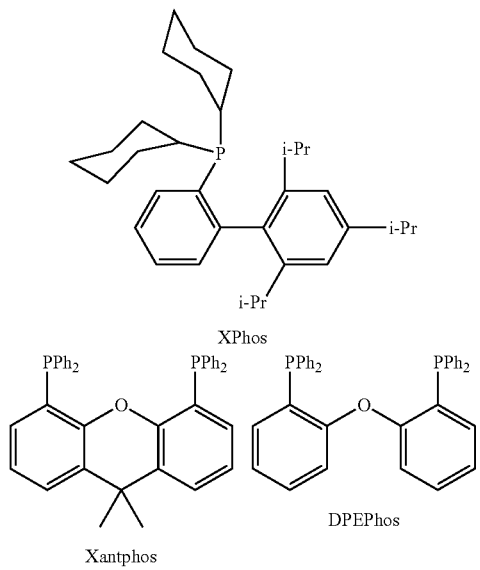

In some aspects, the catalyst comprises a palladium(II) species, a phosphine ligand, and at least one palladium-carbon bond. For example, the catalyst may be selected from: a cationic palladium species comprising an inorganic or organic counterion X; and a neutral palladium species comprising a coordinated inorganic or organic ligand X. X may be a halogen; a carboxylate, such as, but not limited to, CH$_3$C(O)O$^-$, tBuC(O)O$^-$, or CF$_3$C(O)O$^-$; a sulfonate such as, but not limited to, triflate (CF$_3$SO$_3$—), tosylate, besylate, or nosylate; or an inorganic anion, such as, but not limited to, PF$_6^-$, BF$_4^-$, B(C$_6$F$_5$)$_4^-$, NO$_3^-$, or SO$_4^{2-}$. In some aspects, the Pd catalyst is neutral or cationic; and may further comprises a counterion. In some aspects, the catalyst is [(SPhos)Pd(allyl)]CF$_3$SO$_3$, [(SPhos)Pd(allyl)]CH$_3$CO$_2$, [(SPhos)Pd(allyl)]NO$_3$, [(SPhos)Pd(allyl)Cl], [(SPhos)Pd(crotyl)Cl], [(SPhos)Pd(allyl)]PF$_6$, or [(SPhos)Pd(allyl)]CF$_3$CO$_2$. In some other aspects, the catalytic source is a preformed catalyst. Non-limiting examples of preformed catalysts include Pd(dppf)Cl$_2$, Pd(dppe)Cl$_2$, Pd(PCy$_3$)$_2$Cl$_2$, bis(triethylphospine)palladium(II) chloride, Pd(t-Bu$_3$P)$_2$Cl$_2$, Pd[P(o-tol)$_3$]$_2$Cl$_2$, Pd(PPh$_3$)$_2$Cl$_2$, Pd(OAc)$_2$(PPh$_3$)$_2$, and Pd(CH$_3$CN)$_2$Cl$_2$. In some such aspects, the preformed catalyst is Pd(dppf)Cl$_2$. In some further aspects, the catalyst source or preformed catalyst may complex with a solvent such as dichloromethane, chloroform or acetonitrile. Non-limiting examples of such complexes include Pd(dppf)Cl$_2$·DCM, Pd$_2$(dba)$_3$·CHCl$_3$ and Pd(PPh$_3$)$_2$Cl$_2$·ACN.

As used herein, a "borylation reagent" refers to any borylation reagent capable of cross-coupling with an aryl halide to form an aryl boronate. Examples of borylation reagents include, without limitation, tetrahydroxyboron, catecholborane, 4,4,5,5-tetramethyl-1,3,2-dioxaborolane, 4,6,6-trimethyl-1,3,2-dioxaborinane, diisopropylamine borane, bis(neopentyl glycolato)diboron, bis(catecholato)diboron, bis(hexylene glycolato)diboron, bis(pinacolato)diboron, 4-(4,4,5,5-tetramethyl-1,3,2-dioxaborolan-2-yl)-5-(trifluoromethyl)-1-(triisopropylsilyl)-1H-pyrrolo[2,3-b]pyridine, bis(2,4-dimethylpentane-2,4-glycolato)diboron, phenyl boronic acid, diisopropoxy methyl borane, and methyl boronic acid.

As used herein "reducing agent" refers to a compound that donates an electron. Non-limiting examples of reducing agents include sodium borohydride, potassium borohydride, sodium bis(2-methoxyethoxy)aluminum hydride, sodium bisulfite, sodium hydrogensulfite, sodium hydrosulfite, sodium tetrahydroborate, potassium tetrahydroborate, sodium triacetoxyborohydride, trichlorosilane, triphenylphosphite, triethylsilane, trimethylphosphine, triphenylphosphine, diborane, diethoxymethylsilane, diisobutylaluminum hydride, diisopropylaminoborane, lithium aluminum hydride, and lithium triethylborohydride.

As used herein "protecting group" refers to group used for protection of remote functionality (e.g., primary or secondary amine) of intermediates. The need for such protection will vary depending on the nature of the remote functionality and the conditions of the preparation methods. Suitable amino-protecting groups include acetyl trifluoroacetyl, t-butoxycarbonyl (BOC), benzyloxycarbonyl (Cbz) and 9-fluorenylmethyleneoxycarbonyl (Fmoc). For a general description of protecting groups and their use, see T. W. Greene, *Protective Groups in Organic Synthesis*, John Wiley & Sons, New York, 1991.

Some embodiments herein refer to purity or content (e.g., of a desired compound or an undesired compound) using area % as measured by HPLC. Suitable methods of HPLC to evaluate area % are known to those of skill in the art, and include the methods, for example, that were used in Examples 6-9 of the present disclosure, and which are described in detail in the Analytical Methods section.

As used herein, "predominant" and "predominantly" refer to greater than 50%, at least 75%, at least 90%, at least 95%, at least 99% or at least 99.9% on any of a weight, volume, molar, equivalent, v/w %, w/w %, w/v % or v/v % basis.

As used herein, the term "amorphous" or "amorphous form" indicates the substance, component, or product is not essentially crystalline as determined, for instance, by XRPD. In certain aspects, a sample comprising an amorphous form of a substance may be essentially free of other amorphous forms and/or crystalline forms.

As used herein, the terms "crystalline" and "crystal" refer to a crystalline solid form of a chemical compound, including, but not limited to, a single-component or multiple-component crystal form, e.g., a polymorph of a compound; or a solvate, a hydrate, a clathrate, a co-crystal, a salt of a compound, or a polymorph thereof. The term "crystal forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof. Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding and solvent-drop grinding.

Techniques for characterizing crystal forms and amorphous forms are known in the art and include, but are not limited to, thermogravimetric analysis ("TGA"), differential scanning calorimetric ("DSC"), X-ray powder diffraction ("XRPD"), single crystal X-ray diffractometry, vibrational spectroscopy, e.g., IR and Raman spectroscopy, solid-state nuclear magnetic resonance ("NMR"), optical microscopy, hot stage optical microscopy, scanning electron microscopy ("SEM,") electron crystallography and quantitative analysis, particle size analysis ("PSA"), surface area analysis, solubility studies and dissolution studies.

Preparation of Compound 190

In some aspects of the present invention, compound 190, stereoisomers thereof, geometric isomers thereof, tautomers thereof, and salts thereof, may be prepared from compounds 170 and 181 according to the following reaction scheme:

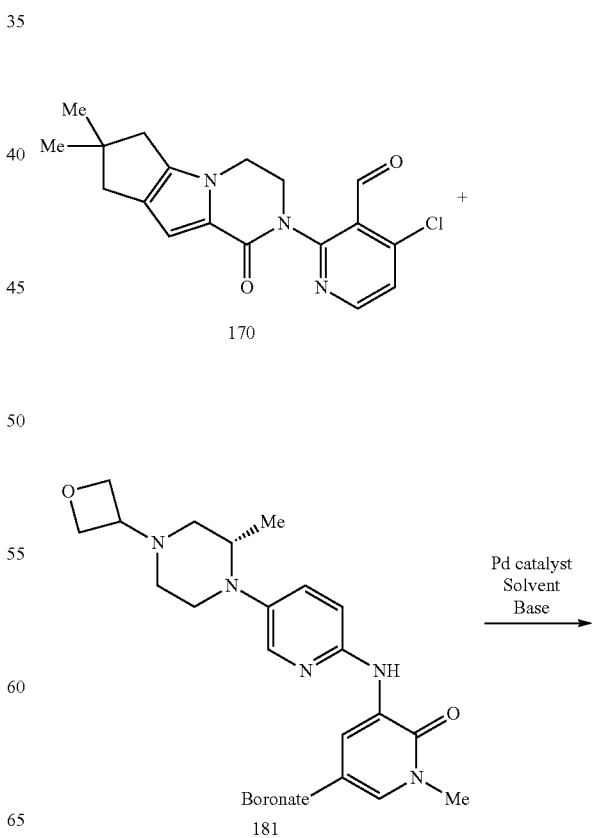

-continued

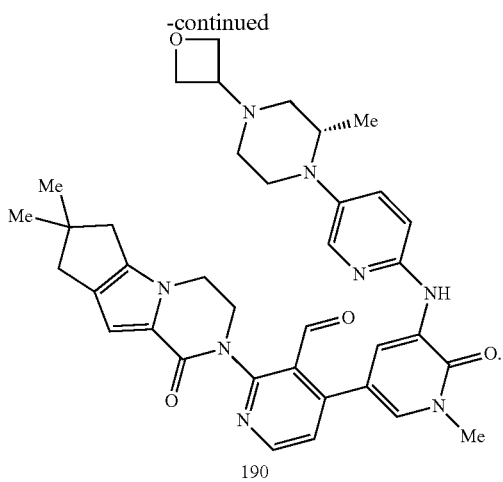

190

Figure 5A:
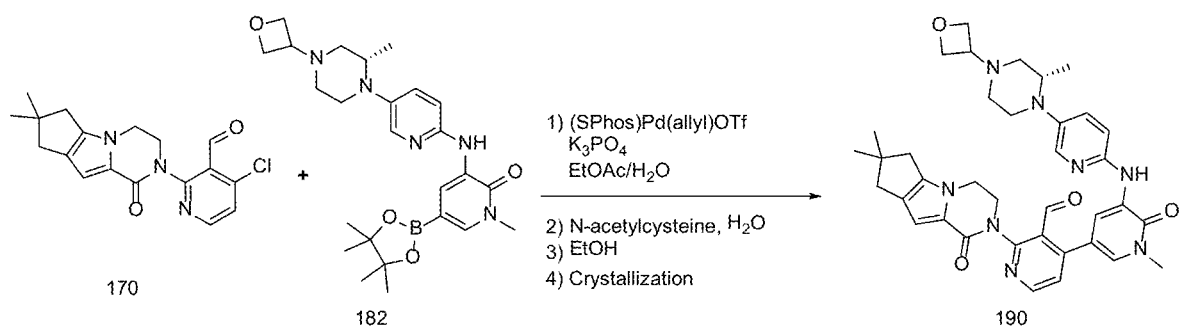
FIG. 5A shows a first method for the preparation of compound 190.
Figure 5B:
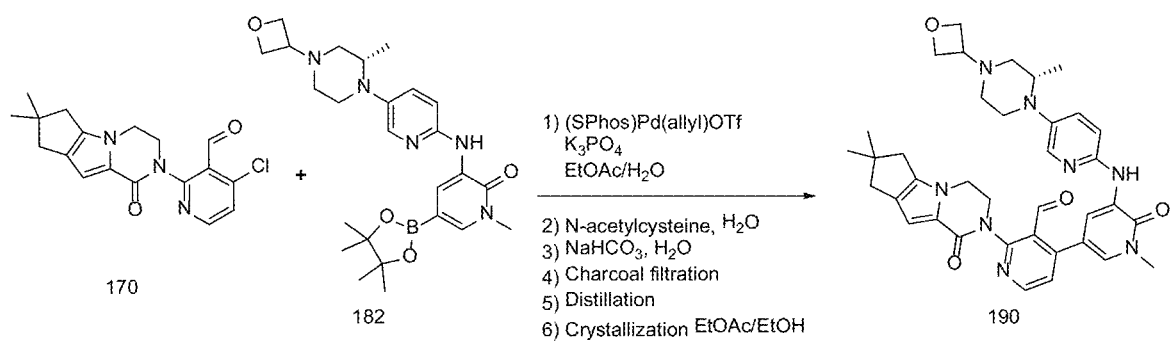
FIG. 5B shows a second method for the preparation of compound 190.

In some aspects, compound 190 (or a stereoisomer, geometric isomers, tautomer, or salt thereof) may be prepared according to the method depicted in FIG. 5A and in FIG. 5B.

Compound 190 (or a stereoisomer, geometric isomers, tautomer, or salt thereof) is prepared from a reaction mixture comprising compound 170, compound 181, a palladium catalyst, a solvent system comprising water, and a base, and reacting the reaction mixture to form a reaction product mixture comprising compound 190, or a stereoisomer, geometric isomer, tautomer, or salt thereof. In certain embodiments, the solvent system further comprises a polar aprotic solvent. In some embodiments, the polar aprotic solvent is an ester, such as a low molecular weight ester. In certain embodiments, the solvent system comprises a low molecule weight ester, such as a lower-alkyl ester of acetic acid. In some embodiments, the low molecular weight ester is ethyl acetate or isopropyl acetate. In certain embodiments, the solvent system comprises water and ethyl acetate. In some embodiments of the methods provided herein, using a solvent system comprising water and an ester, such as a low molecular weight ester, produces compound 190, or a stereoisomer, geometric isomer, tautomer, or salt thereof, at a higher yield, or with lower level of impurities, or both, than methods using a different solvent system.

In some embodiments, in the reaction mixture, the equivalent ratio of compound 181 to compound 170 is greater than 1:1, from greater than 1:1 to about 1.5:1, about 1.01:1, about 1.05:1, about 1.1:1, about 1.15:1, about 1.2:1, about 1.25:1, about 1.3:1, about 1.35:1, about 1.4:1, about 1.45:1 or about 1.5:1, and any range constructed therefrom.

The palladium catalyst may be a palladium catalyst as described elsewhere herein. In some particular aspects, the palladium catalyst comprises a palladium(II) species containing a phosphine ligand and at least one palladium-carbon bond. In some aspects, the fragment giving rise to the palladium-carbon bond is an allyl derivative of the formula:

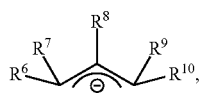

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring. In some particular aspects of the allyl derivative: each of $R^6$ to $R^{10}$ is H; $R^6$ is —$CH_3$ and each of $R^7$ to $R^{10}$ is H; $R^7$ is —$CH_3$ and each of $R^6$ and $R^8$ to $R^{10}$ is H; $R^8$ is —$CH_3$ and each of $R^6$, $R^7$, $R^9$ and $R^{10}$ is H; $R^6$ is -phenyl and each of $R^7$ to $R^{10}$ is H; or $R^7$ is -phenyl and each of $R^6$ and $R^8$ to $R^{11}$ is H.

In some aspects, $R^6$ and $R^{10}$ together with the atoms to which they are attached form a fused bicycle comprising an aromatic ring. In some embodiments, $R^6$ and $R^{10}$ together with the atoms to which they are attached form a five-membered carbocycle fused to a phenyl ring. In some such embodiments, $R^7$, $R^8$, and $R^9$ are H. In other embodiments, two of $R^7$, $R^8$, and $R^9$ are H, and the remainder is $C_{1-10}$ alkyl.

For example, in some aspects, the fragment giving rise to the palladium-carbon bond is an indenyl of the formula

wherein $R^{11}$ is $C_{1-10}$ alkyl. In some particular aspects, the allyl derivative of the structure:

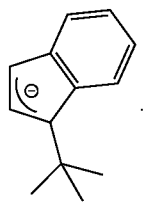

In some aspects, the phosphine ligand is of the formula:

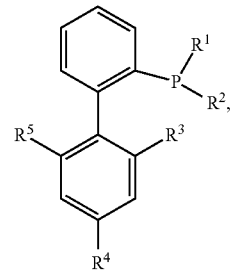

wherein $R^1$ and $R^2$ are each independently selected from the group consisting of: optionally substituted $C_{1-12}$ alkyl, optionally substituted $C_3$-$C_{20}$ cycloalkyl, and optionally substituted $C_5$ or $C_6$ aryl; or $C_{1-4}$ alkyl, and $C_{3-6}$ cycloalkyl. In some aspects, $R^3$ to $R^5$ are each independently selected from the group consisting of: H, optionally substituted $C_{1-6}$ alkyl, alkoxide of the formula —O—$C_{1-6}$ alkyl, and amine of the formula —N($R^{12}$)($R^{13}$) wherein $R^{12}$ and $R^{13}$ are independently selected from H and $C_{1-6}$ alkyl. In some aspects, $R^3$ to $R^5$ are each independently —O—$C_{1-4}$ alkyl and $R^{12}$ and $R^{13}$ are independently selected from H and $C_{1-4}$ alkyl. In some aspects, the phosphine ligand is SPhos, having the following structure:

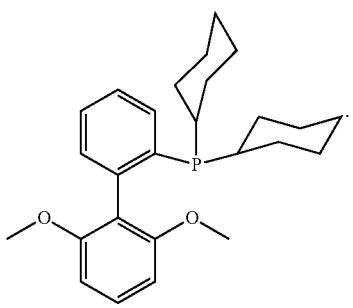 [SMILES: COc1cccc(OC)c1-c1ccccc1P(C1CCCCC1)C1CCCCC1]

In some aspects, the Pd catalyst is selected from: a cationic palladium species comprising an inorganic or organic counterion X; and a neutral palladium species comprising a coordinated inorganic or organic ligand X. In such aspects, X may be selected from a halogen, a carboxylate, a sulfonate, and an inorganic anion. In such aspects, the carboxylate may be as defined elsewhere herein, such as CH$_3$C(O)O$^-$, tBuC(O)O$^-$, or CF$_3$C(O)O$^-$. In such aspects, the sulfonate may be as defined elsewhere herein, such as triflate (CF$_3$SO$_3$—), tosylate, besylate, or nosylate. In such aspects, the inorganic anion may be as defined elsewhere herein, such as PF$_6^-$, BF$_4^-$, B(C$_6$F$_5$)$_4^-$, NO$_3^-$, and SO$_4^{2-}$. In one aspect, X is CF$_3$SO$_3^-$.

In some aspects, the Pd catalyst is neutral or cationic. In certain embodiments, the catalyst further comprises a counterion, such as a cationic catalyst further comprising an anionic counterion. In some aspects, the catalyst is selected from the group consisting of [(SPhos)Pd(allyl)]CF$_3$SO$_3$, [(SPhos)Pd(allyl)]CH$_3$CO$_2$, [(SPhos)Pd(allyl)]NO$_3$, [(SPhos)Pd(allyl)]Cl], [(SPhos)Pd(crotyl)Cl], [(SPhos)Pd(allyl)]PF$_6$, and [(SPhos)Pd(allyl)]CF$_3$CO$_2$. In one aspect, the catalyst is [(SPhos)Pd(allyl)]CF$_3$SO$_3$.

The equivalent ratio of the palladium catalyst to compound 170 is about 0.001:1, about 0.0015:1, about 0.002:1, about 0.0025:1, about 0.003:1, about 0.004:1, about 0.0045:1, about 0.005:1, about 0.006:1, about 0.007:1, about 0.008:1, about 0.009:1, or about 0.01:1, and any range constructed therefrom, such as from about 0.001:1 to about 0.01:1, from about 0.001:1 to less than 0.05:1, from about 0.001:1 to about 0.0045:1, or from about 0.001:1 to about 0.003:1.

In some aspects, the reaction mixture base is an inorganic base. In some particular aspects, the base is K$_3$PO$_4$ or K$_2$HPO$_4$.

In some aspects, the reaction mixture solvent system comprises, predominantly comprises, consists essentially of, or consists of water and at least one aprotic solvent as defined elsewhere herein. The volume ratio of aprotic solvent to water is about 1:0.05, about 1:0.1, about 1:0.5, about 1:1, about 1:1.5, or about 1:2, and any range constructed therefrom, such as from about 1:0.05 to about 1:2, or from about 1:0.1 to about 1:1. In some particular embodiments, the aprotic solvent is an ester. In certain embodiments, the aprotic solvent is a low molecular weight ester, such as an ester of acetic acid with C$_{1-6}$alkyl, such as C$_{1-3}$alkyl. In some embodiments, the ester is isopropyl acetate, or ethyl acetate. In some particular aspects, the solvent system comprises water and ethyl acetate, predominantly comprises water and ethyl acetate, consists essentially of water and ethyl acetate, or consists of water and ethyl acetate. In some aspects, the ratio of the solvent system volume in the reaction mixture to compound 170 weight may be less than 20:1 L/kg, about 5:1 L/kg, about 7.5:1 L/kg, about 10:1 L/kg, about 12.5:1 L/kg, about 15:1 L/kg, about 20:1 L/kg, about 25:1 L/kg, or about 30:1 L/kg, and ranges thereof, such as from about 5:1 to about 30:1 L/kg, from about 5:1 to about 20:1 L/kg, from about 5:1 to about 15:1 L/kg, or from about 7.5:1 to about 12.5:1 L/kg. In certain embodiments, using a solvent system comprising water and an ester (such as ethyl acetate) results in higher product yield, or a lower amount of impurities, or both, compared to using other solvent systems. In some embodiments, the ratio of ethyl acetate to water is from about 1:0.1 to about 1:1, or about 1:0.1 to about 1:0.8, or about 1:0.1 to about 1:0.5, or about 1:0.1 to about 1:0.3.

In some aspects, the catalyst is [(SPhos)Pd(allyl)]CF$_3$SO$_3$, the solvent system predominantly comprises ethyl acetate and water wherein the volume ratio of ethyl acetate to water is from about 1:0.1 to about 1:1 (such as about 1:0.3), and the boronate is 4,4,5,5-tetramethyl-1,3,2-dioxaborolane of the structure:

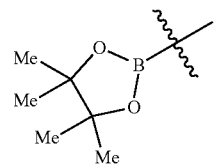

In some embodiments, the reaction temperature for forming compound 190 is greater than about 40° C., greater than about 50° C., greater than about 60° C., greater than about 70° C., or between about 40° C. to about 80° C., between about 50° C. to about 80° C., between about 60° C. to about 80° C., between about 65° C. to about 75° C., is about 60° C., is about 70° C., or is about 80° C. In some embodiments, the reaction temperature is about 70° C. In some embodiments, the solvent system comprises ethyl acetate and water, and a temperature of about 70° C. is used.

The reaction may be deemed complete when the area % concentration by HPLC of compound 170 is less than 2, less than 1, less than 0.5 or less than 0.1. In some embodiments, the reaction is deemed complete when the area % concentration by HPLC of compound 170 is less than 0.5, or not detectible. The reaction time to completion may be about 1 hour, about 2 hours, about 3 hours, about 4 hours, about 5 hours, about 6 hours, about 7 hours, about 8 hours, about 9 hours, about 10 hours, about 11 hours, or about 12 hours. In some aspects, the reaction time to completion is less than 5 hours, such as less than 2 hours or less than 3 hours. In some embodiments, the reaction time is about 1 hour, or about 2 hours.

Without wishing to be bound by theory, the combination of solvent system, catalyst, and temperature described herein may lead to lower reaction times than other combinations. For example, in some embodiments, a combination of a catalyst comprising palladium(II) species containing a phosphine ligand and at least one palladium-carbon bond, solvent system comprising water and an ester (such as a low molecular weight ester, such as ethyl acetate), and a reaction temperature of between about 60° C. to about 80° C. (such as between about 65° C. to about 75° C., such as about 70° C.), may lead to the production of compound 190 or a salt thereof at higher yields in a shorter period of time (such as less than 5 hours, less than 3 hours, or less than 2 hours), or with lower impurities, or both, compared to other conditions.

In some aspects of the invention, the methods of producing compound 190 (or a stereoisomer, geometric isomers, tautomer, or salt thereof) further comprise one or more purification steps. In some embodiments, the one or more purification steps comprise one or more aqueous washes, for example two aqueous washes, or three aqueous washes. In certain embodiments, the one or more purification steps comprise an aqueous N-acetyl-cysteine wash followed by an aqueous base wash, and then a water wash. In certain embodiments, additional purification steps are included, such as filtration.

In some such aspects, the temperature of the reaction product mixture may be adjusted from about 10° C. to about 35° C. or from about 15° C. to about 30° C. or from about 15° C. to about 25° C. (such as about 20° C.) and combined with agitation with aqueous N-acetyl-L-cysteine having a N-acetyl-L-cysteine concentration of about 3 wt. %, about 5.5 wt. %, about 6 wt. % or about 9 wt. %, and ranges thereof, such as from about 3 wt. % to about 9 wt. %. The weight ratio of N-acetyl-L-cysteine to compound 190 may be from about 1:5 to about 1:25, or from about 1:10 to about 1:20, or about 1:15. The ratio of aqueous N-acetyl-L-cysteine volume (such as about 3 wt. % to about 9 wt. % aqueous N-acetyl-L-cysteine) to compound 190 weight may be about 1 L/kg, about 2 L/kg or about 3 L/kg, and ranges thereof, such as from about 1 L/kg to about 3 L/kg. Following agitation with aqueous N-acetyl-L-cysteine, in some embodiments additional organic solvent is added with agitation. The additional organic solvent may be the same organic solvent present in the reaction, for example a low molecular weight ester such as ethyl acetate. In some embodiments, the ratio of additional organic solvent to compound 190 weight is from about 1:3 to about 1:1, or about 1:2 to about 1:1, or about 1:2.5. An aqueous layer is separated and an organic layer comprising compound 190 is collected. The organic layer may be further optionally combined with a base solution, wherein the concentration of base may be from about 3 wt. % to about 7 wt. %, or about 5 wt. %. In some embodiments, the base is sodium bicarbonate (NaHCO₃). In certain embodiments, the ratio of the base solution volume to compound 190 weight may be about 0.5 L/kg, about 1 l/kg, about 1.5 L/kg, about 2 L/kg, or about 2.5 L/kg and ranges thereof, such as from about 0.5 L/kg to about 2.5 L/kg. In such aspects, an aqueous layer is separated and an organic layer comprising compound 190 is collected. The organic layer comprising compound 190 may, in some embodiments, undergo additional washing steps, such as a water wash. In some embodiments, the organic layer comprising compound 190 is combined with water under agitation. In certain embodiments, the ratio of water volume to compound 190 weight may about 0.5 L/kg, about 1 L/kg, about 2 L/g, about 3 L/kg, or about 4 L/kg, or ranges thereof, such as from about 0.5 L/kg to about 4 L/kg, or from about 1 L/kg to about 3 L/kg, or about 2 L/kg. In such aspects, an aqueous layer is separated and an organic layer comprising compound 190 is collected. In some aspects, any of the various organic layers comprising compound 190 may be contacted with activated charcoal, such filtration through a charcoal bed or by suspending activated charcoal in the organic phase followed by charcoal separation and removal such as by filtration or centrifugation. In certain embodiments, a stereoisomer, geometric isomer, tautomer, or salt of compound 190 is produced, and all comparisons and/or ratios made relative to the amount of compound 190 are instead relative to the amount of stereoisomer, geometric isomer, tautomer, or salt of compound 190.

Compound 190 may optionally be isolated from the reaction product mixture or from the organic layer comprising compound 190 from the work up step(s). Such isolation may include, for example, one or more solvent swap, distillation, and/or crystallization steps. In some such aspects, the collected organic layer comprising compound 190, may be processed by a solvent swap step where the aprotic solvent may be swapped for a polar protic solvent as described elsewhere herein. In some aspects, the polar protic solvent is an alcohol. In some such aspects, the polar protic solvent is ethanol. In some such aspects, the solvent swap may be done by reducing the volume of the composition comprising compound 190 by vacuum distillation, and the reduced volume comprising compound 190 may be diluted with the polar protic solvent. For example, a reduced volume comprising compound 190 may be diluted with a polar protic solvent at a ratio of 1:6, 1:5, 1:4, 1:3, or 1:2, or any ranges therein, such as from 1:6 to 1:1, or 1:5 to 1:4, or about 1:4.5. In some embodiments, the ratio of volume of polar protic solvent to compound 190 weight is about 20 L/kg, 15 L/kg, 10 L/kg, 5 L/kg, or ranges therein, such as from about 20 L/kg to about 5 L/kg, or about 15 L/kg to about 5 L/kg, or is about 10 L/kg. In some embodiments, polar protic solvent is added to the reduced volume comprising compound 190 to a total solvent volume of from about 20 to about 5 L solvent per kg of compound 190, or from about 8 to about 12 L solvent per kg of compound 190 to produce a diluted solution of compound 190. The diluted mixture may optionally be treated with activated carbon as describe herein. The volume of the solution of purified compound 190 may be reduced by distillation to a reduced volume of such as from about 3 to about 13 L, from about 3 to about 7 L, from about 6 to about 10 L, or from about 7 to about 9 L of solvent per kg of compound 190. The polar protic solvent (ethanol) dilution and distillation step may be repeated one or more times. In some embodiments, the polar protic solvent dilution and distillation steps is performed one or more times until the content of residual aprotic solvent is less than 10% w/w, or less than 8% w/w, or less than 6% w/w, or less than 4% w/w. In some embodiments, the methods herein further comprise crystallizing compound 190, or stereoisomer, geometric isomer, tautomer, or salt thereof. Such crystallization may, for example, follow the solvent swap and/or distillation steps described herein. The solution of compound 190 may be cooled, such as to less than 25° C., to crystalize purified compound 190. In some embodiments, the solution is cooled to from about 70° C. to about 80° C., such as about 75° C., then cooled to from about 0° C. to about 10° C., such as about 5° C. The purified compound 190 crystals may be collected, such as by filtration or centrifugation, and dried to yield purified dry compound 190 crystals, or stereoisomer, geometric isomer, tautomer, or salt thereof. In some embodiments, the solution of compound 190 is seeded with crystals of compound 190 to promote crystallization. In some embodiments, seed crystals are added as a solid composition (e.g., as dry crystals, or essentially dry crystals, or crystals comprising less than 5% or less than 1% solvent). In other embodiments, the solution of compound 190 is seeded with a suspension of compound 190 in protic solvent to promote crystallization. In some such embodiments, the suspension comprises from about 2.5% to about 10% by weight, or from about 5% to about 8% by weight, of compound 190 in protic solvent (such as an alcohol, for example ethanol). In certain embodiments, the solution is seeded at a temperature of about 70° C. to about 80° C., such as about 75° C., then the seeded solution is cooled to from about 0° C. to about 10° C., such as about 5° C., to produce crystals. In some embodiments, the cooled solution is stirred for at least 5 hours, at least 7 hours, at least 9 hours, at least 11 hours, or between, for example, 5 to 15 hours, and then the crystals are isolated. Compound 190 crystals may be collected by filtration or centrifugation and washed with cold $C_{1-4}$ alcohol and/or water. In some such aspects, the crystals may be washed with alcohol, water/alcohol (e.g., in a 1:1 v/v ratio), and then alcohol. In some such aspects, the alcohol is methanol. The washed compound 190 crystals may be dried under vacuum, e.g., at a temperature of from about 30° C. to about 70° C. (such as from about 35° C. to about 65° C., or from about 45° C. to about 55° C.) and a vacuum of from about 2-10 mbar.

The yield of compound 190, or stereoisomer, geometric isomer, tautomer, or salt thereof, based on compound 170 is at least 80%, at least 85%, at least 90%, or at least 95%. In some embodiments, the yield is at least 910%. In some embodiments, the yield is at least 93%. In certain embodiments, the yield is at least 96%. In some embodiments, the purity of compound 190 is at least 99 area %, at least 99.5 area %, at least 99.6 area %, at least 99.7 area %, at least 99.8 area %, or at least 99.9 area % by HPLC. In some embodiments, the content of compound 190, or stereoisomer, geometric isomer, tautomer, or salt thereof is at least 98.5% w/w, at least 99% w/w, at or at least 99.5% w/w. The content of a dimer impurity, depicted below, is less than 0.15 area %, less than 0.1 area %, less than 0.05 area %, or is undetectable as measured by an HPLC method according to the present disclosure. In some embodiments, the content of a dimer impurity, depicted below, is less than 0.29% w/w, or less than 0.25% w/w, or less than 0.2% w/w, or less than 0.15% w/w, or less than 0.1% w/w. In some embodiments, the combined content of a ketone and alcohol impurity, depicted below, is less than 0.3 area %, less than 0.25 area %, less than 0.2 area %, less than 0.15 area %, less than 0.1 area %, less than 0.05 area %, no more than 0.05 area %, or is undetectable as measured by HPLC. In certain embodiments, area % is evaluated using the HPLC method according to the present disclosure.

The catalytic system of the present disclosure displays much higher activity for the coupling of compounds 170 and 181 to yield compound 190 as compared to previously disclosed catalytic systems employing a $Pd(dppf)Cl_2$ catalyst. The higher activity results in a catalysts loading of as low as about 0.1 mol % or about 0.2 mol % (0.001 eq or about 0.002 eq) based on compound 170 as compared to previously disclosed loading of about 1 mol %. The improved catalyst system has the advantage of higher yields and lower byproduct impurities, as has been described herein and is illustrated in the Examples. For example, in some embodiments the present catalytic system provides for compound 190 yield, based on compound 170, of at least 90%, or at least 93%; and dimer impurity content of less than 0.15 area %, or less than 0.1 area %, or is undetectable. The increased yield and decreased impurity profile using the improved catalytic system described herein may be reflected in particular at higher batch sizes, such as when using greater than 100 g of starting material 170, such as at least 100 g, at least 250 g, at least 500 g, at least 750 g, at least 1 kg, or at least 2 kg of compound 170. In previously described processes for producing compound 190, increasing batch size (such as from 50 g to 0.75 kg starting material 170) resulted in a decrease in yield of compound 190 obtained. Thus, in certain aspects the presently described catalytic system advantageously results in higher yields of compound 190 with lower levels of impurities such as dimer, alcohol, and ketone impurities, when preparing larger batch sizes of compound 190 (e.g., at least 1 kg, or at least 5 kg, or at least 50 kg, or at least 100 kg, or at least 150 kg, or about 175 kg, such as 160-185 kg). Further, in some embodiments, the catalytic system described herein exhibits higher activity in a solvent system comprising water and an aprotic ester solvent, compared to previously used solvent systems. Using a solvent system comprising water and an aprotic solvent, wherein the solvent is an ester, in combination with the catalytic system described herein results in a higher yield, or lower level of impurities, or both, compared to prior systems using other solvents. In addition, the methods described herein may be carried out at higher temperatures, and/or shorter reaction times, compared to prior methods, and the change of these parameters may have additional advantages.

The present combination of catalyst, solvent, and base, referred to as the catalytic system, further provides for compound 190 purity on the order of about 99.8 area % (HPLC) or greater as compared to purity of up to 99.5 area % described by previous methods. Concomitant with an improved impurity profile, the present catalytic system provides for a significant reduction in the generation of certain impurities that are difficult to remove, thereby obviating the need for certain purification steps. For instance, three impurity byproducts of the compound 170-181 coupling reaction include a dimer impurity, a sec-alcohol impurity, and a ketone impurity as follows:

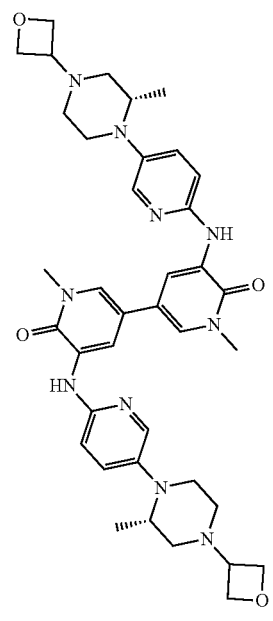

Dimer

-continued

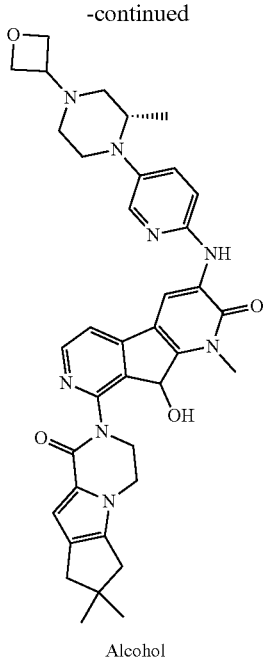

Alcohol

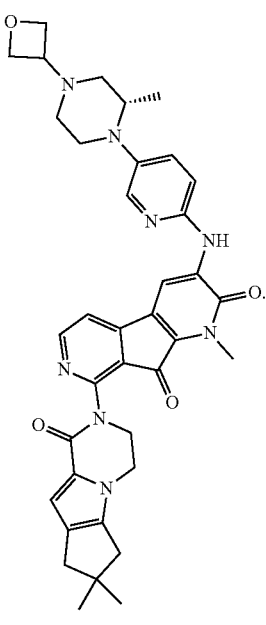

Ketone

Representative compound 190 impurity profiles for the previously disclosed and present catalytic systems are shown in the table below, using the same HPLC method for quantification.

| Impurity | Previous catalytic system | Present catalytic system |
|---|---|---|
| Dimer | About 0.3 to about 0.5 w/w % | Not Detected |
| sec-Alcohol | Not Detected | Not Detected |
| Ketone | Up to about 0.3 area % | Up to about 0.06 area % |

The combination of catalytic system described herein, solvent system comprising an ester, and increased reaction temperature compared to previous methods, advantageously provides one or more (including a combination of some, or all) of: higher yields of compound 190 (particularly at larger batch sizes), lower levels of impurities (including decreasing some impurities below detectable levels), a more efficient reaction work-up, and shorter reaction times than previously required.

Further provided herein are compositions comprising compound 190, or stereoisomer, geometric isomer, tautomer, or salt thereof, with low levels of impurities. Such compositions may comprise, for example, at least 98.5 w/w %, at least 99.0 w/w %, at least 99.3 w/w %, at least 99.5 w/w %, or at least 99.7 w/w % compound 190, or stereoisomer, geometric isomer, tautomer, or salt thereof. In some embodiments, the composition has a compound 190 purity of at least 99 area %, at least 99.5 area %, at least 99.6 area %, at least 99.7 area %, at least 99.8 area %, or at least 99.9 area % by HPLC. In some embodiments, the composition has a content of a dimer impurity of less than 0.15 area %, less than 0.10 area %, less than 0.05 area %, or is not detectible, based on compound 190; or has a dimer impurity content less than 0.29% w/w, less than 0.25% w/w, less than 0.2% w/w, less than 0.15% w/w, or less than 0.10% w/w; wherein the dimer impurity is of the structure

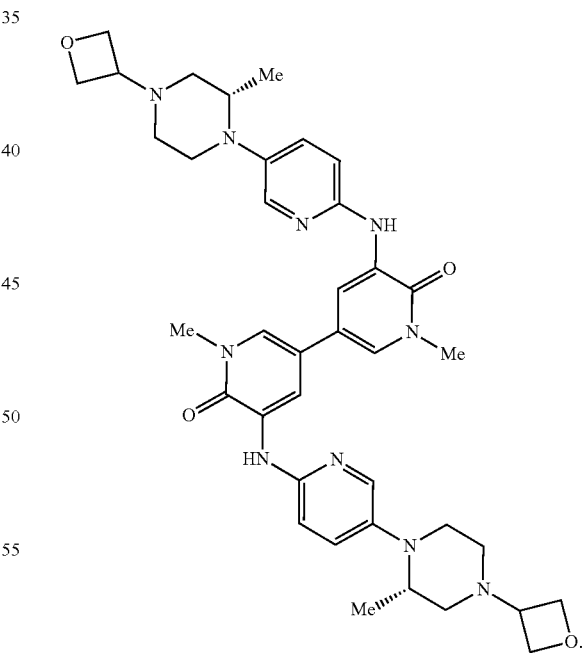

In some embodiments, the composition has a combined content of an alcohol and a ketone impurity based on compound 190 that is less than 0.35 area %, less than 0.30 area %, less than 0.25 area %, less than 0.20 area %, less than 0.15 area %, less than 0.1 area %, less than 0.05 area %, no more than 0.05 area %, or is undetectable, wherein the alcohol and ketone impurities are of the structure:

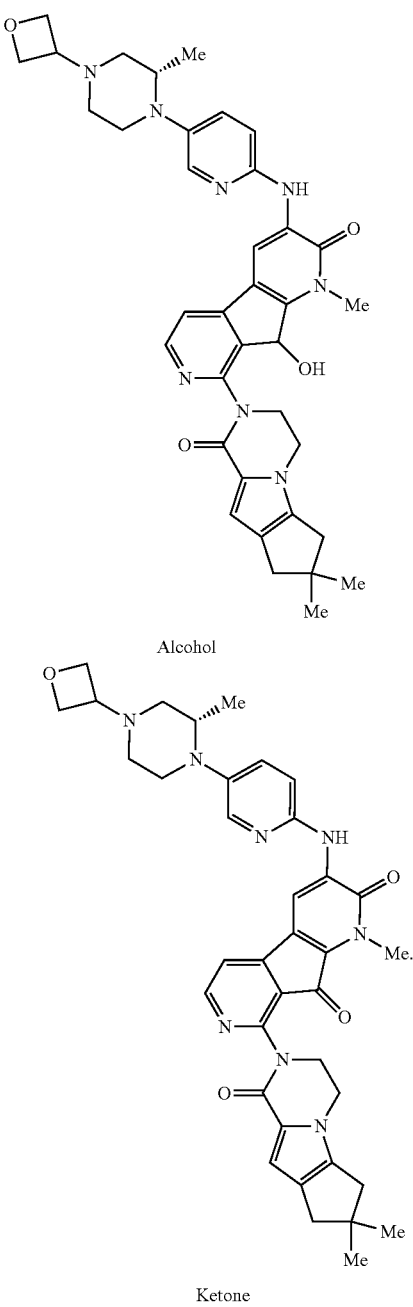

Alcohol and

Ketone

In some embodiments, the composition comprises at least 1 kg, at least 2 kg, at least 5 kg, at least 25 kg, at least 50 kg, at least 75 kg, at least 100 kg, at least 125 kg, at least 150 kg, or at least 175 kg of compound 190, for example between 1-200 kg, or between 5-100 kg, or between 50-200 kg, or between 100-200 kg of compound 190.

In certain embodiments, a stereoisomer, geometric isomer, tautomer, or salt of compound 190 is produced, and all comparisons and/or ratios made relative to the amount of compound 190 are instead relative to the amount of stereoisomer, geometric isomer, tautomer, or salt of compound 190.

Preparation of Compound 200

Compound 200 (or a stereoisomer, geometric isomer, tautomer, or salt thereof) is prepared from a second reaction mixture comprising compound 190 (or stereoisomer, geometric isomer, tautomer, or salt thereof), a reducing agent, a base and a solvent. The second reaction mixture is reacted to reduce the aldehyde moiety of compound 190 and form a reaction product mixture comprising compound 200 as generally depicted below

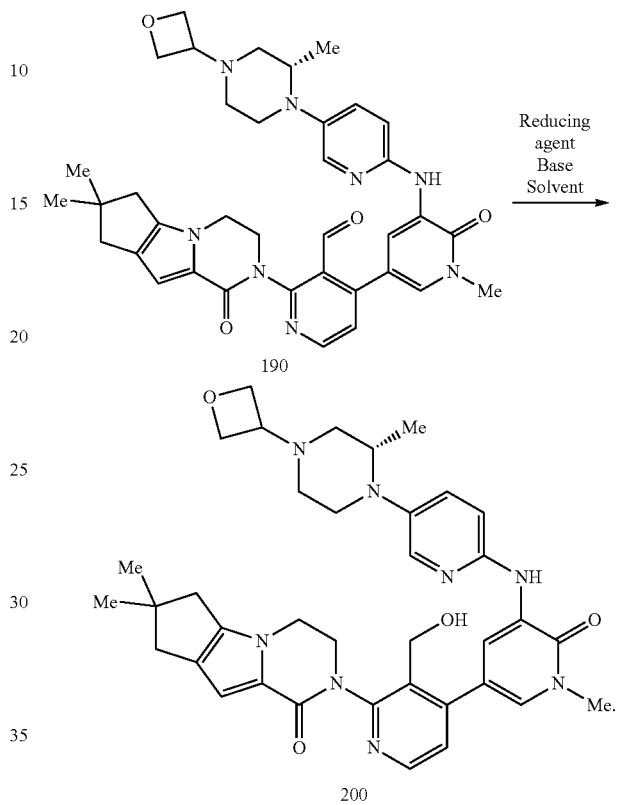

Figure 6:
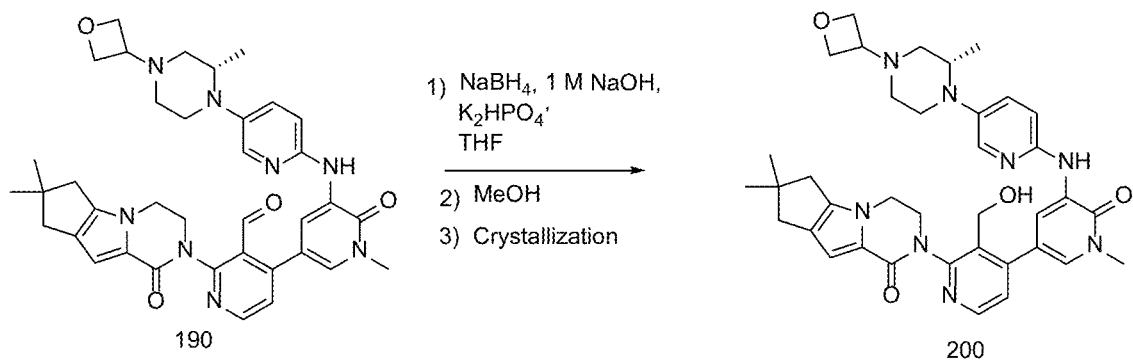
FIG. 6 shows a method for the preparation of compound 200.

In some aspects, compound 200 may be prepared according to the method depicted in FIG. 6.

In some aspects, the solvent is selected from $C_{1-4}$ alcohols, ethers and cyclic ethers. In some particular aspects, the solvent an aprotic solvent, such as THF, methyl tert-butyl ether, or 2-Me-THF. The ratio of solvent volume to compound 190 weight may be about 2:1 L/kg, about 3:1 L/kg, about 4:1 L/kg, about 5:1 L/kg, about 6:1 L/kg, about 7:1 L/kg, about 8:1 L/kg, about 9:1 L kg, about 10:1 L/kg, and ranges thereof, such as from about 2:1 to about 10:1 L/kg, or from about 4:1 to about 8:1 L/kg. In some aspects, the solvent predominantly comprises or consists of THF. In some aspects, the base in the reaction mixture is an inorganic base, such as an alkali hydroxide. In one such aspect, the base is sodium hydroxide. The equivalent ratio of base to compound 190 is about 0.1:1, about 0.2:1, about 0.3:1, about 0.4:1, about 0.5:1, about 0.6:1, about 0.7:1, about 0.8:1, or about 0.9:1, and ranges thereof, such as from about 0.1:1 to about 0.9:1 or from about 0.3:1 to about 0.7:1. In any of the various aspects, the reducing agent is as described elsewhere herein. In some particular aspects, the reducing agent is sodium borohydride. The equivalent ratio of the reducing agent to compound 190 is about 0.1:1, about 0.2:1, about 0.3:1, about 0.4:1, about 0.5:1, about 0.6:1, about 0.7:1, about 0.8:1, or about 0.9:1, and ranges thereof, such as from about 0.1:1 to about 0.9:1 or from about 0.2:1 to about 0.8:1. In some embodiments, the base and reducing agent are added to the reaction mixture in the form of solids, or an aqueous solution, or a combination. In some embodiments, the base and reducing agent are added separately, while in other embodiments, they are added together. In some embodiments, the base and the reducing agent are added to the reaction mixture together, for example as an aqueous mixture. In certain embodiments, the molar ratio of base: reducing agent is from about 0.5:1 to 0.5:2, such as about 0.5:1.25 to 0.5:1.75, for example about 0.5:1.57.

The reaction temperature for forming compound 200 is suitably about 20° C., about 25° C., about 30° C., about 35° C., about 40° C., about 45° C., about 50° C., about 55° C., or about 60° C. The reaction may be deemed complete when the area % concentration by HPLC of compound 200 is less than 2, less than 1, less than 0.5 or less than 0.1. In some aspects, the reaction time to completion may be 0.5 hours, 1 hour, 2 hours, 4 hours, 6 hours, or more. The yield of compound 200 or salt thereof is at least 60%, at least 70%, at least 80%, at least 85%, at least 90%, at least 91%, at least 92%, at least 93%, at least 94%, or at least 95%, and the purity of compound 200 is at least 99 area %, at least 99.5 area %, at least 99.9 area %, or 100 area % by HPLC. In some embodiments, the yield of compound 200 or salt thereof is at least 90%, and the purity is at least 99.9 area % by HPLC.

In some aspects, compound 200 may be isolated from the reaction product mixture. In some such aspects, compound 200 may be isolated by admixing the second reaction product mixture with an aqueous solution of a base, such as an inorganic base (e.g., monopotassium phosphate); or admixing with an aqueous solution of an inorganic acid, such as phosphoric acid (i.e. $H_3PO_4$). In some embodiments, the aqueous base or inorganic acid in a volume ratio to compound 200 weight of from about 0.5 L to about 2 L of about 10 percent by weight to about 25 percent by weight aqueous base or acid (e.g., monopotassium phosphate or phosphoric acid) solution per kg of compound 200. In some embodiments, such admixing is performed at a temperature of about 15° C. to about 50° C., such as about 20° C., or about 30° C., or about 40° C. An aqueous layer is separated and an organic layer comprising compound 200 in solution is collected. The organic layer comprising compound 200 may optionally be treated with activated charcoal. The organic layer comprising compound 200 may be filtered.

In some aspects where the solvent is an aprotic solvent (e.g., THF), the filtrate may be distilled to a volume of from about 2 to about 4 L/kg of compound 200. A suitable solvent, such as a $C_{1-4}$ alcohol (e.g., methanol) may be added to the distilled filtrate to a total volume of from about 6 to about 8 L/kg of compound 200. In some aspects, from about 0.2 to about 0.8 percent by weight compound 200 seed crystals may be added to form a mixture. The mixture may be distilled to reduce the volume by at least 1 L/kg of compound 200, for instance about 2 L/kg, about 3 L/kg, about 4 L/kg, about 5 L/kg, about 6 L/kg, about 7 L/kg, or about 8 L/kg. In some aspects, the distillate may be aged for at least one hour, such as about 1 hour, about 2 hours, about 3 hours, or about 4 hours at a temperature of at least 40° C., for instance about 45° C., about 50° C., about 55° C., about 40° C., or about 65° C. The distilled mixture of compound 200 may be cooled, such as to less than 20° C., to form a slurry of crystallized compound 200 from the cooled mixture. In some embodiments, crystals may begin to form prior to distillation. The slurry may be aged for an amount of time, such as for instance about 30 minutes, about 1 hour, about 2 hours, about 3 hours, or about 4 hours. Compound 200 crystals may be optionally collected and dried. Drying may suitably be done under vacuum and an inert gas purge (e.g., argon or nitrogen) at a temperature of, for instance, about 30° C., about 35° C., about 40° C., about 45° C., about 50° C., about 55° C., or about 60° C. to for a time sufficient to remove the desired amount of solvent, such as for instance about 6 hours, about 12 hours, about 18 hours, about 24 hours, or about 30 hours.

In some aspects, the purified compound 200 crystals may be recrystallized in a purification step. In some such aspects, compound 200 may be combined with a $C_{1-4}$ alcohol (e.g., ethanol) at a ratio of alcohol volume to compound 200 weight of from about 1 L/kg to about 10 L/kg or from about 1 L/kg to about 5 L/kg or from about 4 L/kg to about 10 L/kg or from about 6 L/kg to about 8 L/kg, and with toluene at a ratio of toluene volume to compound 200 weight of from about 1 L/kg to about 5 L/kg or from about 1.5 L/kg to about 3.5 L/kg and with agitation. The mixture may be heated, such as to from about 65 to about 85° C., with agitation and held until a solution is obtained. The solution may then be cooled, such as to from about 60° C. to about 70° C., or from about 65° C. to about 75° C., and combined with additional alcohol and seed crystals. In some embodiments, the cooled solution is first combined with additional alcohol, for example with sufficient additional alcohol such that the alcohol:toluene ratio is about 90:10, or about 80:20, or about 70:30, or any ranges within, and then seed crystals are added, such as from about 0.5 wt % to about 4 wt %, or from about 0.5 wt. % to about 3 wt. %, or from about 0.5 wt. % to about 1.5 wt. % compound 200 seed crystals, to form a slurry. In some embodiments, the solution is further cooled between alcohol addition and seed crystal addition. Alternatively, the solution is first combined with seed crystals and then additional alcohol, such as from about 0.5 wt % to about 4 wt %, or from about 0.5 wt. % to about 3 wt. %, or from about 0.5 wt. % to about 1.5 wt. % compound 200 seed crystals, to form a slurry; and then combined with alcohol at a ratio of alcohol volume to compound 200 weight of from about 5 L/kg to about 25 L/kg or from about 10 L/kg to about 20 L/kg. In either aspect, the slurry may be further cooled, such as to from about −5 to about 15° C., and held for at least 15 minutes, at least 30 minutes, at least 1 hour, at least 2 hours, at least 4 hours, or at least 8 hours to crystallize compound 200. In some embodiments, one or more thermocycles are involved after the initial cooling step, such as raising the temperature to between about 30° C. to about 50° C., or about 35° C. to about 50° C., holding for at least 15 minutes, or at least 30 minutes, or at least 1 hour, then cooling again to from about −5 to about 15° C. and holding to crystallize compound 200. The crystals may be collected, such as by filtration or centrifugation, and washed with alcohol. The washed crystals may be dried under vacuum with a $N_2$ purge at from about 40 to about 60° C. for at least 4 hours, at least 8 hours, at least 12 hours, or at least 20 hours to produce purified compound 200.

Preparation of Compound 141

In some aspects of the present disclosure, compound 141 may be prepared from compound 140 according to the following reaction scheme:

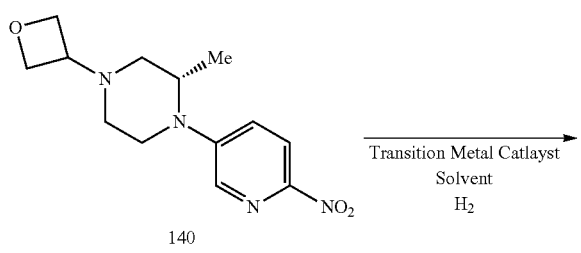

-continued

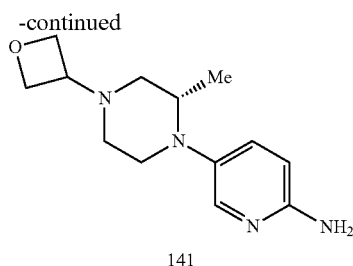

141

The method for preparing compound 141 comprises forming a reaction mixture comprising compound 140, a transition metal catalyst, hydrogen, and a suitable solvent. In some embodiments, the method comprises: forming a reaction mixture comprising compound 140 and a solvent comprising organic solvent and water; and contacting said reaction mixture with a transition metal catalyst in the presence of hydrogen to form a product mixture comprising compound 141.

Compound 141 may be produced via batch processing or continuous flow processing methods.

In some embodiments, the transition metal catalyst is one that comprises one or more transition metals, and may optionally comprise one or more additional components such as one or more non-transition metals, non-metals, metal oxides, solid supports, or any combinations thereof. In some embodiments, the one or more transition metals are selected from the group consisting of Pd, Pt, Co, Ra, and Ni. The transition metal catalyst is suitably selected from Pd/C, Sponge-Ni (which may include Ra—Ni), Ra—Co, Pt/V@C, and Beller type catalysts such as Co@Chitin, Ni-phen@SiO$_2$, or Ni-phen@TiO$_2$. In some aspects, the catalyst is suitably selected from Ra—Ni, Ra—Co, Pt/V@C, and Beller type catalysts such as Co@Chitin, Ni-phen@SiO$_2$, or Ni-phen@TiO$_2$. In some aspects, the catalyst is suitably selected from Pd/C, Sponge-Ni (which may include Ra—Ni), Pt/V@C, Co@Chitin, and Ni-phen@TiO$_2$. In one aspect, the catalyst is Pt/V@C. Pt/V@C (that is, platinum and vanadium supported on carbon) may also be known as Pt—V/C or Pt/V/C. In some embodiments, such catalyst is used in a batch processing method. In some embodiments, the catalyst comprises Pd, Pt, Al, or C, or any combinations thereof, such as comprising Pd or Pt and Al or C. In some embodiments, the catalyst is Pd/Al$_2$O$_3$, Pt/Al$_2$O$_3$, Pd/C, or Pt/C. In some embodiments, the catalyst comprises Pd and Al, for example is Pd/Al$_2$O$_3$. As known to those of skill in the art, there exist alternative formats of describing catalysts—for example, a support may sometimes be referenced using the "@" symbol in some formats, or alternatively using "/". For example, Pt/V@C may also be referred to as Pt/V/C or Pt—V/C; Pd/C may be referred to as Pd@C; Co@Chitin, Ni-phen@SiO$_2$, and Ni-phen@TiO$_2$ may alternatively be referenced as Co/Chitin, Ni-phen/SiO$_2$, and Ni-phen/TiO$_2$, respectively; and so on.

In some embodiments, such catalyst is used in a continuous flow processing method. A catalyst used in continuous flow processing may be in the form of, for example, a packed bed catalyst or an immobilized catalyst. Immobilized catalysts may include those formed by electroplating, spray coating, or slurry coating the catalyst on a solid support. Suitable solid supports may include, for example, polymer-based, carbon-based, or metal-based supports, or any combination thereof (for example, polymer-based carbon supports). In some embodiments, the immobilized catalyst comprises a catalytic static mixer (CSM) support. One or more of such supports may be used. Such CSMs may be prepared, for example, via methods comprising selective laser-melting or 3D printing techniques.

Beller type catalysts are known in the art. See, for instance: Formenti, D. et al., "A State-of-the-Art Heterogeneous Catalyst for Efficient and General Nitrile Hydrogenation", Chem. Eur. J. 2020, 26, 15589; Sahoo, B., et al., "Biomass-Derived Catalysts for Selective Hydrogenation of Nitroarenes", ChemSusChem 2017, 10, 3035; and Bachmann, S., et al., "Nitrogen containing biopolymer-based Catalysts, a Process for their Preparation and Uses thereof", WO2018/114777. These references are incorporated herein in their entirety. The catalysts may suitably comprise a transition metal content of about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 20 wt. %, or about 25 wt. %, and any range constructed therefrom, such as from about 1 wt. % to about 25 wt. %, from about 1 wt. % to about 15 wt. %, or from about 2 wt. % to about 10 wt. %. In some aspects, Ni and Co catalysts may suitably comprise a transition metal content of about 0.5 mol %, 1 mol %, 1.5 mol %, 2 mol %, 2.5 mol %, 3 mol %, 3.5 mol %, 4 mol %, 4.5 mol %, 5 mol %, 6 mol %, 7 mol %, 8 mol %, 9 mol %, or 10 mol %, and any range constructed therefrom, such as from about 0.5 mol % to about 10 mol %, from about 1 mol % to about 7 mol %, or from about 2 mol % to about 5 mol %. The catalytic amount of transition metal is suitably about 0.1 wt. %, about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, or about 10 wt. %, and any range constructed therefrom, such as from about 0.1 wt. % to about 10 wt. %, from about 0.1 wt. % to about 5 wt. %, from about 1 wt. % to about 5 wt. %, or from about 2 wt. % to about 4 wt. %. In the case of Ni and Co catalysts, the catalytic amount is about 0.5 mol %, about 1 mol %, about 1.5 mol %, about 2 mol %, about 2.5 mol %, about 3 mol %, about 3.5 mol %, about 4 mol %, about 5 mol %, about 6 mol %, or about 7 mol %, and any range constructed therefrom, such as from about 0.5 mol % to about 7 mol %, from about 1 mol % to about 5 mol %, or from about 2 mol % to about 4 mol %. In reference to catalyst amount, wt % may refer to the weight of a wet catalyst, such as a catalyst that contains some water and has not been fully dried. For example, catalysts such as Pt—V@C and Pd/C, if not fully dried, may contain about 50% water by weight, or between about 50% to about 70% water by weight, such as about 60% to about 65% water by weight. Thus, in some embodiments, as an example, about 2% w/w catalyst loading of a wet catalyst may correspond to about 0.76% w/w of dry catalyst. In some embodiments, the catalyst loading is from about 0.5% w/w to about 1% w/w dry catalyst. In other embodiments, wt % may refer to the weight of a dry catalyst; for example Beller-type catalysts are typically dry. References to mol % refer to the molar amount of the catalytic species irrespective of water content.

In some aspects, the solvent is selected from a non-polar solvent, a polar aprotic solvent, and a polar protic solvent. In some aspects, the solvent is selected from alcohols, ethers, esters, toluene, dichloromethane, water, and combinations thereof. In some aspects, the solvent is selected from ethers (including cyclic ethers), alcohols, and combinations thereof. In some aspects, the solvent is selected from methanol, ethanol, isopropanol, dioxane, toluene, THF and Me-THF, water, and combinations thereof. In some aspects, the solvent predominantly comprises water and a co-solvent. In some aspects, the solvent predominantly comprises THF, predominantly comprises toluene and methanol, or predominantly comprises THF and water. In aspects wherein the solvent predominantly comprises water and a co-solvent, the volume ratio of the co-solvent to water is about 50:1, about 40:1, about 30:1, about 20:1, about 10:1, of about 1:1, and any range constructed therefrom, such as from about 1:1 to about 50:1, from about 10:1 to about 40:1, or from about 10:1 to about 30:1. When the solvent system predominantly comprises the combination of two organic solvents (e.g., toluene and methanol), the volume ratio between the solvents is suitably about 10:1, about 5:1, about 3:1, about 2:1, about 1:1, about 1:2, about 1:3, about 1:5, or about 1:10. In some aspects, the solvent predominantly comprises THF, e.g., no or essentially no co-solvent is used (e.g., none is intentionally included or added). In some embodiments, water may be present. For example, a small amount of water may be included when using certain catalysts that are not dried before use, even when no further water is separately added. In certain embodiments, no additional water is intentionally included or added beyond that which accompanies a catalyst. The presence of residual water associated with a catalyst may occur, for example, in batch processing methods. Water may in some embodiments be produced during the reaction though not added to the initial reaction mixture, for example in batch processing methods. In other embodiments, additional water may be included in the reaction mixture, for example in certain continuous flow processing methods. The ratio of the solvent volume to compound 140 weight is about 3:1 L/kg, about 5:1 L/kg, about 10:1 L/kg, about 15:1 L/kg, or about 20:1 L/kg, and range thereof, such as from about 3:1 to about 20:1 L/kg, from about 3:1 to about 10:1 L/kg, or from about 4:1 to about 6:1 L/kg. On a wt. % basis, the concentration of compound 140 in the reaction mixture is suitably about 5 wt. %, about 10 wt. %, about 15 wt. %, about 20 wt. %, about 25 wt. %, about 30 wt. %, or about 35 wt. %, and any range constructed therefrom, such as from about 5 wt. % to about 35 wt. %, or from about 10 wt. % to about 25 wt. %.

The reaction for forming compound 141 may be done with $N_2$ purging prior to introducing $H_2$. The reaction is typically done at a temperature of about 20° C., about 30° C., about 40° C., about 50° C., about 60° C., about 70° C., about 80° C., about 90° C., about 100° C., about 125° C., about 150° C., about 175° C., or about 200° C., and any range constructed therefrom, such as from about 20° C. to about 200° C., or from about 40° C. to about 80° C. The hydrogen pressure in the reaction is suitably about 0.1 bar, about 0.5 bar, about 1 bar, about 2 bar, about 3 bar, about 4 bar, about 5 bar, about 6 bar, about 7 bar, about 8 bar, about 9 bar, about 10 bar, about 20 bar, about 30 bar, about 40 bar, about 45 bar, about 50 bar, about 60 bar, about 70 bar, about 80 bar, about 90 bar, about 100 bar, about 125 bar, about 150 bar, about 175 bar, or about 200 bar, and any range constructed therefrom, such as from about 0.1 bar to about 200 bar, from a§ bout 0.5 bar to about 100 bar, or from about 1 bar to about 45 bar. For a Pt/V@C catalyst, the preferred hydrogen pressure range is from about 1 bar to about 10 bar, from about 2 bar to about 8 bar, or about 4 bar. For Ni-phen and Co@chitin catalysts, the preferred hydrogen pressure range is from about 10 bar to about 100 bar, from about 20 bar to about 70 bar, or about 40 bar. In some aspects, the reaction time to completion may be about 4 hours, about 6 hours, about 12 hours, about 18 hours, about 24 hours, or more. The reaction may be deemed complete when the area % concentration by HPLC of compound 140 is less than 2, less than 1, less than 0.5, or less than 0.1. The reaction product mixture comprises compound 141 in solution. The reaction product mixture may be optionally filtered.

In some embodiments, the method of producing compound 141 comprises: forming a reaction mixture comprising compound 140, a catalyst comprising platinum, a solvent, and hydrogen; and reacting the reaction mixture to form a product mixture comprising compound 141. In some embodiments, the catalyst comprising platinum is a Pt/V on carbon catalyst. In certain embodiments, the catalyst loading is 1-4%, or about 1-3%, or about 2%, as weight %. In some embodiments, the catalyst loading refers to wet catalyst, that is, catalyst that has not been fully dried and may contain some water. In some such embodiments, the amount of water present is from about 50% to about 70%, or from about 60% to about 65%. Thus, for example, in some embodiments the catalyst loading is about 1-4%, or about 1-3%, or about 2%, as weight % of wet catalyst; or about 0.35-1.6% w/w, or about 0.5-1.0% w/w, or about 0.7-0.8% w/w dry catalyst. In some embodiments, the solvent is a polar aprotic solvent. In some embodiments the polar aprotic solvent is THF. In still further embodiments, the reaction mixture is reacted at a temperature between 20-200° C., such as 40-80° C., for example about 60° C. In yet additional embodiments, the hydrogen pressure is 0.1-200 bar, such as 1-45 bar, for example 1-8 bar, or about 4 bar. In certain embodiments, the combination of a platinum catalyst (such as Pt/V on carbon), catalyst loading of 1-4 wt % (such as 1-3 wt %, or about 2 wt %), polar aprotic solvent (such as THF), temperature between 40-80° C. (such as 50-70° C., or about 60° C.), and hydrogen pressure of 1-45 bar (such as 1-8 bar, or about 4 bar), results in conversion of compound 140 to 141 in a higher yield, or higher selectivity, or both, compared to previously used methods. Such yield may be, for example, greater than 99%, or greater than 99.5%, or greater than 99.8%, or greater than 99.9%. In some embodiments, the selectivity is greater than 99%, such as at least 99.1%, at least 99.2%, at least 99.3%, or at least 99.4%. In certain embodiments, such methods are performed using batch processing.

In some aspects, the reaction mixture comprises about 10 wt. % compound 141 in THF and about 2 wt. % Pt/V@C catalyst, and the reaction is run at about 60° C. under about 4 bar hydrogen for a reaction time of about 16 hours. In some such embodiments, the catalyst is a "wet" catalyst, comprising about 50% to about 70%, or from about 60% to about 65% water by weight.

In other embodiments, the method of producing compound 141 comprises a continuous flow process. In some such embodiments, the method comprises: forming a reaction mixture comprising compound 140 and a solvent; and contacting said reaction mixture with a transition metal catalyst in the presence of hydrogen to form a product mixture comprising compound 141, wherein the method is a continuous flow reaction. In some embodiments, the solvent is organic solvent, such as polar aprotic solvent. In some embodiments, the solvent optionally comprises water. In some embodiments, the solvent does comprise water. In yet other embodiments, the solvent does not comprise water, or is essentially free of water, or comprises less than 1% water, or less than 0.5% water, or less than 0.10% water v/v. In some embodiments, compound 140 is present in the reaction mixture at a concentration of between 0.1 to 0.8 M, 0.2 to 0.6 M, 0.3 to 0.5 M, 0.35 M to 0.45 M, or about 0.4 M. In some embodiments, the continuous flow reaction is performed at a temperature of between 80° C. to 140° C., or between 100° C. to 140° C., or between 110° C. to 130° C., or about 100° C. or about 120° C. In certain embodiments, the transition metal catalyst comprises palladium or platinum, for example Pd/Al$_2$O$_3$ or Pt/Al$_2$O$_3$. In some embodiments, the catalyst is Pd/Al$_2$O$_3$. In some embodiments, the transition metal catalyst is in the form of a packed bed catalyst. In some embodiments, the transition metal catalyst is an immobilized catalyst, for example formed by electroplating, spray coating, or slurry coating a solid support with the catalyst. Such solid support may be any suitable support, which may include one or more catalytic static mixers (CSMs). In some embodiments, the catalyst comprises solid support. For examples the solid support is in the form of spheres or granules. In some embodiments, said supports are metal or carbon. In certain embodiments, the supports comprise alumina, or carbon. In certain embodiments, the catalyst comprises between about 3-5% loading of Pt or Pd, on a solid support comprising alumina or carbon. In some embodiments, the catalyst is 3% Pd on Al$_2$O$_3$ spheres, or 3% Pt on Al$_2$O$_3$ spheres, or 3% Pt on activated C granules, or 3% Pd on activated C granules, or 5% Pd on Al$_2$O$_3$ spheres, or 5% Pt on Al$_2$O$_3$ spheres, or 5% Pt on activated C granules, or 5% Pd on activated C granules, wherein the metal loading is wt %. In some embodiments, this loading is dry wt %. In still further embodiments, the solvent comprising organic solvent and water comprises a polar aprotic solvent and about 1-10 equivalents water, or about 2-8 equivalents water, or about 4, about 6, or about 8 equivalents water, compared to the amount of compound 140. In some embodiments, the solvent consists essentially of the organic solvent and water, such as consisting essentially of a polar aprotic solvent and water. In some embodiments, the polar aprotic solvent is THF. In some embodiments, hydrogen is present in excess, compared to the amount of compound 140. For example, in some embodiments hydrogen is present at greater than 3 equivalents, between 3 to 5 equivalents, between 3 to 4 equivalents, or about 3.3 equivalents, or about 3.75 equivalents compared to the amount of compound 140. In some embodiments, the flow of hydrogen to the continuous flow reactor is adjusted such that an excess of hydrogen is provided. In some embodiments, the continuous flow reaction is carried out at a pressure of between 1-50 bar, between 1-40 bar, between 10-30 bar, between 15-25 bar, or about 20 bar. In some embodiments, the flow rate of reactor is 2-40 mL/min, 2-35 mL/min, 10-40 mL/min, 20-40 mL/min, 15-30 mL/min, 2-20 mL/min, 2-12 mL/min, 4-10 mL/min, 2-8 mL/min, 6-8 mL/min, about 2 mL/min, about 4 mL/min, about 6 mL/min, about 8 mL/min, about 16 mL/min, about 20 mL/min, about 24 mL/min, about 27 mL/min, or about 30 mL/min. In some embodiments, the method of producing compound 141 comprises: forming a reaction mixture comprising compound 140 and a solvent comprising THF and about 2-8 equivalents water; and contacting said reaction mixture with a transition metal catalyst comprising Pd (such as Pd/Al$_2$O$_3$) in the presence of excess hydrogen to form a product mixture comprising compound 141; wherein the water and hydrogen is in comparison to compound 140, wherein the reaction is a continuous flow reaction, and the reaction is carried out at a pressure between 10-30 bar, the flow rate is about 2-8 mL/min, and the temperature is between 110° C. to 130° C. In some embodiments, the method of producing compound 141 comprises: forming a reaction mixture comprising compound 140 and a solvent comprising THF; and contacting said reaction mixture with a transition metal catalyst comprising Pd or Pt (such as Pd/Al$_2$O$_3$ or Pt/Al$_2$O$_3$) in the presence of excess hydrogen to form a product mixture comprising compound 141; wherein the hydrogen is in comparison to compound 140, wherein the reaction is a continuous flow reaction, and the reaction is carried out at a pressure between 10-30 bar, the flow rate is about 2-8 mL/min, and the temperature is between 110° C. to 130° C. In some embodiments, water is also included in the solvent system. In some embodiments, wherein the catalyst is included as one or more catalytic static mixers, water is included in the solvent system. In other embodiments, wherein the catalyst is included in a form other than one or more catalytic static mixers, such as when the catalyst is included on solid supports, e.g. spheres or granules, the solvent system does not comprise water, or is essentially free of water, or comprises less than 1% or less than 0.5% v/v water. In some embodiments, water is included when the catalyst is included on solid supports, or water has little impact on yield and impurities when the system comprises catalyst on solid supports (such as 3-5% Pd on Al$_2$O$_3$ on spheres or activated C granules, or 3-5% Pt on Al$_2$O$_3$ spheres or activated C granules). In some embodiments, this catalyst loading is dry wt %.

In certain embodiments, the combination of a solid-supported transition metal catalyst (such as one comprising Pd, for example Pd/Al$_2$O$_3$), the inclusion of water in the solvent system (for example about 2-8 equivalents water, or about 4, about 6, or about 8 equivalents water), temperature between 100-140° C. (such as 110-130° C., or about 120° C.), and flow rate of 2-40 mL/min (for example 20-40 mL/min, about 30 mL/min, 2-10 mL/min, 4-8 mL/min, or about 4 mL/min, 6 mL/min, or 8 mL/min) result in a high conversion of compound 140 to 141 while maintaining low levels of undesired impurities. In some embodiments, the flow rate is 4 mL/min and about 2-8 equivalents of water are included. In some embodiments, the flow rate is 6 mL/min and about 8 equivalents of water are included. In some embodiments, the flow rate is 8 mL/min and about 8 equivalents of water are included. In some embodiments, the flow rate is 4-8 mL/min and about 8 equivalents of water are included.

In certain embodiments, the combination of a solid-supported transition metal catalyst (such as one comprising Pt, for example Pt/C, such as 5% Pt/activated C granules); a solution of about 0.1-1M compound 140 in a solvent system essentially free of water, or less than 1% v/v or less than 0.5% v/v water; temperature between 80-140° C. (such as 90-110° C., or about 10° C.); the ratio of flow rate of hydrogen:solution is in the range of about 50 to 5 mL/min, or about 40 to 10 mL/min, or about 35 to 25 mL/min, or is about 30 mL/min; the system pressure of about 10-30 bar, or about 15-25 bar, or about 20 bar; the ratio of hydrogen to compound 140 is in the range of about 5 to 1, about 4 to 2, about 3.5 to 2.5, or is about 3; results in a high conversion of compound 140 to 141 while maintaining low levels of undesired impurities. In some embodiments, the solvent system is polar aprotic, such as THF. In some embodiments, the reduction of compound 140 occurs at a rate of about 40 g/h to 80 g/h, or about 50 g/h to about 70 g/h, or about 60 g/h. In some such embodiments, compound 141 is achieved at a purity of greater than 98%, or greater than 98.5%, or greater than 99%, or greater than 99.1%, as measured by HPLC. In some embodiments, compound 141 is achieved in greater than 70% yield relative to compound 140, or greater than 75% yield, or greater than 80% yield, or greater than 85% yield. In some embodiments, the combined azo and azoxy impurities are less than 0.05%; the dimer impurity is less than 0.2%, such as less than 0.015%; and other impurities are less than 1%, less than 0.75%, less than 0.6%, or less than 0.5%.

Some conditions used in the continuous process methods provided herein may not be achievable in certain types of batch processing, for example batch processing methods that cannot reach similarly high temperatures, or achieve the low residence times possible with continuous flow. Such situations would be apparent to one of skill in the art. The combination of including water in the solvent system, high temperature, and increased flow rate used in the continuous processing methods described herein may achieve unexpectedly synergistic effects that are not observed by adjusting only one of these parameters; and further may achieve a higher total output over time of desired product while maintaining acceptably low levels of undesired impurities compared to other methods, including certain types of batch processing methods. In some embodiments, the continuous processing methods described herein achieve conversion of compound 140 to 141 at a yield of greater than 98.5 area %, greater than 99 area %, or greater than 99.5 area %, or greater than 99.8 area %, or greater than 99.9 area %. In certain embodiments, the yield conversion may be similar or lower than other methods, however the higher throughput using continuous processing at the conditions described herein may achieve greater total output of product per time period while maintaining low impurity levels, and thus be advantageous compared to other methods. In certain embodiments, the combined level of azo and azoxy impurities (shown below) is maintained below 0.1 area %, below 0.09 area %, below 0.08 area %, below 0.07 area %, below 0.06 area %, below 0.05 area %, below 0.04 area %, or below 0.03 area %. In certain embodiments, the level of the dimer impurity (shown below) is maintained below 0.1 area %, below 0.09 area %, below 0.08 area %, below 0.07 area %, below 0.06 area %, below 0.05 area %, below 0.04 area %, or below 0.03 area %. In some embodiments, the level of dimer impurity, and the combined level of azo and azoxy impurities, are respectively below 0.04 area % and below 0.09 area %; below 0.05 area % and below 0.09 area %; or below 0.04 area % and below 0.08 area %. In some embodiments, the total combined content of the azo, azoxy, and dimer impurities (shown below) is maintained below 0.20 area %, or below 0.15 area %, or below 0.13 area %, or below 0.1 area %.

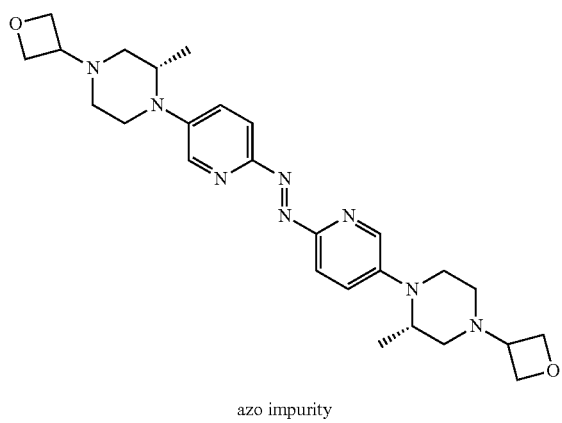

azo impurity

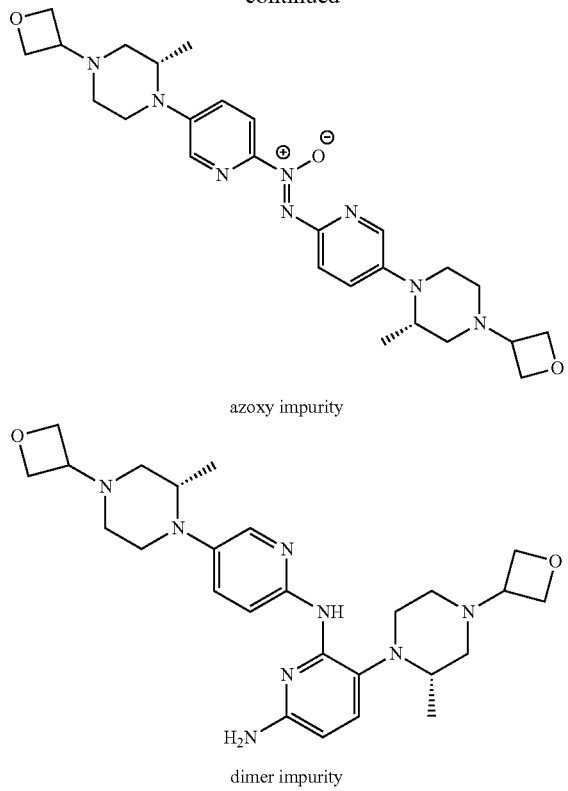

azoxy impurity dimer impurity

In some aspects, the reaction product mixture comprising compound 141 in solution may be subjected to a solvent exchange step to swap the solvent in the reaction product mixture for the solvent system for the reaction for coupling compounds 141 and 90 to form compound 180. Solvent exchange may be done by methods known in the art, for instance and without limitation distillation or evaporation to dryness to remove solvent followed by dissolution in the replacement solvent or by solvent exchange distillation. For instance and without limitation, alcohols, ethers, esters, toluene, dichloromethane, water, and combinations thereof present in the reaction product mixture comprising compound 141 may be exchanged for an aprotic solvent by methods as described elsewhere herein for the reaction mixture comprising compounds 141 and 90. In some aspects, the aprotic solvent is selected from THF, toluene, Me-THF, 1,4-dioxane, anisole and combinations thereof. In some particular aspects, the solvent is 1,4-dioxane, anisole, or a combination thereof. In one particular aspect, the reaction product mixture comprising compound 141 predominantly comprises THF, and the THF is exchanged for anisole. The concentration of compound 141 after solvent exchange may suitably be about 5:1 L/kg, about 10:1 L/kg or about 15:1 L/kg or about 20:1 L/kg and ranges thereof, such as from about 5:1 to about 20:1 L/kg or from about 5:1 to about 15:1 L/kg. In some such aspects, the final concentration of compound 141 is from about 5 to about 15 percent by weight.

In some aspects, compound 141 may be optionally isolated from the reaction product mixture as a residue by concentration of the filtrate to almost dryness. In some aspects, compound 141 may be optionally crystallized from the reaction product mixture by concentration to remove solvent followed by the addition of an anti-solvent such as n-heptane and cooling thereof. In some aspects, the concentration may be done in a vacuum at a temperature below 60° C. In some embodiments, the yield of compound 141 is at least 90% or at least 95%.

Preparation of Compound 180

In some aspects of the present disclosure, compound 180 may be prepared from compounds 90 and 141 according to the following reaction scheme where "LG" is a leaving group:

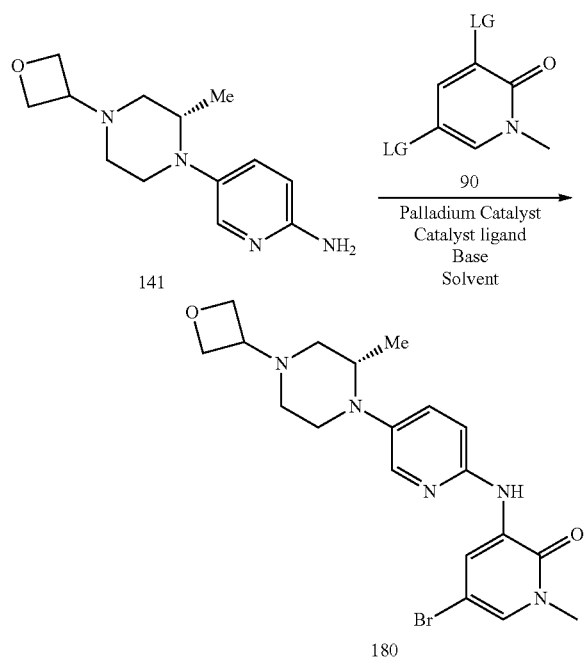

In some aspects, the leaving group is a halogen or triflate. In one aspect, the leaving group is Br.

Figure 2:
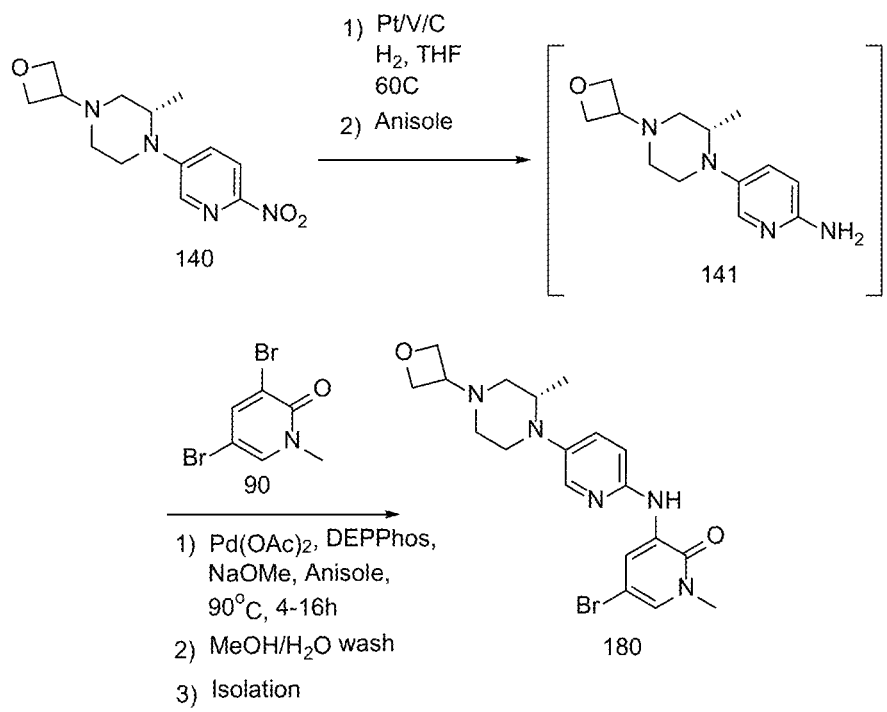
FIG. 2 shows a method for the preparation of compound 141, and another method for the preparation of compound 180.
Figure 3:
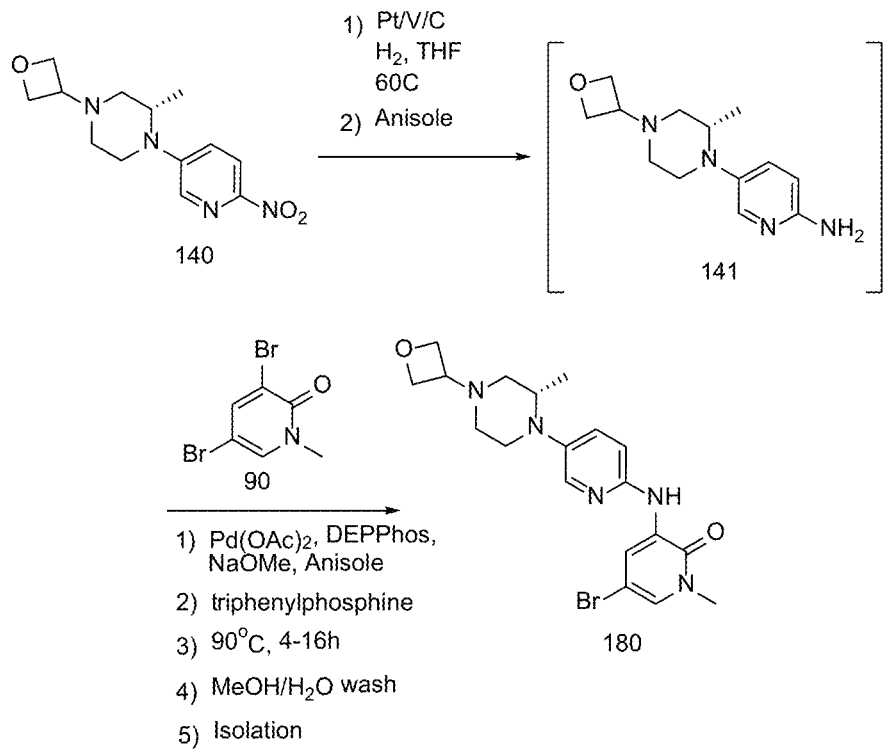
FIG. 3 shows a method for the preparation of compound 141 and another method for the preparation of compound 180.

In some aspects, compound 180 may be prepared by any of the methods depicted in FIGS. 1 to 3.

The method for preparing compound 180 comprises forming a reaction mixture comprising compound 141, compound 90, a palladium catalyst and an aryl phosphate catalyst ligand, a base, and an aprotic solvent. The reaction mixture is reacted to form a reaction product mixture comprising compound 180. Compound 180 is optionally isolated from the reaction product mixture.

In some aspects for the preparation of compound 180, compound 141 is used directly and is not isolated. In such aspects, the solvent in the reaction product mixture comprising compound 141 may be exchanged for a solvent for the formation of the reaction mixture comprising compound 141, compound 90, the Pd catalyst and ligand and base. Solvent exchange may be done by methods known to those skilled in the art as described elsewhere herein. In one such aspect, a portion of the solvent contained in the compound 141 reaction product mixture (e.g., THF) may be removed by distillation under reduced pressure. For instance, about 40%, about 50%, about 60%, about 70% or about 80% of the solvent may be stripped. In one aspect, the solvent content can be reduced from about 10 volumes (V) to about 2 to 3V. Solvent for the compound 141/90 reaction mixture (e.g., anisole) may then be added followed by distillation to predominantly remove the remainder of the solvent from the compound 141 reaction product mixture and achieve a total volume of, for instance, about 3V, 4V, 5V, 6V or 7V.

The reaction mixture comprises approximately equimolar amounts of compounds 90 and 141 to a slight stoichiometric excess of compound 90, such as an equivalent ratio 1.05:1 or 1.1:1. The reaction mixture solvent may suitably be an aprotic solvent as described elsewhere herein, or a polar aprotic solvent as described herein. Non-limiting examples of suitable solvents include THF, 2-Me-THF, tert-butyl methyl ether, cyclopropylmethyl ether, toluene, anisole, trifluorotoluene, chlorobenzene, and mixtures thereof. In some aspects, the solvent is anisole.

The concentration of compound 141 in solution is suitably about 10 wt. %, about 10 wt. %, about 15 wt. %, about 20 wt. %, about 25 wt. % or about 30 wt. %, and any range constructed therefrom, for instance from about 5 wt. % to about 30 wt. %, from about 10 wt. % to about 25 wt. %, from about 10 wt. % to about 20 wt. %, or from about 15 wt. % to about 25 wt. %.

The palladium catalyst is suitably a Pd complex and a ligand. In some aspects, the Pd complex is preformed. In some aspects, the Pd complex is formed in situ. In either aspect, the Pd complex is formed from Pd precursor Pd(II) complexes, for instance and without limitation, $Pd(OAc)_2$, $[PdCl(allyl)]_2$, or $[PdCl(cinnamyl)]_2$ or from Pd(O) complexes such as $[Pd(PPh_3)_4]$, $[Pd(P(oTol)_3)_2]$, $Pd_2(dba)_3$ or $Pd(dba)_2$. In some aspects the ligand is a phosphine ligand. Non-limiting examples of phosphine ligands include Xantphos, DPEPhos, dppf, and dppp. In some aspects, the catalyst is $Pd(OAc)_2$ and the ligand is XantPhos. In some aspects, the catalyst is $Pd(OAc)_2$ and the ligand is DPEPhos. In some aspects, the palladium catalyst is $Pd_2(dba)_3$ and the catalyst ligand is Xantphos. The equivalent ratio of the palladium catalyst to compound 141 is from about 0.005:1 to about 0.05:1, from about 0.01:1 to about 0.03:1, or from about 0.01:1 to about 0.02:1. The mole ratio of the catalyst ligand to the catalyst is about 1.2:1, about 1.5:1, about 1.6:1, about 1.7:1, about 1.8:1, about 1.9:1, about 2:1, about 2.1:1, about 2.2:1, about 2.3:1, about 2.4:1, about 2.5:1, or about 3:1, and any range constructed therefrom, such as from about 1.2:1 to about 3:1, from about 1.5:1 to about 2.5:1, or from about 1.8:1 to about 2.2:1.

In some aspects, the base is an inorganic base as described elsewhere herein. In some such aspects, the base is an alkali metal carbonate of the formula $M_2CO_3$ where M is Na or K. In some such aspects, the base is an organic base as described elsewhere herein, such as of the formula MOR' where M is Na or K and wherein R' is $C_{1-6}$ alkyl, such as methyl, ethyl, n-propyl, i-propyl, or t-amyl. In some such aspects, the organic base is NaOMe. The equivalent ratio of the base to compound 141 is suitably from about 1.2:1 to about 3:1, such as about 1.5:1 or about 2:1.

The reaction mixture may optionally comprise an additive. One example of additive is triphenyl phosphine ("$PPh_3$"). Suitable additive concentrations are about 1 mol %, about 2 mol %, about 3 mol %, about 4 mol %, about 4.5 mol %, about 5 mol %, or about 6 mol %, and any range constructed therefrom, such as from about 1 mol % to about 6 mol %, from about 3 mol % to about 5 mol %, or from about 4 mol % to about 5 mol %.

The reaction for forming compound 180 may be done under an inert atmosphere, for example with Ar or $N_2$ purging and/or an Ar or $N_2$ blanket. The reaction may be done at a temperature of about 20° C., about 30° C., about 40° C., about 50° C., about 60° C., about 70° C., about 80° C., about 90° C., about 100° C., about 110° C., about 115° C., about 120° C., about 130° C., about 140° C., or about 150° C., and any range constructed therefrom, such as from about 20° C. to about 150° C., from about 70° C. to about 120° C., or from about 20° C. to about 115° C. The reaction may be deemed complete when the area % concentration by HPLC of compound 180 is less than 2, less than 1, less than 0.5, or less than 0.1. In some aspects, the reaction time to completion may be about 4 hours, about 6 hours, about 12 hours, about 16 hours, about 18 hours, about 24 hours, about 30 hours, or more.

In some particular aspects, the catalyst is Pd(OAc)$_2$, the ligand is DPEPhos, and the base is an organic base. In some such aspects, the organic base is sodium or potassium methoxide. In some such aspects, the reaction mixture solvent predominantly comprises anisole and the reaction temperature is from about 80° C. to about 100° C., such as about 90° C. The reaction time to full conversion is about 2 hours, 4 hours, about 8 hours, about 12 hours, or about 16 hours. In some optional aspects, the reaction mixture may further comprise aa additive, such as PPh$_3$.

In some particular aspects, the catalyst is Pd(OAc)$_2$, the ligand is XantPhos, and the base is an inorganic base. In some such aspects, the inorganic base is sodium or potassium carbonate. In some such aspects, the reaction mixture solvent predominantly comprises anisole and water, and the reaction temperature is from about 100° C. to about 125° C., such as from about 110° C. to about 115° C. The reaction time to full conversion is about 8 hours, about 12 hours, about 15 hours, about 18 hours, about 21 hours, or about 24 hours.

In some particular aspects, the catalyst is Pd(OAc)$_2$, the ligand is DPEPhos, and the base is NaOMe. In some embodiments, the additive PPh$_3$ is included. In some particular aspects, about 0.5 to 2.5 mol % Pd(OAc)$_2$, about 2 to 4 mol % DPEPhos, and about 1 to 1.5 eq NaOMe are used, optionally with about 3 to 6 mol % PPh$_3$. In certain embodiments, the reaction temperature is about 90° C. In some particular aspects, the catalyst is Pd(OAc)$_2$ (about 1.5 mol %), the ligand is DPEPhos (about 3 mol %), the additive is PPh$_3$ (about 4.5 mol %), and the base is NaOMe (about 1.2 eq), and the reaction temperature is about 90° C.

In some embodiments, producing compound 180 using Pd(OAc)$_2$, DPEPhos, PPh$_3$, and NaOMe, may be done with shorter reaction times, lower reaction temperature, and a less complicated work-up than previously-used methods of preparing compound 180. For example, in some embodiments, methods of producing compound 180 using Pd(OAc)$_2$, XantPhos, and K$_2$CO$_3$ may require longer reaction times, higher reaction temperatures, and a more complex work-up process to isolate compound 180.

In some aspects, compound 180 may be isolated from the reaction product mixture.

In aspects wherein the catalyst is Pd(OAc)$_2$ and the ligand is XantPhos, the reaction product mixture may be washed with water. In such aspects, additional solvent may optionally be added with stirring to the reaction product mixture followed by addition of water in a volume ratio of reaction product mixture or diluted reaction product mixture to water of about 5:1, about 3:1, about 2:1, about 1:1 or about 1:2. The temperature may suitably be from about 40° C. to about 100° C., such as for instance, about 50° C., about 60° C., about 70° C., about 80° C., about 85° C., about 90° C., or about 95° C. Water may be removed by phase separation, and the collected washed reaction product mixture organic phase may be distilled to reduce the volume. The concentration of compound 180 after volume reduction may suitably be about 0.2 g/mL, about 0.25 g/mL, about 0.3 g/mL, about 0.35 g/mL, about 0.4 g/mL, about 0.45 g/mL, about 0.5 g/mL, about 0.55 g/mL, or about 0.6 g/mL, and any range constructed therefrom, such as from about 0.2 g/mL to about 0.6 g/mL, from about 0.3 g/mL to about 0.5 g/mL, or from about 0.35 g/mL to about 0.45 g/mL.

The compound 180 concentrate may be washed with water. In some such aspects, the compound 180 concentrate may be combined with mixing with an organic protic anti-solvent (e.g., a C$_{1-6}$ alcohol) and water. In such aspects, the volume ratio of organic protic anti-solvent to water may be about 3:1, about 2.5:1, about 2:1, about 1.5:1, about 1:1, about 1:1.5, about 1:2, about 1:2.5 or about 1:3, and any range constructed therefrom, such as from about 3:1 to about 1:3, from about 2:1 to about 1:1.5, or from about 1.5:1 to about 1:1. In such aspects, the volume ratio of organic protic solvent to compound 180 concentrate may be about 3:1, about 2.5:1, about 2:1, about 1.5:1, about 1:1, about 1:1.5, or about 1:2, and any range constructed therefrom, such as from about 3:1 to about 1:2, from about 2.5:1 to about 1:1, or from about 2:1 to about 1.5:1. Water may be removed by phase separation, and the collected washed compound 180 concentrate organic phase comprising the aprotic solvent and protic solvent may be distilled to reduce the volume. The concentration of compound 180 after volume reduction may suitably be about 0.15 g/mL, about 0.2 g/mL, about 0.25 g/mL, about 0.3 g/mL, about 0.35 g/mL, about 0.4 g/mL, about 0.45 g/mL, about 0.5 g/mL, about 0.55 g/mL, or about 0.6 g/mL, and any range constructed therefrom, such as from about 0.15 g/mL to about 0.6 g/mL, from about 0.2 g/mL to about 0.4 g/mL, or from about 0.25 g/mL to about 0.35 g/mL. Additional protic anti-solvent may be added in a volume ratio of compound 180 concentrate to added anti-solvent of about 3:1, about 2.5:1, about 2:1, about 1.5:1, about 1:1, or about 1:1.5, and any range constructed therefrom, such as from about 3:1 to about 1:1.5, from about 2:1 to about 1:1, or from about 1.5:1 to about 1:1. In some aspects, the protic anti-solvent is methanol, ethanol or 1-butanol. In one aspect, the protic anti-solvent is 1-butanol.

The mixture of compound 180 and anti-solvent may be cooled to less than 0° C. with mixing, such as to about −5° C. or −10° C., at a suitable rate, such as from about 5° C./hour, 10° C./hour, 15° C./hour, to crystallize compound 180. The crystal slurry may be aged at the final temperature for at least 2 hours, at least 4 hours or at least 6 hours to complete the crystallization. Compound 180 crystals may be collected by filtration or centrifugation and washed with cold protic anti-solvent and water. In some aspects, when the anti-solvent is 1-butanol, the collected crystals may be washed with chilled (e.g., −5° C.±5° C.) methanol or ethanol and water (e.g., at volume ratio of alcohol to water of from about 3:1 to about 1:3, such as about 1:1) followed by a wash with chilled 1-butanol. The washed compound 180 crystals may be dried under vacuum, e.g., at a temperature of from about 30° C. to about 80° C. (such as from about 60° C. to about 75° C.) and a vacuum of from about 2-10 mbar.

In aspects wherein the catalyst is Pd(OAc)$_2$ and the ligand is DPEPhos, the reaction product mixture may be quenched with water and the reaction product mixture comprises a suspension of compound 180. The volume ratio of water to reaction product mixture may suitably be about 3:1, about 2:1, about 1.5:1, about 1:1, about 1:1.5, about 1:2, or about 1:3, and any range constructed therefrom, such as from about 3:1 to about 1:3 or from about 1.5:1 or about 1:1.5. The quenched reaction product mixture may then be cooled to about 0° C., about 5° C., about 10° C., about 15° C., or about 20° C., and any range constructed therefrom, such as from about 0° C. to about 20° C., or from about 5° C. to about 15° C. The cooling rate may suitably be about 0.5° C./min, about 1° C./min, about 1.5° C./min, about 2° C./min, about 2.5° C./min, or about 3° C./min, and any range constructed therefrom, such as from about 0.5° C./min to about 3° C./min, or from about 0.5° C./min to about 1.5° C./min. Compound 180 crystals may be collected by filtration or centrifugation and washed with cold $C_{1-4}$ alcohol and/or water. In some such aspects, the crystals may be washed with alcohol, water/alcohol (e.g., in a 1:1 v/v ratio), and then alcohol. In some such aspects, the alcohol is methanol. The washed compound 180 crystals may be dried under vacuum, e.g., at a temperature of from about 30° C. to about 70° C. (such as from about 35° C. to about 55° C.) and a vacuum of from about 2-10 mbar.

In some embodiments, the yield of compound 180 is about 70%, about 75% or about 80%. The purity of compound 180 is at least 98.5 area %, at least 99 area %, at least 99.5 area %, 99 area %, 99.1 area %, 99.2 area %, 99.3 area %, 99.4 area %, 99.5 area %, 99.6 area %, 99.7 area %, or 99.8 area %.

Preparation of Compound 181

In some aspects of the present disclosure, compound 181 may be prepared from compound 180 according to the following reaction scheme:

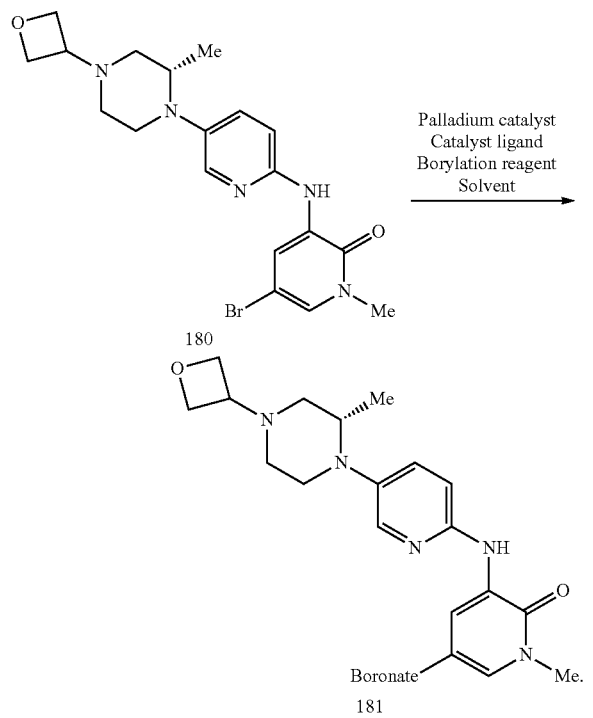

The method for preparing compound 181 comprises forming a reaction mixture comprising compound 180, a palladium catalyst, a catalyst ligand, a borylation reagent, and a polar aprotic solvent. The reaction mixture may also comprise an alkali metal acetate salt. The reaction mixture is reacted to form a reaction product mixture comprising compound 181. Compound 181 is optionally isolated from the reaction product mixture.

The palladium catalyst and the catalyst ligand are as generally described elsewhere herein. In some aspects, the palladium catalyst is $Pd_2(dba)_3$ and the catalyst ligand is an aryl phosphate ligand. In some such aspects, the aryl phosphate ligand is XPhos. The equivalent ratio of palladium catalyst to compound 180 is about 0.001:1, about 0.002:1, about 0.003:1, about 0.004:1, or about 0.005:1, and ranges thereof, such as from 0.001:1 to about 0.005:1. The equivalent ratio of catalyst ligand to catalyst is about 1.3:1, about 1.5:1, about 1.7:1, about 1.9:1, about 2.5:1 or about 3:1, and ranges thereof, such as from about 1.3:1 to about 3 or from about 1.5:1 to about 2.5:1. The borylation reagent is as described elsewhere herein. The solvent is a polar aprotic solvent as described elsewhere herein. In some aspects, the polar aprotic solvent is THF. The ratio of solvent volume to compound 180 weight is about 3:1 L/kg, about 5:1 L/kg, about 10:1 L/kg, about 20:1 L/kg, or about 25:1 L/kg, and ranges thereof, such as from about 3:1 to about 25:1 L/kg, from about 5:1 to about 20:1 L/kg, or from about 5:1 to about 15:1 L/kg. In some aspects, the reaction mixture comprises a compound 180 concentration of about 0.1 moles/L, about 0.2 moles/L, about 0.3 moles/L, about 0.4 moles/L, or about 0.5 moles/L, and ranges thereof, such as from about 0.1 to about 0.5 moles/L. The equivalent ratio of the alkali metal acetate salt to compound 180 is greater than 1:1. In some aspects, the alkali metal acetate salt is potassium acetate. In some aspects, the borylation reagent is bis(pinacolato)diboron and the boronate is 4,4,5,5-tetramethyl-1,3,2-dioxaborolane. The equivalent ratio of borylation reagent to compound 180 is greater than 1:1, about 1.2:1, about 1.5:1 or about 2:1, and ranges thereof, such as between 1:1 and 2:1. In some aspects, the borylation reagent is bis(pinacolato)diboron and the boronate is 4,4,5,5-tetramethyl-1,3,2-dioxaborolane. In such aspects, boronate compound 181 is the species of compound 182:

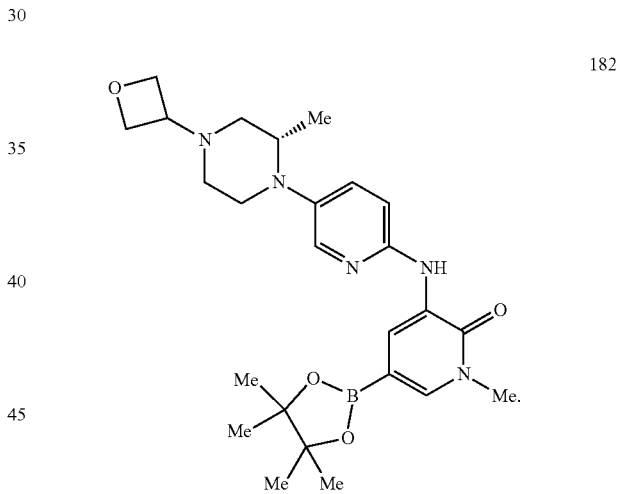

Figure 4:
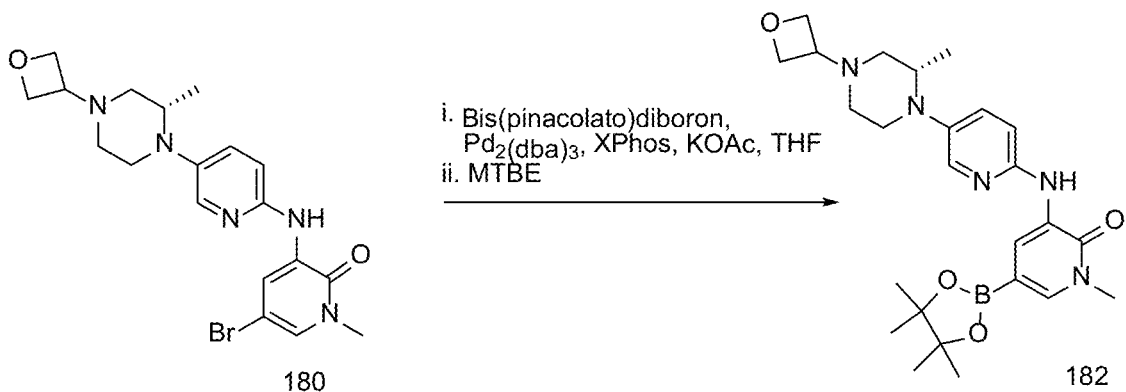
FIG. 4 shows a method for the preparation of compound 182.

In some aspects, compound 182 may be prepared according to the method depicted in FIG. 4.

The reaction for forming compound 181 or 182 may be done under an inert atmosphere, for example with $N_2$ purging and/or a $N_2$ blanket. The reaction may be done at reflux temperature, typically between about 60° C. and about 80° C. The reaction may be deemed complete when the area % concentration by HPLC of compound 160 is less than 1, less than 0.5, or less than 0.1. In some aspects, the reaction time to completion may be about 6 hours, about 12 hours, about 18 hours, about 24 hours, or more.

In some aspects, compound 181 or 182 may be isolated from the reaction product mixture. In some such aspects, the reaction product mixture may be combined with water at a ratio of water volume to compound 181 or 182 weight of about 2 L/kg, about 3 L/kg, about 4 L/kg or about 5 L/kg, and ratios thereof, such as from about 1 to about 5 L/kg or from about 2 to about 4 L/kg. An aqueous layer may be separated and an organic layer comprising compound 181 or 182 in solution is collected. The organic layer may be distilled to a reduced volume at a ratio of volume to compound 181 or 182 weight of about 2 L/kg, about 3 L/kg, about 4 L/kg or about 5 L/kg, and ranges thereof, such as from about 2 to about 5 L/kg. Distillation is suitably vacuum distillation, such as for instance, at a temperature of at least 40° C. Alternatively, the distillation may be performed at atmospheric pressure. The reduced volume comprising compound 181 or 182 may be diluted with a polar aprotic solvent, such as THF, in a ratio of solvent volume to compound 181 or 182 weight of about from about 5 L/kg to about 8 L/kg, the diluted mixture is optionally filtered, and the diluted mixture may be distillated to a reduced volume of from about 2 to about 4 L per kg of compound 181 or 182. The polar aprotic solvent dilution and distillation step may be repeated one or more times. The reduced volume may be combined with a non-polar solvent, such as MTBE, at a ratio of non-polar solvent volume to compound 181 or 182 weight of about 5 L/kg, about 10 L/kg, about 15 L/kg or about 20 L/kg, and ranges thereof, such as from about 5 to about 20 L/kg or from about 5 to about 15 L/kg. The mixture may be cooled to from about 0 to about 15° C. to form compound 181 or 182 as a solid dispersion. Solid compound 181 or 182 may be collected, such as by filtration or centrifugation, and dried to form solid compound 181 or 182.

Alternatively, after completion of the reaction to form compound 181 or 182, inorganic salts may be filtered off at 60-65° C. The filtrate is cooled, such as to 40-45° C., and filtered over charcoal. The volume of the filtrate may then be reduced at atmospheric pressure. The reduced volume may be combined with a non-polar solvent, such as MTBE, at a ratio of non-polar solvent volume to compound 181 or 182 weight of about 5 L/kg, about 10 L/kg, about 15 L/kg or about 20 L/kg, and ranges thereof, such as from about 5 to about 20 L/kg or from about 5 to about 15 L/kg.

The yield of compound 181 or 182 based on compound 180 is at least 80%, at least 85% or at least 90%. The purity of compound 181 or 182 is at least 95 area %, at least 98 area % or at least 99 area % by HPLC.

Preparation of Compound 160

In some aspects, compound 160 may be prepared according to methods disclosed in International Publication Number WO 2018/109050 as generally depicted in the three schemes below and as further depicted the reaction schemes of FIGS. 8-10:

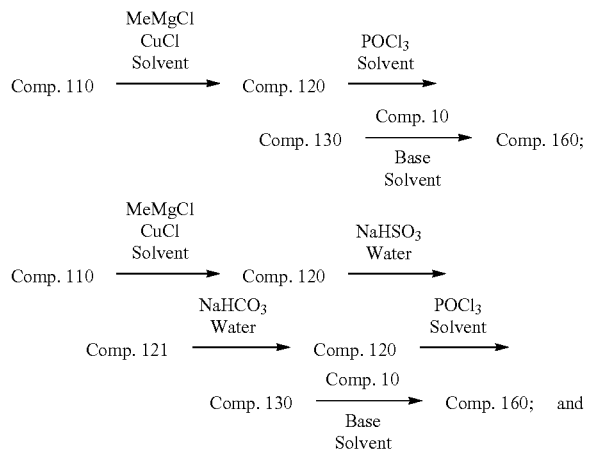

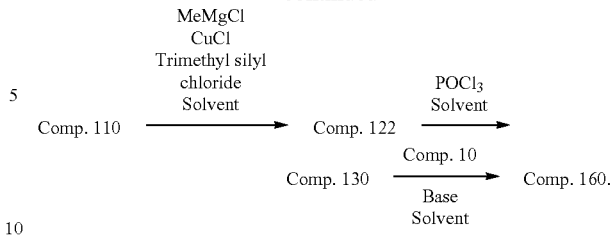

Figure 8:
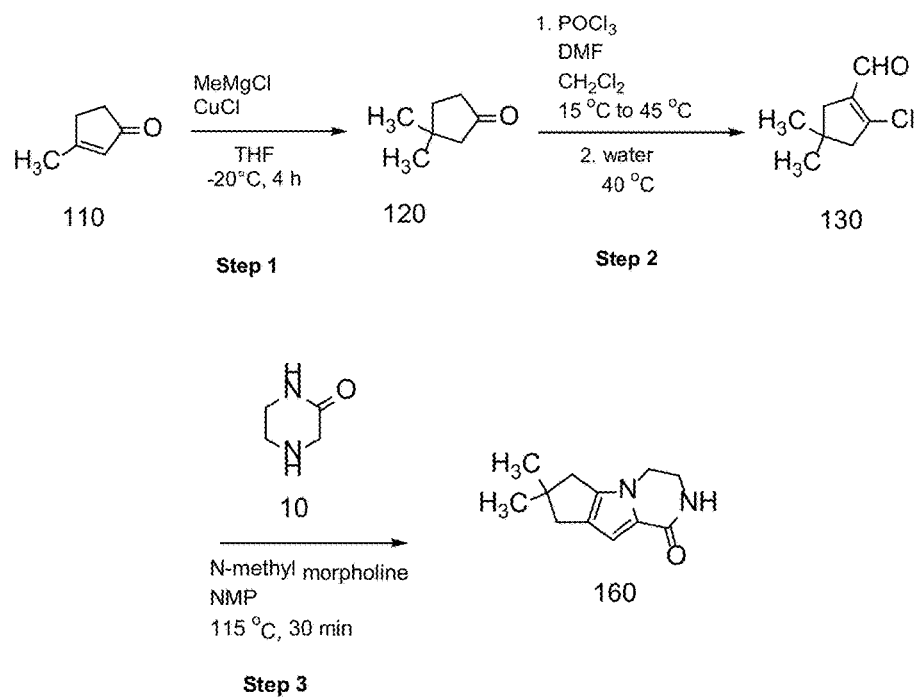
FIG. 8 shows a method for the preparation of compounds 120, 130, and 160.

In some such aspects, compounds 120, 130, and 160 may be prepared according to the methods described in WO 2018/109050, depicted in FIG. 8.

In some aspects, compound 120 may be prepared from compound 110 according to the following reaction scheme:

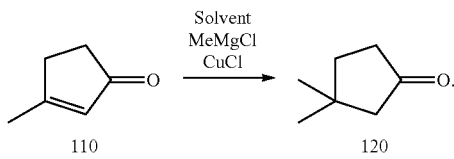

The method for preparing compound 120 comprises forming a reaction mixture comprising a polar aprotic solvent, methyl magnesium chloride, copper (I) chloride and compound 110. The reaction mixture is reacted to form a reaction product mixture comprising compound 120.

The polar aprotic solvent is as described elsewhere herein. In some aspects, the polar aprotic solvent is THF.

The reaction mixture may be formed under a $N_2$ blanket and/or with an $N_2$ purge. In some aspects, the polar aprotic solvent may be charged to a reactor and admixed with CuCl and MeMgCl. The ratio of polar aprotic solvent volume to compound 110 starting material weight is from about 3 to about 20 L/kg, or from about 5 to about 15 L/kg. The equivalent ratio of CuCl to compound 110 starting material is from about 0.1:1 to about 0.5:1 or from about 0.1:1 to about 0.3:1. The equivalent ratio of MeMgCl to compound 110 starting material is from about 0.05:1 to about 0.3:1 or from about 0.05:1 to about 0.15:1. The mixture is stirred at a temperature of from about −30 to about −10° C. followed by addition of compound 110 to the reactor while maintaining the temperature. Additional MeMgCl is added to the reactor at a temperature of from about −30 to about −10° C. wherein the equivalent ratio of the additional MeMgCl to compound 110 of from about 0.9:1 to about 1.5:1 or from about 1:1 to about 1.2:1. A reaction product mixture comprising compound 120 in solution is formed. In some aspects, the reaction time to completion may be at least 1 hour, or more. The reaction may be deemed complete when the area % concentration by HPLC of compound 110 is less than 5, less than 2, less than 1, less than 0.5, or less than 0.1.

Compound 120 may be isolated from the reaction product mixture. In some such aspects, the pH of the reaction product mixture may be adjusted to from about 3 to about 4 with an aqueous mineral acid solution, for instance 3 to 10 w/w % HCl. The resultant aqueous phase and organic phase (e.g., THF) comprising compound 10 in solution may be separated. The aqueous phase may be extracted with a non-polar solvent (e.g., MTBE) at a volume ratio of solvent to compound 110 starting material weight of from about 2 L/kg to about 10 L/kg or from about 3 L/kg to about 7 L/kg. The organic phases may be combined and washed with aqueous inorganic base (e.g., NaHCO$_3$) followed by a brine wash. The washed organic phase may then be dried with a drying agent, for instance over Na$_2$SO$_4$. The drying agent may be removed, such as by filtration or centrifugation. The organic phases may be concentrated to a volume ratio to compound 110 starting material weight of from about 3 to about 15 L/kg, such as about 5 L/kg or about 10 L/kg. Concentration may suitably be done at atmospheric pressure at from about 50 to about 70° C.

In some aspects, compound 120 may be purified by fractional distillation as follows. The combined organic phases or concentrated organic phases may be first distilled at a temperature of less than about 60° C. to remove a first (front) fraction predominantly comprising solvent. Distillation may continue to produce a compound 120 product fraction collected at a temperature of between 60° C. and 90° C. (P≤−0.09 MPa). In such aspects, the yield of compound 120 is at least 40% or at least 50% and the HPLC purity of compound 120 is at least 95 area %, at least 98 area % or at least 99 area % by HPLC. Distillation may optionally be continued to remove one or more additional fractions.

In some particular aspects, the solvent is THF, the mole ratio of methyl magnesium chloride to compound 110 in the reaction mixture is between 1:1 and 2:1, or from about 1.1:1 to about 1.4:1, and the mole ratio of copper (I) chloride to compound 110 in the reaction mixture is from about 0.1:1 to about 0.5:1, or from about 0.15:1 to about 0.25:1.

In some such aspects, compound 130 may be prepared from compound 120 according to the following reaction scheme:

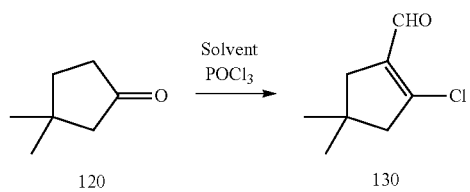

The method for preparing compound 130 comprises forming a reaction mixture comprising a polar aprotic solvent, a non-polar solvent, phosphorous oxychloride and compound 120. The reaction mixture may be reacted to form a reaction product mixture comprising compound 130.

The polar aprotic solvent is as described elsewhere herein. In some aspects, the polar aprotic solvent is DMF. The non-polar solvent is as described elsewhere herein. In some aspects, the non-polar solvent is DCM.

The reaction mixture may be formed as follows, and the reaction may be done under a N$_2$ blanket and/or with a N$_2$ purge. A reactor is charged with the non-polar solvent (e.g., DCM) at a ratio of non-polar solvent volume to compound 120 starting material weight of from about 3 to about 15 L/kg or from about 5 to about 11 L/kg, and with the polar aprotic solvent (e.g., DMF) at an equivalent ratio to compound 120 starting material of from about 1.5:1 to about 5:1 or from about 2:1 to about 3:1. The temperature of the solvent combination is adjusted to from about 5 to about 25° C., and POCl$_3$ is added to the reactor wherein the equivalent ratio of POCl$_3$ to compound 120 is from about 1.5:1 to about 3:1 or from about 2:1 to about 2.25:1. The mixture may be optionally stirred at temperature for at least 0.5 hours. Compound 120 is then added to the reactor, at a temperature such as from about 5 to about 25° C., to form the reaction mixture. The reaction mixture may then be heated, such as to from about 35 to about 55° C., to form a reaction product mixture comprising compound 130. In some aspects, the reaction time to completion may be at least 6 hours, or more. The reaction may be deemed complete when the area % concentration by HPLC of compound 120 is less than 5, less than 2, less than 1, less than 0.5, or less than 0.1.

Compound 130 may be optionally purified. In some such aspects, the reaction product mixture may be admixed with water wherein the ratio of water volume to compound 120 starting material weight is from about 3 to about 20 L/kg, or from about 5 to about 15 L/kg. The temperature may suitably be from about 30 to about 50° C. and the mixture may be agitated for at least 0.25 hours, at least 0.5 hours or at least 1 hour. The mixture may be cooled, such as to from about 15 to about 35° C., and filtered through a filter media, such as diatomaceous earth. The filtrate may be allowed to separate into an aqueous phase and an organic phase, and the organic phase may be collected and optionally washed with water and brine. The organic phase may then concentrated, such as for instance to ratio of volume to compound 120 starting material weight of from about 2 to about 5 L/kg or from about 2 to about 4 L/kg. An organic solvent (e.g., toluene or NMP) may be combined with the concentrated organic phase at a ratio of organic solvent to compound 120 starting material weight of about 1 to about 2 L/kg. The volume may be reduced, for instance, under vacuum and at a temperature below 40° C., to produce a solution of compound 130. In some aspects, the organic solvent is DCM and compound 130 is in solution in DCM.

Compound 160 may be prepared forming a reaction mixture comprising an organic solvent, an organic base, and compounds 130 and 10, and reacting the reaction mixture to form a reaction product mixture comprising the tricyclic lactam of compound 160.

The organic base is as described elsewhere herein. In some aspects, the organic base is a tri-C1-6 alkyl amine. In some particular aspects, the organic base is selected from 4-methylmorpholine and N-ethyldiisopropylamine.

In some aspects, the organic solvent is a polar aprotic solvent as described elsewhere herein. In some particular aspects, the solvent is selected from NMP and DMF.

In some aspects, the concentration of compound 130 in the reaction mixture is from about 0.25 to about 2 moles/L, from about 0.5 to about 1.5 moles/L or from about 0.5 to about 1 moles/L. In some aspects, the ratio of solvent volume to compound 130 weight is from about 1.5:1 to about 10:1 L/kg, from about 2:1 to about 6:1 L/kg, or from about 2:1 to about 4:1 L/kg. The equivalent ratio of the organic base to compound 130 is from about 1:1 to about 2:1, from about 1.05:1 to about 1.9:1, or from about 1.1:1 to about 1.5:1. In some aspects, compound 130 is present in stoichiometric excess over compound 10. In some aspects the equivalent ratio of compound 10 to compound 130 is between 0.7:1 and 1:1, such as from about 0.75:1 to about 0.95:1.

The reaction for forming a reaction product mixture comprising compound 160 may be done with N$_2$ purging and/or with an N$_2$ blanket. In some aspects, the organic solvent, organic base and compound 10 are combined in a reactor with agitation at a temperature of from about 95 to about 125° C. or from about 100 to about 120° C. Compound 130 is then added to the reactor with agitation while maintaining the temperature. In some aspects, compound 130 is in solution in an organic solvent (e.g., toluene or NMP) as described elsewhere herein. In some aspects, the reaction time to completion may be about 0.25 hours, about 0.5 hours, about 1 hour, about 2 hours, about 3 hours, or more.

The reaction may be deemed complete when the area % concentration by HPLC of compound 130 is less than 5, less than 2, less than 1, less than 0.5, or less than 0.1.

Compound 160 may be isolated from the reaction product mixture. In some isolation aspects, the reaction product mixture may be cooled, such as for instance to from about 80 to about 95° C. Water may then be combined with the reaction product mixture to form a mixture wherein the ratio of water volume to compound 130 starting material weight is from about 3:1 to about 15:1 L/kg or from about 5:1 to about 10:1 L/kg. The mixture is cooled to from about 5 to about 30° C. and stirred at temperature for at least 0.5 hours to form a slurry comprising solid compound 160. Solid compound 160 may be collected, such as by filtration or centrifugation. The solids may optionally be subjected to a second water slurry and collection step. Acetone may then be combined with the solid compound 160 to form a slurry, for instance at a temperature of from about 10 to about 30° C., wherein the ratio of acetone volume to compound 130 starting material weight is from about 1.5:1 to about 6:1 L/kg or from about 2:1 to about 4:1 L/kg. The slurry may be agitated for at least 1 hour. Solid compound 160 may be isolated, such as by filtration or centrifugation. The collected solids may be optionally washed with acetone. The solid compound 160 may be dried. In some drying aspects, drying may be done under vacuum at a temperature of from about 25 to about 50° C. The yield of compound 160 is at least 50% at least 60% or at least 70%. The purity of compound 160 by HPLC is at least 98 area %, at least 99 area %, or at least 99.5 area % by HPLC.

Figure 9:
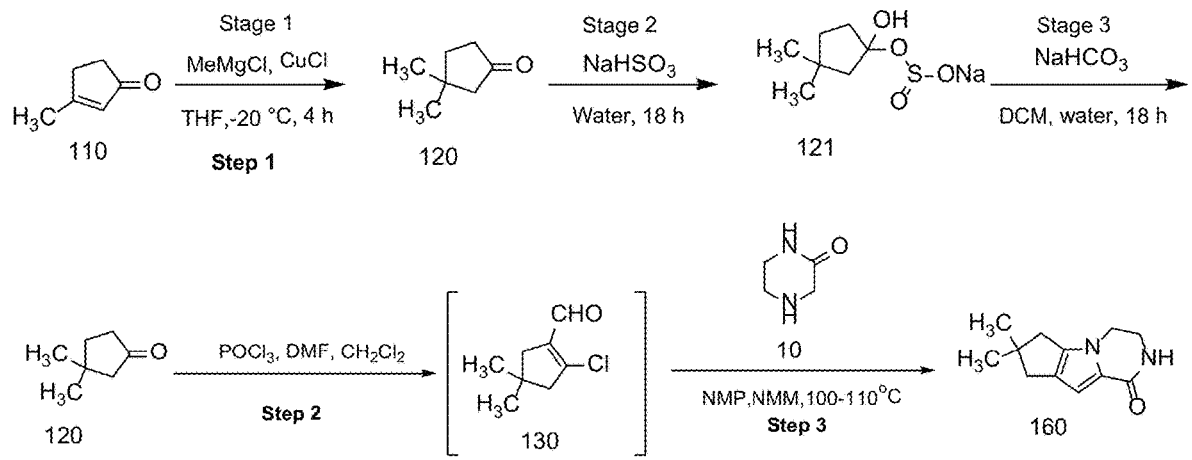
FIG. 9 shows a method for the preparation of compounds 120, 121, 130, and 160.

In some particular aspects, compounds 120, 130 and 160 may be prepared according to the method of WO 2018/109050, depicted in FIG. 9.

In some such aspects, compound 120 may be prepared according to FIG. 8. Compound 120 may be purified by a solid ketone bisulfite adduct route depicted in FIG. 9. The purification method comprises forming a first reaction mixture comprising crude compound 120, an organic solvent that is not miscible with water (e.g., heptane), and an aqueous solution of sodium bisulfite, and reacting the first reaction mixture to form a first reaction product mixture comprising the solid ketone bisulfite adduct of compound 121:

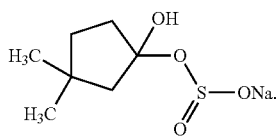

121

Compound 121 is isolated from the first reaction product mixture. A second reaction mixture is formed comprising isolated compound 121, water, a low boiling solvent that is not miscible with water, and sodium bicarbonate. In some aspects, the solvent is DCM. The second reaction mixture is reacted to form a second reaction product mixture comprising a first phase comprising the solvent and the predominant amount of purified compound 120 is in solution in the first phase, and a second phase comprising water. The first phase comprising the purified compound 120 is separated from the aqueous phase.

In such aspects, the pH of the reaction product mixture comprising crude compound 120 may be adjusted to less than 5 with an aqueous mineral acid solution, for instance, aqueous HCl providing about 1.2 to about 1.4 equivalent of HCl per equivalent of compound 120.

In the first reaction mixture, the pH-adjusted reaction product mixture may be combined with a solvent that is not miscible with water (e.g., hexane) wherein crude compound 120 is soluble in said solvent. In some aspects, the ratio of solvent volume to compound 120 weight of from about 5 L/kg to about 25 L/kg, from about 10 L/kg to about 20 L/kg, or from about 10 L/kg to about 15 L/kg. The ratio of water volume to the crude compound 120 weight in the first reaction mixture is from about 1:1 L/kg to about 10:1 L/kg, from about 1.5:1 L/kg to about 4:1 L/kg, or from about 2:1 L/kg to about 3:1 L/kg. The equivalent ratio of sodium bisulfite to compound 120 in the first reaction mixture is from about 2:1 to about 5:1 or from 3:1 to about 5:1.

The first reaction mixture is formed by combining the pH-adjusted reaction product mixture with the solvent that is not miscible with water with agitation at a temperature of from about 10 to about 30° C. The resulting mixture is combined with a filter aid (e.g., diatomaceous earth) and the solids are removed, such as by centrifugation or filtration. The filtrate is separated to form an organic phase comprising compound 120 and an aqueous phase. The organic phase is concentrated below at temperature of about 75° C. by reducing the volume to a ratio of total volume to compound 120 weight of from about 1.5 L/kg to about 4 L/kg, or from about 1.5 L/kg to about 2.5 L/kg. The reduced volume organic phase is cooled, for instance, to about 10 to about 30° C., optionally filtered, and combined with aqueous $NaHSO_3$ solution providing from about 2 to about 5 equivalents of $NaHSO_3$ per equivalent of compound 120 or from about 3 to about 4.5 equivalents of $NaHSO_3$ per equivalent of compound 120 to form a slurry comprising solid compound 121. Solid compound 121 is isolated, such as by filtration or centrifugation, and the collected solids are slurried in the solvent that is not miscible with water (e.g., hexane). The ratio of solvent volume to compound 121 weight is suitably from about 3 L/kg to about 13 L/kg, or from about 5 L/kg to about 9 L/kg. Solid compound 121 is isolated, such as by filtration or centrifugation. The isolated compound 121 solids are optionally washed with the low boiling solvent volume that is not miscible with water (e.g., DCM).

The second reaction mixture comprises a ratio of water volume to isolated solid 121 weight of from about 5:1 L/kg to about 15:1 L/kg, or from about 7.5:1 L/kg to about 10.5:1 L/kg. The ratio of water volume to the low boiling solvent volume that is not miscible with water (e.g., DCM) in the second reaction mixture is from about 1:1 to about 3:1 or from about 1.5:1 to about 2.5:1. The ratio of the volume of solvent that is not miscible with water and compound 121 weight is from about 2 L/kg to about 9 L/kg, from about 3 L/kg to about 7 L/kg, or from about 4 L/kg to about 6 L/kg. The equivalent ratio of sodium bicarbonate to compound 121 in the second reaction mixture is between 1:1 and 2:1, or from about 1.25:1 to about 1.75:1. In some aspects, the sodium bicarbonate is an aqueous solution of sodium bicarbonate.

The second reaction mixture is formed by combining the compound 121 solids with water and with agitation. The low boiling solvent that is not miscible with water is added and followed by addition of the solution of sodium bicarbonate to form a second reaction product mixture comprising compound 120. The resulting mixture may be combined with a filtration aid (e.g., diatomaceous earth) and the solids are removed from the mixture, such as by filtration or centrifugation. The filtrate or centrifugate is allowed to separate into an organic phase and an aqueous phase, and the phases are separated and collected. The aqueous phase may optionally be extracted with the low boiling solvent that is not miscible with water, and the organic phases are combined. The combined organic phase may be washed with brine. The washed combined organic phase may be concentrated at a temperature of less than about 70° C. to a total volume to compound 120 weight of from about 1.5 L/kg to about 4 L/kg or from about 1.5 L/kg to about 2.5 L/kg and comprises compound 120 in solution. The assay of the solution is suitably from about 30% to about 50%, from about 35% to about 45%, or about 40%. The yield of compound 120 is at least 50%, at least 60% or at least 70%.

In some aspects, compound 130 may be prepared from compound 120 according to the method depicted in FIG. 8.

Compound 160 may be isolated from the reaction product mixture. In some isolation aspects, the reaction product mixture may be cooled, such as for instance to from about 80° C. to about 95° C. Water may then be combined with the reaction product mixture to form a mixture wherein the ratio of water volume to compound 130 starting material weight is from about 3:1 to about 15:1 L/kg or from about 5:1 to about 10:1 L/kg. The mixture is cooled to from about 5° C. to about 30° C. and stirred at temperature for at least 0.5 hours to form a slurry comprising solid compound 160. Solid compound 160 may be collected, such as by filtration or centrifugation. The solids may optionally be subjected to a second water slurry and collection step. Acetone may then be combined with the solid compound 160 to form a slurry, for instance at a temperature of from about 10° C. to about 30° C., wherein the ratio of acetone volume to compound 130 starting material weight is from about 1.5:1 to about 6:1 L/kg or from about 2:1 to about 4:1 L/kg. The slurry may be agitated for at least 1 hour. Solid compound 160 may be isolated, such as by filtration or centrifugation. The collected solids may be optionally washed with acetone. The solid compound 160 may be dried. In some drying aspects, drying may be done under vacuum at a temperature of from about 25 to about 50° C. The yield of compound 160 is at least 50% at least 60% or at least 70%. The purity of compound 160 by HPLC is at least 98 area %, at least 99 area %, or at least 99.5 area % by HPLC.

Figure 10:
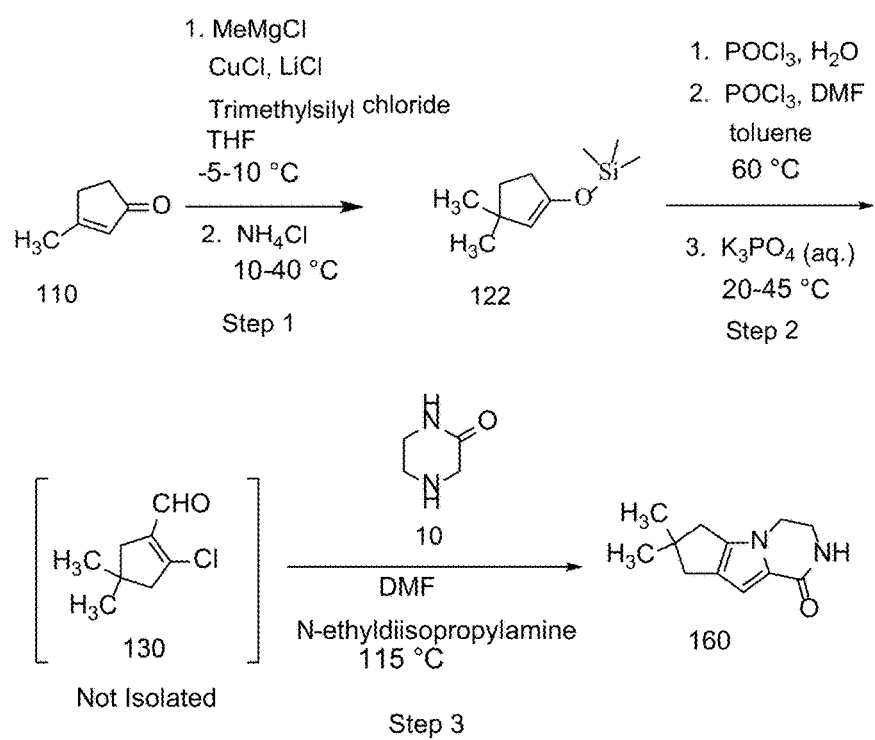
FIG. 10 shows a method for the preparation of compounds 122, 130, and 160.

In some particular aspects, compounds 130 and 160 may be prepared according to method described in WO 2018/109050, depicted in FIG. 10.

In some such aspects of the present disclosure, compound 130 in the below reaction scheme may be prepared from a trimethyl silyl intermediate of compound 120, designated as compound 122 in the below reaction scheme. The reaction scheme is as follows:

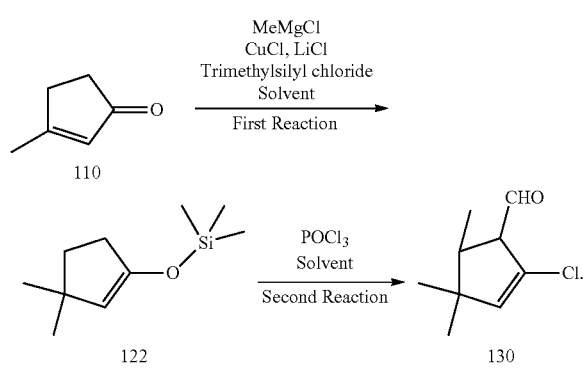

The method for preparing compound 130 comprises forming a first reaction mixture comprising a first polar aprotic solvent, methyl magnesium chloride, copper (I) chloride, lithium chloride, chlorotrimethylsilane (TMSCl), and compound 110. The first reaction mixture is reacted to form a first reaction product mixture comprising compound 122. The first reaction product mixture is quenched with a first quenching agent in aqueous solution and a non-polar water-immiscible solvent is added to the quenched reaction product mixture. The phases are separated and an organic phase comprising the predominant amount of compound 122 is collected and concentrated to obtain compound 122 in solution. A second reaction mixture comprising a second polar aprotic solvent, phosphorous oxychloride, and the solution of compound 122 is formed. The second reaction mixture is reacted to form a second reaction product mixture comprising compound 130. The second reaction product mixture is quenched with a second quenching agent in aqueous solution. The phases are separated and an organic phase comprising the predominant amount of compound 130 in solution is collected.

The first and second polar aprotic solvents are as described elsewhere herein. In some aspects, the first polar aprotic solvent is THF. In some aspects, the second polar aprotic solvent is DMF. In some aspects, the first quenching agent is ammonium chloride. In some aspects, the second quenching agent is potassium phosphate.

In some aspects, the first reaction mixture comprises from about 0.25 to about 2 moles per liter of compound 110, or from about 0.5 to about 1.1 moles per liter of compound 110. In some other aspects, the ratio of the volume of the first polar aprotic solvent volume to compound 110 weight is from about 3 to about 11 L/kg, or from about 5 L/kg to about 9 L/kg. MeMgCl is present in stoichiometric excess as compared to compound 110. In some aspects, MeMgCl is in solution in THF, such as a 3M solution. In some aspects, the mole ratio of MeMgCl to compound 110 is between 1:1 and 1.5:1, or is from about 1.1:1 to about 1.3:1. TMSCl is present in stoichiometric excess as compared to compound 110. In some aspects, the mole ratio of TMSCl to compound 110 is between 1:1 and 1.2:1, or from about 1.01:1 to about 1.1:1. The mole ratio of CuCl to compound 110 is from about 0.05:1 to about 0.2:1, or from about 0.05:1 to about 0.15:1. The mole ratio of LiCl to compound 110 is from about 0.05:1 to about 0.2:1, or from about 0.07:1 to about 0.15:1.

In some aspects, the second reaction product mixture comprises from about 0.5 to about 2 moles per liter or from about 0.7 to about 1.3 moles per liter compound 122. The mole ratio of phosphorous oxychloride to compound 122 is from about 1.5:1 to about 3.1:1, or from about 2.1:1 to about 2.6:1.

In the first reaction, in some aspects, CuCl, LiCl, and the first polar aprotic solvent may be combined in an $N_2$ atmosphere in a reactor at a temperature of from about 10 to about 35° C. and cooled to from about −10 to about 10° C. Compound 110 and TMSCl are added to the reactor at from about −10 to about 10° C. A first reaction product mixture comprising compound 122 is formed. In some aspects, the reaction time to completion may be at least 0.5 hours, at least 1 hour, or more. The reaction may be deemed complete when the area % concentration by HPLC of compound 110 is less than 5, less than 2, less than 1, less than 0.5, or less than 0.1. The reaction is quenched, such as with an aqueous ammonium chloride solution wherein the equivalent ratio of ammonium chloride to compound 110 is greater than 1:1, about 1.1:1, about 1.2:1 or about 1.3:1. The ratio of ammonium chloride solution volume to compound 110 is from about 2:1 to about 10:1 L/kg, or from about 3:1 to about 7:1 L/kg. Organic and aqueous phases are separated and collected. The organic layer comprises compound 122 in solution and may optionally be washed with brine. The optionally washed organic layer may be concentrated until the ratio of the distillate volume collected to compound 110 weight is from about 8 L/kg to about 10 L/kg. The concentrated first reaction product mixture may be diluted with a non-polar solvent (e.g., toluene) wherein the ratio of the added non-polar solvent volume to compound 110 weight is from about 1 L/kg to about 3 L/kg. In such aspects, the diluted mixture may concentrated to remove an approximate volume of the added non-polar solvent to produce a solution of compound 122. The compound 122 assay in the solution is from about 40 w/w % to about 60 w/w %, or from about 45 w/w % to about 55 w/w %. The yield of compound 122 based on compound 110 is at least 60%, at least 70% or at least 80% and the HPLC purity of compound 122 is at least 85 area % or at least 90 area % by HPLC.

In the second reaction, the solution from the first reaction is diluted with the non-polar solvent to achieve a compound 122 assay of from about 25 to about 45 w/w % or from about 30 to about 40 w/w % or about 35 w/w %. In some aspects, the non-polar solvent is toluene. A first $POCl_3$ addition may be done wherein the equivalent ratio of $POCl_3$ to compound 110 weight is from about 0.2:1 to about 0.4:1 or about 0.3:1 and wherein the temperature is from about 5 to about 35° C. DMF is added after $POCl_3$ at an equivalent ratio to compound 110 of from about 1.5:1 to about 3:1 or from about 1.5:1 to about 2.5:1. A second $POCl_3$ addition is done wherein the equivalent ratio of $POCl_3$ to compound 110 weight is from about 1.5:1 to about 2.5:1 or about 2:1, and the mixture is heated to from about 50 to about 70° C. to form a second reaction product mixture comprising compound 130. In some aspects, the reaction time to completion may be at least 2 hours, or more. The reaction may be deemed complete when the area % concentration by HPLC of compound 110 is less than 5, less than 2, less than 1, less than 0.5, or less than 0.1. The reaction product mixture is combined with an aqueous potassium phosphate solution providing an equivalent ratio of potassium phosphate to compound 110 is from about 1.2:1 to about 2:1 or from about 1.4:1 to about 1.8:1. The ratio of potassium phosphate solution volume to compound 110 weight is from about 3 to about 12 L/kg or from about 6 to about 9 L/kg. Organic and aqueous phases are formed that are separated and collected. The organic layer is washed with potassium phosphate solution and water to obtain a washed organic phase (e.g., toluene) comprising compound 130 in solution and having a pH in excess of 7. The organic phase is filtered to generated compound 130 in solution (e.g., toluene). The yield of compound 130 based on compound 110 is at least 70% or at least 75%, and the purity of compound 130 is at least 85% or at least 88% by HPLC.

In some aspects, compound 130 may be prepared from compound 120 according to the method depicted in FIG. 8.

Preparation of Compound 170

In some aspects, compound 170 may be prepared according to methods disclosed in International Publication Number WO 2018/10905.

Figure 7:
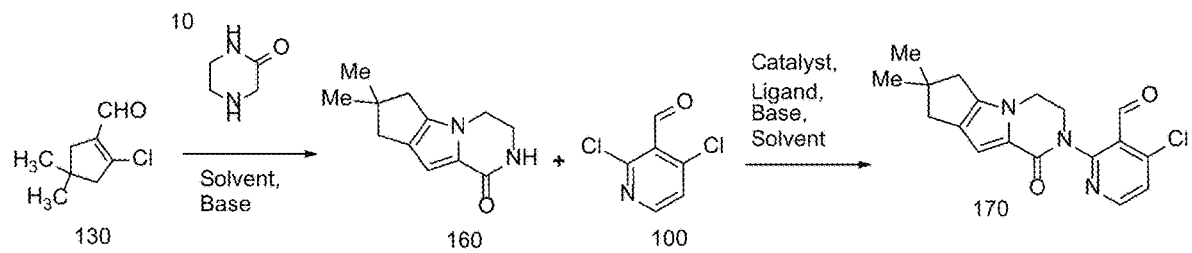
FIG. 7 shows a method for the preparation of compounds 160 and 170.

In some such aspects, compound 170 may be prepared according to the method of WO 2018/10905, depicted in FIGS. 7 and 13 and reproduced below, by forming a reaction mixture comprising compound 160, a stoichiometric excess of compound 100, a palladium catalyst and a catalyst ligand, a base and a polar aprotic solvent:

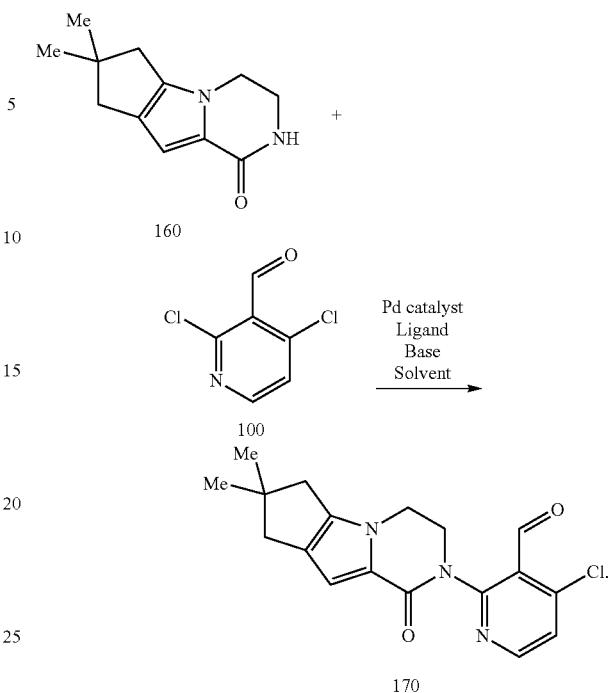

The reaction mixture is reacted to form a reaction product mixture comprising compound 170. Compound 170 may optionally be isolated from the reaction mixture.

The equivalent ratio of compound 100 to compound 160 in the reaction mixture is greater than 1:1, such as between 1:1 and 1.7:1, from about 1.05:1 to about 1.5:1 or from about 1.05:1 to about 1.2:1. The palladium catalyst may be any palladium catalyst that affects the rate and conversion of a chemical substrate compound to a product compound as a commercially acceptable yield and conversion. In some aspects, the catalytic palladium species is a palladium source selected from the following non-excusive listing: [Pd(allyl)Cl]$_2$, Pd(MeCN)$_2$Cl$_2$, Pd(benzonitrile)$_2$Cl$_2$, Pd(dba)$_2$, Pd(OAc)$_2$, PdCl$_2$, PdBr$_2$, Pd(TFA)$_2$, Pd(MeCN)$_4$(BF$_4$)$_2$, Pd$_2$(dba)$_3$, PdCy$_3$Cl$_2$, Pd(acac)$_2$, and Pd(PPh$_3$)$_4$. In some such aspects, the palladium catalyst is Pd$_2$(dba)$_3$ or Pd(OAc)$_2$, or is Pd(OAc)$_2$. Non-limiting examples of ligands include DPPF, DTPBF, BINAP, DPPE, DPPP, DCPE, RuPhos, SPhos, APhos (amphos), CPhos, XPhos, t-BuXPhos, Me$_4$t-BuXPhos, neopentyl(t-Bu)$_2$P, (t-Bu)$_2$PMe, (t-Bu)$_2$PPh, PCy$_3$, PPh$_3$, XantPhos, and N-XantPhos. In some aspects, the ligand is DPPF. The polar aprotic solvent is as described elsewhere herein. In some aspects, the solvent is THF. The ratio of solvent volume to compound 160 weight in the reaction mixture may be about from about 2:1 to about 30:1 L/kg, from about 5:1 to about 20:1 L/kg, or from about 5:1 to about 15:1 L/kg. The concentration of compound 160 in the reaction mixture may be from about 0.1 mol/L to about 1 mol/L, or from about 0.2 to about 0.5 mol/L. The equivalent ratio of catalyst to compound 160 may be from about 0.01:1 to about 0.05:1 or from about 0.01:1 to about 0.03:1. The equivalent ratio of the ligand to the catalyst may from about 1.2:1 to about 3:1 or from about 1.5:1 to about 2.5:1. In some aspects, the base is an inorganic base, such as without limitation, an alkali metal hydroxide, alkali metal carbonate, or alkali metal bicarbonate. One such inorganic base is potassium carbonate. The equivalent ratio of the base to compound 160 is suitably between 1:1 and 2:1, or from about 1.2:1 to about 1.8:1. The reaction may be done at reflux temperature, typically between about 60° C. and about 80° C. The reaction may be deemed complete when the area % concentration by HPLC of compound 160 is less than 3, less than 2, less than 1 or less than 0.5. In some aspects, the reaction time to completion may be 2 hours, 6 hours, 10 hours, 14 hours, 18 hours, 22 hours, or more.

Compound 170 may be isolated from the reaction product mixture. In some aspects, water may be combined with the reaction product mixture at a ratio of water volume to compound 160 weight of from about 2:1 to about 20:1 or from about 2:1 to about 10:1. The temperature may be reduced to induce crystallization of compound 170 and form a suspension of solid compound 170, such as from about 5° C. to about 30° C. or from about 15° C. to about 25° C. and held at that temperature for at least 1 hour. Solid compound 170 may be isolated from the reaction mixture, such as by filtration or centrifugation. Isolated compound 170 may optionally be dried. In some drying aspects, drying is done under a partial vacuum with a $N_2$ purge at a temperature of from about 15° C. to about 60° C. or from about 30° C. to about 60° C. or from about 15° C. to about 50° C. or from about 15° C. to about 40° C. or from about 15° C. to about 30° C. for at least 2 hours. The yield of compound 170 based on compound 160 is at least 80%, at least 85% or at least 90%. The purity of compound 170 is at least 95 area %, at least 98 area % or at least 99 area % by HPLC.

Figure 11:
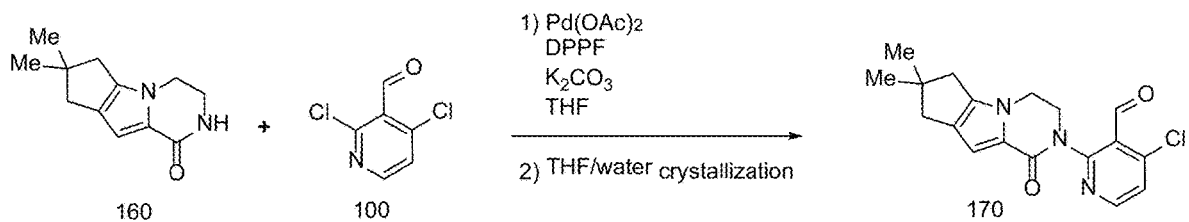
FIG. 11 shows a method for the preparation of compound 170.

In some particular aspects, compound 170 may be prepared according to the method disclosed in International Publication Number WO 2018/10905 as depicted in FIG. 11.

Preparation of Compound 140

Figure 12A:
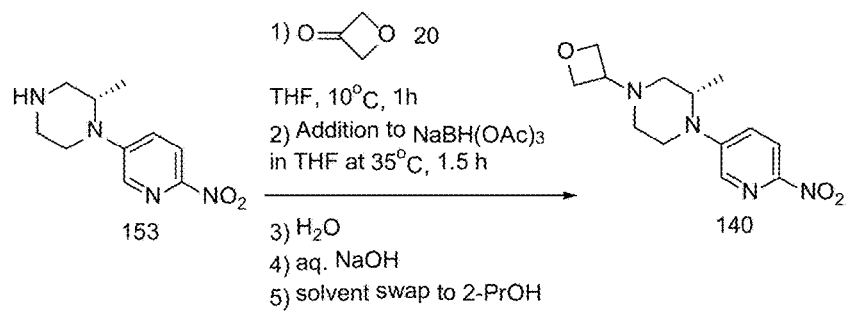
FIG. 12A shows a method for the preparation of compound 140.

In general, compound 140 may be prepared from compounds 153 and 20 according to the following scheme:

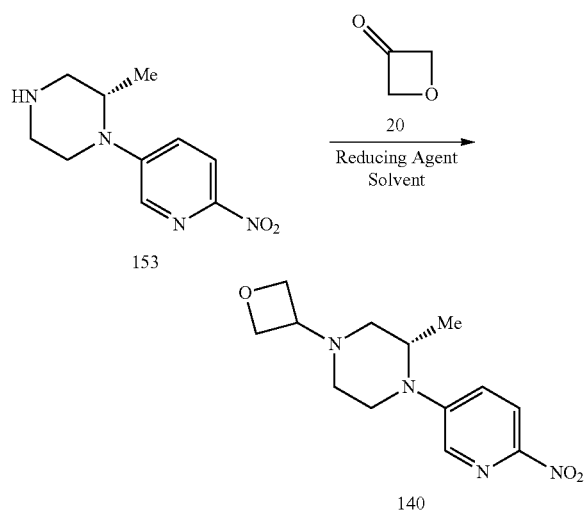

Wherein the secondary amine of compound 153 is alkylated with compound 20 in a reductive alkylation reaction in the presence of a reducing agent to form compound 140. In some aspects, compound 140 may be prepared as depicted in FIG. 12A, and further described herein.

In some aspects, provided herein is a method of preparing compound 140, the method comprising:
(a) forming a reaction mixture comprising compound 153, compound 20, NaBH(OAc)$_3$, and a solvent; and
(b) reacting the reaction mixture to form a reaction product mixture comprising compound 140 according to the following scheme:

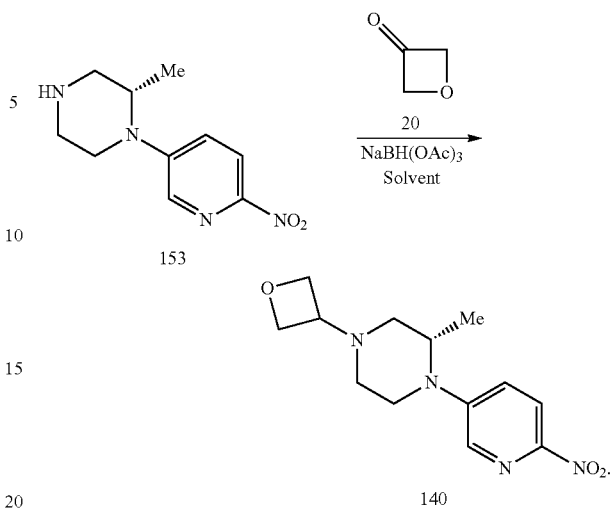

In some aspects, acetic acid is not separately added, though some may form from the presence of residual water. In some aspects, the reaction product mixture formed in step (a) comprises less than 10% by weight, less than 5% by weight, less than 1% by weight, or is essentially free of acetic acid. In some embodiments, the ratio of NaBH$^-$ to combined total of OAc$^-$ and HOAc is less than 1:3.1, or less than 1:3.05, or less than 1:3.01. The solvent may be, for example, an organic solvent, such as an aprotic organic solvent. In some aspects, the solvent is THF or Me-THF. In some aspects, the solvent is THF. In some aspects, the source of compound 153 and compound 20 is a solution of compound 153 and compound 20 in the solvent, for example as about from 20 wt % to about 50 wt % compound 153, or about 30 wt % to about 40 wt % compound 153; and from about 5 wt % to about 20 wt % compound 20, or from about 10 wt % to about 20 wt % compound 20. In some aspects this solution is prepared by adding compound 153 to a solution of compound 20 in the solvent at a temperature between about 5° C. to about 15° C., or about 10° C. In some aspects, a solution of compound 153 and compound 20 in the solvent is combined with a suspension of NaBH(OAc)$_3$ in the solvent to form the reaction mixture. In any of the various aspects, the concentration of compound 153 in the reaction mixture may be from about 10 wt % to about 30 wt %, or from about 15 wt % to about 25 wt %, or about 20 wt %. In any of the various aspects, the concentration of compound 20 in the reaction mixture may be from about 5 wt % to about 15 wt %, or about 6 wt % to about 10 wt %, or about 8 wt %. The equivalent ratio of compound 20 to compound 153 in the reaction mixture may be from about 1.1:1 to about 1.9:1, or from about 1.2:1 to about 1.4:1, or about 1.3:1. The equivalent ratio of NaBH(OAc)$_3$ to compound 153 may be from about 2:1 to about 1:1, or about 1.7:1 to about 1.3:1, or about 1.5:1. The reaction for forming compound 140 may be done with $N_2$ purging and/or with an $N_2$ blanket. The reaction is typically done at a temperature of from about 25° C. to about 45° C., or about 30° C. to about 40° C., or about 35° C. In some aspects, the reaction time to completion may be about 0.5 hours, about 1 hour, about 2 hours, about 4 hours, or more. The reaction may be deemed complete when the area % concentration by HPLC of compound 153 is less than 2, less than 1, less than 0.5, or less than 0.1.

In some aspects, the reaction product mixture is subsequently combined with water and a base, wherein the water and base may be added separately. The reaction product mixture may be combined with water at a ratio of water volume to compound 140 weight of from about 1:1 to about 5:1 L/kg or from about 2:1 to about 3:1 L/kg. In certain aspects, the weight ratio of water added to solvent in the mixture is from about 0.4:1 to about 0.8:1, or is about 0.6:1. The phases may then be separated to form an aqueous phase and an organic phase, and a base added. In some aspects, the base is an inorganic base. In certain aspects, the base is NaOH. The base may be added, for example, as an aqueous solution, for example as an aqueous solution of NaOH at a concentration of from about 20 wt % to about 40 wt %, or about 30 wt %. An amount of base may be added such that the pH of the aqueous phase reaches about 12. Base may be added, for example, at a ratio of base to compound 140 of from about 3:1 to about 1:1, or about 2:1.

Compound 140 may then be isolated, which may include, for example, one or more solvent swap, distillation, and/or crystallization steps. For example, in some aspects, following addition of base, the organic layer comprising compound 140 is isolated, optionally filtered, and the solvent in the organic phase comprising compound 140 is be exchanged for another solvent. Solvent exchange may be done by methods known to those skilled in the art as described elsewhere herein. In one such aspect, a portion of the solvent in the organic phase comprising compound 140 (e.g., THF) may be removed by distillation under reduced pressure. For instance, about 40%, about 50%, about 60%, about 70% or about 80% of the solvent may be stripped, such as under reduced atmosphere, for example at from about 250 mbar to 350 mbar, or about 300 mbar. The stripped may be replaced with another solvent, such as an organic protic solvent. The organic protic solvent may be an alcohol. In some aspect, the organic protic solvent is isopropanol. In some aspects, the methods herein further comprise crystallizing compound 140. Such crystallization may, for example, follow the solvent swap steps described herein. The solution of compound 140 may be cooled, such as to less than 40° C., less than 20° C., or about 5° C., and stirred while crystals of compound 140 form. The crystals may then be isolated, such as by filtering, optionally washed with additional solvent, and dried under reduced pressure to yield purified dry compound 140 crystals. In some embodiments, the solution of compound 140 is seeded with crystals of compound 140 to promote crystallization. The yield of compound 140 may be at least 85% or at least 90%. The purity of compound 140 may at least 95%, at least 98% or at least 98.5% by HPLC.

Figure 12B:
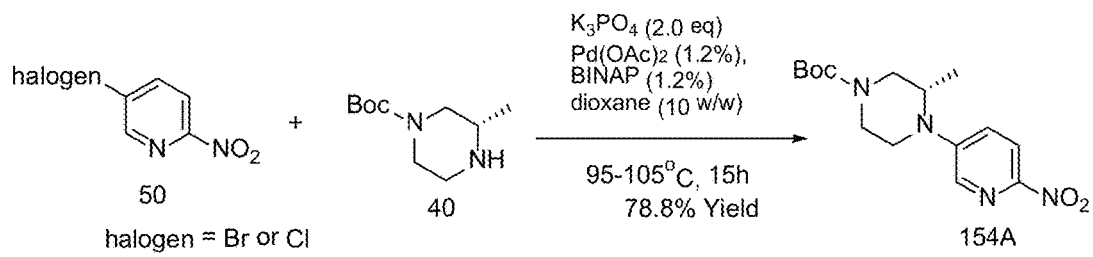
FIG. 12B shows methods for the preparation of compounds 154A, 153, and 140.
Figure 12B:
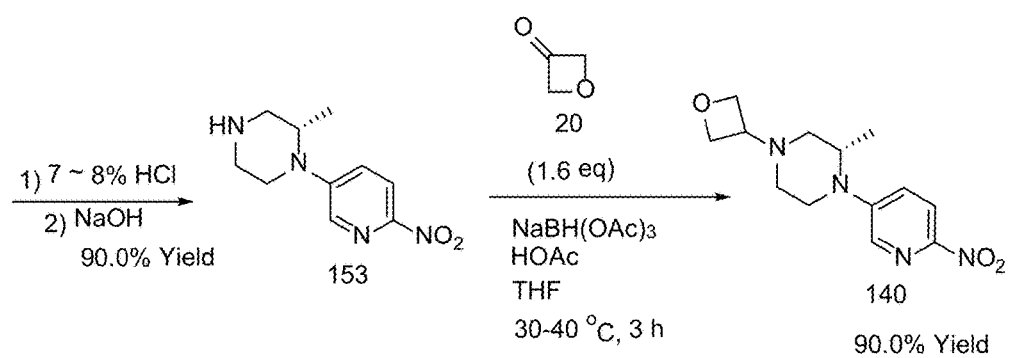

In other aspects, compound 140 may be prepared according to the method of WO 2018/10905 as depicted in the last step of FIG. 12B.

Preparation of Compound 153

In general, compound 153 may be prepared according to the following scheme:

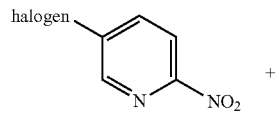

50 halogen = Br or Cl

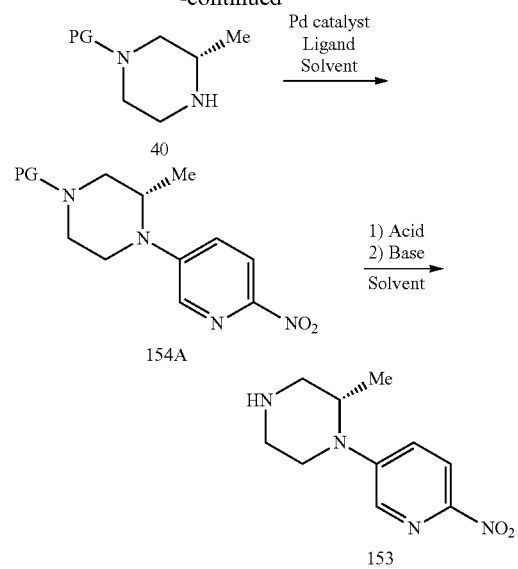

In such aspects, compound 154A may be prepared from a reaction mixture comprising compound 50, compound 40, dioxane, $K_3PO_4$, $Pd(OAc)_2$ catalyst, and BINAP ligand. In the reaction mixture, the concentration of compound 50 in dioxane is about 10 w/w %, the equivalent ratio of $K_3PO_4$ to compound 50 is about 2, the equivalent ratio of $Pd(OAc)_2$ catalyst to compound 50 is about 0.012:1, and the equivalent ratio of $Pd(OAc)_2$ catalyst to BINAP ligand is about 1:1. The reaction mixture is reacted at from about 95° C. to about for about 105° C. for about 15 hours to form a reaction product mixture comprising BOC-protected compound 154 at a yield of about 79%. A reaction mixture comprising compound 154A, methanol, 10% palladium on carbon catalyst and hydrogen is formed. In the reaction mixture, the ratio of methanol volume to compound 154A weight is about 5:1, and the weight ratio of the palladium on carbon catalyst to compound 154A is about 0.05:1. In some aspects, where the PG is BOC, compound 154A is designated as compound 154.

In such aspects, compound 153 may be prepared from compound 154A according to the following reaction scheme:

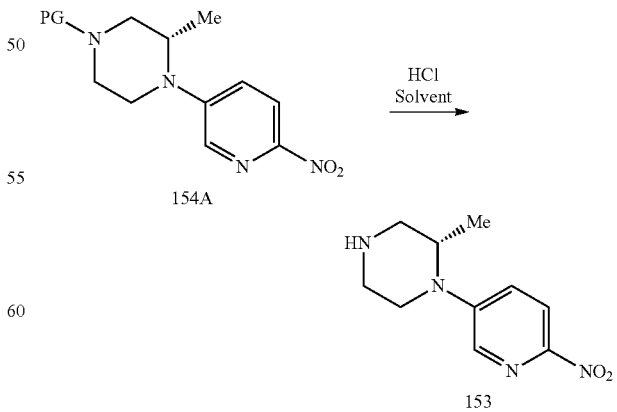

The method for preparing compound 153 comprises forming a reaction mixture comprising compound 154A having a protecting group moiety, PG, hydrochloric acid, and a solvent comprising water. The reaction mixture is reacted to form a reaction product mixture comprising deprotected compound 154A. Compound 153 may optionally be isolated from the reaction product mixture.

The reaction for forming compound 153 may be done with $N_2$ purging and/or with an $N_2$ blanket. The reaction is typically done at a temperature of from about 40 to about 70° C. or from about 50 to about 60° C. In some aspects, the reaction time to completion may be at last 1 hour, or more. The reaction may be deemed complete when the area % concentration by HPLC of compound 154A is less than 2, less than 1, less than 0.5, or less than 0.1.

In some aspects, compound 153 may be isolated from the reaction product mixture. In such aspects, the reaction product mixture may be cooled, such as for instance to from about 10 to about 30° C., and the reaction mixture may be extracted with a non-polar solvent as described elsewhere herein (e.g., DCM) at a ratio of solvent volume to compound 153 weight of from about 3:1 L/kg to about 11:1 L/kg or from about 5:1 L/kg to about 9 L/kg. The aqueous phase may be collected and the pH thereof adjusted to greater than 11 with an aqueous strong inorganic base, for instance, about 30% NaOH. The pH-adjusted aqueous phase may be extracted with a non-polar solvent (e.g., DCM) at a ratio of solvent volume to compound 153 weight of from about 5:1 L/kg to about 20:1 L/kg or from about 8:1 L/kg to about 15:1 L/kg. A second aqueous phase extraction with the non-polar solvent may be done. The organic phases are combined and may be washed at least once with water in a volume generally consistent with the volume of each non-polar solvent extraction. The combined washed organic phases may then be dried with a drying agent (e.g., MgSO4) and filtered. The filtrate comprises compound 153 in solution at a concentration of from about 2 to about 8 w/w % or from about 2 to about 6 w/w %. In some aspects, solid compound 153 may be obtained by solvent evaporation under vacuum. In some embodiments, the solvent used is an ester. In certain embodiments, solid compound 153 is obtained by solvent evaporation from isopropyl acetate. In some other aspects, the solution of compound 153 may be used directly for the preparation of compound 140. The yield of compound 153 is at least 80% or at least 90%.

Overall Process

Figure 13:
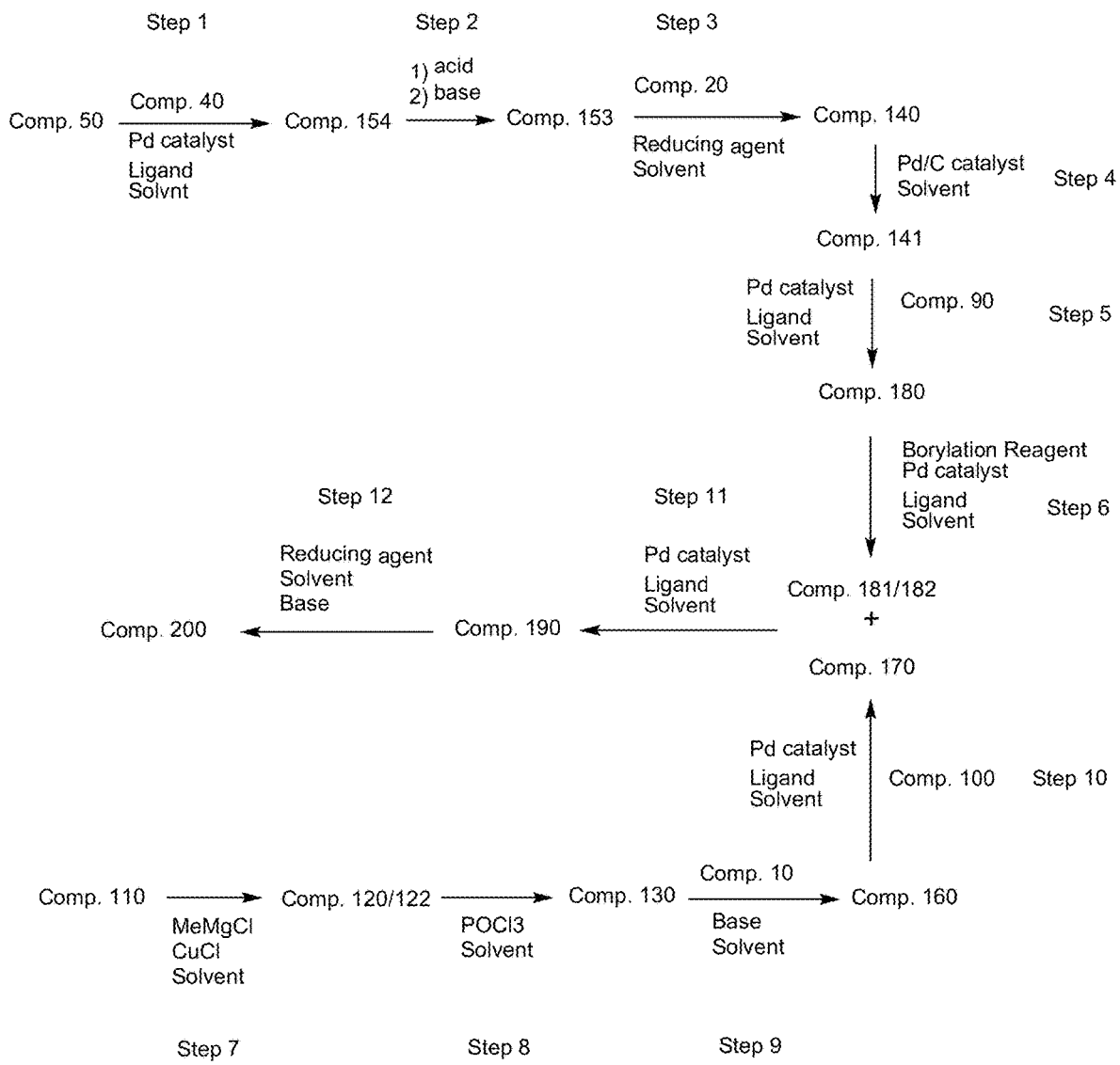
FIG. 13 shows an overall process for the process for the preparation of compound 200, where "Comp" refers to compound.

Compound 200 may be prepared in an overall process as depicted in FIG. 13 where steps 1-3 and 7-10 relate to the general methods of International Publication Number WO 2018/109050 described elsewhere herein, and where steps 4-6 and 10-12 relate to reactions of the present disclosure.

Solvates of Compound 200

Further provided herein are solvates of compound 200, such as those that may be produced during manufacturing of compound 200. In some embodiments, said solvates are crystalline solvates. In certain embodiments, the crystalline solvate is an ethanol hemi-solvate. In some embodiments, the crystalline solvate is a toluene solvate. In some embodiments, the crystalline solvate is an ethanol solvate.

Figure 17:
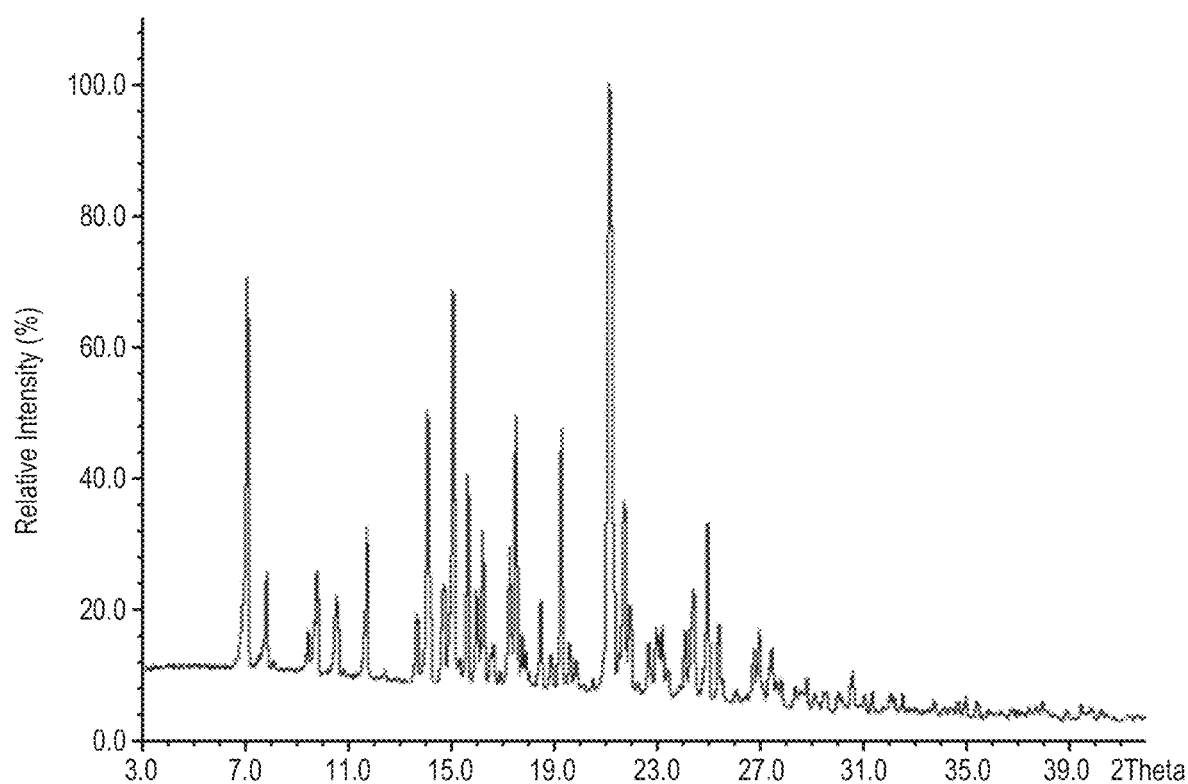
FIG. 17 is an XRPD spectrum of the crystalline ethanol hemi-solvate form of fenebrutinib, obtained in Example 14.

In some embodiments, the crystalline ethanol hemi-solvate is characterized by an XRPD pattern comprising one or more (e.g., one, two, three, four, five, six, seven, eight, nine, ten, or greater than ten; or at least two, at least three, at least four, at least five, at least six, at least seven, at least eight, at least nine, or at least ten) characteristic peaks selected from Table X. In some embodiments, the crystalline ethanol hemi-solvate is characterized by an XRPD pattern comprising at least four, at least five, or all six of the following peaks: 7.04, 14.05, 15.03, 17.48, 19.23, and 21.11 (+0.2° 2Theta). In some embodiments, the crystalline ethanol hemi-solvate has an XRPD pattern essentially as provided in FIG. 17.

Figure 18:
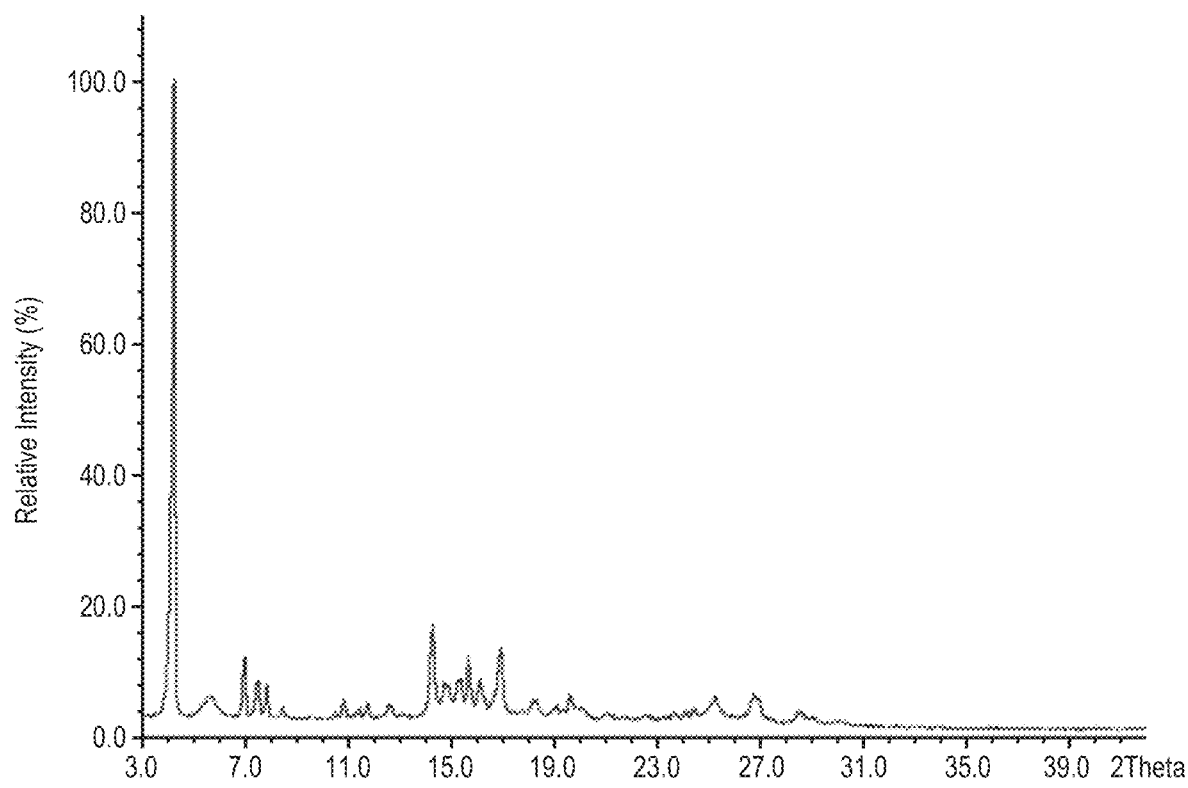
FIG. 18 is an XRPD spectrum of the crystalline ethanol hemi-solvate form of fenebrutinib, obtained in Example 14.

In some embodiments, the crystalline toluene solvate is characterized by an XRPD pattern comprising one or more (e.g., one, two, three, four, five, six, seven, eight, nine, ten, or greater than ten; or at least two, at least three, at least four, at least five, at least six, at least seven, at least eight, at least nine, or at least ten) characteristic peaks selected from Table X. In some embodiments, the crystalline toluene solvate has an XRPD pattern essentially as provided in FIG. 18. In some embodiments, the crystalline toluene solvate is characterized by an XRPD pattern comprising at least four, or all five of the following peaks: 4.18, 6.91, 14.20, 15.59, and 16.83 (+0.2° 2Theta).

Figure 19:
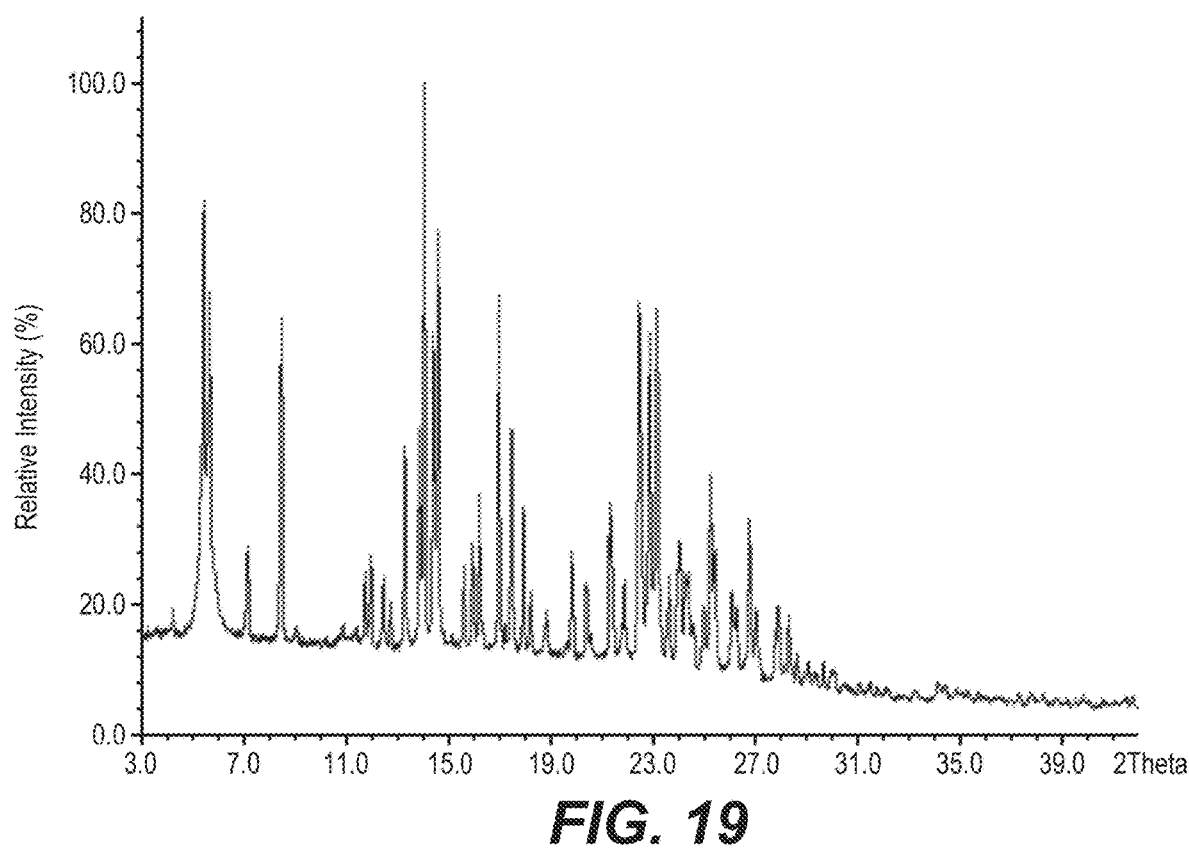
FIG. 19 is an XRPD spectrum of the crystalline ethanol hemi-solvate form of fenebrutinib, obtained in Example 14.

In some embodiments, the crystalline ethanol solvate is characterized by an XRPD pattern comprising one or more (e.g., one, two, three, four, five, six, seven, eight, nine, ten, or greater than ten; or at least two, at least three, at least four, at least five, at least six, at least seven, at least eight, at least nine, or at least ten) characteristic peaks selected from Table X. In some embodiments, the crystalline ethanol solvate has an XRPD pattern essentially as provided in FIG. 19. In some embodiments, the crystalline ethanol solvate is characterized by an XRPD pattern comprising at least four, at least five, at least six, or all seven of the following peaks: 5.41, 5.64, 8.46, 13.83, 14.02, 14.56, and 16.96 (+0.2° 2Theta).

TABLE X

XRPD Peak list for selected compound 200 solvate polymorphs. The positional error for each individual peak is ±0.2° 2Theta.

| Ethanol Hemi-Solvate | | Toluene Solvate | | Ethanol Solvate | |
|---|---|---|---|---|---|
| Unique peaks [°2Theta] | rel. Intensity [%] | Unique peaks [°2Theta] | rel. Intensity [%] | Unique peaks [°2Theta] | rel. Intensity [%] |
| 7.04 | 62 | 4.18 | 100 | 5.41 | 79 |
| 7.78 | 15 | 6.91 | 10 | 5.64 | 64 |
| 9.41 | 7 | 7.43 | 6 | 7.14 | 17 |
| 9.65 | 9 | 7.78 | 5 | 8.46 | 57 |
| 9.76 | 16 | 8.40 | 2 | 11.71 | 14 |
| 10.51 | 13 | 10.76 | 3 | 11.94 | 17 |
| 11.68 | 24 | 11.36 | 2 | 12.41 | 12 |
| 13.63 | 11 | 11.68 | 3 | 12.70 | 9 |
| 14.05 | 44 | 12.54 | 2 | 13.26 | 37 |
| 14.67 | 16 | 14.20 | 15 | 13.83 | 40 |
| 15.03 | 65 | 14.66 | 6 | 14.02 | 100 |
| 15.61 | 35 | 15.21 | 7 | 14.38 | 57 |
| 15.95 | 16 | 15.28 | 7 | 14.56 | 77 |
| 16.19 | 25 | 15.59 | 10 | 15.58 | 16 |
| 16.61 | 7 | 16.04 | 6 | 15.93 | 20 |
| 17.24 | 23 | 16.83 | 11 | 16.20 | 28 |
| 17.48 | 45 | 18.09 | 3 | 16.96 | 64 |
| 17.71 | 9 | 19.53 | 4 | 17.45 | 41 |
| 17.85 | 6 | 25.16 | 4 | 17.90 | 26 |
| 18.44 | 15 | 26.63 | 5 | 18.19 | 11 |
| 18.84 | 6 | | | 18.82 | 8 |
| 19.23 | 42 | | | 19.80 | 18 |
| 19.55 | 8 | | | 20.36 | 14 |
| 19.81 | 6 | | | 21.26 | 28 |
| 21.11 | 100 | | | 21.35 | 26 |
| 21.67 | 32 | | | 21.84 | 14 |
| 21.91 | 15 | | | 22.42 | 65 |
| 22.63 | 9 | | | 22.83 | 59 |
| 22.93 | 12 | | | 23.11 | 64 |
| 23.17 | 12 | | | 23.56 | 16 |
| 24.05 | 12 | | | 24.00 | 23 |
| 24.35 | 18 | | | 24.32 | 18 |
| 24.91 | 30 | | | 24.94 | 12 |
| 25.35 | 13 | | | 25.20 | 36 |
| 26.70 | 9 | | | 25.36 | 20 |

TABLE X-continued

XRPD Peak list for selected compound 200 solvate polymorphs. The positional error for each individual peak is ±0.2° 2Theta.

| Ethanol Hemi-Solvate | | Toluene Solvate | | Ethanol Solvate | |
|---|---|---|---|---|---|
| Unique peaks [°2Theta] | rel. Intensity [%] | Unique peaks [°2Theta] | rel. Intensity [%] | Unique peaks [°2Theta] | rel. Intensity [%] |
| 26.90 | 13 | | | 26.05 | 16 |
| 27.39 | 10 | | | 26.21 | 13 |
| | | | | 26.71 | 28 |
| | | | | 26.98 | 13 |
| | | | | 27.74 | 10 |
| | | | | 27.86 | 14 |
| | | | | 28.26 | 13 |

EXEMPLARY EMBODIMENTS

E1. A method of preparing compound 190, or a stereoisomer, geometric isomer, tautomer, or salt thereof, the method comprising:

(a) forming a reaction mixture comprising compound 170, compound 181, a palladium catalyst, and a solvent system comprising a base, and wherein the equivalent ratio of the palladium catalyst to compound 170 is from about 0.001:1 to less than 0.005:1; and (b) reacting the reaction mixture to form a reaction product mixture comprising compound 190 according to the following scheme:

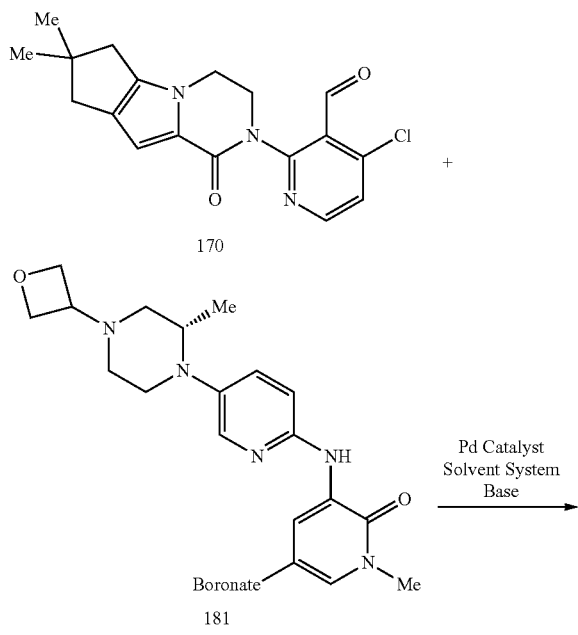

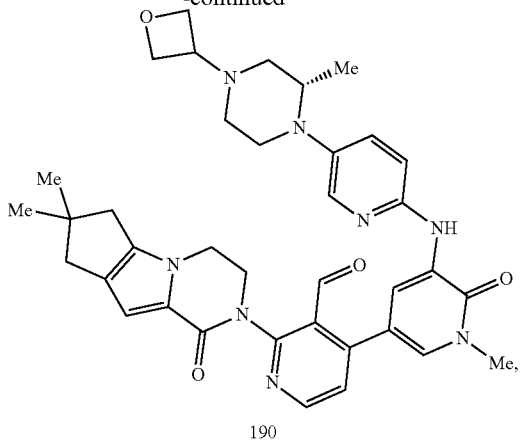

wherein the Pd catalyst comprises a palladium(II) species containing a phosphine ligand and at least one palladium-carbon bond, wherein:
(i) the fragment giving rise to the palladium-carbon bond is an allyl derivative of the formula

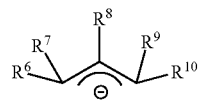

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring;

wherein the yield of compound 190, or a stereoisomer, geometric isomer, tautomer, or salt thereof, is at least 50% based on compound 170.

E2. The method of E1, wherein the fragment giving rise to the palladium-carbon bond is an indenyl of the formula

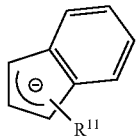

wherein $R^{11}$ is $C_{1-10}$ alkyl.

E3. The method of E1 or E2 wherein the allyl derivative is selected from:
(a) a derivative wherein each of $R^6$ to $R^{10}$ is H;
(b) a derivative wherein $R^6$ is —CH$_3$ and each of $R^7$ to $R^{10}$ is H;
(c) a derivative wherein $R^7$ is —CH$_3$ and each of $R^6$ and $R^8$ to $R^{10}$ is H;
(d) a derivative wherein $R^8$ is —CH$_3$ and each of $R^6$, $R^7$, $R^9$ and $R^{10}$ is H;
(e) a derivative wherein $R^6$ is -phenyl and each of $R^7$ to $R^{10}$ is H;

(f) a derivative wherein $R^7$ is -phenyl and each of $R^6$ and $R^8$ to $R^{10}$ is H; and (g) the structure

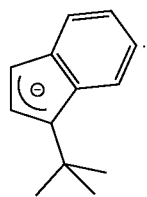

E4. The method of any one of E1 to E3, wherein phosphine ligand is of the formula

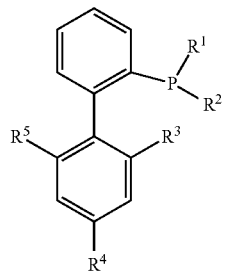

wherein:
$R^1$ and $R^2$ are each independently selected from optionally substituted $C_{1-12}$ alkyl, optionally substituted $C_3$-$C_{20}$ cycloalkyl, and optionally substituted $C_5$ or $C_6$ aryl; and
$R^3$ to $R^5$ are each independently selected from H, optionally substituted $C_{1-6}$ alkyl, alkoxide of the formula —O—$C_{1-6}$ alkyl, and amine of the formula —N($R^{12}$)($R^{13}$) wherein $R^{12}$ and $R^{13}$ are independently selected from H and $C_{1-6}$ alkyl.

E5. The method of any of E1 to E4, wherein the phosphine ligand is SPhos of the following structure

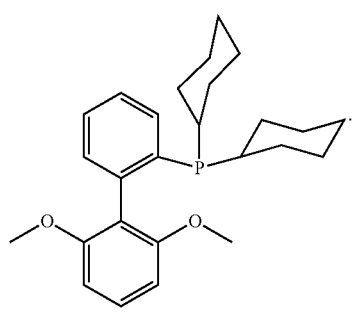 [SMILES: COc1cccc(OC)c1-c1ccccc1P(C1CCCCC1)C1CCCCC1]

E6. The method of any one of E1 to E5, wherein the Pd catalyst is selected from:
(a) a cationic palladium species comprising an inorganic or organic counterion X; and (b) a neutral palladium species comprising a coordinated inorganic or organic ligand X.

E7. The method of E6, wherein X is selected from a halogen, a carboxylate, a sulfonate, and an inorganic anion.

E8. The method of E7, wherein:
(a) the carboxylate is selected from $CH_3C(O)O^-$ and $tBuC(O)O^-$;
(b) the sulfonate is selected from $CF_3SO_3^-$, tosylate, besylate, and nosylate; and
(c) the inorganic anion selected from $PF_6^-$, $BF_4^-$, $B(C_6F_5)_4^-$, $NO_3^-$, and $SO_4^{2-}$.

E9. The method of E7 or E8, wherein X is $CF_3SO_3^-$.

E10. The method of any one of E1 to E9, wherein the palladium catalyst comprises a $CF_3SO_3^-$ organic counterion, wherein the phosphine ligand is SPhos, and wherein each of $R^6$ to $R^{10}$ is H.

E11. The method of any one of E1 to E10, wherein the solvent system predominantly comprises an aprotic low molecular weight ester solvent and water, wherein the volume ratio of the aprotic low molecular weight ester solvent to water is from about 1:0.1 to about 1:1, and wherein the reaction mixture is heated to from about 60° C. to about 80° C.

E12. The method of any one of E1 to E11 wherein the equivalent ratio of compound 181 to compound 170 is greater than 1:1, and the equivalent ratio of the palladium catalyst to compound 170 is from about 0.001:1 to about 0.003:1, or about 0.002:1.

E13. The method of any one of E1 to E12, wherein:
(a) the catalyst is [(SPhos)Pd(allyl)] $CF_3SO_3$;
(b) the solvent system predominantly comprises ethyl acetate and water wherein the volume ratio of ethyl acetate to water is from about 1:0.1 to about 1:1; and
(c) the boronate is 4,4,5,5-tetramethyl-1,3,2-dioxaborolane of the structure:

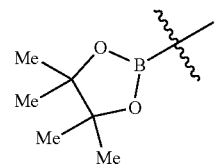

E14. The method of any one of E1 to E13, wherein:
the yield of compound 190, or a stereoisomer, geometric isomer, tautomer, or salt thereof, is at least 60%, at least 70%, at least 80% or at least 90%, and the purity of compound 190, or a stereoisomer, geometric isomer, tautomer, or salt thereof, is at least 99 area % or at least 99.5 area %.

E15. The method of any one of E1 to E14, wherein:
(a) the content of a dimer impurity is less than 0.1 area % based on compound 190, or a stereoisomer, geometric isomer, tautomer, or salt thereof, wherein the dimer impurity is of the structure

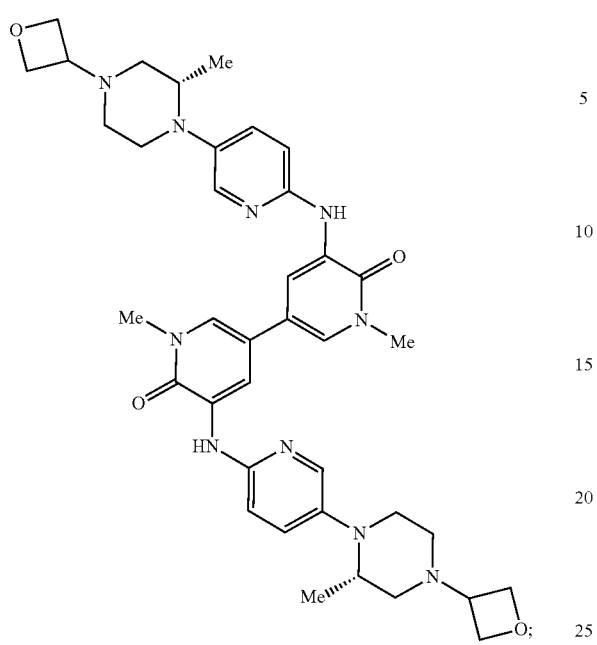

and (b) the combined content of an alcohol and a ketone impurity is less than 0.25 area % based on compound 190, or a stereoisomer, geometric isomer, tautomer, or salt thereof, wherein the alcohol and ketone impurities are of the structure

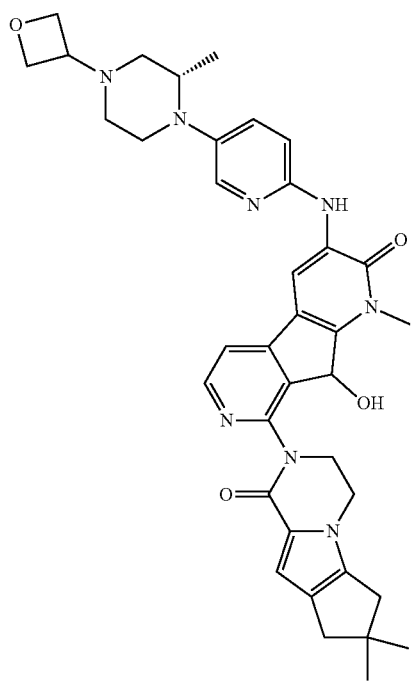

Alcohol

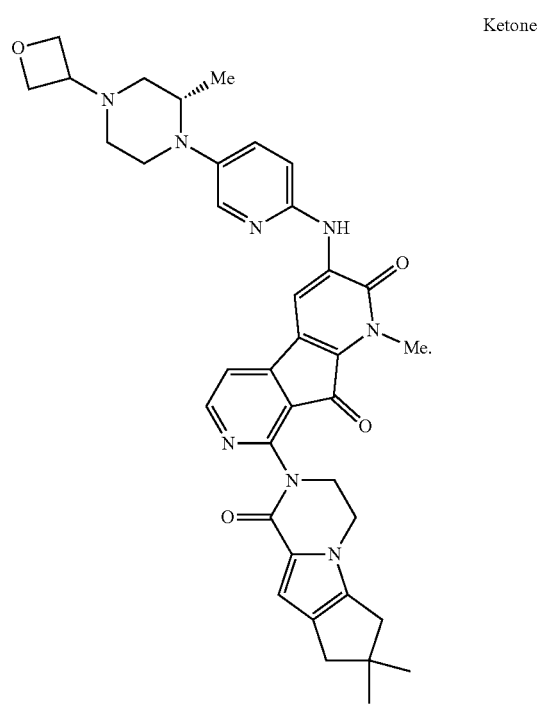

Ketone

E16. The method of any one of E1 to E15, further comprising reacting compound 190, or a stereoisomer, geometric isomer, tautomer, or salt thereof, to form compound 200, or a stereoisomer, geometric isomer, tautomer, or salt thereof, the reacting comprising:

(a) contacting compound 190, or the stereoisomer, geometric isomer, tautomer, or salt thereof, with a reducing agent and a base in the presence of a solvent to form compound 200, or the stereoisomer, geometric isomer, tautomer, or salt thereof, according to the following scheme

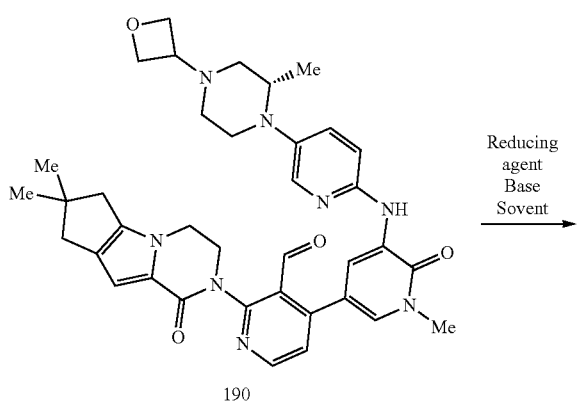

-continued

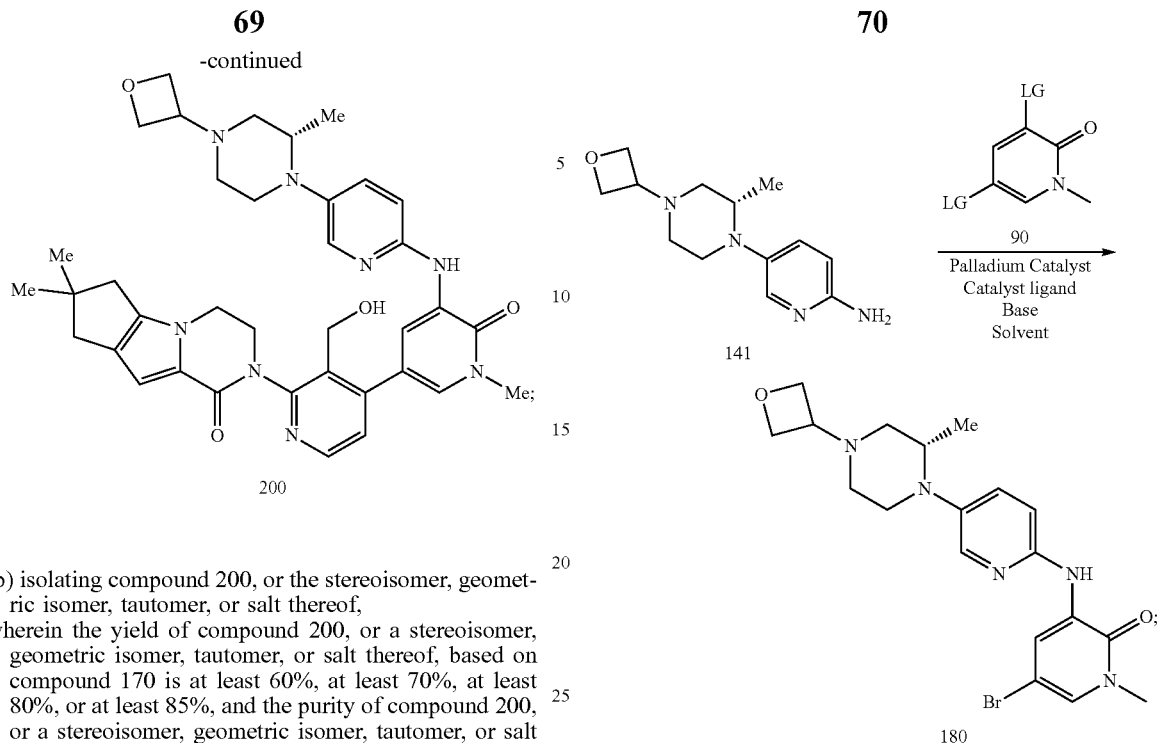
200 and
(b) isolating compound 200, or the stereoisomer, geometric isomer, tautomer, or salt thereof,
wherein the yield of compound 200, or a stereoisomer, geometric isomer, tautomer, or salt thereof, based on compound 170 is at least 60%, at least 70%, at least 80%, or at least 85%, and the purity of compound 200, or a stereoisomer, geometric isomer, tautomer, or salt thereof, is at least 99 area % or at least 99.5 area %.

E17. The method of any one of E1 to E16 further comprising isolating compound 190, or a stereoisomer, geometric isomer, tautomer, or salt thereof, from the reaction product mixture E18. The method of any one of E1 to E17 wherein compound 181 is prepared by:
(a) forming a first reaction mixture comprising compound 140, a platinum/vanadium on carbon catalyst, a solvent, and hydrogen;
(b) reacting the first reaction mixture to form a first reaction product mixture comprising compound 140 according to the following scheme

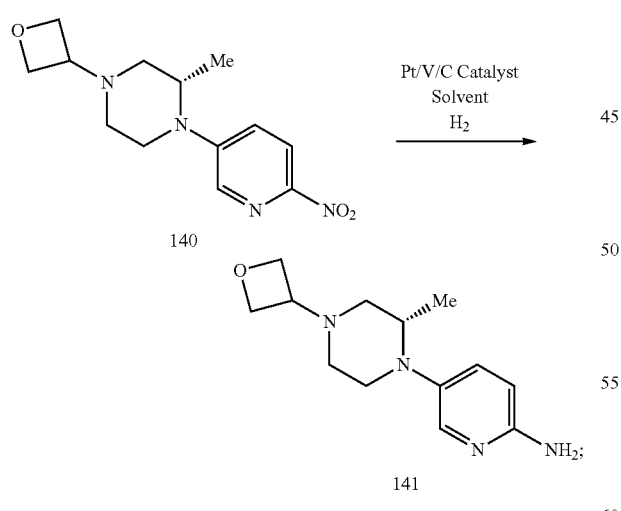

(c) forming a second reaction mixture comprising compound 141, compound 90, a palladium catalyst, a catalyst ligand, a base, and a solvent; and
(d) reacting the second reaction mixture to form a second reaction product mixture comprising compound 180 according to the following scheme where LG is a leaving group

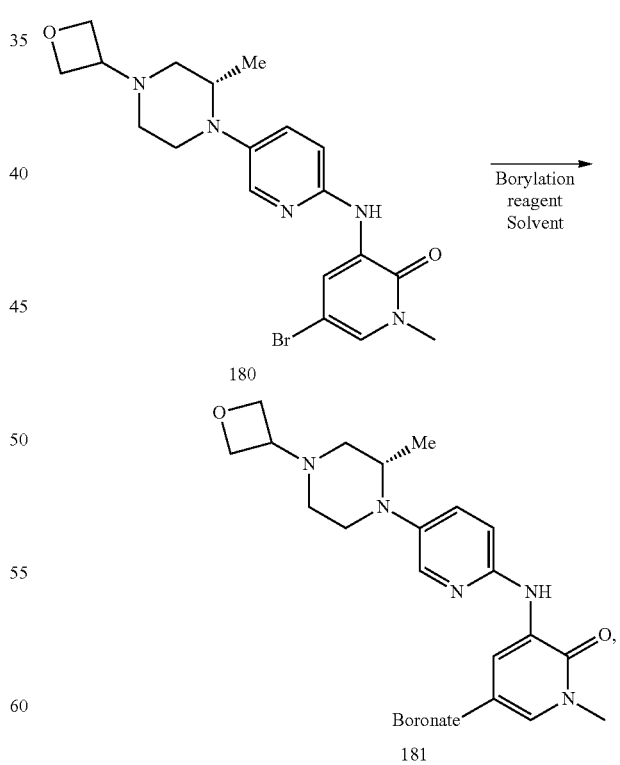

(e) reacting compound 180 with a borylation agent in the presence of a solvent to form compound 181 according to the following scheme wherein the yield of compound 141 based on compound 140 is at least 90% or at least 95%, and wherein the yield of compound 180 based on compound 141 is at least 60%, at least 70%, at least 80%, and the purity of compound 180 is at least 95%, at least 98%, or at least 99%.

E19. The method of any one of E1 to E17 wherein compound 181 is prepared by:

(a) a process of forming a first reaction mixture comprising compound 140 and a solvent comprising organic solvent and water; and contacting said reaction mixture with a transition metal catalyst in the presence of hydrogen to form a first product mixture comprising compound 141, wherein the process is a continuous flow process

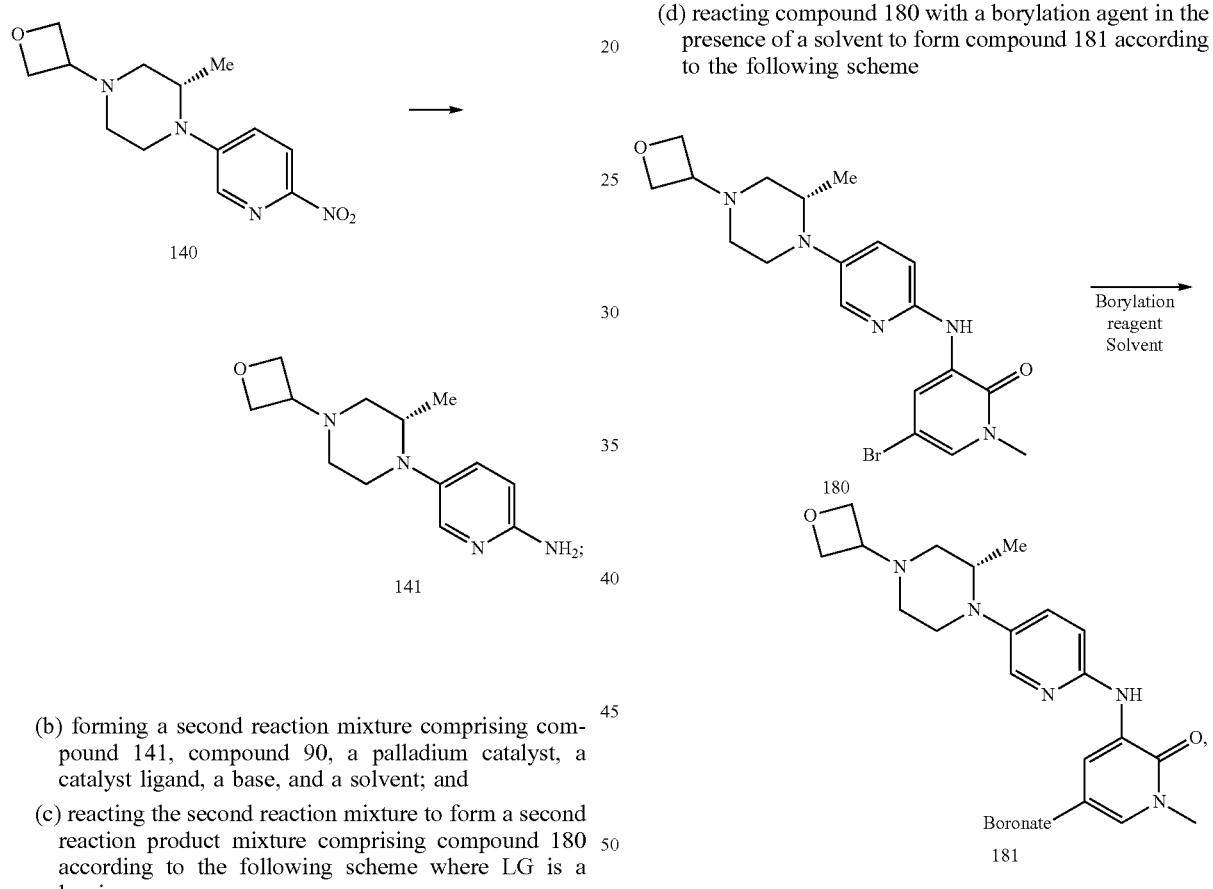

(b) forming a second reaction mixture comprising compound 141, compound 90, a palladium catalyst, a catalyst ligand, a base, and a solvent; and (c) reacting the second reaction mixture to form a second reaction product mixture comprising compound 180 according to the following scheme where LG is a leaving group

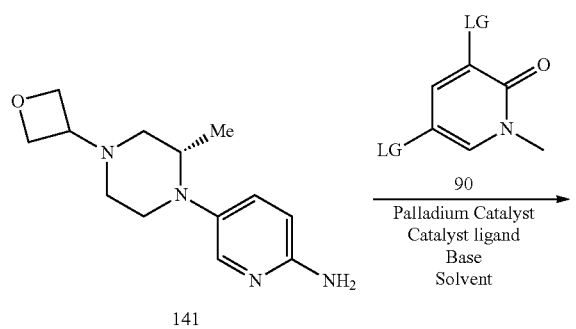

and (d) reacting compound 180 with a borylation agent in the presence of a solvent to form compound 181 according to the following scheme

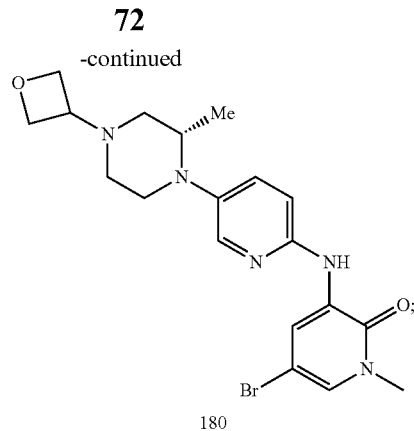

wherein the yield of compound 141 based on compound 140 is at least 90% or at least 95%, and wherein the yield of compound 180 based on compound 141 is at least 60%, at least 70%, at least 80%, and the purity of compound 180 is at least 95%, at least 98%, or at least 99%.

E20. The method of E18 or E19, wherein the palladium catalyst is Pd(OAc)$_2$; the ligand is Xantphos, the base is K$_2$CO$_3$; and the solvent predominantly comprises anisole.

E21. The method of E20, wherein: the palladium catalyst is Pd(OAc)$_2$; the ligand is DPEPhos, the base is NaOMe; and the solvent predominantly comprises anisole.

E22. The method of any one of E18 to E21, wherein leaving group is a halogen or triflate, or is Br.

E23. The method of any one of E18 to E22, wherein compound 141 is isolated from the first reaction product mixture prior to formation of the second reaction mixture.

E24. The method of any one of E18 to E23, wherein compound 140 is prepared by:
  (a) forming a reaction mixture comprising compound 153, compound 20, NaBH(OAc)₃, and a solvent; and
  (b) reacting the reaction mixture to form a reaction product mixture comprising compound 140 according to the following scheme:

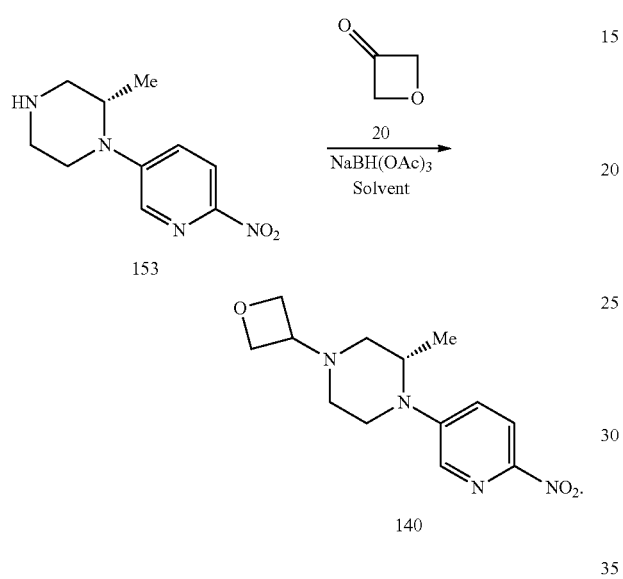

E25. The method of E24, wherein the solvent in step (a) is, an organic solvent, optionally an aprotic organic solvent, optionally THF or Me-THF.

E26. The method of E24 or E25, wherein the ratio of NaBH⁻ to combined total of OAc⁻ and HOAc is less than 1:3.1; and the solvent in step (a) is THF.

E27. A method of reducing byproduct formation in a Suzuki coupling reaction, the method comprising:
  (a) forming a reaction mixture comprising compound 170, compound 181, a palladium catalyst, a solvent system, and a base, wherein the equivalent ratio of the palladium catalyst to compound 170 is from about 0.001:1 to less than 0.005:1; and
  (b) reacting the reaction mixture to form a reaction product mixture comprising compound 190, or a stereoisomer, geometric isomer, tautomer, or salt thereof, according to the following scheme:

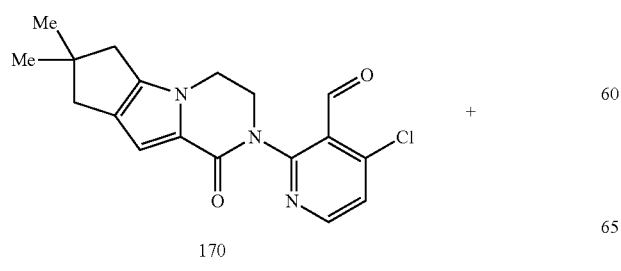

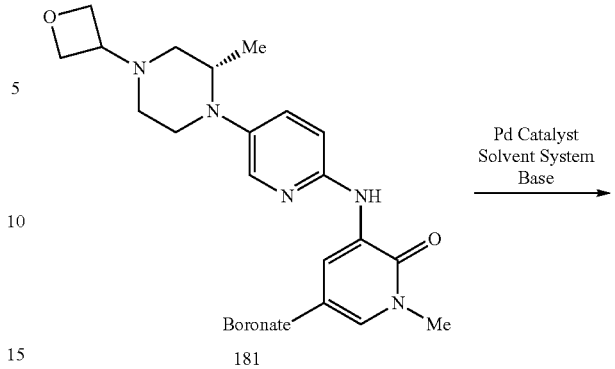

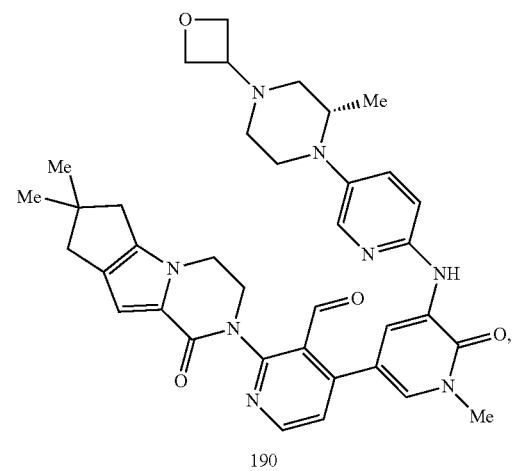

wherein the Pd catalyst comprises a palladium(II) species containing a phosphine ligand and at least one palladium-carbon bond, wherein:
  (i) the fragment giving rise to the palladium-carbon bond is an allyl derivative of the formula

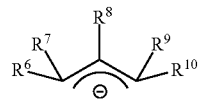

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring;

wherein:
  (a) the content of a dimer impurity is less than 0.1 area % based on compound 190, or a stereoisomer, geometric isomer, tautomer, or salt thereof, wherein the dimer impurity is of the structure

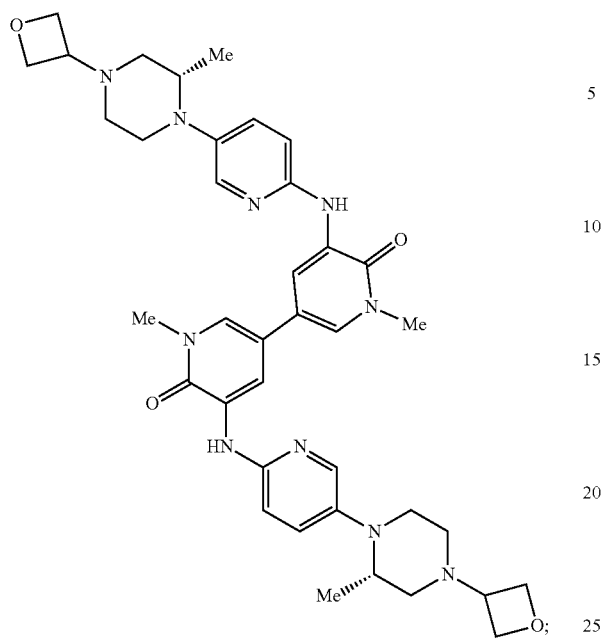

and (b) the combined content of an alcohol and a ketone impurity is less than 0.25 area % based on compound 190, or a stereoisomer, geometric isomer, tautomer, or salt thereof, wherein the alcohol and ketone impurities are is of the structure

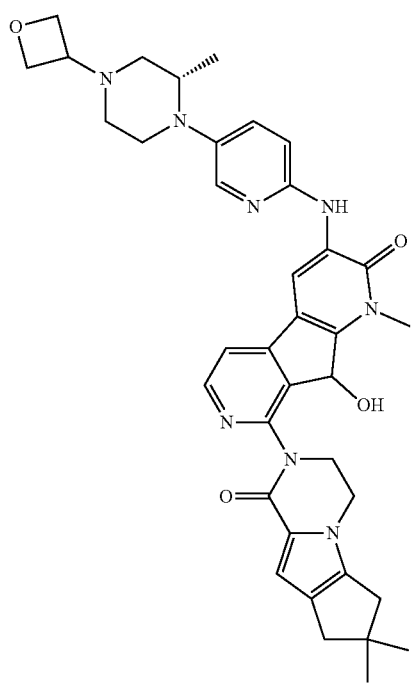

Alcohol

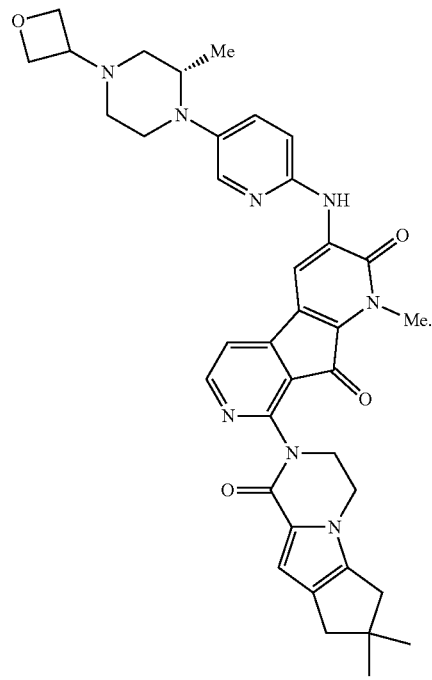

Ketone

E28. The method of E27, wherein the fragment giving rise to the palladium-carbon bond is an indenyl of the formula

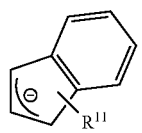

wherein $R^{11}$ is $C_{1-10}$ alkyl.

E29. The method of E27 or E28, wherein the allyl derivative is selected from:
(a) a derivative wherein each of $R^6$ to $R^{10}$ is H;
(b) a derivative wherein $R^6$ is —$CH_3$ and each of $R^7$ to $R^{10}$ is H;
(c) a derivative wherein $R^7$ is —$CH_3$ and each of $R^6$ and $R^8$ to $R^{10}$ is H;
(d) a derivative wherein $R^8$ is —$CH_3$ and each of $R^6$, $R^7$, $R^9$ and $R^{10}$ is H;
(e) a derivative wherein $R^6$ is -phenyl and each of $R^7$ to $R^{10}$ is H;
(f) a derivative wherein $R^7$ is -phenyl and each of $R^6$ and $R^8$ to $R^{10}$ is H; and
(g) a derivative of the structure

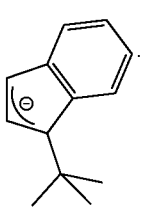

E30. The method of any one of E27 to E29, wherein phosphine ligand is of the formula

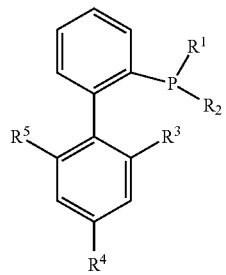

wherein:
$R^1$ and $R^2$ are each independently selected from optionally substituted $C_{1-12}$ alkyl, optionally substituted $C_3$-$C_{20}$ cycloalkyl, and optionally substituted $C_5$ or $C_6$ aryl; and
$R^3$ to $R^5$ are each independently selected from H, optionally substituted $C_{1-6}$ alkyl, alkoxide of the formula —O—$C_{1-6}$ alkyl, and amine of the formula —N($R^{12}$)($R^{13}$) wherein $R^{12}$ and $R^{13}$ are independently selected from H and $C_{1-6}$ alkyl.

E31. The method of any one of E27 to E30, wherein the phosphine ligand is SPhos of the following structure

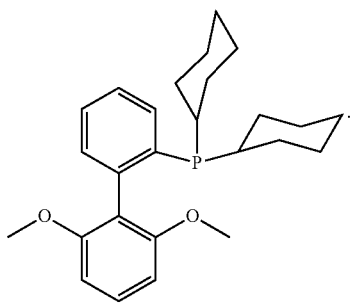 [SMILES: COc1cccc(OC)c1-c1ccccc1P(C1CCCCC1)C1CCCCC1]

E32. The method of any one of E27 to E31, wherein the Pd catalyst is selected from:
(a) a cationic palladium species comprising an inorganic or organic counterion X; and
(b) a neutral palladium species comprising a coordinated inorganic or organic ligand X.

E33. The method of E32, wherein X is selected from a halogen, a carboxylate, a sulfonate, and an inorganic anion.

E34. The method of E33, wherein:
(a) the carboxylate is selected from $CH_3C(O)O^-$ and $tBuC(O)O^-$;
(b) the sulfonate is selected from $CF_3SO_3^-$, tosylate, besylate, and nosylate; and
(c) the inorganic anion selected from $PF_6^-$, $BF_4^-$, $B(C_6F_5)_4^-$, $NO_3^-$, and $SO_4^{2-}$.

E35. The method of E33 or E34, wherein X is $CF_3SO_3^-$.

E36. The method of any one of E27 to E35, wherein the palladium catalyst comprises a $CF_3SO_3^-$ organic counterion, wherein the phosphine ligand is SPhos, and wherein each of $R^6$ to $R^{10}$ is H.

E37. The method of any one of E27 to E36, wherein the solvent system predominantly comprises an aprotic low molecular weight ester solvent and water, wherein the volume ratio of the aprotic low molecular weight ester solvent to water is from about 1:0.1 to about 1:1, and wherein the reaction mixture is heated to from about 60° C. to about 80° C.

E38. The method of any one of E27 to E37, wherein the equivalent ratio of compound 181 to compound 170 is greater than 1:1, and the equivalent ratio of the palladium catalyst to compound 170 is from about 0.001:1 to about 0.003:1, or about 0.002:1.

E39. The method of any one of E27 to E38, wherein:
(a) the catalyst is [(SPhos)Pd(allyl)] $CF_3SO_3$;
(b) the solvent system predominantly comprises ethyl acetate and water wherein the volume ratio of ethyl acetate to water is from about 1:0.1 to about 1:1; and
(c) the boronate is 4,4,5,5-tetramethyl-1,3,2-dioxaborolane of the structure:

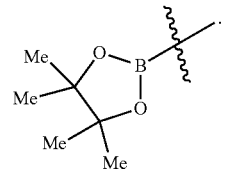

E40. The method of any one of E27 to E39, wherein:
the yield of compound 190 based on compound 170 is at least 60%, at least 70%, at least 80% or at least 90%, and the purity of compound 190 is at least 99 area % or at least 99.5 area %.

E41. A method of improving yield in a Suzuki coupling reaction, the method comprising:
(a) forming a reaction mixture comprising compound 170, compound 181, a palladium catalyst, a solvent system, and a base, wherein the equivalent ratio of the palladium catalyst to compound 170 is from about 0.001:1 to less than 0.005:1; and
(b) reacting the reaction mixture to form a reaction product mixture comprising compound 190, or a stereoisomer, geometric isomer, tautomer, or salt thereof, according to the following scheme:

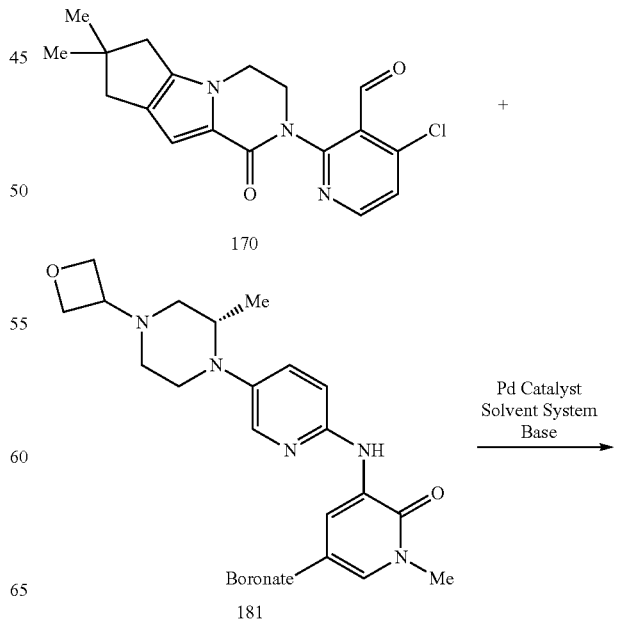

-continued

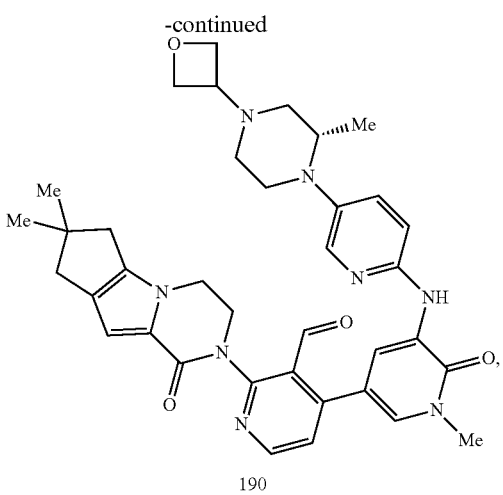

190 wherein the Pd catalyst comprises a palladium(II) specie containing a phosphine ligand and at least one palladium-carbon bond,
wherein:
(i) the fragment giving rise to the palladium-carbon bond is an allyl derivative of the formula

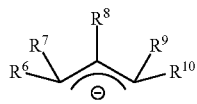

wherein each of $R^6$ to $R^{10}$ is independently selected from the group consisting of H, optionally substituted $C_{1-6}$ alkyl, optionally substituted $C_6$ aryl, and optionally substitute heteroaryl; and $R^6$ and $R^{10}$ may optionally come together to form a fused bicycle comprising an aromatic ring
wherein the yield of compound 190, or a stereoisomer, geometric isomer, tautomer, or salt thereof, based on compound 170 is at least 80% or at least 85%.

E42. The method of E41, wherein the fragment giving rise to the palladium-carbon bond is an indenyl of the formula

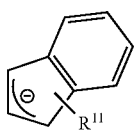

wherein $R^{11}$ is $C_{1-10}$ alkyl.

E43. The method of E41 or E42, wherein the allyl derivative is selected from:
(a) a derivative wherein each of $R^6$ to $R^{10}$ is H;
(b) a derivative wherein $R^6$ is —$CH_3$ and each of $R^7$ to $R^{10}$ is H;
(c) a derivative wherein $R^7$ is —$CH_3$ and each of $R^6$ and $R^8$ to $R^{10}$ is H;
(d) a derivative wherein $R^8$ is —$CH_3$ and each of $R^6$, $R^7$, $R^9$ and $R^{10}$ is H;
(e) a derivative wherein $R^6$ is -phenyl and each of $R^7$ to $R^{10}$ is H;
(f) a derivative wherein $R^7$ is -phenyl and each of $R^6$ and $R^8$ to $R^{10}$ is H; and (g) a derivative of the structure

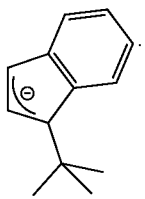

E44. The method of any one of E41 to E43, wherein phosphine ligand is of the formula

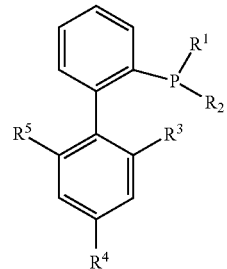

wherein:
$R^1$ and $R^2$ are each independently selected from $C_{1-6}$ alkyl and $C_5$ or $C_6$ aryl; and
$R^3$ to $R^5$ are each independently selected from H, $C_{1-6}$ alkyl, ether, and amine.

E45. The method of any of E41 to E44, wherein the phosphine ligand is SPhos of the following structure

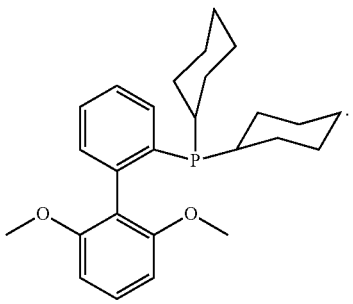 [SMILES: COc1cccc(OC)c1-c1ccccc1P(C1CCCCC1)C1CCCCC1]

E46. The method of any one of E41 to E45, wherein the Pd catalyst is selected from:
(a) a cationic palladium species comprising an inorganic or organic counterion X; and
(b) a neutral palladium species comprising a coordinated inorganic or organic ligand X.

E47. The method of E46, wherein X is selected from a halogen, a carboxylate, a sulfonate, and an inorganic anion.

E48. The method of E47, wherein:
(a) the carboxylate is selected from $CH_3C(O)O^-$ and $tBuC(O)O^-$;
(b) the sulfonate is selected from $CF_3SO_3$—, tosylate, besylate, and nosylate; and
(c) the inorganic anion selected from $PF_6^-$, $BF_4^-$, $B(C_6F_5)_4^-$, $NO_3^-$, and $SO_4^{2-}$.

E49. The method of E47 or E48, wherein X is $CF_3SO_3^-$.

E50. The method of any one of E41 to E49, wherein the palladium catalyst comprises a $CF_3SO_3^-$ organic counterion, wherein the phosphine ligand is SPhos, and wherein each of $R^6$ to $R^{10}$ is H.

E51. The method of any one of E41 to E50, wherein the solvent system predominantly comprises an aprotic low molecular weight ester solvent and water, wherein the volume ratio of the aprotic low molecular weight ester solvent to water is from about 1:0.1 to about 1:1, and wherein the reaction mixture is heated to from about 60° C. to about 80° C.

E52. The method of any one of E41 to E51, wherein the equivalent ratio of compound 181 to compound 170 is greater than 1:1, and the equivalent ratio of the palladium catalyst to compound 170 is from about 0.001:1 to about 0.003:1, or about 0.002:1.

E53. The method of any one of E41 to E52, wherein:
  (a) the catalyst is [(Sphos)Pd(allyl)] $CF_3SO_3$;
  (b) the solvent system predominantly comprises ethyl acetate and water wherein the volume ratio of ethyl acetate to water is from about 1:0.1 to about 1:1; and
  (c) the boronate is 4,4,5,5-tetramethyl-1,3,2-dioxaborolane of the structure:

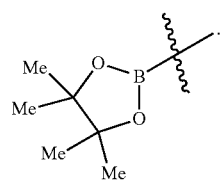 [SMILES: *B1OC(C)(C)C(C)(C)O1]

E54. The method of any one of E41 to E53, wherein:
  (a) the content of a dimer impurity is less than 0.1 area % based on compound 190, wherein the dimer impurity is of the structure

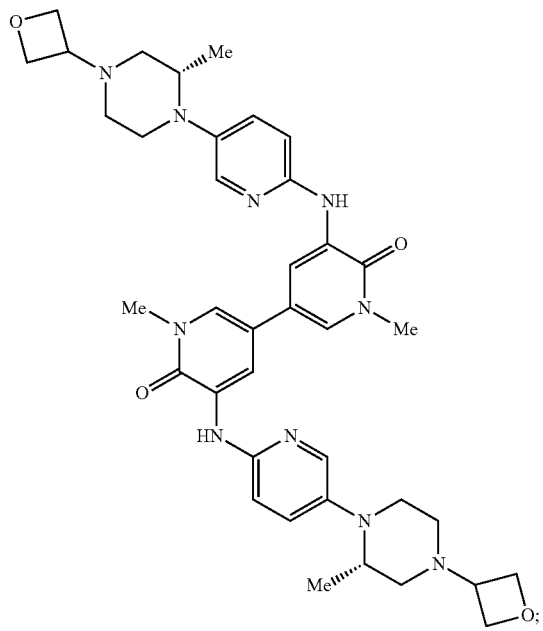 [SMILES: C[C@H]1CN(C2COC2)CCN1c1ccc(Nc2cc(-c3cc(Nc4ccc(N5CCN(C6COC6)C[C@@H]5C)cn4)c(=O)n(C)c3)cn(C)c2=O)nc1]

(b) the combined content of an alcohol and a ketone impurity is less than 0.25 area % based on compound 190, wherein the alcohol and ketone impurities are of the structure

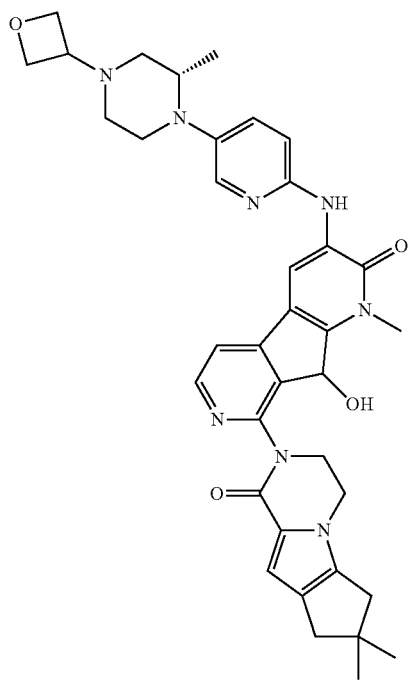

Alcohol

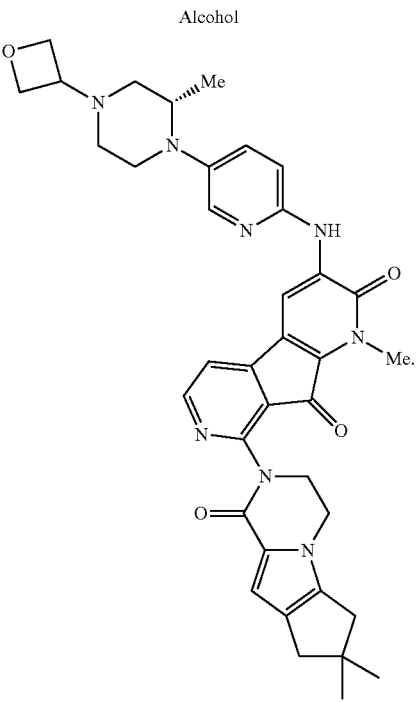

Ketone and;
  (c) the purity of compound 190 is at least 99 area % or at least 99.5 area %.

E55. A method of preparing compound 180, stereoisomers thereof, geometric isomers thereof, tautomers thereof, and salts thereof, the method comprising:
  (a) forming a first reaction mixture comprising compound 140, a platinum/vanadium on carbon catalyst, a solvent, and hydrogen;

83

(b) reacting the first reaction mixture to form a first reaction product mixture comprising compound 141 according to the following scheme

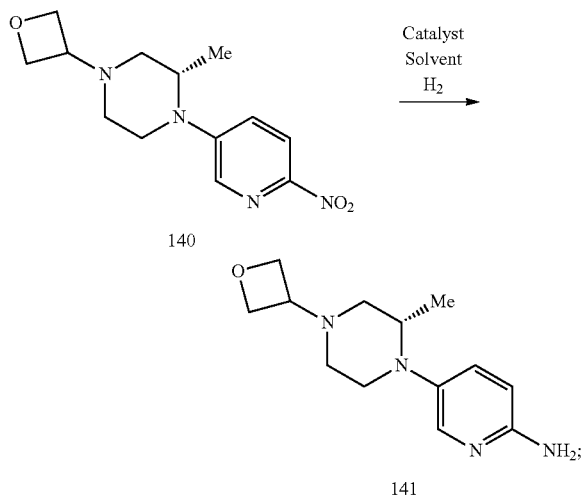

(c) forming a second reaction mixture comprising compound 141, compound 90, a palladium catalyst, a catalyst ligand, a base, and a solvent; and (d) reacting the second reaction mixture to form a second reaction product mixture comprising compound 180 according to the following scheme

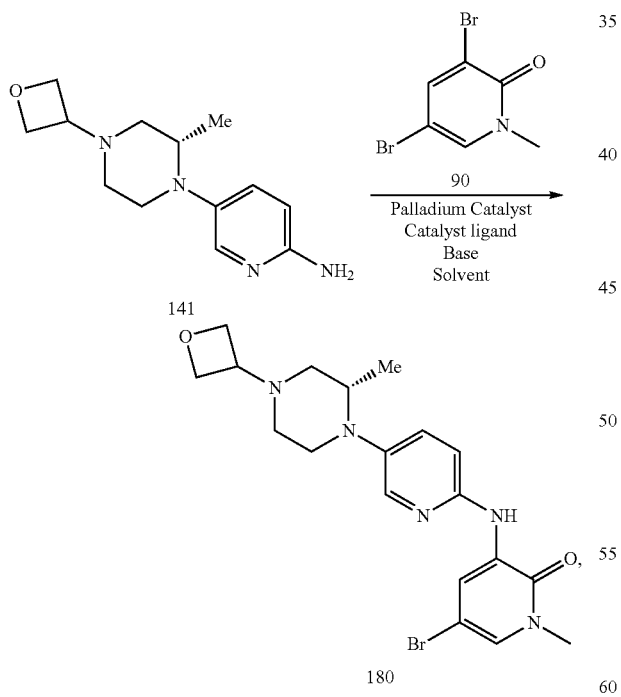

wherein the first reaction mixture catalyst is selected from the group consisting of Ra—Ni, Ra—Co, Pt/V@C, Co@Chitin, Ni-phen@SiO$_2$, and Ni-phen@TiO$_2$, wherein the yield of compound 141 based on compound 140 is at least 90% or at least 95%, and

84 wherein the yield of compound 180 based on compound 141 is at least 60%, at least 70%, at least 80%, and the purity of compound 180 is at least 95%, at least 98%, or at least 99%.

E56. A method of preparing compound 180 stereoisomers thereof, geometric isomers thereof, tautomers thereof, and salts thereof, the method comprising:

(a) a process of forming a first reaction mixture comprising compound 140 and a solvent comprising organic solvent and water; and contacting said reaction mixture with a transition metal catalyst in the presence of hydrogen to form a first product mixture comprising compound 141, wherein the process is a continuous flow process

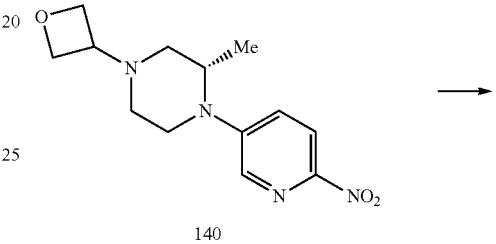

(b) forming a second reaction mixture comprising compound 141, compound 90, a palladium catalyst, a catalyst ligand, a base, and a solvent; and (c) reacting the second reaction mixture to form a second reaction product mixture comprising compound 180 according to the following scheme where LG is a leaving group

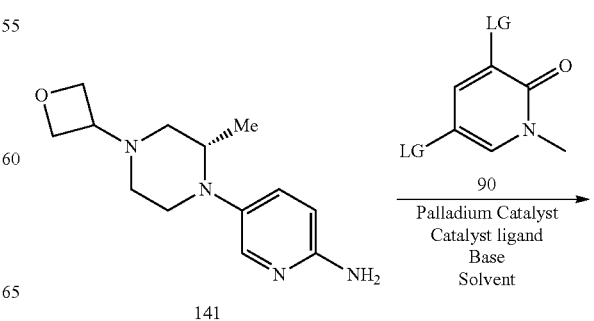

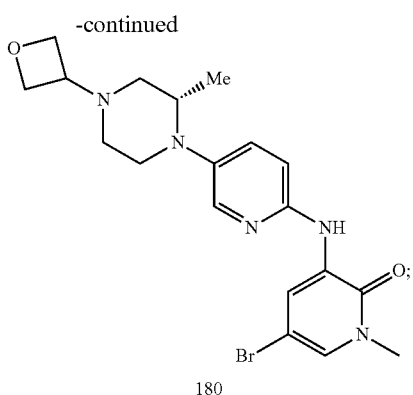

and (d) reacting compound 180 with a borylation agent in the presence of a solvent to form compound 181 according to the following scheme

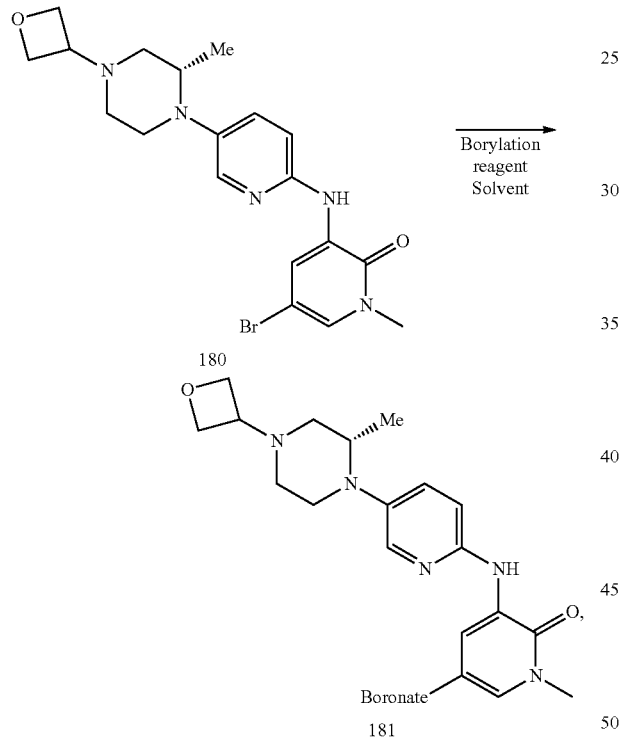

wherein the yield of compound 141 based on compound 140 is at least 90% or at least 95%, and wherein the yield of compound 180 based on compound 141 is at least 60%, at least 70%, at least 80%, and the purity of compound 180 is at least 95%, at least 98%, or at least 99%.

E57. The method of E55 or E56, wherein compound 141 is not isolated from the first reaction product mixture prior to formation of the second reaction product mixture.

E58. The method of any one of E55 to E57, wherein, the first reaction mixture solvent and the second reaction mixture solvent each predominantly comprise a polar aprotic solvent.

E59. The method of E58, wherein the first reaction mixture solvent predominantly comprises tetrahydrofuran.

E60. The method of any one of E51 to E59, further comprising a solvent exchange step wherein the first reaction product mixture solvent is predominantly replaced with a polar aprotic solvent prior to forming the second reaction mixture.

E61. The method of E60, wherein the first reaction product mixture solvent is predominantly replaced with anisole, and where the second reaction mixture solvent predominantly comprises anisole.

E62. The method of any one of E55 to E61, wherein the palladium catalyst is $Pd(OAc)_2$ and the catalyst ligand is XantPhos or DPEPhos.

E63. The method of any one of E55 to E62, wherein the palladium catalyst is $Pd(OAc)_2$, the catalyst ligand is XantPhos, and the base is $K_2CO_3$; or wherein the palladium catalyst is $Pd(OAc)_2$; the catalyst ligand is DPEPhos, and the base is NaOMe.

E64. The method of any one of E55 to E62, wherein the first reaction mixture catalyst is Pt/V@C.

E65. The method of any one of E56 to E62, wherein the first reaction mixture catalyst is $Pd/Al_2O_3$, $Pt/Al_2O_3$, Pd/C, or Pt/C.

E66. The method of any one of E56 to E65, further comprising isolating compound 180 by the following order of steps comprising:

(e) contacting the second reaction with an aqueous wash;
(f) isolating and concentrating the organic phase, said organic phase comprising predominantly all of compound 180 contained in the second reaction product mixture;
(g) combining the concentrated organic phase with an alcohol and water;
(h) isolating the organic phase comprising the second reaction product mixture solvent, the alcohol, predominantly all of compound 180;
(i) concentrating the isolated organic phase;
(j) combining the concentrated organic phase with alcohol and cooling thereof to form crystalline compound 180; and
(k) isolating crystalline compound 180.

E67. The method of E65, wherein the alcohol is 1-butanol.

E68. A composition, comprising at least 98.5 w/w % compound 190, or stereoisomer, geometric isomer, tautomer, or salt thereof,

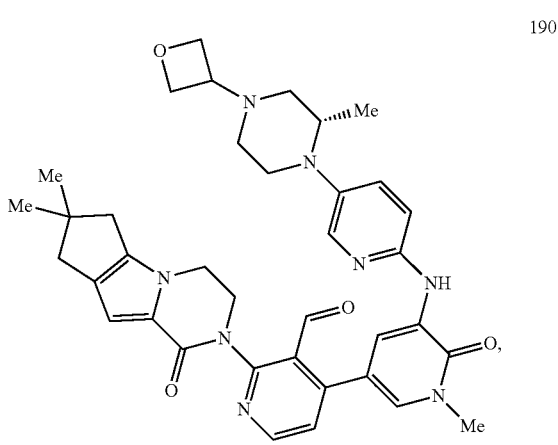 [SMILES: C[C@H]1CN(C2COC2)CCN1c1ccc(Nc2cc(-c3ccnc(N4CCn5c(cc6c5CC(C)(C)C6)C4=O)c3C=O)cn(C)c2=O)nc1]

and wherein (a) the content of a dimer impurity is less than 0.15 area % based on compound 190, wherein the dimer impurity is of the structure

87

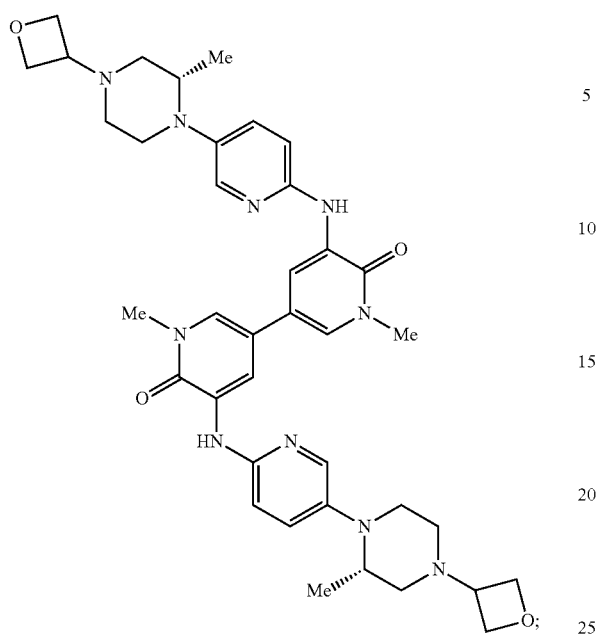

and (b) the combined content of an alcohol and a ketone impurity is less than 0.35 area % based on compound 190, wherein the alcohol and ketone impurities are of the structure

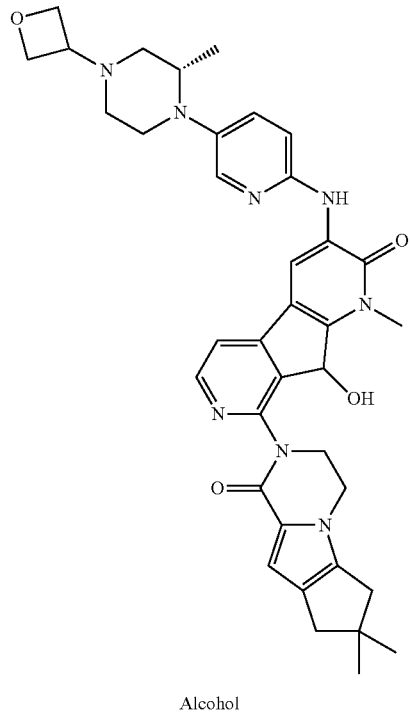

Alcohol

88

-continued

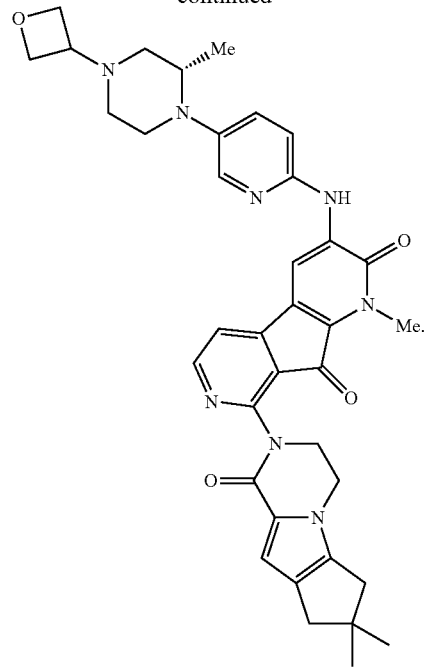

Ketone

E68-1. A method of preparing compound 180 stereoisomers thereof, geometric isomers thereof, tautomers thereof, and salts thereof, the method comprising:

(a) a process of forming a first reaction mixture comprising compound 140 and a solvent comprising organic solvent; and contacting said reaction mixture with a transition metal catalyst in the presence of hydrogen to form a first product mixture comprising compound 141, wherein the process is a continuous flow process

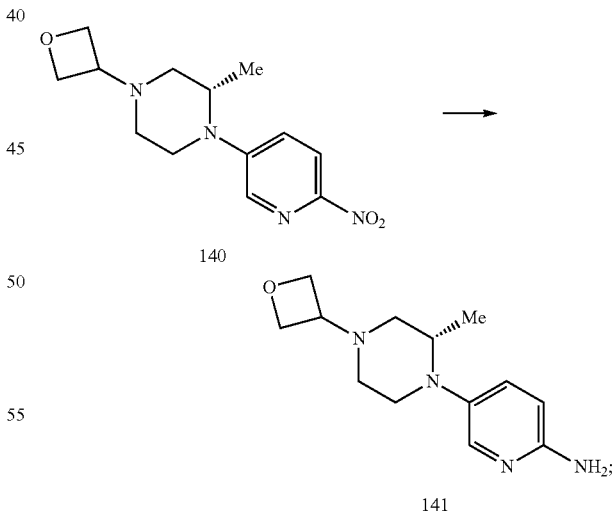

(b) forming a second reaction mixture comprising compound 141, compound 90, a palladium catalyst, a catalyst ligand, a base, and a solvent; and (c) reacting the second reaction mixture to form a second reaction product mixture comprising compound 180 according to the following scheme where LG is a leaving group

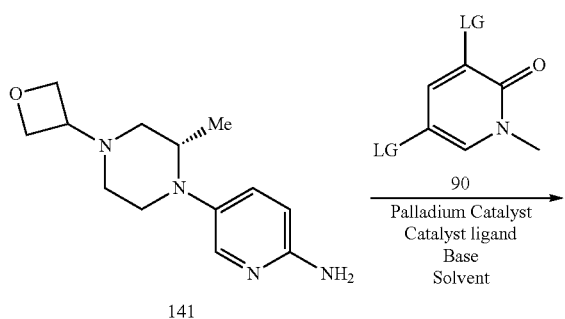

141

90

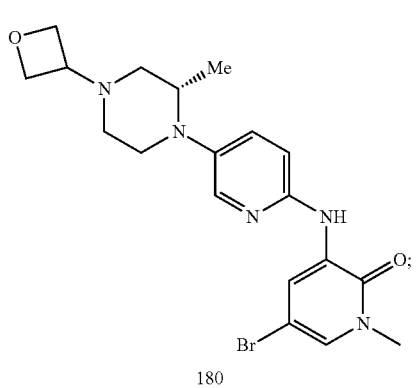

180 and (d) reacting compound 180 with a borylation agent in the presence of a solvent to form compound 181 according to the following scheme

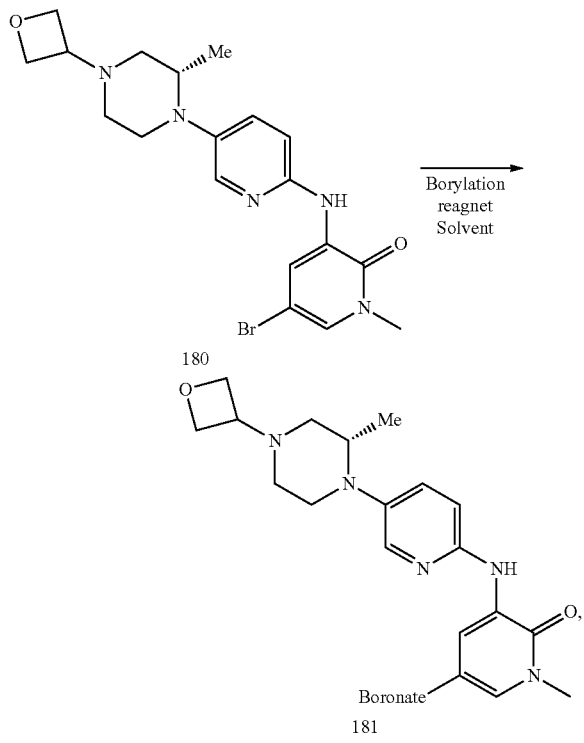

180

181 wherein the yield of compound 141 based on compound 140 is at least 90% or at least 95%, and wherein the yield of compound 180 based on compound 141 is at least 60%, at least 70%, at least 80%, and the purity of compound 180 is at least 95%, at least 98%, or at least 99%.

E69. The composition of E68 or E68-1, wherein the content of the dimer impurity is less than 0.10 area % based on compound 190.

E70. The composition of E69, wherein the content of the dimer impurity is less than 0.05 area % based on compound 190.

E71. The composition of any one of E68 to E70, wherein the combined content of the alcohol and ketone impurities is less than 0.30 area % based on compound 190.

E72. The composition of E71, wherein the combined content of the alcohol and ketone impurities is less than 0.25 area % based on compound 190.

E73. The composition of E72, wherein the combined content of the alcohol and ketone impurities is less than 0.20 area % based on compound 190.

E74. The composition of any one of E68 to E73, comprising at least 99.0 w/w % compound 190, or stereoisomer, geometric isomer, tautomer, or salt thereof.

E75. The composition of E74, comprising at least 99.5 w/w % compound 190, or stereoisomer, geometric isomer, tautomer, or salt thereof.

EXAMPLES

The Figures and Examples provide exemplary methods for preparing the disclosed compounds; those skilled in the art will appreciate that other synthetic routes may be used to synthesize the compounds. Although specific starting materials and reagents are depicted and discussed in the Figures and Examples, other starting materials and reagents may be substituted to provide a variety of derivatives and/or reaction conditions. In addition, many of the described and exemplary methods may be further modified in light of this disclosure using conventional chemistry well known to those skilled in the art.

In the Examples, equivalents and equivalent ratios are based on the referenced starting material for each reaction. Volume per weight values, such as L/kg and mL/g, refer to a volume of a liquid component based on the weight of the referenced starting material for each reaction.

Analytical Methods

High pressure liquid chromatography (HPLC) may be performed as follows.

HPLC Method 1—Examples 2-10; and Comparative Examples 4-6: Instruments and column. HPLC system: Agilent Series 1260, quaternary pump, and autosampler. Integration system: Waters Empower. Configuration: Jetweaver V380 mixer not used, pulse compensation, 0.12 mm capillaries (red), and 10 mm flow cell. Delay volume: 0.51 mL. Dosage: Automatic burettes (e.g., Metrohm 725 Dosimat) or volumetric pipettes, Piston-stroke pipettes for μL range. Stationary phase: Poroshell 120 Bonus-RP, L=150 mm, ID=4.6 mm, 2.7 μm.

Solutions. Buffer solution: 20 mM ammonium acetate in water, 1.52-1.56 g ammonium acetate, 1000 mL water, pH 5.8±0.1, adjust pH if necessary with acetic acid. Mobile Phase A: 950 mL buffer solution, 50 mL acetonitrile. Mobile Phase B: 950 mL Acetonitrile, 50 mL buffer solution. Diluent: Water/acetonitrile 1:9 v/v (e. g. 100 mL water and 900 mL acetonitrile).

Pump program.

| Flow (mL/min) | Time (min) | A (%) | B (%) | Remarks |
|---|---|---|---|---|
| 1.0 | 0.0 | 80 | 20 | |
| 1.0 | 1.0 | 80 | 20 | isocratic |
| 1.0 | 15.0 | 50 | 50 | linear gradient |
| 1.0 | 18.5 | 50 | 50 | isocratic |
| 1.0 | 25.0 | 20 | 80 | linear gradient |
| 1.0 | 26.0 | 20 | 80 | isocratic |
| 1.0 | 26.1 | 80 | 20 | equilibration |
| 1.0 | 30.0 | 80 | 20 | |

Column oven temperature: 25° C. Column back pressure: About 300 bar (initial conditions). Injection volume: 3.0 μL. Needle wash: Wash vial. Sampler thermostat temperature: 5° C. Column flushing: Water/acetonitrile 2:8. Column storage: acetonitrile. Detection: DAD: 245 nm, band width 4 nm. Reference wavelength: Off. Slit: 4 nm. Data rate: 5 Hz, by peak width>0.05 min, response time 1 s.

Sample preparation. The blank solution was the diluent. For stock solution 1, the following reference standards were dissolved in 10.0 mL diluent: 7.0 to 8.0 Des-Brom impurity; 7.0 to 8.0 mg Cysteine adduct impurity; 7.0 to 8.0 mg Regioisomer impurity (compound 190 regioisomer); and 7.0 to 8.0 mg Chloride (compound 170). For stock solution 2, 7.0 to 8.0 Boronate (compound 182) was dissolved in 10.0 mL acetonitrile. For stock solution 3, the following reference standards were dissolved in 100.0 mL methylene chloride: 7.0 to 8.0 mg Dimer impurity; 7.0 to 8.0 mg sec Alcohol impurity; 7.0 to 8.0 mg Ketone impurity. For the system suitability test ("SST") solution 1 (0.05%), 7.0 to 8.0 reference standard compound 200 was dissolved in 9.93 mL diluent followed by addition of 5.0 μL of stock solution 1, 5.0 μL of stock solution 2, and 50.0 μL of stock solution 3. For the SST solution 2 (for peak assignment of the THF-Impurity), 7.0 to 8.0 mg of the THF impurity was dissolved in 10.0 mL diluent. Sample reaction mixtures were prepared by dissolving a 50 μL organic phase sample in 10.0 mL diluent.

System suitability test. Blank chromatogram: The blank chromatogram was compared with the chromatogram depicted in the analytical method; System peaks or peaks resulting from the chemicals used must not interfere with the analysis. Selectivity: The chromatograms of the SST solutions were comparable to the enclosed chromatogram with respect to selectivity and retention times. Sensitivity, peak symmetry: The chromatogram of the SST solutions were checked by visual inspection. Action: In the case of failure, the sample analysis was not valid. After correcting the source of error, the blank, SST(s) and sample analysis were repeated.

The identity of a compound corresponds if the retention time of the main peak in the sample chromatogram corresponds to the retention time of the main peak in the SST solution chromatograms. Area percent is $$x_i = \frac{A_i}{\sum_{j=1}^{n} A_j} \cdot 100\%$$

where: $x_i$=percentage of analyte i (% area); Ai=area of the peak obtained for the analyte i (mAU*s) or (pA*s) or (counts*s); and Aj=area of the peak obtained for the analyte j=1 to n (mAU*s) or (pA*s) or (counts*s). The reduced area percent took into account only the selected analytes.

Integration range. Area percent: Peaks present in the blank chromatogram were disregarded for area percent analysis. Reduced area percent analysis: Integrate only Chloride impurity and aldehyde impurity; The reaction was determined to be finished if the reduced area percent of compound 170 ("Chloride") is below the specification limit.

Integration parameters. The integration parameters are adjusted in order to integrate all peaks ≥half of the reporting level ("RL"). The peak of any impurity that is not completely separated from the main peak was preferably integrated by valley-to-valley extrapolation (tangential skim).

The peak table is as follows:

| Analyte | RRT (approx.) | RL (area %) |
|---|---|---|
| Des-Brom impurity | 0.34 | 0.05 |
| Dimer impurity | 0.62 | 0.05 |
| Cystein adduct impurity | 0.63 | 0.05 |
| Boronate (compound 182) | 0.83 | 0.05 |
| Regioisomer impurity | 0.91 | 0.05 |
| sec. Alcohol impurity | 0.93 | 0.05 |
| Aldehyde (compound 190) | 1.00 | — |
| EtOH Hemiacetal impurity [a] | 1.04 | 0.05 |
| Chloride (compound 170) | 1.18 | 0.05 |
| Ketone impurity | 1.20 | 0.05 |
| Other impurities | — | — |

[a] Only in SST solutions

Peak table, for peak assignment/information only

| Analyte | RRT (approx.) | RL (area %) |
|---|---|---|
| Boronate acid impurity | 0.24 | 0.05 |
| THF impurity | 0.34 | 0.05 |
| Lactam impurity | 0.56 | 0.05 |
| Dimer impurity | 1.44 | 0.05 |
| Toluene | 0.98 | — |

The amount of dimer on a % w/w by the HPLC Method 1 described above correlates to the amount of dimer on an area % HPLC method as reported in the correlation table below.

Correlation of dimer % w/w evaluated by HPLC Method 1 with area % as determined by other HPLC methods, from the same sample.

| Sample | % w/w by HPLC Method 1 | area % method |
|---|---|---|
| 1 | 0.35 | 0.31 |
| 2 | 0.29 | 0.27 |
| 3 | 0.51 | 0.52 |
| 4 | 0.38 | 0.39 |

Analytical Methods for Comparative Examples 1-3

Comparative Example 1: Column: Waters Atlantis T3 (4.6*150 mm 3 μm). Mobile Phase A: 10 mM ammonium formate pH 3.7. Mobile Phase B: CH₃CN. Flow Rate: 1.0 mL/min. Injection Volume: 2.0 uL. Column Temperature: 45° C. UV Detection Wavelength: 315 nm. Diluent: ACN.

Comparative Example 3: Column: (1) Agilent PLRP-S 100A, 150 mm×4.6 mm, 3 μm or (2) Agilent PLRP-S 100A, 250 mm×4.6 mm, 5 μm. Mobile phase A: 10 mM aqueous NaOH. Mobile phase B: acetonitrile. Flow Rate: 1.0 mL/min. Injection Volume: 1.0 uL. Column temperature: (1) 20° C.; (2) 15° C.

Liquid chromatograph mass spectrometry (LCMS) may be performed as follows. Column: XDB-C18 4.6 mm×50 mm, 1.8 μm. Mobile Phase A: Water/0.05% TFA. Mobile Phase B: CH3CN/0.05% TFA. Flow Rate: 1.2 mL/min. Injection Volume: 10.0 uL. Column Temperature: 40° C. Diluent: 30:70 (v/v) CH₃CN/H₂O. Interface Type: ES-API+. Drying Gas Temp: 250° C. Nebulizer Pressure: 35 psig. Drying Gas Flow: 13 L/min. Capillary Voltage: 3000 V. Scan Range: 150-600 m/z.

Gas chromatography (GC) may be performed as follows. An Agilent 7890A series GC system with an Agilent HP-5 (30 m*0.32 mm*0.25 μm) column. Flow rate: 2.0 mL/min. Injection volume: 10.0 uL. Carrier gas: N₂. Diluent: methanol.

Mass spectrometry (MS) may be performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) may be performed using any suitable instrument, including, but not limited to, a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

Example 1

Compound 140 was prepared as according to the reaction scheme in FIG. 12A, and as depicted below:

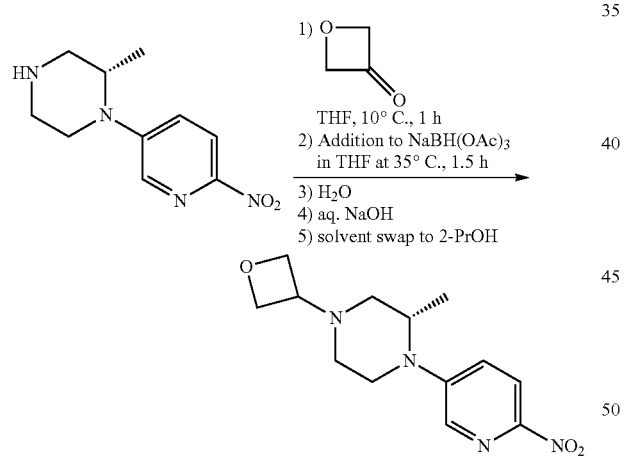

To a warm suspension (35° C.) of NaBH(OAc)₃ (71.5 g, 337 mmol) in THF (110 g) was added a cold (10° C.) preformed mixture of (S)-2-methyl-1-(6-nitropyridin-3-yl) piperazine (50 g, 225 mmol; compound 153) and oxetan-3-one (21.2 g, 292 mmol; compound 20) in THF (136.4 g) over a period of 1-2 h. The mixture was stirred at 35° C. until full conversion was achieved (typically 1 h). Then the reaction mixture was cooled to 25° C. and quenched upon addition to water (135 g) at 40° C. After phase separation, NaOH (99.6 g, 28%) was added at 40° C. to achieve pH 12. After phase separation, the organic phase was polish filtered at 40° C., concentrated and followed by a continuous exchange of THF with 2-PrOH under vacuum (300 mbar), whereupon the crystallization was initiated. The crystal slurry was cooled to 5° C. and stirred for at least 2 h. The crystals were filtered off, washed with cold 2-PrOH and dried under reduced pressure until constant weight was attained. The compound (S)-2-methyl-1-(6-nitropyridin-3-yl)-4-(oxetan-3-yl)piperazine (compound 140) was isolated in 89% yield (55.8 g) as yellow crystals. ¹H-NMR (600 MHz, DMSO-d6) δ ppm 8.22 (d, 1H), 8.11-8.18 (m, 1H), 7.44 (dd, 1H), 4.40-4.62 (m, 3H), 4.30-4.40 (m, 1H), 3.83 (br d, 1H), 3.42 (q, 1H), 3.08-3.18 (m, 1H), 2.79-2.90 (m, 1H), 2.66 (br d, 1H), 2.08-2.20 (m, 1H), 1.92-2.03 (m, 1H), 1.21 (d, 3H). HR-MS (ESI): calc. for C₁₃H₁₈N₄O₃: 278.1379; found: 278.1406.

Example 2

Compounds 141 and 180 were prepared according to the reaction scheme in FIG. 1, and as depicted in more detail below:

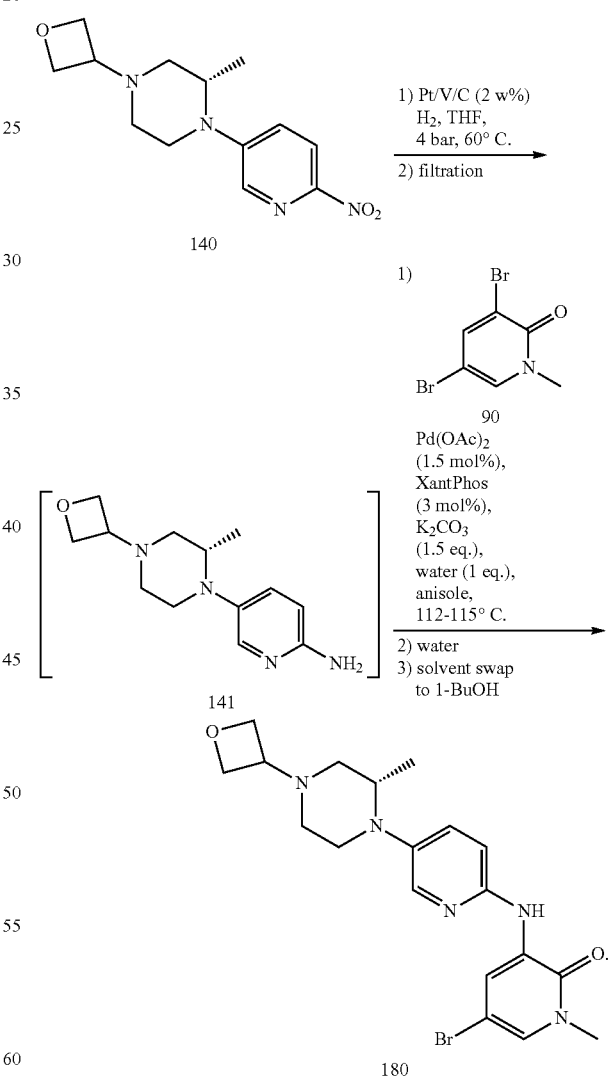

A solution of (S)-2-methyl-1-(6-nitropyridin-3-yl)-4-(oxetan-3-yl)piperazine (56 g, 201.3 mmol) (compound 140) in THF (495.8 g) was transferred to a steel autoclave and hydrogenated in the presence of a Pt/V@C catalyst (1.12 g, 2 w %) at 60° C. and 4 bar of hydrogen for 16 h to produce a solution of (L54-(2-methyl-4-(oxetan&-3-ylpiperazin-1-yl)pyridin-2-amine (compound 141). After pressure release, the catalyst was filtered off, the autoclave was rinsed with THF, and the filter cake was washed with THF. THF was distilled off from the solution to achieve a reactor volume of ca 120 mL. Anisole was added and the remaining THF was removed by distillation under reduced pressure (120-150 mbar, Ti 90±5° C.) to achieve a reactor volume of 250 mL (5V).

To the solution of compound 141, 3,4-dibromo-1-1methylpyridin-2-one (compound 90) (1.05 eq.) and K$_2$CO$_3$ (1.5 eq.) were then added at a temperature of 90° C. under an argon/nitrogen stream, followed by the dropwise addition of water (1.0 eq.). Finally, Xantphos (3 mol %) and Pd(OAc)$_2$ (1.5 mol %) were added to form a mixture. The mixture was heated to a temperature of 112-114° C. and stirred until full conversion to compound 180 was achieved (15-20 h). The reaction mixture was diluted with anisole (2V) followed by water addition (4V) resulting in a temperature of 90° C. The organic and aqueous phases were separated. Anisole was partially removed from the organic phase under vacuum (120-150 mbar) to achieve a reactor volume of 150 mL (3 V). 1-butanol (5 V) and water (4 V) were then added followed by separation of the organic and aqueous phases. The organic phase comprising anisole, 1-butanol and compound 180 was transferred to a pre-heated (90° C.) reactor and the volume of the reaction mixture was reduced under vacuum (120-150 mbar) to achieve a reactor volume of 200 mL, whereupon the crystallization was initiated. 1-butanol (3 V) was added to achieve a crystallization volume of 350 mL. The suspension was cooled to a temperature of −10° C. at a rate of 10° C./h and stirred for at least 6 h at a temperature of −10° C. The crystals were collected by filtration, washed with cold (−5±2° C.) MeOH/H$_2$O (1:1 v/v, 1.5V) and with cold (−5±2° C.) 1-butanol (2.5 V), and dried at 70° C. under vacuum (2-10 mbar) until weight constancy to give compound 180 as beige-yellowish solid in 75-78% yield and >99.0 w % assay. $^1$H NMR (600 MHz, DMSO-d6) δ ppm 8.47-8.62 (m, 2H), 7.92 (d, 1H), 7.33-7.51 (m, 2H), 7.26 (d, 1H), 4.39-4.69 (m, 4H), 3.73 (br d, 1H), 3.51 (s, 3H), 3.38-3.45 (m, 1H), 3.08-3.17 (m, 1H), 2.90-3.04 (m, 1H), 2.58 (br d, 1H), 2.27-2.40 (m, 2H), 2.18 (br t, 1H), 0.96 (d, 3H). HR-MS (ESI): calc. for C$_{19}$H$_{24}$BrN$_5$O$_2$ 433.1113; found: 433.1130.

Example 3

Compounds 141 and 180 were prepared as according to the reaction scheme in FIG. 2, and as depicted in more detail below:

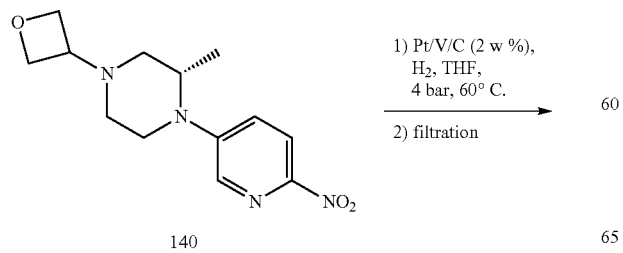

1) Pt/V/C (2 w %), H$_2$, THF, 4 bar, 60° C.
2) filtration

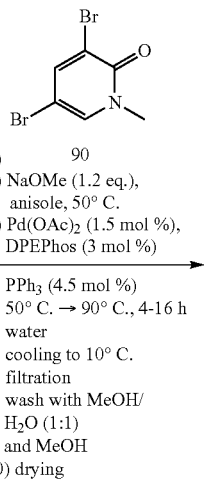

1) 90
2) NaOMe (1.2 eq.), anisole, 50° C.
3) Pd(OAc)$_2$ (1.5 mol %), DPEPhos (3 mol %)
4) PPh$_3$ (4.5 mol %)
5) 50° C. → 90° C., 4-16 h
6) water
7) cooling to 10° C.
8) filtration
9) wash with MeOH/ H$_2$O (1:1) and MeOH
10) drying

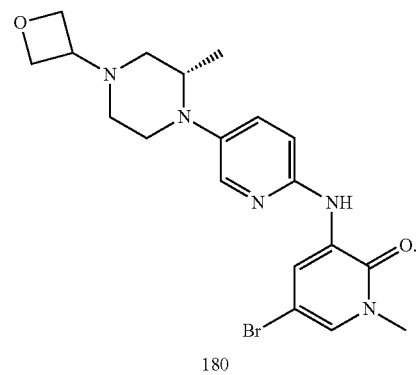

180

Compound 141 was prepared by the method of Example 2. A solution of compound 141 (152.04 g containing 15 g of compound 141) in THF was heated to 85° C. and the THF was replaced by anisole by continuous distillation to result in a reactor volume of about 75 mL. The mixture was cooled to 50° C., followed by the sequential addition of compound 90 (16.93 g, 63.42 mmol, Eq: 1.05), sodium methoxide anhydrous (3.92 g, 72.48 mmol, Eq: 1.2) and finally, a premixed, red suspension of palladium (II) acetate (203.4 mg, 906.1 µmol, Eq: 0.015) and DPEphos (975.9 mg, 1.812 mmol, Eq: 0.030) in anisole (6.93 g, 7 ml). The reaction mixture was then heated to 92° C., whereupon a suspension was formed. The mixture was then stirred until full conversion was achieved, then quenched upon the addition of water (120 g). The reaction mixture was then cooled to 10° C. at a rate of 1° C./min. Crystalline compound 180 was then isolated by filtration and washed with a sequence of MeOH (45 mL), H$_2$O/MeOH (1:1 v/v, 20 mL), and MeOH (30 mL). The crystals were dried at 45° C. under vacuum until weight constancy to yield compound 180 as beige solid in 82.5% yield (12.6 g) and in >99 area % purity.

Example 4

Example 3 was repeated except where triphenylphosphine (4.5 mol %) was added to the reaction mixture comprising the solution of compound 141. The reaction provided 82.4% yield at 98.3% purity.

Example 5

Compound 141 was prepared and isolated from solution according to the following scheme:

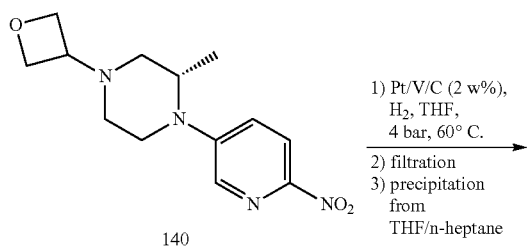

A solution of compound 140 (300 g, 1.078 mol) in THF (1.06 kg) was placed in an autoclave and hydrogenated in the presence of a Pt/V/@C catalyst (6.0 g, 2 w %) at 60° C. and 4 bar of hydrogen for 16 h to produce compound 141 in solution. After cooling to ambient temperature and release of the pressure, the catalyst was collected by filtration, the autoclave was rinsed with THF, and the filter cake is washed with THF (177.8 g total THF rinse). From the combined solutions, THF was distilled off (70° C., 350 mbar) to achieve a reactor volume of about 1.5 L followed by cooling to 37° C. n-heptane (1 L) was added, whereupon compound 141 crystallization was initiated and the suspension is stirred at 27° C. for 1.5 h. Additional n-heptane (1.25 L) was added then, the suspension was stirred at 25° C. for 15 minutes, and then cooled to 3-5° C. and stirred for 30 min. The crystals were then collected by filtration, washed with n-heptane (1 L), and dried under vacuum to give compound 141 in 90.7% yield (242.8 g) and in >99 area % purity. $^1$H-NMR (600 MHz, CDCl$_3$): δ ppm 7.86 (dd, 1H), 7.26 (dd, 1H), 6.49 (dd, 1H), 4.53-477 (m, 4H), 4.27 (br s, 2H), 3.45-3.62 (m, 1H), 3.19-3.35 (M, 1H), 2.98-3.06 (m, 2H), 2.51-2.70 (m, 2H), 2.27-2.46 (m, 1H), 2.06 (dd, 1H), 0.92 (d, 3H). HR-MS (ESI): calc. for $C_{13}H_{20}N_4O$: 248.1637; found: 248.1647. XRF: <1 ppm Pt; <2 ppm V.

Example 6

Catalysts for the preparation of compound 141 from compound 140 were evaluated according to the method of Example 5. The results are reported in Table 1 below.

TABLE 1

Summary of compound 141 syntheses

| Exp | Catalyst (loading) | Solvent | Additive (eq.) | Temp. (° C.) | Press. (bar) | Conv. (%) | Selec. (%) |
|---|---|---|---|---|---|---|---|
| 1 | 1% Pt/2% V@ C (2 wt. %) | THF | — | 60 | 4 | >99.9 | 99.4 |
| 2 | 1% Pt/2% V@ C (2 wt. %) | Toluene/MeOH (1:1) | AcOH (0.5) | 60 | 4 | >99.9 | 85.9 |
| 3 | 10% Pd@C (2 wt. %) | THF | — | 60 | 4 | >99.9 | 98.8 |
| 4 | 10% Pd@C (2 wt. %) | Toluene/MeOH (1:1) | AcOH (0.5) | 60 | 4 | >99.9 | 95.2 |
| 5 | Ra—Ni (14 wt. %) | THF | — | 60 | 4 | 99.8 | 96.5 |
| 6 | Co@Chitin-700 (3 mol % Co) | THF/H$_2$O (20:1) | NEt$_3$ (0.5) | 110 | 40 | >99.9 | 99.3 |
| 7 | Co@Chitin-MgO-700 (3 mol % Co) | THF/H$_2$O (20:1) | NEt$_3$ (0.5) | 110 | 40 | 99.9 | 97.9 |
| 8 | Co$_3$O$_4$/NGr@Al$_2$O (3 mol % Co) | THF/H$_2$O (20:1) | NEt$_3$ (0.5) | 110 | 40 | >99.9 | 96.4 |
| 9 | Ni-Phen@SiO$_2$-1000 (3 mol % Ni) | THF/H$_2$O (20:1) | NEt$_3$ (0.5) | 110 | 40 | 99.9 | 98.6 |
| 10 | Ni-Phen@TiO$_2$-1000 (3 mol % Ni) | THF/H$_2$O (20:1) | NEt$_3$ (0.5) | 110 | 40 | >99.9 | 98.7 |

In the above table, experiments 1 and 3 used 50-56 g compound 140, 10V solvent, a 1.5 L autoclave with glass insert, and 16 hour reaction time. The catalyst for experiment 1 was Noblyst P8078, and the catalyst for experiment 3 was E101 NE/W. Experiments 2, 4 and 5 used 5 g compound 140, TOV solvent, a 185 mL autoclave, and a 16 hour reaction time. Experiments 6-10 used 200 mg compound 140, TOV solvent, a 35 mL autoclave with glass insert and shaker, and a 16 hour reaction time.

-continued

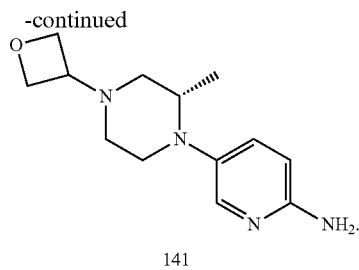

Example 7

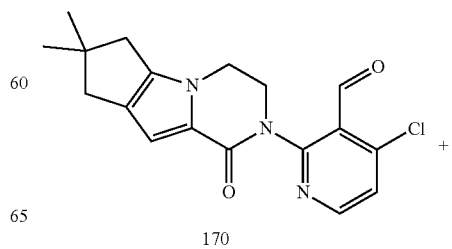

-continued

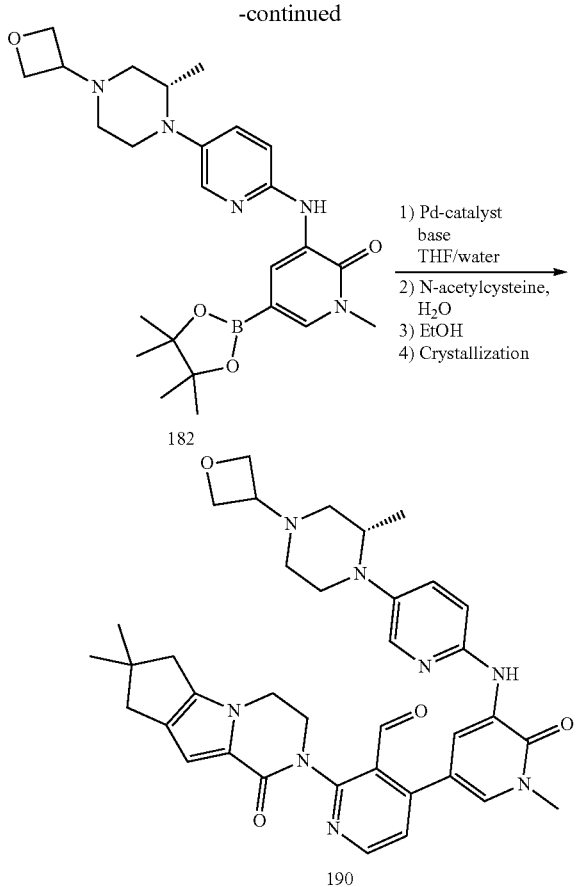

182

190

Compound 190 was prepared from compounds 170 and 182, utilizing various catalysts at two catalyst concentrations of 0.001 equivalent per equivalent of compound 170 (0.1 mol %), or 0.01 equivalent per equivalent of compound 170 (1 mol %). In each experiment, the solvent was THF and water at a volume ratio of THF to water was 4:1, the ratio of solvent volume to compound 170 was 10:1 L/kg, the equivalent ratio of compound 182 to compound 170 was 1.1:1, the base was $K_3PO_4$, (1.5 eq based on compound 170), the reaction temperature was 50° C., and the reaction time was 18 hours. After 18 hours, 0.25 equivalents of acetyl cysteine as a 60 mg/mL solution in $H_2O$ was added to the reaction mixture; the mixture stirred for 10 minutes; and a sample removed for HPLC analysis. The results are reported below in Tables 2 and 3 where: "Comp. 190" refers to compound 190; "Comp. 170" refers to compound 170; "ketone" refers to the ketone impurity; "sec alcohol" refers to the sec alcohol impurity; "dimer" refers to the dimer impurity; "Comp. 182" refers to compound 182; "des brom" refers to the DesBr impurity depicted below; and the results are reported in HPLC area %.

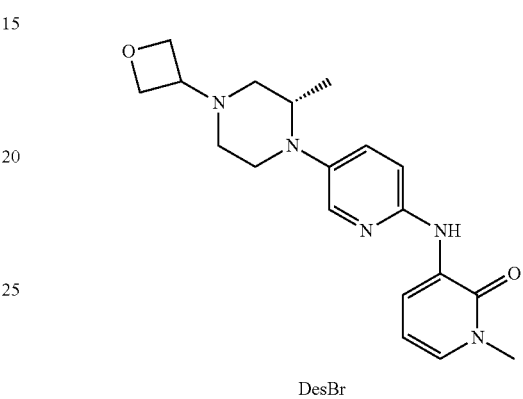

DesBr

The results in Tables 2 and 3 are in-process values expressed in HPLC area % measured after 18 hours of reaction time at 50° C.

Table 2 reports the activity of cationic and neutral Pd(S-Phos)(allyl) compounds at 1 mol % catalyst loading. This table demonstrates that, compared to previously disclosed [Pd(dppf)Cl$_2$] catalyst, the amount of compound 190 produced was greater and the amount of dimer formed was much less (0.87 for Pd(dppf)Cl$_2$ vs. 0.02-0.08 for Pd(SPhos) (allyl) catalysts). Table 3 demonstrates that among the catalysts that performed better at 1 mol %, [(SPhos)Pd (allyl)]OTf performed the best at 0.1 mol % (higher amount of compound 190, and lower amount of dimer).

TABLE 2

Summary of results using 1 mol % loading of various cationic and neutral Pd(SPhos)(allyl) catalysts, and previously used catalyst Pd(dppf)Cl$_2$

| Catalyst | [Pd(dppf)Cl$_2$] | [(SPhos)Pd(allyl)]OTf | [(SPhos)Pd(allyl)Cl] | [(SPhos)Pd(crotyl)Cl] | [(SPhos)Pd(allyl)]PF$_6$ | [(SPhos)Pd(allyl)]CF$_3$CO$_2$ |
|---|---|---|---|---|---|---|
| Comp. 190 | 91.95 | 96.81 | 96.62 | 90.73 | 95.36 | 95.71 |
| Comp. 170 | 0.04 | 0 | 0.08 | 2.65 | 1 | 0.82 |
| Ketone | 0.03 | 0.04 | 0.1 | 0.29 | 0.31 | 0.09 |
| Sec Alcohol | 0.04 | 0.06 | 0.09 | 0.45 | 0.43 | 0.26 |
| Dimer | 0.87 | 0.07 | 0.05 | 0.02 | 0.05 | 0.08 |
| Comp. 182 | 0.03 | 0.33 | 0.03 | 0 | 0.02 | 0.02 |
| Des Brom | 2.46 | 0.82 | 0.85 | 3.83 | 1.04 | 1.26 |

TABLE 3

Summary of results using 0.1 mol % loading of various cationic and neutral Pd(SPhos)(allyl) catalysts

| Catalyst | [(SPhos)Pd(allyl)]-OTf | [(SPhos)Pd(allyl)]-CH$_3$CO$_2$ | [(SPhos)Pd(allyl)]-NO$_3$ | [(SPhos)Pd(allyl)Cl] |
|---|---|---|---|---|
| Comp. 190 | 96.42 | 93.53 | 88.36 | 92.99 |
| Chloride | 0.17 | 0.06 | 0.68 | 2.25 |
| Ketone | 0 | 0 | 0 | 0 |
| Sec Alcohol | 0.04 | 0.01 | 0.03 | 0.02 |
| Dimer | 0.06 | 0.18 | 0.1 | 0.22 |
| Boronate | 0.15 | 1.07 | 0.09 | 0.58 |
| Des Brom | 1.59 | 2.59 | 1.57 | 2.34 |

The data demonstrate that an improved impurity profile is achieved using (SPhos)Pd(allyl)-counter anion catalysts as described in the present disclosure, compared to previously used catalysts.

Example 8

Compound 190 was prepared from compounds 170 and 182 according to the reaction scheme in FIG. 5B. Compound 170 (27.5 g, 80.0 mmol, 1.0 eq) and compound 182 (46.3 g, 88.0 mmol, 1.1 eq) were suspended with stirring in ethyl acetate (222 mL, 200 g) at 70° C. followed by thorough degassing for 10 min. [(SPhos)Pd(allyl)]OTf catalyst (113 mg) was added in one portion and the suspension was heated to 70° C.±3° C. in 25-35 minutes. A solution of potassium phosphate (25 g) in in water (60.0 g) at 70° C.±5° C. was then added over a period of 55-65 minutes. The reaction product mixture was stirred at 70° C. until an in-process control indicated less than 1.0 area % compound 170. The reaction time was 1-2 hours.

The reaction product mixture was cooled to 20° C. Ti and then combined with a solution of N-acetyl cysteine (3.27 g) in water (60.0 g) that had been degassed with Ar by bubbling. The aqueous N-acetyl cysteine vessel and transfer line were washed forward into the reaction product mixture with ethyl acetate (22.4 g, 25.0 mL). The mixture was stirred for 15 minutes at 20° C.±3° C. After phase separation, the lower aqueous phase was removed. The remaining organic phase was combined with stirring with 5% aqueous NaHCO$_3$ solution (100 g, 98 mL) at 20° C.±3° C. The stirring was stopped allowing for phase separation (15 minutes). The lower aqueous phase was removed and the remaining organic phase was combined with water (100 g). The mixture was stirred for 15 minutes at 20° C.±3° C. The stirring was stopped allowing for phase separation (15 minutes). The lower aqueous phase was removed and the remaining organic phase was heated to 40° C.±3° C. and then filtered over activated charcoal R55SP. The filtrate was collected in a Schott flask and the vessel formerly containing the organic phase and the filter were rinsed twice with ethyl acetate (22.4 g, 25 mL for each rinse) into the flask containing the filtrate.

The filtrate was concentrated under about 200-300 mbar vacuum at about 85° C. to a residual volume of about 100 mL. Ethanol (350 g, 450 mL) was then added at 50° C. to 70° C. to form a suspension. The suspension was concentrated at reflux (about 85° C.) and atmospheric pressure to a residual volume of about 400 mL. At reflux, as solution was obtained which was maintained throughout the concentration step. An in process control sample was collected and tested for residual ethyl acetate, and concentration was continued until the fraction of EtOAc in the EtOAc/EtOH mixture was no more than 6.0%. If that level is not achieved then additional ethanol may be added to the solution followed by concentration to about 400 mL. After the EtOAc content was reduced to no more than 6.0%, the solution was cooled to 75° C.±2° C. and seeded with a suspension of compound 190 (273 mg compound 190 in 10.0 mL ethanol). The formed suspension was stirred for 30 minutes at 75° C.±2° C. and then cooled to 5° C.±3° C. at a rate of 10° C. per hour (about 7 hours). The suspension was aged for at least 7 hours at 5° C.±3° C. Compound 190 was isolated by filtration over a nutsche with filter paper at a vacuum of about 500 mbar. The collected solid compound 190 was washed two times with 4° C. to 6° C. ethanol at a total ethanol volume of 74.9 g. The compound 190 product was dried overnight at 50° C. under 5 mbar vacuum to yield 48.6 g of compound 190 (99.7 area % assay and 91.4% yield).

The above method for preparing compound 190 was repeated in triplicate (experiments 1 to 3) with the exception that the solvent exchange from ethyl acetate to ethanol in experiment 3 was done as follows: The organic phase was concentrated to 80 mL and ethanol (268 g, 340 mL) was added. The results are presented in Table 4 below where "IPC" refers to in process control test results; "IPC water" refers to the water content as measured in the IPC EtOAc fraction test.

TABLE 4

Summary of experimental characterization in process (IPC) and after completion, for three triplicate experiments preparing compound 190 using [(SPhos)Pd(allyl)]OTf and ethyl acetate.

| | Experiment 1 | Experiment 2 | Experiment 3 |
|---|---|---|---|
| Batch size | 80.0 mmol | 80.0 mmol | 80.0 mmol |
| IPC test time | 2 hours | 2 hours | 2 hours |
| IPC compound 190 | 96.3 area % | 95.3 area % | 95.6 area % |
| IPC compound 170 | Not detected | Not detected | Not detected |
| IPC des-brom impurity | 1.2 area % | 0.91 area % | 2.11 area % |
| IPC dimer impurity | 0.26 area % | 0.12 area % | 0.28 area % |
| IPC compound 182 | 0.77 area % | 0.97 area % | 0.39 area % |
| IPC sec alcohol impurity | 0.04 area % | 0.10 area % | 0.06 area % |
| IPC EtOAc fraction | 3.6% | 4.9% | 7.2% |
| IPC water | 0.4% | 0.16% | 0.4% |
| Crystallization time | 15 h | 13.5 h | 11 h |
| Compound 190 results | | | |
| Compound 190 weight | 48.9 g | 48.6 g | 48.9 g |
| Compound 190 assay | 98.9 w/w % | 99.7 w/w % | 99.1 w/w % |
| Compound 190 purity | 99.4 area % | 99.7 area % | 99.4 area % |
| Compound 190 yield | 91.3% | 91.4% | 91.4% |
| Compound 170 | Not detected | Not detected | Not detected |
| Des-brom impurity | Not detected | Not detected | <0.05 area % |
| Dimer impurity | 0.12 area % | Not detected | 0.15 area % |
| Compound 182 | Not detected | Not detected | Not detected |
| Sec alcohol impurity | Not detected | Not detected | Not detected |
| EtOH-hemiacetal impurity | 0.23 area % | 0.10 area % | 0.30 area % |

TABLE 4-continued

Summary of experimental characterization in process (IPC) and after completion, for three triplicate experiments preparing compound 190 using [(SPhos)Pd(allyl)]OTf and ethyl acetate.

|  | Experiment 1 | Experiment 2 | Experiment 3 |
|---|---|---|---|
| Ketone impurity | Not detected | Not detected | Not detected |
| Ethyl acetate | Not detected | Not detected | 123 ppm |
| Ethanol | <100 ppm | 380 ppm | 251 ppm |
| Water | 1.27 w/w % | 0.43 w/w % | 0.45 w/w % |

Example 9

The reaction of the present disclosure for preparing compound 190 from compounds 182 and 170 was compared to a previously used reaction for preparing compound 190 from compounds 182 and 170. The reaction conditions are summarized in Table 5. Using the old catalytic system of Pd(dppf)Cl$_2$, a ketone impurity was observed over a wide range, and up to 0.29 area % (see Table 5). In contrast, using the new catalytic system, the amount of ketone impurity observed is maintained within a narrow range, with a much lower upper bound (up to 0.06 area %).

TABLE 5

Summary of conditions from previously-used and presently-described methods. Yield, purity, and by-product content were evaluated in isolated compound after work-up. The "Present Disclosure" values are an average over 3 batches, 800 kg product in total.

| Parameter | Previous Process | Present Disclosure |
|---|---|---|
| Catalyst | Pd(dppf)Cl$_2$ | [(SPhos)Pd(allyl)]OTf |
| Solvent | THF/water | Ethyl acetate/water |
| Catalyst content based on Compound 170 (mol %) | 1.0 | 0.2 |
| Reaction Temp (° C.) | 50 | 70 |
| Reaction Mode | Full batch | Semi batch (aq K$_3$PO$_4$ added at 70° C. over 1-3 hours) |
| Reaction time (h) | 15 | 1-2 |
| Solvent exchange 1 (after reaction) | THF → toluene for extraction | None |
| Solvent exchange 2 | Toluene → ethanol | Ethyl acetate → ethanol |
| Yield (%) | 75.0 | 84.7 |
| Purity (area %) | 99.1-99.5 | 99.8 |
| Dimer (% w/w) | 0.29-0.40 | Not detected |
| Alcohol impurity (area %) | Not detected | Not detected |
| Ketone impurity (area %) | <0.05-0.29 | 0.03-0.06 |

The dimer, alcohol and ketone impurities are depicted below.

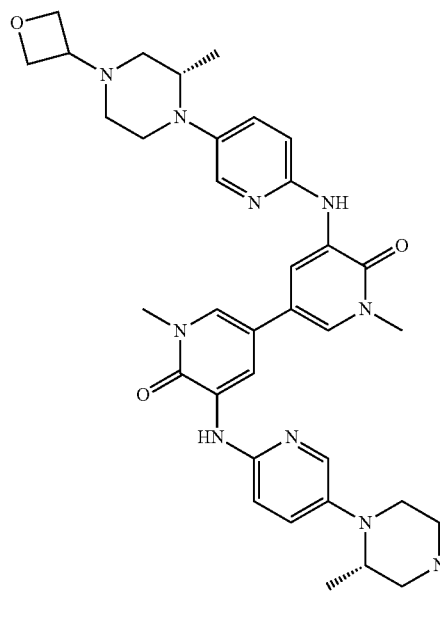

Dimer

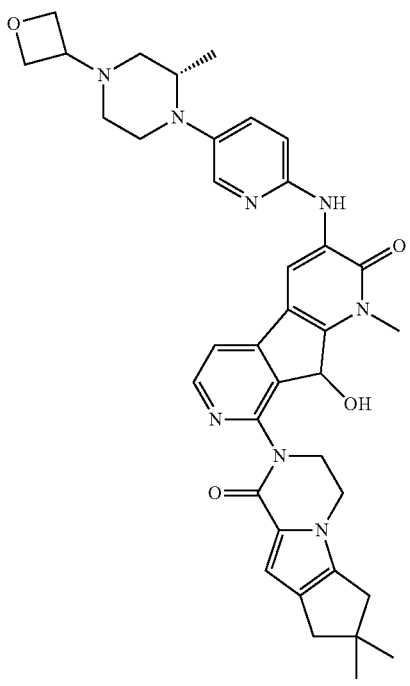

Alcohol

105

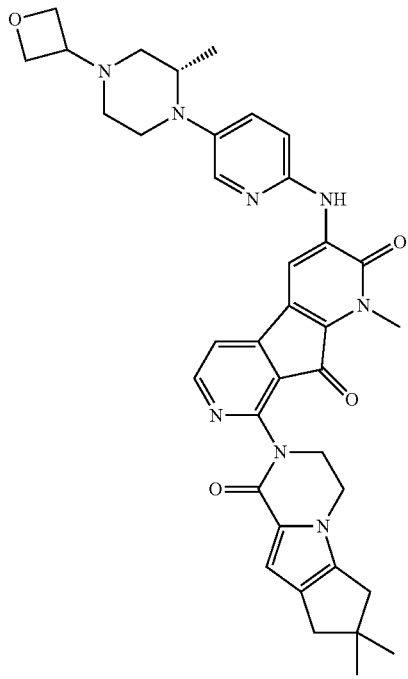

Ketone

The alcohol impurity that may be formed during this reaction may be oxidized to the corresponding ketone impurity before detection.

Example 10

Compound 200 was prepared from Compound 190 as provided in the following scheme:

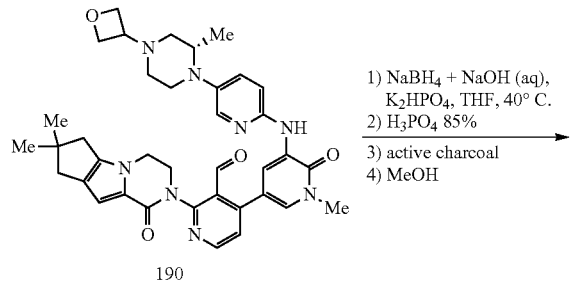

190

106

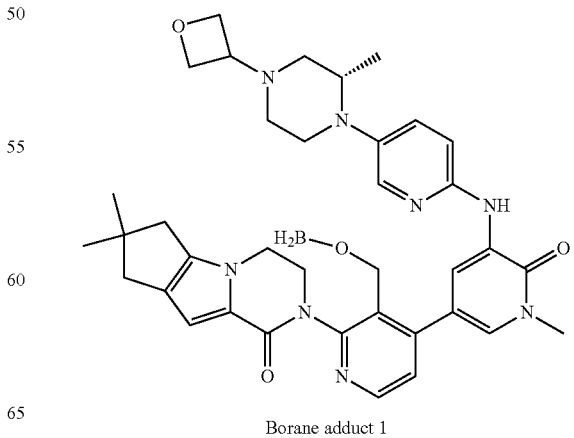

200

Compound 190 (50 g, 75.4 mmol, 1 eq) was charged to a reactor. THF (267 g) was added, followed by $K_2HPO_4$ (6.16 g, 35.4 mmol, 0.469 eq) and water (42.5 g). The mixture was heated to 40-45° C. and agitated for about 20 minutes. Then, an aqueous mixture of sodium hydroxide and sodium borohydride (12 w/w $NaBH_4$, 40 w/w NaOH, 11.9 g total aqueous solution added) was added over 10-20 minutes while maintaining a temperature of 40-45° C. The reactor contents were monitored until the concentration of compound 190 remaining was less than or equal to 0.20 area % (about one hour). 85% aqueous phosphoric acid (10.5 g) then added to the reaction product mixture comprising product compound 200, the reactor heated to 60° C., and the contents agitated until the content of borane adducts fell to at or below 0.05 area % (about 2 hours).

Borane adduct 1

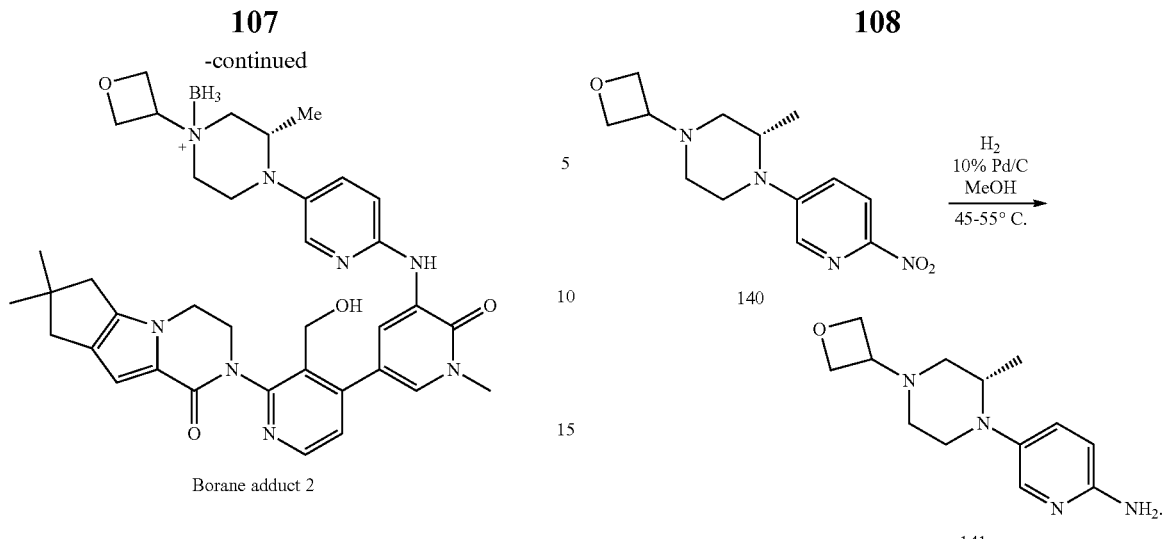

Borane adduct 2

The contents were agitated for another three hours, then cooled to 40-45° C., and an organic phase separated, removed, and filtered over activated charcoal. The filtrate was then solvent-swapped by concentrating under atmospheric pressure at 65° C. to a minimum volume of 2.6 L/kg starting material compound 190, and methanol added to a final volume of 6.6 L/kg starting material compound 190. The mixture was seeded to begin crystallization of compound 200, and the solvent swap continued at constant volume until the THF concentration fell at or below 5.0% w/w. The resulting suspension was aged for at least 30 min, cooled to 5° C. over 5 h, and held for at least 3 h at 5° C. before filtering off crystals of compound 200 using a nutsche and washing twice with methanol. Crystals were dried under reduced pressure until constant weight was attained (90% yield, assay: 99.1% w/w, purity: 99.7 area %).

Example 11

Compound 200 obtained from the synthesis outlined in Example 10 was recrystallized from toluene/ethanol in a cooling crystallization process.

Crude compound 200 was suspended in a 60:40 w/w toluene:ethanol mixture in a first reactor at ambient temperature, and then heated to between 70-75° C. The suspension was transferred via a polish filter unit into a second reactor, followed by a rinse of the first reactor with 60/40 w/w toluene/ethanol. The concentration of compound 200 in the second reactor was about 20% w/w. Ethanol was added, maintaining a temperature of 70-75° C., until a 20:80 w/w ratio of toluene:ethanol was reached. This solution was cooled to 50° C., seeded with a 10% w/w suspension of compound 200 in ethanol (to about 2% w/w). The seeded suspension was aged for four hours, cooled to −10° C., aged for 10 min, heated to 45° C. within 15 min, and aged for 30 minutes. This thermocycle was repeated three times (heat to 45° C., age, cool to −10° C., age), and after the fourth thermocycle, the suspension cooled to between −15° C. to −10° C. After further aging for at least six hours, the suspension is filtered, the filter cake washed with ethanol (−10° C.), and the washed filter cake dried at 50° C. at reduced pressure overnight.

Comparative Example 1

This comparative example presents a previously-used method for synthesizing compound 141. Compound 141 was prepared from compound 140 as follows:

Methanol (675 mL) was charged to a reaction flask. Compound 140 (135 g, 98.9 A %, 537.7 mmol, 1 eq.) was charged to the reaction flask with agitation followed by 10% palladium on carbon catalyst (27 g, 20 w/w %, 59% wet). The reaction flask was evacuated and filled with $N_2$ three times and was then evacuated and filled with $H_2$ three times. The mixture was heated to 45 to 55° C. for 15 hours. The mixture was cooled to 20 to 25° C. and was then filtered. The filtrate was concentrated in vacuo at a temperature of less than 60° C. to almost dryness to form a residue. The residue was combined with dioxane (675 mL) and the resulting mixture was concentrated in vacuo at a temperature of less than 60° C. to almost dryness to form a residue. The residue was diluted with dioxane (1200 mL) to form a solution of compound 141 in dioxane (1295.5 g). The compound 141 yield was 90.3%, the assay was 8.3%, and the methanol residue was 0.13% as measured by GC.

Various solvents were evaluated for the preparation of compound 141 from compound 140 according to the above method. The results are summarized in Comparative Example 1 Table 6 below where "Exp." refers to experiment; "C 140" refers to compound 140; "C 141" refers to compound 141; "Pd/C" refers to palladium on carbon catalyst and the 10% Pd/C catalyst was 59% wet; and "Crude" refers to the assay in area % HPLC purity of the referenced compound in the reaction product mixture and prior to work-up (filtration).

Comparative Example 1 Table 6

| | | Conditions | | Crude | |
|---|---|---|---|---|---|
| Exp. | C 140 | 10% Pd/C | Solvent | Rx Time | C 140 | C 141 |
| 1 | 3.6 mmol | 2 w/w % | Ethanol | 16 h | 56.8 A % | 31.9 A % |
| 2 | 3.6 mmol | 2 w/w % | Dioxane | 16 h | 73.2 A % | 21.1 A % |
| 3 | 3.6 mmol | 5 w/w % | Dioxane | 16 h | 25.5 A % | 72 A % |
| 4 | 54 mmol | 2 w/w % | Methanol | 10 h | 0.13 A % | 90.1 A % |

Palladium on carbon catalyst loading was evaluated for the preparation of compound 141 from compound 140 according to the above method. The results are summarized in Comparative Example 1 Table 7 below where "Exp." refers to experiment; "C 140" refers to compound 140 where the compound 140 purity was 98.4 A %; "C 141" refers to compound 141; "Crude" refers to the assay in area % by HPLC of the referenced compound in the reaction product mixture and prior to work-up (filtration).

Comparative Example 1 Table 7

| Exp. | C 140 | Pc/C loading | Crude | | |
|---|---|---|---|---|---|
| | | | C 141 | Impurity 1 | Impurity 2 |
| 1 | 15 g | 2 w/w % | 90.1 A % | 2 A % | 4.1 A % |
| 2 | 5 g | 5 w/w % | 95.8 A % | 0.6 A % | 2 A % |
| 3 | 166 g | 10 w/w % | 97.5 A % | 0.43 A % | 0.77 A % |
| 4 | 5 g | 20 w/w % | 98.2 A % | 0.18 A % | 0.27 A % |

Recovery and reuse of palladium on carbon catalyst was evaluated for the preparation of compound 141 from compound 140 according to the above method where the starting amount of compound 140 in each of experiments 1 to 4 below was 35.9 mmol. The results are summarized in Comparative Example 1 Table 8 below where "Exp." refers to experiment; "C 140" refers to compound 140 where the compound 140 purity was 98.4 A %; "Pd/C" refers to palladium on carbon catalyst; "Crude" refers to the compound 140 assay in area % by HPLC of the referenced compound in the reaction product mixture and prior to work-up (filtration); and "RT" refers to reaction time in minutes.

Comparative Example 1 Table 8

| Exp. | 10% Pd/C | IPC | | | | |
|---|---|---|---|---|---|---|
| | | RT: 4.93 | RT: 5.21 | RT: 5.32 | RT: 6.89 | RT: 7.39 |
| 1 | 2.0 g, 20 w/w % | 98.3 A % | 0.69 A % | 0.13 A % | 0.48 A % | 0.1 A % |
| 2 | Recycle from Exp. 1 + 0.2 g fresh catalyst | 98.2 A % | 0.35 A % | 0.12 A % | 0.71 A % | 0.03 A % |
| 3 | Recycle from Exp. 2 + 0.2 g fresh catalyst | 98 A % | 0.47 A % | 0.14 A % | 0.78 A % | 0.08 A % |
| 4 | Recycle from Exp. 2 + 0.2 g fresh catalyst | 97.9 A % | 0.52 A % | 0.14 A % | 0.91 A % | 0.06 A % |

Comparative Example 2

This comparative example presents a previously-used method of preparing compound 180. Compound 141 as prepared in Comparative Example 1 was reacted with compound 90 to form compound 180 according to the following scheme:

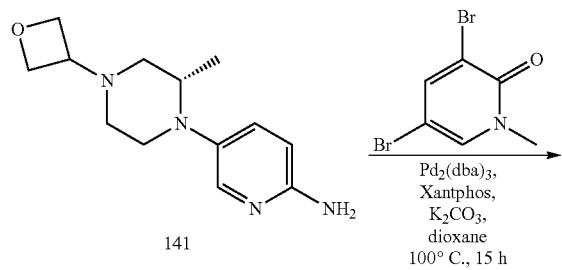

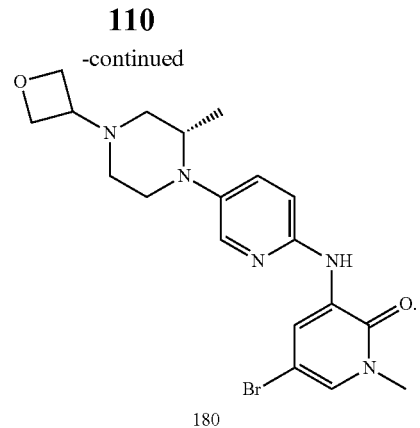

A solution of compound 141 in dioxane (1295.5 g, 8.3% assay, 433 mmol, 1 eq.) was charged to a reaction flask. Compound 90 (119.5 g, 96.7% assay, 433 mmol, 1 eq.) and $K_2CO_3$ (121 g, 99% assay, 17.3 mmol, 2 eq.) were charged to the reaction flask with agitation. The reaction flask was evacuated and refilled with $N_2$ three times. $Pd_2(dba)_3$ catalyst (9.05 g, 99% assay, 8.66 mmol, 0.02 eq.) and Xantphos ligand (10.2 g, 98% assay, 17.3 mmol, 0.04 eq.) were charged to the reaction flask with agitation. The reaction flask was evacuated and refilled with $N_2$ three times and the mixture was heated to 105 to 115° C., and the mixture was stirred under $N_2$ for 24 hours. The mixture was cooled to 65 to 75° C. and filtered. The collected solids were rinsed with hot dioxane. The filtrate and dioxane wash were combined and concentrated to almost dryness in vacuo at 55 to 65° C. to form a residue.

Methanol (550 mL) was combined with the residue, the mixture was stirred at 0° C. for 2 hours, the mixture was filtered to collect crude compound 180 as a solid, and the collected crude compound 180 was washed with cold methanol. The crude compound 180 was dried in vacuo at 55 to 65° C. for 1 hour. The crude product was weighed and assayed by HPLC to yield 151 g compound 180 having a purity of 97.6 area %. The crude was combined with dioxane (211 g) and the mixture was heated to reflux and stirred at reflux for 15 minutes. i-propanol (500 mL) was added dropwise to the mixture while maintaining reflux. The mixture was cooled to 15 to 25° C. and stirred for 1 hour at that temperature. The mixture was filtered and the collected compound 180 solids were rinsed with i-propanol and were dried in vacuo at 60 to 70° C. for 5 hours. Compound 180 (188 g) was collected having a purity of 99.1 area % by HPLC, an assay of 97.6%, and an assay yield of 74.1%.

$K_3PO_4$ was evaluated for the preparation of compound 180 from compounds 141 and 90 according to the above method. The results are presented in Comparative Example 2 Table 10 below where "Exp." refers to experiment; "C 141" refers to compound 141; "C 180" refers to compound 180; "C 90" refers to compound 90; "catalyst" refers to $Pd_2(dba)_3$ catalyst; and "Crude" refers to the assay in area % of the referenced compound in the reaction product mixture after a reaction time of 14.3 minutes and prior to work-up.

Comparative Example 2 Table 10

| | | | | IPC | | |
|---|---|---|---|---|---|---|
| Exp. | C 141 | C 90 | Base | C 141 | C 90 | C 180 |
| 1 | 8 mmol | 8 mmol | $K_2CO_3$, 2 eq. | 0.78 A % | 3.3 A % | 74.9 A % |
| 2 | 8 mmol | 8 mmol | $K_3PO_4$, 2 eq. | 0.74 A % | 3 A % | 74.6 A % |

The solvents dioxane and toluene were evaluated as solvents for palladium-catalyzed coupling reactions for the preparation of compound 180 from compounds 141 and 90 according to the above method where the reaction time was 15 hours. The results are presented in Comparative Example 2 Table 11 below where the amount of compounds 90 and 141 was 24.2 mmol for each experiment and where the equivalents of catalyst and ligand are based on equivalents of compounds 141 and 90. In the table, "Exp" refers to experiment number.

Comparative Example 2 Table 11

| | | | | Compound 180 | |
|---|---|---|---|---|---|
| Exp. | Solvent | $Pd_2(dba)_3$ | Xantphos | Amount | Purity | Yield |
| 1 | Dioxane | 0.02 eq. | 0.04 eq. | 7.4 g | 98.9 A % | 70.5% |
| 2 | Toluene | 0.02 eq. | 0.04 eq. | 4.7 g | 94.8 A % | 44.8% |

The effect of methanol was evaluated on palladium-catalyzed coupling reactions for the preparation of compound 180 from compounds 141 and 90 according to the above method. The results are presented in Comparative Example 2 Table 12 below where the amount of compounds 90 and 141 was 34.6 mmol for experiments 1 to 3 and was 2 mmol for experiment 4. In the table, "Exp" refers to experiment number; and "RT" refers to reaction time.

Comparative Example 2 Table 12

| | | IPC | | |
|---|---|---|---|---|
| Exp. | MeOH residue | Compound 141 RT = 4.95 min | Compound 180 RT = 9.58 min | Compound 90 RT = 9.37 min |
| 1 | 0.1 w/w % | 1.13 A % | 76 A % | 4.48 A % |
| 2 | 0.5 w/w % | 2.22 A % | 72.6 A % | 10.8 A % |
| 3 | 1 w/w % | 2.38 A % | 75.7 A % | 3.22 A % |
| 4 | 5 w/w % | 10 A % | 74.2 A % | 10.2 A % |

Compound 180 (5 g, 94.3 A %) was crystallized from various solvent systems in a number of experiments. The results are summarized in Comparative Example 2 Table 13 below.

Comparative Example 2 Table 13

| | | | Crystallized compound 180 | | |
|---|---|---|---|---|---|
| Exp. | Solvent (mL) | Solvent (mL) | Weight | Assay | Yield |
| 1 | DCM (10 mL) | MeOH (50 mL) | 4.3 g | 96.4 A % | 87.9% |
| 2 | DCM (6.25 mL) | MeOH (37.5 mL) | 4.38 g | 95.8 A % | 89% |
| 3 | Dioxane (9 mL) | EtOH (22 mL) | 4.27 g | 94.9 A % | 85.9% |
| 4 | Dioxane (7 mL) | i-PrOH (21 mL) | 4.61 g | 94.9 A % | 92.8% |

Comparative Example 3

This comparative example presents a previously-used method of preparing compound 182. Compound 180 prepared as in Comparative Example 2 was boronated to form compound 182 according to the following scheme:

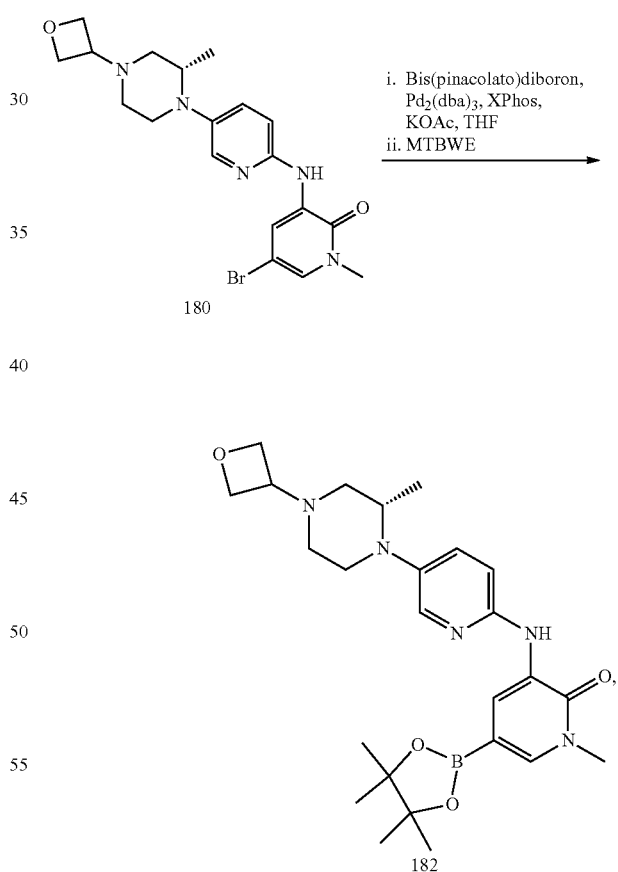

Compound 180 (1.2 kg, 2.763 mol, 1 eq.), bis(pinacolato) diboron (1.052 kg, 4.145 mol, 1.5 eq.), and KOAc (0.542 kg, 5.526 mol, 2 eq.) were charged to an inerted reactor. Excess THF (15 L) was charged to a holding vessel and was sparged subsurface with N₂ for at least 1 hour to form degassed THF. Degassed THF (9.78 kg, 11 L) was charged to the reactor with agitation. Pd₂(dba)₃ (6.52 g, 6.91 mmol, 0.0025 eq.), XPhos (8.15 g, 16.58 mmol, 0.006 eq.) and degassed THF (0.445 kg, 0.5 L) were combined with agitation to form a mixture in a catalyst preparation vessel. The catalyst mixture was then added to the reactor with agitation. The contents of the reactor were sparged subsurface with N₂ for a minimum of 1 hour. The contents of the reactor were heated to 60 to 70° C. and aged for a minimum of 12 hours. The contents of the reactor were sampled and evaluated for compound 170 content by HPLC, and the reaction was continued until the compound 170 content was 0.9 area % by HPLC. The reactor contents were cooled to 20 to 30° C. to form a crude reaction mixture comprising compound 182. Water (3.6 kg, 3 L/kg) was charged to the reactor and the reactor contents were agitated for a minimum of 10 minutes. The aqueous layer was removed from the reactor. The organic layer remaining in the reactor may be optionally washed with brine. The reactor contents were heated to 55 to 65° C. and vacuum distilled to 4 L (3.3 L/kg). THF (7.11 kg, 8 L, 6.7 L/kg) was charged to the reactor, and the reactor contents were heated to 55 to 65° C. and vacuum distilled to 4 L (3.3 L/kg). The THF/distillation step was repeated. The THF/distillation step may be further repeated, as necessary, to reduce the water content in the reactor contents to no more than 3%. The reactor contents were filtered through Celite (0.2 kg) followed by a THF rinse (1.1 kg, 1.2 L, 1 L/kg) to produce a filtrate comprising compound 182. The filtrate was heated to 55 to 65° C. and was vacuum distilled at a temperature of at least 40° C. to a reduced volume of 2 to 3 L. MTBE (8.9 kg, 10 L/kg) was charged to the reduced volume and the resulting mixture was vacuum distilled at a temperature of at least 40° C. to a reduced volume of 2 to 3 L. MTBE (8.9 kg, 10 L/kg) was charged to the reduced volume and the resulting mixture comprising compound 182 was aged at 50 to 60° C. for 2 hours followed by cooling to 0 to 10° C. and aging for a minimum of 2 hours. The mixture was filtered and compound 182 was collected as a filter cake. The filter cake was washed with MTBE (1.86 kg, 2 L/kg) twice. The isolated compound 182 solids were dried under reduced pressure at 50° C. with N₂ sweep for a minimum of 15 hours to provide compound 182 (1.334 kg, 90.3 w/w %, 6.2 wt % THF, 2 wt % MTBE, 1.2% residue on ignition (ROI), 90.6% yield).

The major impurities were a DesBr impurity and a Dimer impurity as follows:

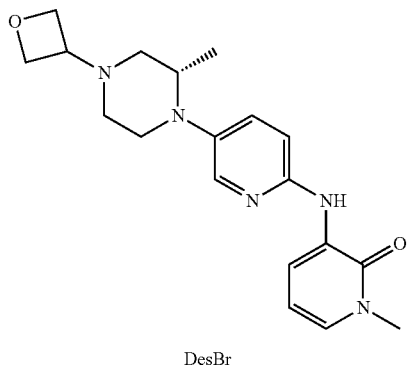 [SMILES: C[C@H]1CN(C2COC2)CCN1c1ccc(Nc2cccn(C)c2=O)nc1]
DesBr

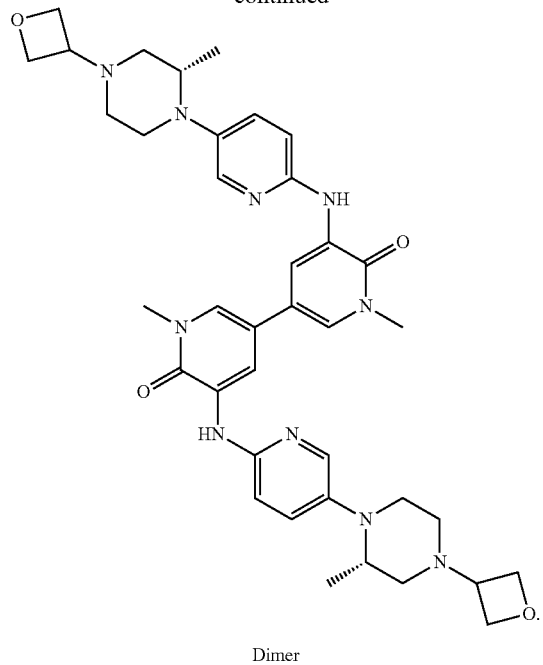
Dimer

The crude reaction mixture contained from 0.5% to 1% DesBr and from 0.1% to 0.5% dimer and the isolated solids contained from 0.1% to 0.4% DesBr and from 0 to 0.1% dimer.

The above method for preparing compound 180 from compound 170 was repeated without the MTBE charge and distillation step. Compound 180 at 92.7 w/w % comprising 2.4 wt % THF, 6.7 wt % MTBE, 0.6% residue on ignition (ROI) and 90.1% yield was produced.

Comparative Example 4

This comparative example presents previously-used methods for preparing compound 190 using a Pd(dppf)Cl₂ catalytic system with THF and H₂O as solvents.

Compound 182 was reacted with compound 170 to form compound 190 according to the following scheme:

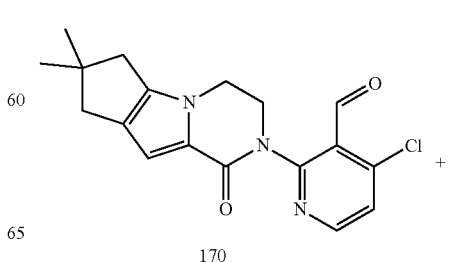
170

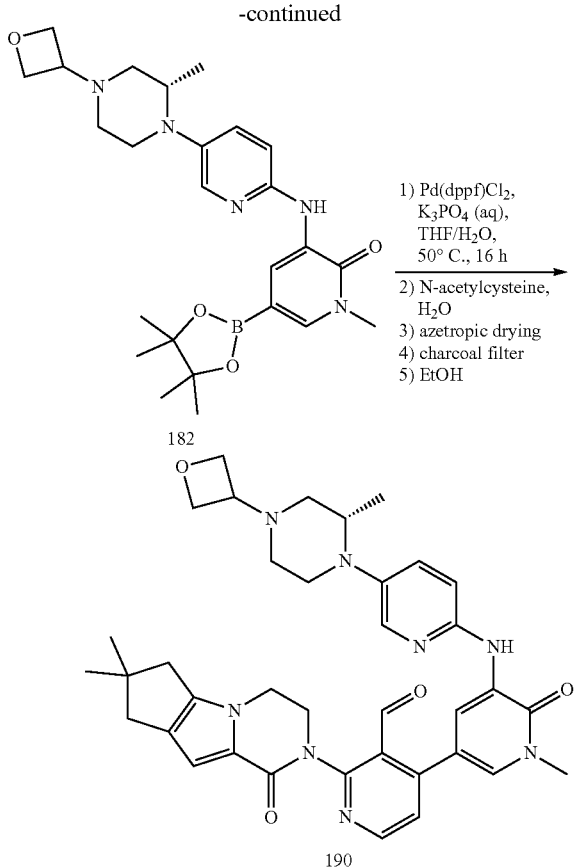

Compound 170 (30.0 g, 1 equiv), Compound 182 (50.1 g, 1.1 equiv), and potassium phosphate (27.8 g, 1.5 equiv) were charged to a reactor with THF (196 g) and water (60 g). The mixture was degassed with argon. Separately, Pd(dppf)Cl₂ (0.639 g) was suspended in THF (8.9 g) and the mixture degassed with argon, then that mixture added to the first reactor. The reactor was heated to 50° C. and stirred until less than 0.2 area % compound 170 was observed (at least 15 h).

The reaction mixture was cooled to 20° C., 6 wt % aqueous N-acetyl cysteine (about 60 mL) added, and the resulting mixture stirred for 15 minutes. The layers were separated, the organic layers washed with saturated aqueous NaCl (about 60 mL), and then dried azeotropically at atmospheric pressure using THF until water was reduced to less than 2.0% w/w. The resulting mixture was filtered over activated charcoal at 40° C., then the filtrate underwent solvent exchange to ethanol by charging to a reactor and distilled to approximately 150 mL at 50° C. under reduced pressure, then addition of ethanol (118 g). Under these conditions, compound 190 crystallizes, and suspension aged for 2 h then cooled to 20° C. over 3 h, and held at 20° C. to promote crystal formation. The resulting crystals were filtered off using a nutsche and washed three times with EtOH, then dried at 50° C. under reduced pressure until constant weight was attained. An isolated yield of 49.7 g compound 190 was obtained as a bright yellow powder (yield: 86%; assay: 99.8% w/w; purity: 99.2 area %), evaluated using the analytical method HPLC Method 1 as described above.

This procedure was repeated three times, obtaining the following results:

|  | Exp. 1 | Exp. 2 | Exp. 3 |
| --- | --- | --- | --- |
| Yield Cmpd. 190 | 51.5 g (89.1%) | 47.9 g (82.9%) | 50.0 g (86.5%) |
| Cmpd. 190 assay (w/w %) | 99.5 | 99.6 | 99.7 |
| Cmpd. 190 purity (area %) | 99.0 | 99.2 | 99.1 |
| Dimer impurity (% w/w) | 0.46 | 0.33 | 0.54 |

Comparative Example 5

The methods for preparing compound 190 as described in Comparative Example 4 ("previous process") and Example 8 ("present process") were repeated at laboratory scale, and then further evaluated at pilot scale and production scale multiple times. The amount of dimer, alcohol, and ketone impurities present in isolated compound 190 (after work-up, including recrystallization) were evaluated, and is summarized below in Table 14. Lab scale batch size was approximately 30 g compound 170; pilot scale was approximately 1.2-2.4 kg compound 170; and production scale was approximately 175 kg compound 170. The amount of dimer present in process (IPC) was also monitored for different batch sizes prepared generally following the procedure of Example 8, and is summarized in Table 15, as area % via HPLC.

TABLE 14

Summary of impurities detected in isolated compound 190 produced according to previously-disclosed methods, compared with methods of the present disclosure, at different batch sizes.

|  | Lab Scale | | Pilot Scale | | Production Scale | |
| --- | --- | --- | --- | --- | --- | --- |
|  | Previous | Present | Previous | Present | Previous | Present |
| Dimer | 0.33-0.54% w/w | <0.05-0.15 area % | 0.38-0.51% w/w | n.d. | 0.29-0.40% w/w | n.d. |
| Alcohol | n.d. | n.d. | n.d. | n.d. | n.d. | n.d. |
| Ketone | n.d. | n.d. | n.d.-0.08 area % | 0.12-0.31 area % | <0.05-0.29 area % | 0.03-0.06 area % |

TABLE 15

Amount of dimer observed in process (IPC) in different batch sizes prepared according to the present process (sample taken when amount of compound 170 remaining was <1%).

| | Batch Size | IPC Dimer (area %) |
| --- | --- | --- |
| Lab Scale | 27.5 g | 0.12-0.28% |
| Pilot Scale | 2.0 kg | <0.05-0.15% |
| Production Scale | 172 kg | ≤0.05% |

Comparative Example 6

Compound 190 was prepared generally following the procedure of Comparative Example 4 ("previous process") and Example 8 ("present process"), on a production scale. The compound 190 from each process was then used to prepare compound 200 and compound 200 isolated as generally described in Examples 10 and 11.

The impurity profiles observed in compound 200 production scale batches prior to the final isolation steps, and after the final isolation steps (as described in Example 11), prepared using compound 190 from the previous compared to the present methods, is summarized in Table 16 below. Preparing compound 190 according to the present methods results in lower impurities in the downstream compound 200 both before and after final isolation, compared to using previously-described methods for preparing compound 190.

TABLE 16

Summary of impurity profiles in compound 200 prior to and after final recrystallization from toluene and ethanol, when using different methods to prepare compound 190 (previous method vs. present method).

|  | Previous Method | | Present Method | |
| --- | --- | --- | --- | --- |
|  | Prior to Final Isolation | After Final Isolation | Prior to Final Isolation | After Final Isolation |
| Dimer | 0.13 to 0.18 area % | 0.13 to 0.22 area % | not detected | Not detected |
| Alcohol | <0.05 area % | <0.05 area % | Not detected | Not detected |
| Ketone | Not detected to 0.06 area % | <0.05 area % | Not detected | Not not detected |

Example 12: Continuous Processing Methods of Compound 140 Hydrogenation

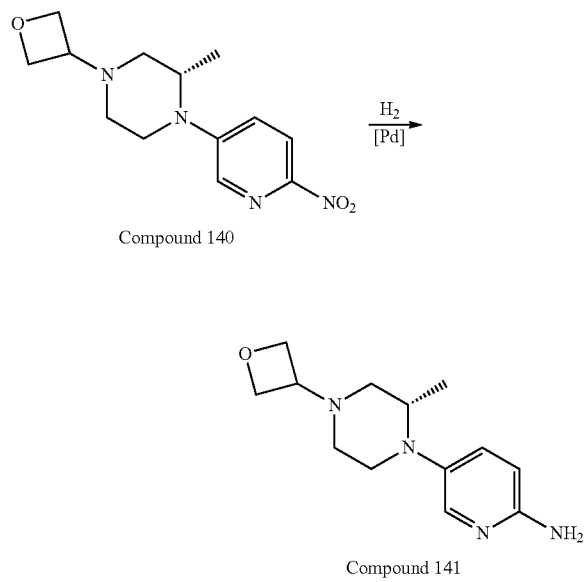

Compound 140

Compound 141

Figure 16:
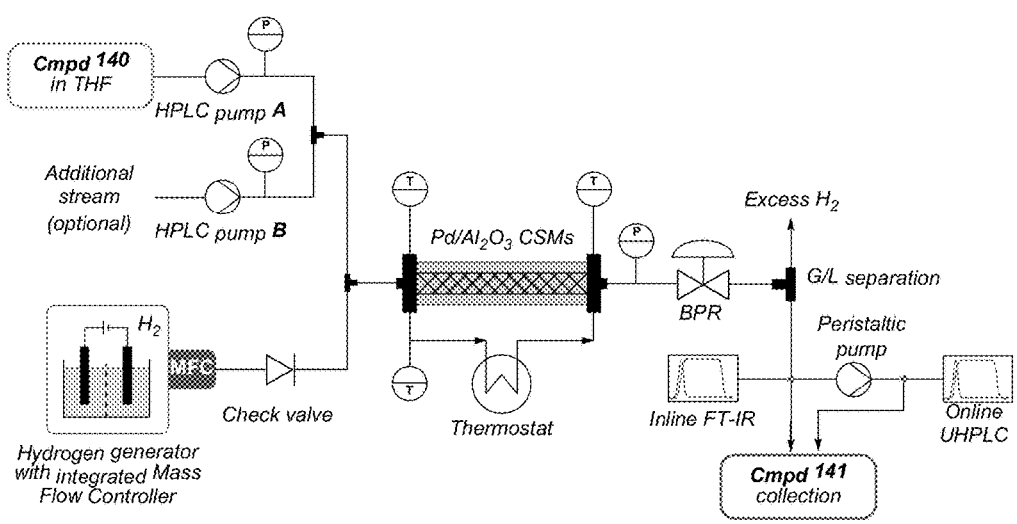
FIG. 16 is a schematic representation of the continuous processing setup described in Example 12, including real-time analysis by inline FT-IR and online UHPLC. P and T denote pressure and temperature sensors, respectively.

The hydrogenation of Compound 140 to produce Compound 141 was performed in an Ehrfeld Miprowa Lab reactor (0224-2-2004-F, Hastelloy C-276), as part of the Ehrfeld Modular MicroReaction System (MMRS). This reactor contains reaction channels with a rectangular cross-section (1.5 mm×12 mm×300 mm). Using a designated flange to reduce the number of channels used, either four (4 CSMs or 8 CSMs setup) or eight (16 CSMs setup) were connected in series. A schematic of the setup is provided in FIG. 16. The catalytic static mixers (CSMs) were manufactured from 316L stainless steel powder by selective laser melting, according to a design by CSIRO (Avril, A. et al., Continuous Flow Hydrogenations Using Novel Catalytic Static Mixers inside a Tubular Reactor. *React. Chem. Eng.* 2017, 2, 180-188; Hornung, C. H. et al., Use of Catalytic Static Mixers for Continuous Flow Gas-Liquid and Transfer Hydrogenations in Organic Synthesis. *Org. Process Res. Dev.* 2017, 21, 1311-1319; Hornung, C. H. et al., Additive Layer Manufacturing of Catalytic Static Mixers for Continuous Flow Reactors. Johnson Matthey Technol. Rev. 2018, 62, 350-360; Lebl, R. et al., Scalable Continuous Flow Hydrogenations Using Pd/Al$_2$O$_3$-Coated Rectangular Cross-Section 3D-Printed Static Mixers. Catal. Today 2020).

Pd CSMs were produced via electroplating. To produce Pd/Al$_2$O$_3$ CSMs, the 3D-printed static mixers were coated with Pd/Al$_2$O$_3$ via a slurry coating technique by CSIRO and Precision Plating Australia. The reactor was filled with CSMs as detailed below. The reactor volume is calculated as 2.7 mL per CSM, when considering the entire channel volume, or estimated as 1.7 mL per CSM, when taking into account only the void volume (channel volume minus volume occupied by the CSM itself).

4 CSM setup: The number of channels was limited to four, using the flange. The first two channels were filled with standard herringbone shaped flow baffles (three layers, 450 angle, strut width 1.0 mm, spacing 2.0 mm, length 300 mm) made of Hastelloy C-276 (6114-1-3244). The last two channels were filled with four Catalytic Static Mixers (CSMs) of 150 mm length each (2 per channel).

8 CSM setup: The number of channels was limited to four, using the flange. All four channels were filled with eight Catalytic Static Mixers (CSMs) of 150 mm length each (2 per channel).

16 CSM setup: The number of channels was expanded to all eight, by opening the flange. All four channels were filled with sixteen Catalytic Static Mixers (CSMs) of 150 mm length each (2 per channel).

Both Online and Offline UHPLC analyses were used to monitor reaction progress and products.

Offline UHPLC: Performed on a Shimadzu Nexera X2, fitted with a Waters XSelect CSH C18 XP column (150×3 mm, 2.5 μm particle size), and the following conditions:

Mobile Phase A: Aqueous ammonium formate (10 mM) adjusted to pH 9.0 with ammonium hydroxide.

Mobile Phase B: Acetonitrile

Total flow rate: 1 mL/min, with the following gradient program:

| Time (min) | A (%) | B (%) |
|---|---|---|
| 0 | 95 | 5 |
| 5 | 95 | 5 |
| 23 | 70 | 30 |
| 25 | 70 | 30 |
| 35 | 5 | 95 |

Analysis was performed at a wavelength of 238 nm. Reporting limit (r.l.) was set at 0.025 area %.

Online UHPLC Analysis: Performed using a Shimadzu Nexera X2 system, fitted with a Kinetex biphenyl column (100×2.1 mm size, 1.7 μm particle size), and the following conditions:

Isocratic method with a fixed concentration of 40% solvent B and a total flow rate of 0.4 mL/min. Samples were analyzed at a wavelength of 238 nm, using a relative absorbance ratio Compound 141:Compound 140 of 2.27.

Solvent A: aqueous $H_3PO_4/KH_2PO_4$ buffer (10 mM), with 0.33 mM n-octyl sodium sulfonate additive.

Solvent B: 67% MeOH, 33% water, $H_3PO_4/KH_2PO_4$ buffer (10 mM) with 0.33 mM n-octyl sodium sulfonate additive.

Representative continuous flow procedure: Input solution of Compound 140 was made up in a volumetric flask, with the required quantity of water (if indicated), then filled to the mark with THF. This solution was degassed with nitrogen while stirring or with sonication. The following startup procedure was followed:

1. Flush the reactor with methanol at the desired reaction flow rate.
2. Set the back pressure regulator to the desired reaction pressure.
3. Begin flushing the reactor with THF at the desired reaction flow rate.
4. Set the thermostat to the desired reaction temperature and allow it to be reached.
5. Allow the system to equilibrate for at least 30 min.
6. Set $H_2$ flow rate and allow pressure to build to the required level.
7. Upon $H_2$ reaching reaction pressure, pause $H_2$ flow.
8. Turn off liquid pump briefly, to allow input to be switched to substrate solution (using a valve).
9. Start pump and $H_2$ flow, as well as UHPLC injections and FT-IR measurement.

References to azo, azoxy, and dimer impurities with respect to the Compound 140 hydrogenation are referring to the following structures:

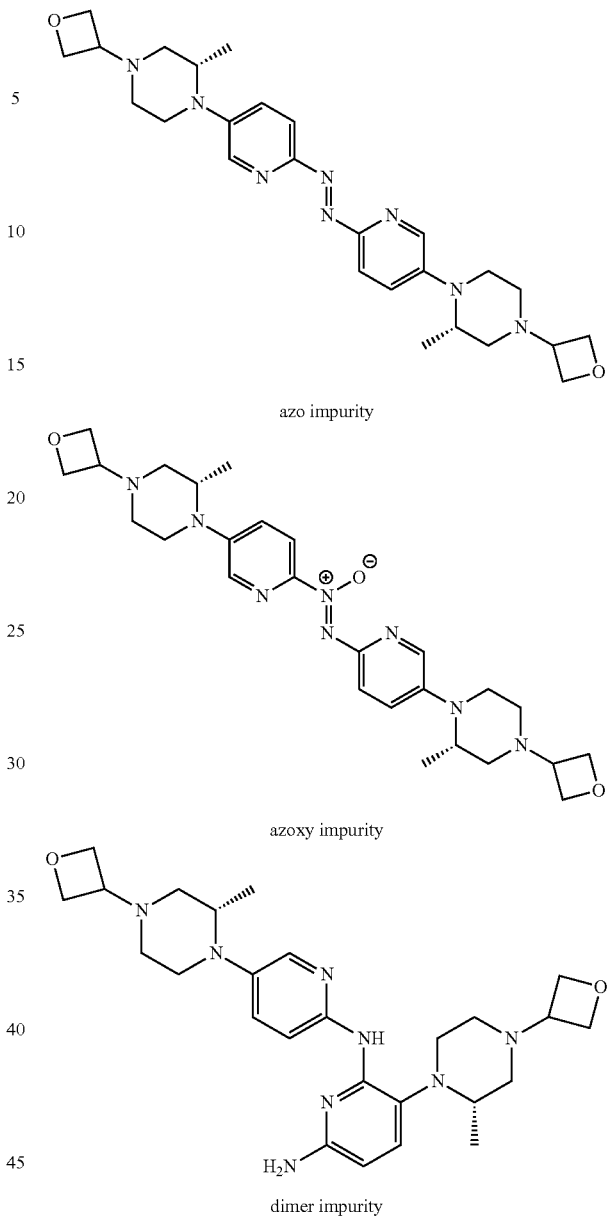

azo impurity azoxy impurity dimer impurity

Initial Evaluation of Continuous Processing Parameters

The initial parameters were: 0.2 M Compound 140 in THF with no added water, 20 bar pressure, 80° C. jacket temperature, using 4 catalytic static mixers (CSMs). Pd-electroplated CSMs displayed only a minimal extent of reaction (~6% conversion), whilst $Pd/Al_2O_3$ slurry coated CSMs were substantially more effective under the same conditions (achieving Compound 141 at 98.632 area %). Without wishing to be bound by theory, this may be attributed to the significantly higher effective surface area of the $Pd/Al_2O_3$ variant.

Increasing the flow rate from 1 to 2 mL/min resulted in incomplete conversion of Compound 140, and the conversion appeared to decrease over the 30 min at which these conditions were applied. This effect was increasingly apparent at higher flow rates (3, 4 and 5 mL/min), which appeared to show a decrease in conversion at a constant gradient. The flow rate was returned to 1 mL/min, where complete substrate conversion was no longer observed (~95% conversion). Results are summarized in Table 17 below.

TABLE 17

Offline UHPLC results from first flow rate screen.

| Liquid flow rate [mL/min] | Cmpd 141 [area %] | Cmpd 140 [area %] | Combined azo + azoxy impurities [area %] | Dimer impurity [area %] |
|---|---|---|---|---|
| 1.0 | 98.355 | 0.060 | 0.130 | 0.023 |
| 2.0 | 94.865 | 2.233 | 0.252 | 0.03 |
| 3.0 | 81.183 | 14.141 | 0.449 | 0.028 |
| 4.0 | 64.712 | 30.178 | 0.469 | 0.022 |
| 5.0 | 50.764 | 44.394 | 0.509 | 0.019 |
| 1.0* | 88.085 | 8.505 | 0.235 | 0.033 |

This type of performance decrease has been observed before using CSMs, and may be attributed to catalyst inhibition over time by reaction species (Lebl, R. et al., Scalable Continuous Flow Hydrogenations Using Pd/Al$_2$O$_3$-Coated Rectangular Cross-Section 3D-Printed Static Mixers. *Catal. Today* 2020). One approach to addressing this problem is the inclusion of protic solvent and a higher reaction temperature.

In a second set of experiments, the jacket temperature was increased from 60 to 140° C. in steps of 20° C.; this appeared to have a significant positive influence on the reaction, in both conversion and in decreasing its erosion over time. The gradient of conversion loss was substantially shallower at 80° C. compared to 60° C. and was not observed at all at 120° C. To determine whether any change had occurred over the duration, the final set of conditions were a replicate of the initial conditions. A substantial difference was observed between the two instances (78% conversion before vs 56% conversion after), implying that some loss of performance was also occurring even at higher temperature and would have an effect in longer term processing.

The approach of adding a protic solvent was also examined, by first adding methanol as a co-solvent. The reactivity and impurity profile were drastically affected by the inclusion of methanol, shown in Table 17 below.

TABLE 17

Offline UHPLC results from reactions using methanol as co-solvent

| MeOH flow rate [mL/min] | MeOH ratio [v/v] | Cmpd 141 [area %] | Cmpd 140 [area %] | Combined azo + azoxy impurities [area %] | Dimer impurity [area %] |
|---|---|---|---|---|---|
| 0.0 | 0.00 | 94.744 | 1.865 | 2.107 | 0.034 |
| 0.5 | 0.20 | 71.976 | 23.378 | 1.472 | 0.042 |
| 1.0 | 0.33 | 78.454 | 16.134 | 2.362 | 0.056 |
| 2.0 | 0.50 | 79.644 | 13.46 | 5.229 | 0.036 |

Water (2 equiv) is generated as a by-product of the hydrogenation reaction, thus it was thought that its presence may not be detrimental to reaction performance. However, the CSMs use Al$_2$O$_3$ as a catalyst support material, leading to concerns over CSM stability and catalyst degradation under aqueous conditions.

To test catalyst degradation, one single CSM was exposed to an increasing quantity of water from 4 to 512 equiv in a control experiment (512 equiv corresponds to a THF:water volumetric ratio of ~2:1.9). Surprisingly, no loss of activity or visible degradation was observed. Inductively coupled plasma mass spectrometry (ICP-MS) analysis of the reactor effluent showed no elevated levels of palladium, indicating that the CSMs were stable, even in the presence of such high levels of water. In view of the surprising stability in the presence of water, reaction condition development was continued without concern for the effect of water on CSM stability.

Using a second HPLC pump, 1 to 4 equiv of water were introduced with the reaction stream. The presence of water appeared to significantly improve the rate of reaction, and also prevented catalyst deactivation over time. The maximum examined value, 4 equiv, provided almost double the level of conversion, versus conditions in the absence of water (38% vs 73%).

The reaction concentration was also examined, using a 0.5 M solution of Compound 140 diluted with THF using a second pump. A downward trend was observed over time at the highest concentration (0.5 M) due to catalyst deactivation under higher concentrations. Reaction conditions: pressure=20 bar, jacket temperature=80° C., H$_2$=4.5 equiv, total liquid flow rate=2.0 mL/min. Results are summarized in Table 18 below. For the remainder of the experiments, 0.4 M Compound 140 was used.

TABLE 18

Offline UHPLC results from Compound 140 concentration screen

| Cmpd 140 Conc. [M] | Liquid flow rate [mL/min] | THF flow rate [mL/min] | H$_2$ flow rate [mLN/min] | Cmpd 141 [area %] | Cmpd 140 [area %] | Combined azo + azoxy impurities [area %] | Dimer impurity [area %] |
|---|---|---|---|---|---|---|---|
| 0.5 | 2.0 | 0.0 | 100 | 64.841 | 29.659 | 0.304 | 0.021 |
| 0.4 | 1.6 | 0.4 | 80 | 61.409 | 33.405 | 0.247 | 0.019 |
| 0.3 | 1.2 | 0.8 | 60 | 62.305 | 32.562 | 0.217 | 0.019 |
| 0.2 | 0.8 | 1.2 | 40 | 65.98 | 29.277 | 0.208 | 0.015 |
| 0.1 | 0.4 | 1.6 | 20 | 74.64 | 20.899 | 0.204 | 0.035 |

Using this reactor set up, a series of reaction parameters were rapidly screened over multiple experimental runs. Temperature, water content, and pressure were all varied. From these experiments (25 in total, including 2 repetitions) it was determined that temperature was by far the most significant parameter, followed by H$_2$O loading. Conversely, reaction pressure had a relatively minimal effect. A contour plot representing predictions of conversion at different conditions was plotted from this data. A clear trend was observed, in which higher temperature and higher H$_2$O loading improved conversion.

Separately, it was experimentally determined that the flow rate of H$_2$ had no effect on reaction performance, so long as sufficient H$_2$ was supplied. The residence time is not affected by excess gas, which may be due to a stratified flow regime within the reactor.

Further Evaluation with 8 CSMs

Figure 14A:
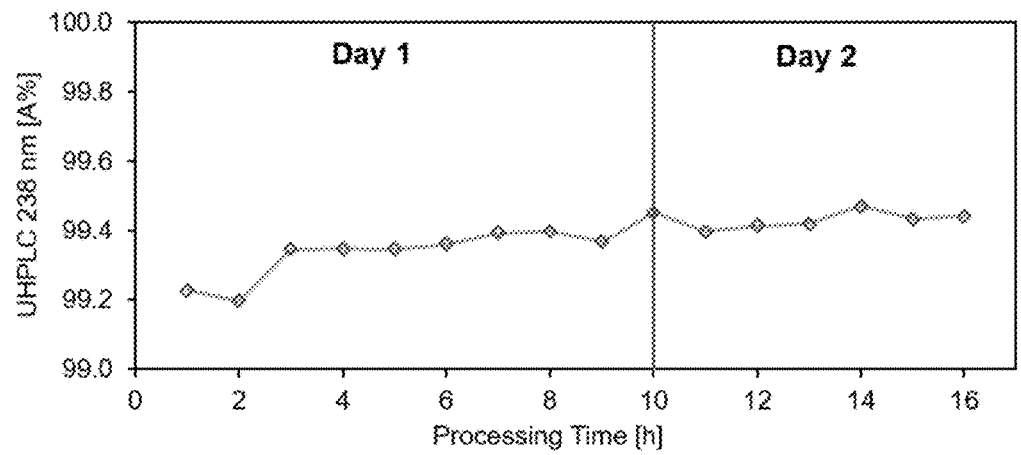
FIG. 14A is a graph of Compound 141 area % as evaluated by ultra-high performance liquid chromatography (UHPLC) measurements from fractionated reactor output, monitoring a continuous processing method for producing Compound 141 from Compound 140, as described in Example 12.
Figure 14B:
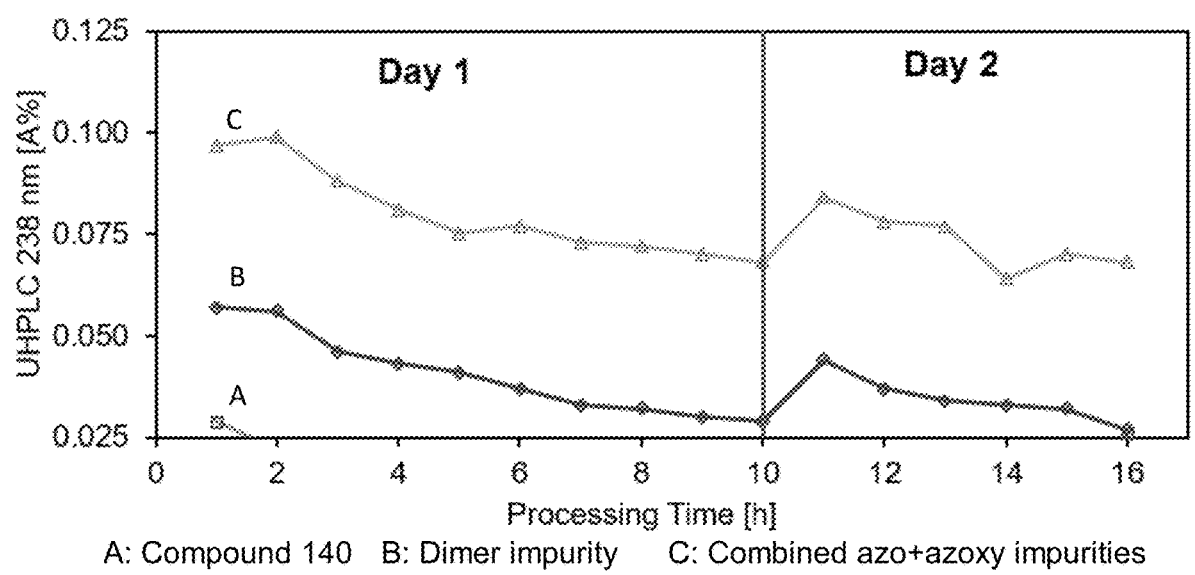
FIG. 14B is a graph of the area % of Compound 140, combined azo+azoxy impurities, and dimer impurity, as evaluated by ultra-high performance liquid chromatography (UHPLC) measurements from fractionated reactor output, monitoring a continuous processing method for producing Compound 141 from Compound 140, as described in Example 12.

Further experiments were performed with 8 CSMs to evaluate potential throughput that could be reached in this reaction system. Key to this evaluation was the quantity of impurities (azo+azoxy total, and dimer) observed with increasing flow rate. Previous experiments with 4 CSMs determined that a higher flow rate resulted in increased levels of these impurities (due to shorter residence time) but also that adding water to the input solution could decrease them. An array of conditions were examined, in which the flow rate and water content were varied (Table 19). The jacket temperature, pressure, and H$_2$ equiv were set at 120° C., 20 bar and 3.3 equiv (10% excess), respectively.

this demonstration were: pressure=20 bar, jacket temperature=120° C., H$_2$=3.3 equiv., liquid flow rate 8 m/min flow rate, 6 equiv H$_2$O, Compound 140 concentration 0.4 M. During the course of this experiment, 16 fractions were collected (1 per hour) for detailed offline analysis. Offline analysis of the fractionated reactor output showed that the quantity of Compound 141 was 99.2 area % in the first fraction measured and showed no decrease over time—in fact a gradual increase was observed (FIG. 14A). Starting material Compound 140 and azo+azoxy (combined) and dimer impurities were low in the first fraction and decreased over time (FIG. 14B). None of the collected fractions provided >0.1 area % of combined azo+azoxy impurities or the dimer impurity. Over this period, 850 g (3.07 mol) of starting material was processed, with no loss in catalyst activity over time. Based on a total Pd loading of 96 mg (0.9 mmol, 12 mg per CSM), this represents an effective catalyst loading of just 0.011 weight %, which is expected to decrease with longer term processing. When considering the long-term stability of such a process, catalyst leaching is a concern. Accordingly, ICP-MS measurements were carried out on six of the fractions collected and compared with measurements of the input reaction mixture and solvent blanks. No detectable level of Al was observed in any samples, implying that there was no degradation of the alumina support over time, in agreement with previous work using this type of CSM (Lebl, R. et al., Scalable Continuous Flow Hydrogenations Using Pd/Al$_2$O$_3$-Coated Rectangular Cross-Section 3D-Printed Static Mixers. *Catal. Today* 2020).

TABLE 19

Offline UHPLC analysis of 8 CSM process, varying flow rate and water inclusion

| Entry | Flow rate [mL/min] | H$_2$O [equiv] | Cmpd 141 [area %] | Cmpd 140 [area %] | Combined azo + azoxy [area %] | Dimer [area %] |
|---|---|---|---|---|---|---|
| 1 | 4.0 | 2.0 | 98.682 | <r.l. | 0.083 | 0.053 |
| 2 | 4.0 | 4.0 | 99.022 | <r.l. | 0.089 | 0.046 |
| 3 | 4.0 | 8.0 | 98.836 | <r.l. | 0.074 | 0.031 |
| 4 | 6.0 | 2.0 | 98.558 | 0.046 | 0.127 | 0.066 |
| 5 | 6.0 | 4.0 | 98.558 | 0.028 | 0.110 | 0.047 |
| 6 | 6.0 | 8.0 | 98.871 | <r.l. | 0.084 | 0.032 |
| 7 | 8.0 | 2.0 | 97.817 | 0.212 | 0.123 | 0.063 |
| 8 | 8.0 | 4.0 | 98.648 | 0.078 | 0.118 | 0.047 |
| 9 | 8.0 | 8.0 | 99.104 | <r.l. | 0.091 | 0.033 | r.l = reporting limit, 0.025 area %

All results (aside from entry 7) showed levels of the desired product >98.5 area %, and <0.1 area % of starting material Compound 141, and there was a clear trend observed in the quantity of the measured impurities. At low flow rate (entry 1-3) all results showed impurity levels <0.1 area %; while at the increased flow rate of 6 mL/min (entry 4-6) and 8 mL/min (entry 7-9) impurity levels were <0.1 area % only when 8 equiv H$_2$O was included in the feed solution. These experiments showed that a flow rate of 8 mL/min (corresponding to 192 mmol/h throughput) may be possible with an acceptable purity profile.

The longer-term stability of the reactor system was then investigated by carrying out a continuous flow reaction over two working days: for 10 h, then for 6 h, with solvent washing in between the two periods; the reactor was stored in MeOH overnight at ambient conditions between the two runs. This evaluated the behavior of the reactor, the impurity profile over time, and to detect any potential catalyst leaching or deactivation. The experimental conditions selected for Maximum Evaluated Throughput Processing (16 CSMs)

The increase in possible throughput from 4 to 8 CSMs was higher than an expected linear scale up (48 mmol/h to 192 mmol/h; a four-fold increase). Without wishing to be bound by theory, this may be caused by improved mixing, which is achieved at higher flow rates, but may also be influenced by minor temperature increase due to reaction exotherm. To evaluate the maximum productivity reachable in the reactor setup used, an additional experiment using a full capacity of 16 CSMs was carried out. Minor modifications were made, including a heat exchanger prior to the reactor and using four additional internal temperature sensors inside the reactor itself (between fluidic channels).

Figure 15:
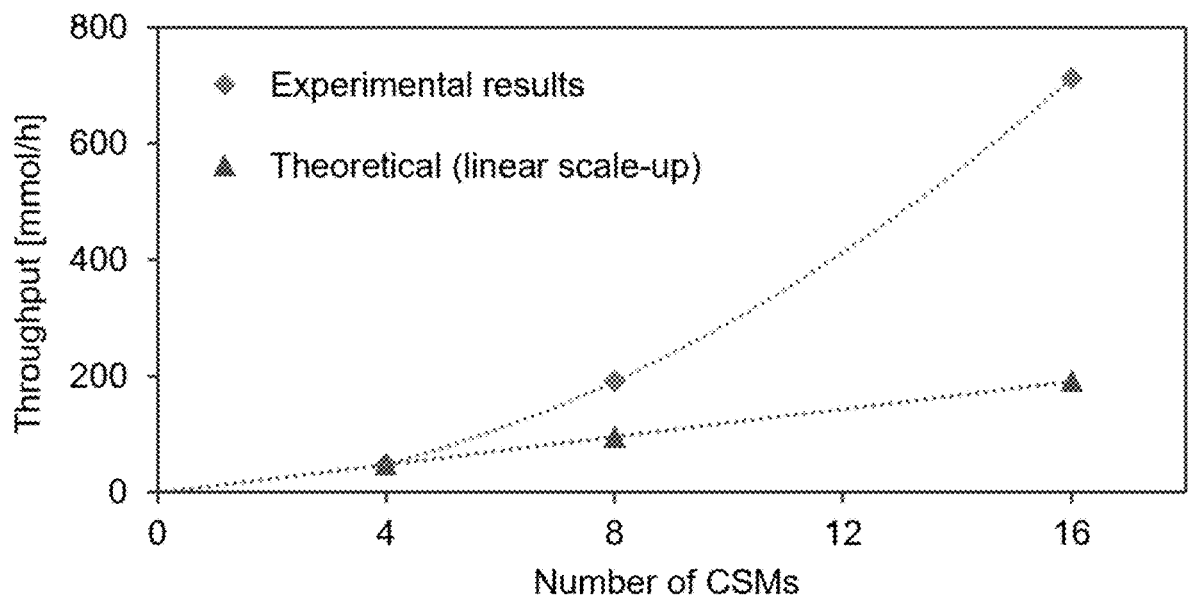
FIG. 15 is a graph of theoretical expected throughput compared to actual achieved experimental output as observed in the continuous processing method described in Example 12.

An initial screening experiment examined the reaction performance at 16 mL/min (according to linear scalability from the 8 CSM setup) as well as 20, 24, 27 and 30 mL/min. Surprisingly, an excellent impurity profile was observed, even at 30 mL/min, with observed levels of azo+azoxy (combined) at 0.082 area %, and an exceptionally low level of dimer impurity (0.039 area %). These conditions were run for 1 h, to ensure stability and process a larger quantity of material. Throughput achieved represents a remarkable improvement compared to the expected value (FIG. 15). This corresponds to an increasing space-time yield with scale-up, possibly due to improved mixing with higher flow rates. The maximum space-time yield achieved here is 26.2 mol/L/h, owing to the small reactor channels used (27.2 mL void volume).

Comparative Example 7: Preparation of Compound 141 Via Two Batch Methods Compared to Continuous Flow Processing Method The continuous flow processing method described in Example 12 and a batch process, both using a THF/water solvent system (approximately 5% vol water), were compared with a previously published batch method using a toluene/methanol solvent system (Zhang, H. et al., Development of an Efficient Manufacturing Process for Reversible Bruton's Tyrosine Kinase Inhibitor GDC-0853. *Org. Process Res. Dev.* 2018, 22, 978-990).

Batch procedure in PhMe/MeOH: In a glass autoclave vessel, compound 140 (4.8 g, 17.2 mmol) was dissolved in a mixture of PhMe and MeOH (1:1 v/v, 27 mL). Then, Pd/C 5% (wet, 56.8% $H_2O$, 222 mg) was added, as well as acetic acid (492 µL) and water (60 µL). The reactor was closed and sealed, purged 3 times with $H_2$ (at 1 bar), then pressurized to 20 bar. The reactor was then heated to 50° C. with slow stirring. The temperature was then controlled by altering the stirring speed to maintain a temperature below 55° C. The reaction was stirred for 3 h, with a temperature increase to 60° C. for the final 1.5 h. The reaction was then cooled to 35° C., then depressurized and sampled for UHPLC analysis, using the UHPLC procedure described in Example 7 above.

Batch procedure in THF/$H_2O$: A glass autoclave vessel was filled with Pd/C 5% (wet, 56.8% $H_2O$, 154 mg) and 30 mL of a 0.4 M compound 140 solution (12 mmol total) in THF, with 2.4 M added water. The reactor was closed and sealed, purged 3 times with $H_2$ (at 1 bar), then pressurized to 20 bar. The reactor was then heated to 50° C. with slow stirring. At the beginning of the reaction, an exotherm was observed, with the reaction temperature reaching 61° C. The temperature was then controlled by decreasing the stirring speed to maintain a temperature below 60° C. The reaction was stirred for 3 h, with a temperature increase to 60° C. for the final 1.5 h. The reaction was then cooled to 35° C., then depressurized and sampled for UHPLC analysis, using the UHPLC procedure described in Example 7 above.

Continuous Flow procedure: The results of the 8 CSM, 16 h (10 h+6 h) run as described in Example 12 above were used. The jacket temperature, pressure, and $H_2$ equiv were set at 120° C., 20 bar and 3.3 equiv (10% excess), respectively; 0.4 M Compound 140 was used; with 8 mL/min flow rate, 6 equiv $H_2O$.

TABLE 20

Offline UHPLC results from batch comparisons, compared with the CSM flow procedure.

| Method | Cmpd 141 [area %] | Starting material Cmpd 140 [area %] | Combined azo and azoxy impurities [area %] | Dimer impurity [area %] |
|---|---|---|---|---|
| Batch (PhMe/MeOH) | 96.572 | <r.l. | 0.182 | 1.196 |
| Batch (THF/$H_2O$) | 99.397 | <r.l. | <r.l. | <r.l. |

TABLE 20-continued

Offline UHPLC results from batch comparisons, compared with the CSM flow procedure.

| Method | Cmpd 141 [area %] | Starting material Cmpd 140 [area %] | Combined azo and azoxy impurities [area %] | Dimer impurity [area %] |
|---|---|---|---|---|
| Flow 16 h extended operation (THF/$H_2O$) | 99.441 | <r.l. | 0.068 | 0.027 | r.l. = reporting limit, 0.025 area %

Example 13: Additional Continuous Processing Methods

Figure 23:
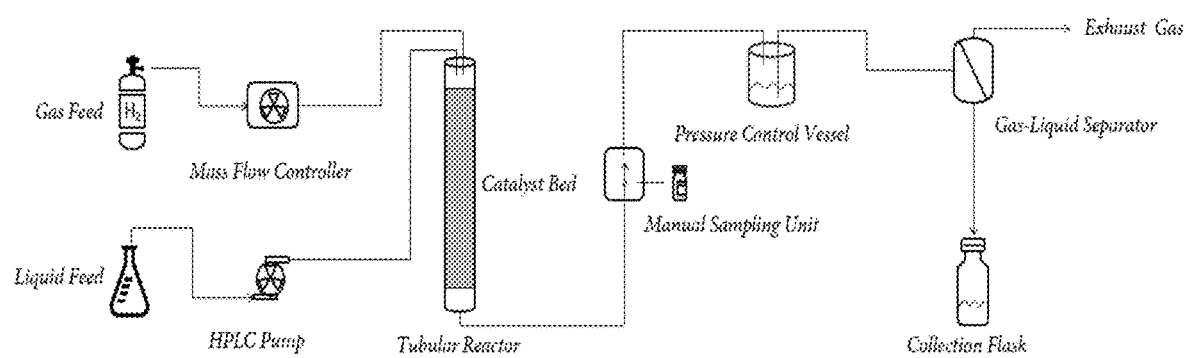
FIG. 23 is a schematic representation of the continuous processing setup described in Example 13, using a fixed-bed catalyst in the form of metal deposited on a solid support and contained in a tubular reactor.

Additional continuous processing experiments were carried out to investigate the impact of using metal catalysts on spherical supports in the preparation of aminopyridine 141. A schematic depiction of the experimental set up used is provided in FIG. 23. A fixed-bed catalyst was housed in a tubular reactor, which was fed continuously with hydrogen gas (feeding controlled by a mass flow controller) and a solution of nitropyridine 140 (feeding controlled by a HPLC pump). After passing through the fixed bed catalyst, the solution resulting from the hydrogenation reaction (containing product aminopyridine 141) was sampled via a manual sampling unit, passed through a pressure control vessel and back-pressure regulator and then collected upon gas/liquid separation.

Initial reaction conditions investigated were using a 3% Pd/$Al_2O_3$ catalyst ($Al_2O_3$ spheres, provided by Johnson Matthey, code 110002). Using a small reactor (internal diameter 0.6 cm, length 15 cm) the reactor temperature was investigated first by feeding the reactor with a solution of nitropyridine 140 in THF (concentration 0.36 M) with a flow of 1 mL/min. The feeding of $H_2$ was kept at 30 mL/min and the pressure of the system at 20 bar. The conversion of nitropyridine 140 into aminopyridine 141 improved when increasing the temperature from 60° C. to higher values. At the same time, the amount of known undesired impurities (azo, azoxy and dimer) was reduced below 0.20 area % each, as judged by HPLC. The sum of unidentified impurities also decreased as summarized in Table 21 with higher temperature, reaching an optimum at $T_{mantel}$=100° C. (entry 3). Further increase of the temperature to $T_{mantel}$=120° C. brought no advantage, as it produced higher amounts of unknown impurities (entry 4).

TABLE 21

HPLC results of the nitro-reduction of compound 140 obtained with a 3% Pd/$Al_2O_3$ catalyst at different reactor temperatures.

| Entry | $T_{mantel}$ [° C.] | Compound 141 [area %] | Starting material cmpd 140 [area %] | Combined azo and azoxy impurities [area %] | Dimer Impurity [area %] |
|---|---|---|---|---|---|
| 1 | 60 | 94.18 | 2.64 | 1.77 | 0.13 |
| 2 | 80 | 98.50 | 0.10 | 0.11 | 0.16 |
| 3 | 100 | 98.90 | <r.l. | 0.09 | 0.13 |
| 4 | 120 | 98.53 | <r.l. | 0.13 | 0.13 |

After setting the reactor temperature to 100° C., the system pressure was briefly investigated, but in the range from 10 to 30 bar no major difference was observed, therefore it was decided to keep this value at 20 bar for further investigations. Regarding $H_2$ feeding, it was observed that a small excess of $H_2$ to what is needed for the stoichiometry of the reaction (i.e. 3 eq. with regard to nitropyridine 140) was necessary but large excesses did not bring any advantage. In contrast to what observed in the case of catalytic static mixers (see example 12), the use of water as additive did not offer any particular advantage (Table 2) and it was decided to continue experimentation in the absence of this additive.

TABLE 22

Results obtained in the presence and absence of water as additive under the conditions reported Table 21, entry 2 ($T_{mantel}$ = 80° C.).

| Water as additive | Compound 141 [area %] | Starting material cmpd 140 [area %] | Combined azo and azoxy impurities [area %] | Dimer Impurity [area %] |
|---|---|---|---|---|
| 4 eq. | 98.43 | 0.05 | 0.17 | 0.12 |
| none | 98.50 | 0.10 | 0.11 | 0.16 |

Figure 20:
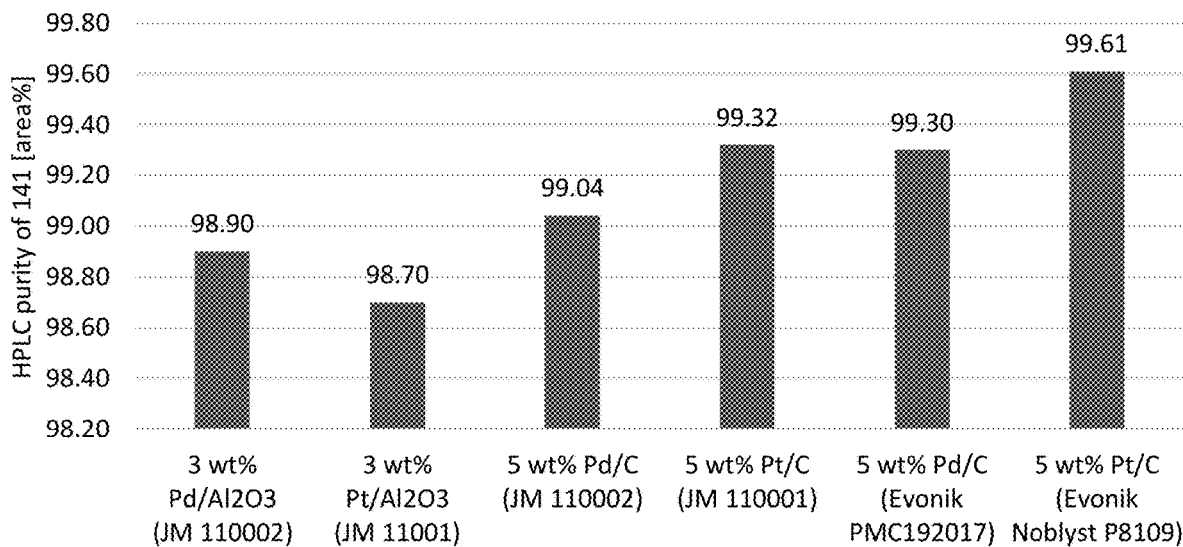
FIG. 20 is a graph summarizing the performance of different catalysts in the flow hydrogenation of 141 under the reaction conditions reported in Table 21, entry 3.

After establishing reaction conditions for the reduction of nitropyridine 140 (see Table 21, entry 3), different catalyst types (metal support=alumina spheres and carbon granules) were tested. Alumina-supported Pd and Pt particles with a metal content of 3% performed very similarly in terms of product purity, reaching 98.90 and 98.70 area % of compound 141 respectively. Next, granules of activated carbon with a metal loading of 5% were tested under the same conditions, yielding product with a purity of >99.0 area %. These carbon-based catalyst further showed that platinum outperformed palladium. The best result of 99.61 area % product purity at full conversion was obtained with the 5% Pt/C catalyst NOBLYST® P8109 supplied by Evonik (FIG. 20). The catalyst loadings provided in this Example 13 are dry wt %.

Figure 21:
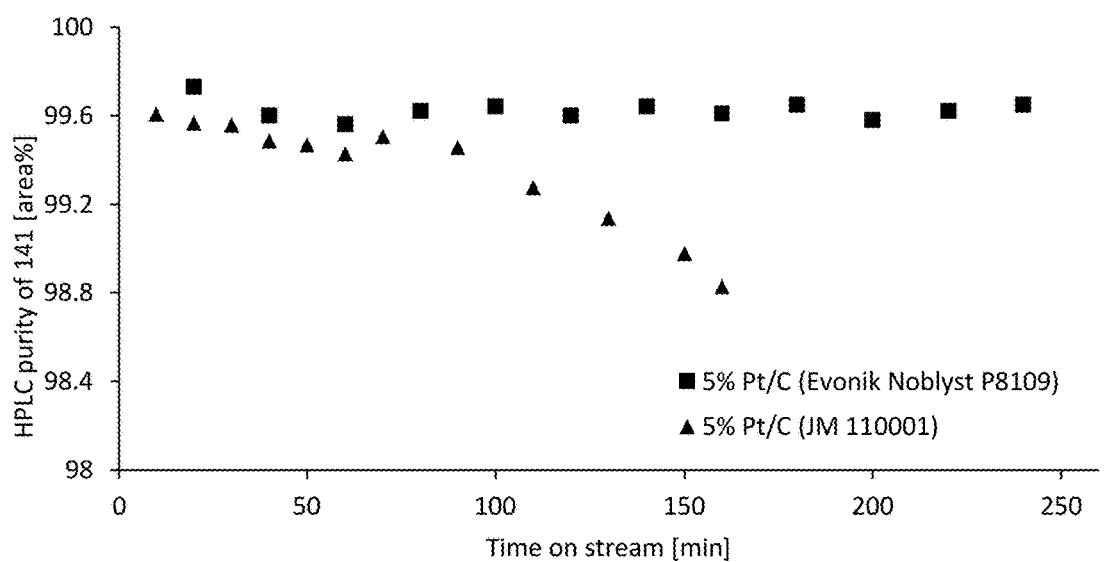
FIG. 21 is a graph summarizing the performance of two different 5% Pt/C catalysts over time in the reduction of compound 140 under the reaction conditions reported in Table 21, entry 3.

The two 5% Pt/C catalysts (one by Johnson Mattehy, type 110001 and one by Evonik, type Noblyst® P8109) were identified as being most promising, and next these catalysts were evaluated over time in the production of compound 141. FIG. 21 summarizes the results observed, which showed a superior activity of NOBLYST® P8109 over a long period of time, while JM 110001 appeared to display reduced performance after about 2 h under the chosen reaction conditions for the reaction under investigation.

Finally, incorporating the evaluations above, the reduction of nitropyridine 140 was scaled up increasing the reactor volume and the throughput of the hydrogenation process as described below.

Liquid feed: A 0.36 M solution of nitropyridine 140 in degassed THF was prepared as a liquid feed for the continuous hydrogenation system.

Catalyst bed: A tubular reactor (internal diameter 1.2 cm, length 15 cm) was filled with the catalyst 5% Pt/C Evonik NOBLYST® P8109 (4.9 g).

Before starting the reaction, the reactor was flushed with THF at 5 mL/min for 20 min. During this time the reactor was heated to the desired temperature ($T_{mantel}$=100° C.) and hydrogen fed to the reactor at a rate of 150 mL/min using a mass flow controller and the system pressure was set at 20 bar. Once the system was pre-conditioned, the liquid feed was switched from THF to the solution of nitropyridine 140 prepared above. The liquid feed rate was kept at 10 mL/min, the $H_2$ feed rate increased at 300 mL/min and the reaction conditions maintained at $T_{mantel}$=100° C. and 20 bar, while sampling the output reaction mixture at regular intervals (every 20 min) and collecting it over time. Hydrogenation was continued for a total of 6 h. After this time the liquid feed was switched again to THF to wash the system, which was then cooled and made inert again by switching the gas feed to argon. On the following day the whole procedure to start the reaction was repeated and the hydrogenation of nitropyridine 140 restarted under the same conditions described above and maintained for 1 h. The goal was to demonstrate that the catalyst bed could be used once again with comparable results. In total, the continuous hydrogenation was performed with the same catalyst bed for a total of 7 h reducing nitropyridine 140 at a rate of 60 g/h.

Figure 22:
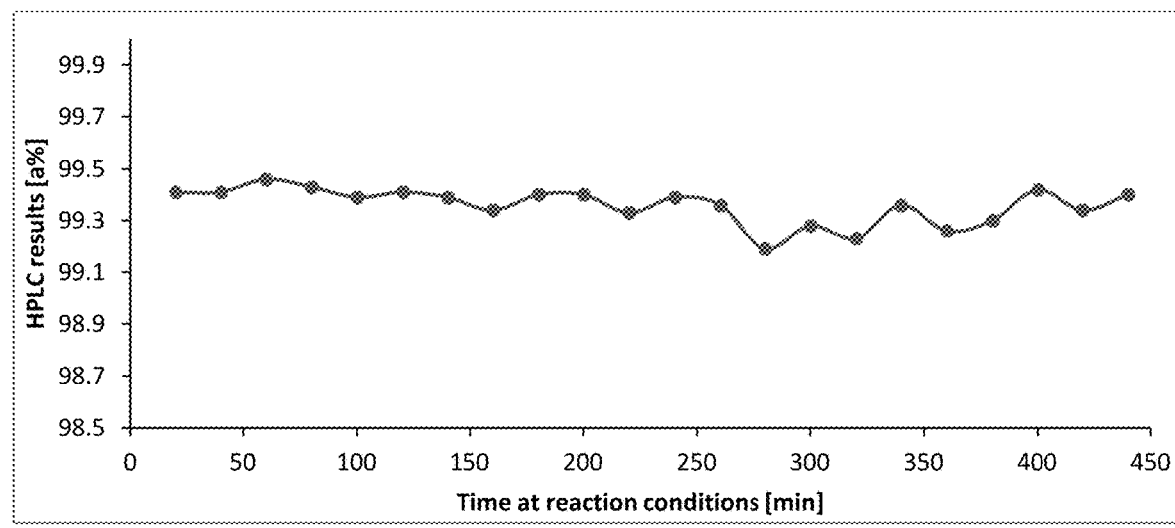
FIG. 22 is a graph of the purity of aminopyridine 141 solution obtained by sampling at regular intervals in the scaled-up continuous flow described in Example 13.

The outcome of the reaction and the stability of the process over time was monitored by HPLC analysis of the sampled reaction solution over time, looking at the purity of the desired product and the formation of undesired impurities. FIG. 22 summarizes the HPLC purity of the aminopyridine 141 sampled from the solution coming out of the fixed bed catalyst over time.

Two portions of the solution resulting from the hydrogenation process were collected separately to evaluate the overall purity and yield of the material, collected at two different stages of the overall process. Portion A consisted of 50 g of solution collected during the first 195 min of the flow process. Portion B consisted of 100 g of solution collected between 195 and 380 min of reaction time. The product present in each portion was isolated by evaporating the solvent under vacuum until constant weight was attained to give aminopyridine 141 in 85.6 and 89.6% yield respectively. The purity of the two isolated materials are reported in Table 23.

TABLE 23

Purity of isolated materials from the flow hydrogenation of 140 using a fixed catalyst bed

| Portion | Compound 141 [area %] | Starting material cmpd 140 [area %] | Combined azo and azoxy impurities [area %] | Dimer Impurity [area %] |
|---|---|---|---|---|
| A | 99.38 | <r.l. | <r.l. | 0.13 |
| B | 99.39 | 0.04 | 0.03 | 0.07 |

XRF analysis of the isolated material from portions A and B did not detect any trace (r.l.=1 ppm) of Pt or other metals, showing that no leaching of the metal into the product has occurred during the process.

Example 14: Preparation of Various Crystalline Solvates of Compound 200

Ethanol hemi-solvate: 100.9 mg of amorphous compound 200 was suspended in 1.2 mL of ethanol and aged at 0° C. for 5 days. The white suspension was isolated at 0° C. by centrifugal filtration. The wet filter cake was dried upon open storage at ambient temperature. The sample was further dried at 50° C. under vacuum for 3 days, then characterized by XRPD. The XRPD spectrum is provided in FIG. 17, and the peak list is provided in Table X.

Toluene solvate: 203.2 mg of amorphous compound 200 was exposed to toluene vapors at ambient temperature for 7 days. The resulting wet powder was gently dried under toluene vapor at 100 mbar/ambient temperature for 2 days, then characterized by XRPD. The XRPD spectrum is provided in FIG. 18, and the peak list is provided in Table X.

Ethanol solvate: 98.1 mg of amorphous compound was dissolved in 10 mL of ethanol at 80° C. The solution was cooled and polished filtered to obtain a particle-free solution. The clear solution was reheated to 80° C. and then rapidly cooled under stirring. The resulting suspension was agitated for 2 days at −10° C. The crystals were isolated by filtration and characterized by XRPD. The XRPD spectrum is provided in FIG. 19, and the peak list is provided in Table X.

XRPD Characterization: X-ray diffraction patterns were recorded at ambient conditions in transmission geometry with a Stoe Stadi P diffractometer (Cu $K_{\alpha 1}$ radiation [1.5406 Å], primary Ge-monochromator, Mythen 1K silicon strip detector, angular range 3° to 42° 2Theta, stepwidth 0.02° 2Theta and 20 seconds measurement time per step). The samples were prepared and analyzed without further processing (e.g. grinding or sieving) of the substance. Measurement and evaluation of the X-ray diffraction data is done using WinXPOW software (STOE & Cie GmbH, Darmstadt, Germany). The positional error for each individual peak is ±0.2° 2Theta.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A method of preparing compound 190, or a salt thereof, the method comprising:
   (a) forming a reaction mixture comprising compound 170, compound 181, a palladium catalyst, and a solvent system comprising a base, wherein the equivalent ratio of the palladium catalyst to compound 170 is from about 0.001:1 to less than 0.005:1; and
   (b) reacting the reaction mixture to form a reaction product mixture comprising compound 190 according to the following scheme:

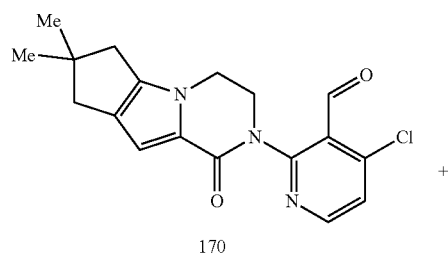
170

+

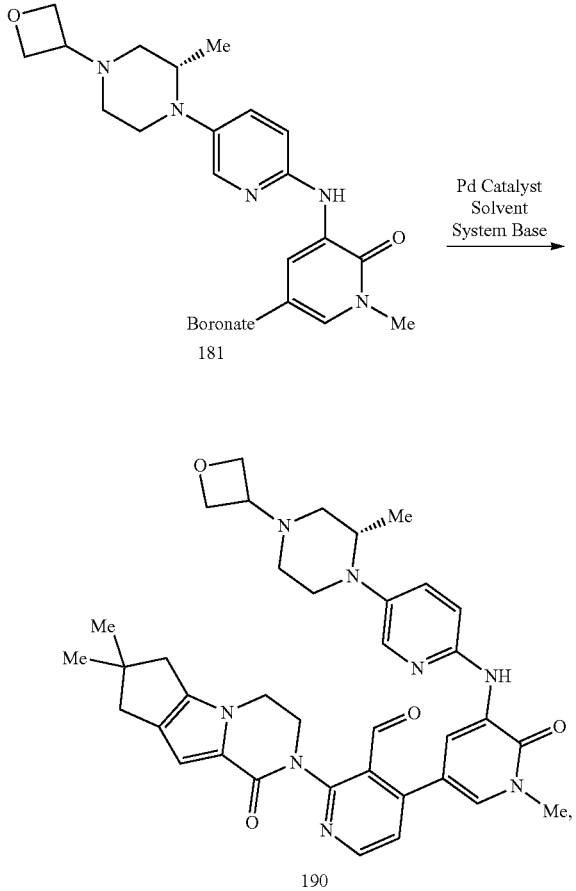

wherein the palladium catalyst comprises a palladium(II) species containing a phosphine ligand and at least one palladium-carbon bond, wherein:
   (i) the fragment giving rise to the palladium-carbon bond is an allyl derivative of the formula

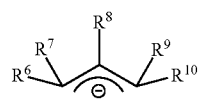

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring;

wherein the yield of compound 190, or salt thereof, is at least 50% based on compound 170.

2. The method of claim 1, wherein the yield of compound 190 or salt thereof is at least 80%, and:
   (a) the content of a dimer impurity is less than 0.1 area % based on compound 190, or salt thereof, wherein the dimer impurity is of the structure

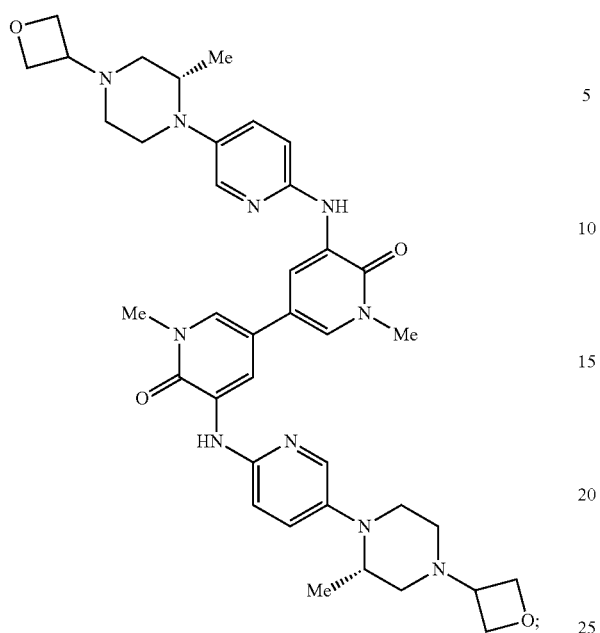

and (b) the combined content of an alcohol and a ketone impurity is less than 0.25 area % based on compound 190, or salt thereof, wherein the alcohol and ketone impurities are of the structures

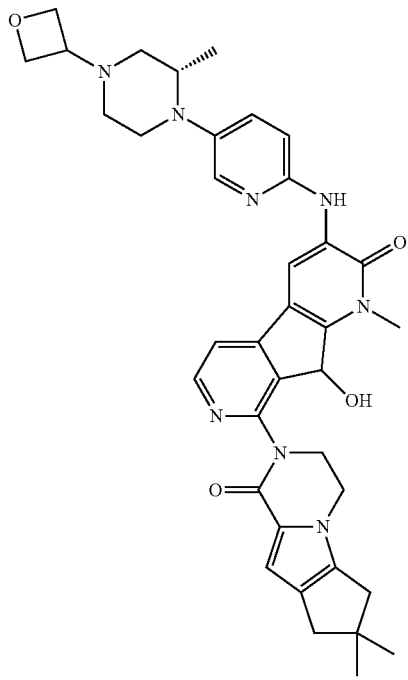

Alcohol

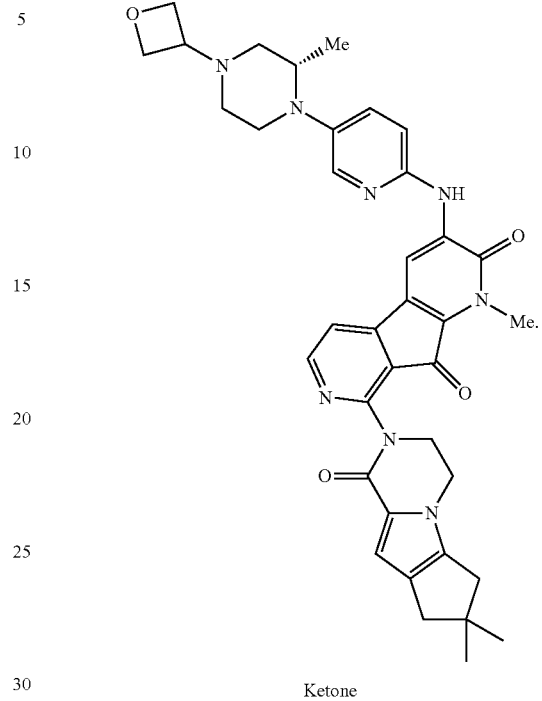

Ketone

3. The method of claim 1, wherein the fragment giving rise to the palladium-carbon bond is an allyl derivative selected from:

(a) a derivative wherein each of $R^6$ to $R^{10}$ is H;

(b) a derivative wherein $R^6$ is —$CH_3$ and each of $R^7$ to $R^{10}$ is H;

(c) a derivative wherein $R^7$ is —$CH_3$ and each of $R^6$ and $R^8$ to $R^{10}$ is H;

(d) a derivative wherein $R^8$ is —$CH_3$ and each of $R^6$, $R^7$, $R^9$ and $R^{10}$ is H;

(e) a derivative wherein $R^6$ is -phenyl and each of $R^7$ to $R^{10}$ is H;

(f) a derivative wherein $R^7$ is -phenyl and each of $R^6$ and $R^8$ to $R^{10}$ is H; and (g) a derivative of the structure

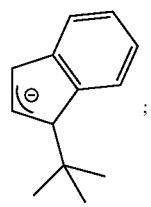

and
the phosphine ligand is of the formula

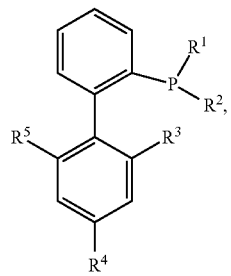

wherein:
R¹ and R² are each independently selected from optionally substituted $C_{1-12}$ alkyl, optionally substituted $C_3$-$C_{20}$ cycloalkyl, and optionally substituted $C_5$ or $C_6$ aryl; and
R³ to R⁵ are each independently selected from H, optionally substituted $C_{1-6}$ alkyl, alkoxide of the formula —O—$C_{1-6}$ alkyl, and amine of the formula —N(R¹²)(R¹³) wherein R¹² and R¹³ are independently selected from H and $C_{1-6}$ alkyl.

4. The method of claim 1, wherein:
each of R⁶ to R¹⁰ in the allyl derivative is H; and
the phosphine ligand is SPhos of the following structure:

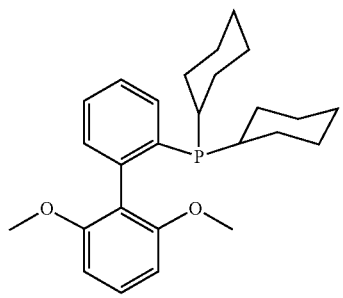

5. The method of claim 4, wherein the palladium catalyst is selected from:
(a) a cationic palladium species comprising an inorganic or organic counterion X; and
(b) a neutral palladium species comprising a coordinated inorganic or organic ligand X;
wherein X is selected from $CH_3C(O)O^-$, $tBuC(O)O^-$, $CF_3SO_3^-$, tosylate, besylate, nosylate, $PF_6^-$, $BF_4^-$, $B(C_6F_5)_4^-$, $NO_3^-$, and $SO_4^{2-}$.

6. The method of claim 5, wherein the palladium catalyst comprises a $CF_3SO_3^-$ organic counterion.

7. The method of claim 1, wherein:
the solvent system predominantly comprises an aprotic low molecular weight ester solvent and water;
the volume ratio of the aprotic low molecular weight ester solvent to water is from about 1:0.1 to about 1:1;
the reaction mixture is heated from about 60° ° C. to about 80° C.;
the equivalent ratio of compound 181 to compound 170 is greater than 1:1; and
the equivalent ratio of the palladium catalyst to compound 170 is from about 0.001:1 to about 0.003:1.

8. The method of claim 7, wherein:
(a) the palladium catalyst is [(SPhos)Pd(allyl)] $CF_3SO_3$;
(b) the solvent system predominantly comprises ethyl acetate and water wherein the volume ratio of ethyl acetate to water is from about 1:0.1 to about 1:1; and
(c) the boronate is 4,4,5,5-tetramethyl-1,3,2-dioxaborolane of the structure:

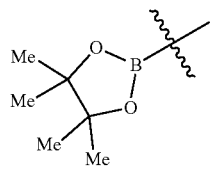

9. The method of claim 2, wherein:
(a) the palladium catalyst is [(SPhos)Pd(allyl)] $CF_3SO_3$;
(b) the solvent system predominantly comprises ethyl acetate and water wherein the volume ratio of ethyl acetate to water is from about 1:0.1 to about 1:1;
(c) the reaction mixture is heated from about 60° C. to about 80° C.;
(c) the boronate is 4,4,5,5-tetramethyl-1,3,2-dioxaborolane of the structure:

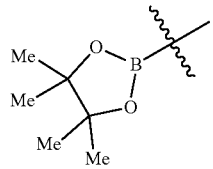

10. The method of claim 9, wherein the purity of compound 190 is at least 99.5 area % by HPLC.

11. The method of claim 1, further comprising reacting compound 190, or salt thereof, to form compound 200, or a salt thereof, the reacting comprising:
(a) contacting compound 190, or salt thereof, with a reducing agent and a base in the presence of a solvent to form compound 200, or salt thereof, according to the following scheme

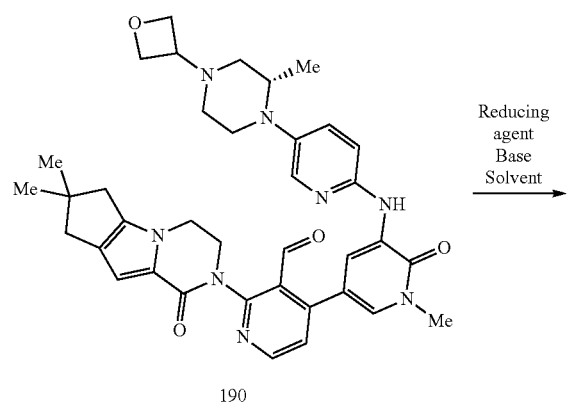

190

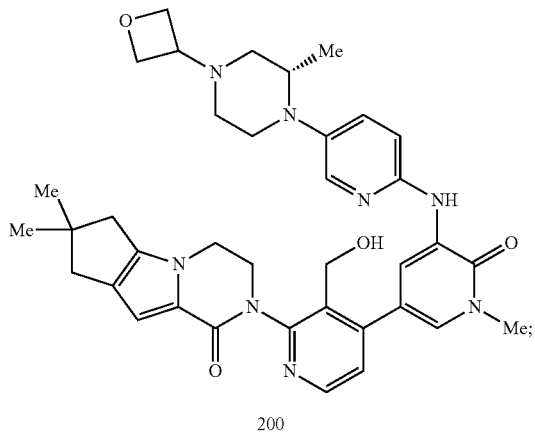

200 and (b) isolating compound 200, or salt thereof, wherein the yield of compound 200, or salt thereof, based on compound 170 is at least 80%, and the purity of compound 200, or salt thereof, is at least 99 area %.

12. A method of reducing byproduct formation in a Suzuki coupling reaction, the method comprising:

(a) forming a reaction mixture comprising compound 170, compound 181, a palladium catalyst, a solvent system, and a base, wherein the equivalent ratio of the palladium catalyst to compound 170 is from about 0.001:1 to less than 0.005:1; and (b) reacting the reaction mixture to form a reaction product mixture comprising compound 190, or salt thereof, according to the following scheme:

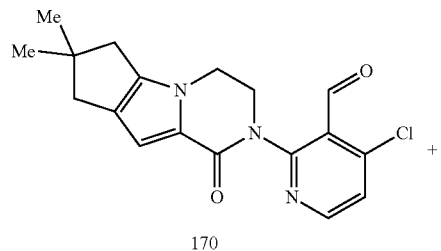

170

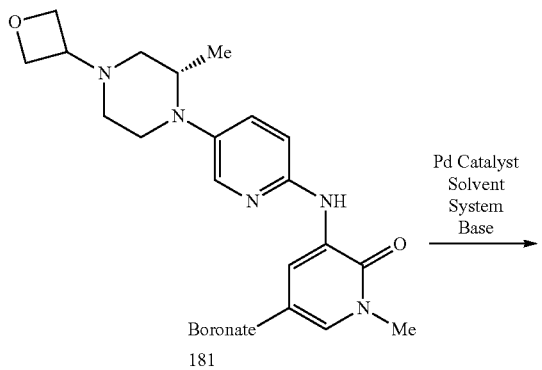

181

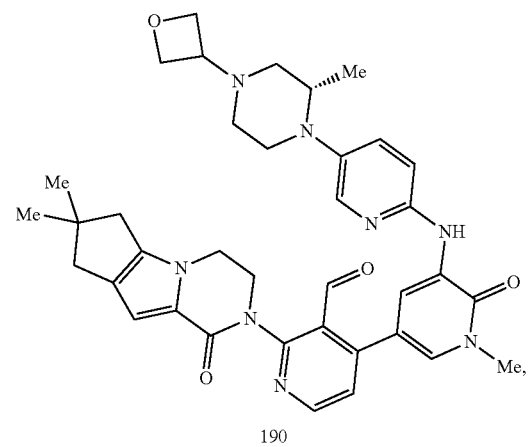

190 wherein the palladium catalyst comprises a palladium(II) species containing a phosphine ligand and at least one palladium-carbon bond, wherein:

(i) the fragment giving rise to the palladium-carbon bond is an allyl derivative of the formula

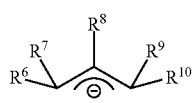

wherein each of $R^6$ to $R^{10}$ is independently selected from the group consisting of H, optionally substituted $C_{1-6}$ alkyl, optionally substituted $C_6$ aryl, and optionally substituted heteroaryl; and $R^6$ and $R^{10}$ may optionally come together to form a fused bicycle comprising an aromatic ring;

wherein:

(a) the content of a dimer impurity is less than 0.1 area % based on compound 190, or salt thereof, wherein the dimer impurity is of the structure

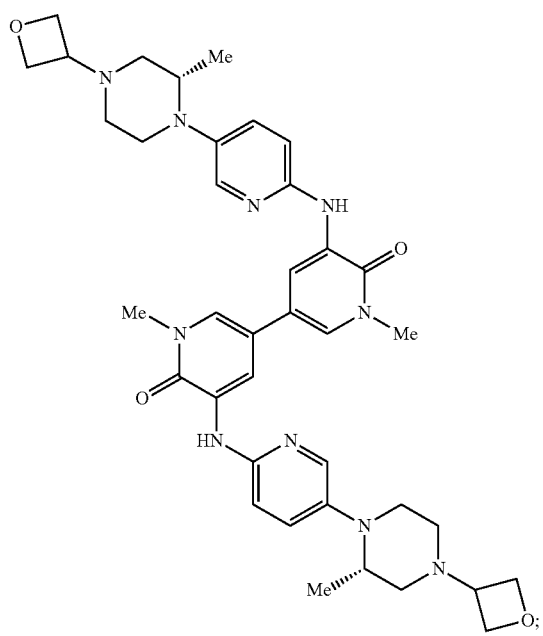 [SMILES: C[C@H]1CN(C2COC2)CCN1c1ccc(Nc2cc(-c3cc(Nc4ccc(N5CCN(C6COC6)C[C@@H]5C)cn4)c(=O)n(C)c3)cn(C)c2=O)nc1]

and (b) the combined content of an alcohol and a ketone impurity is less than 0.25 area % based on compound 190, or salt thereof, wherein the alcohol and ketone impurities are of the structures

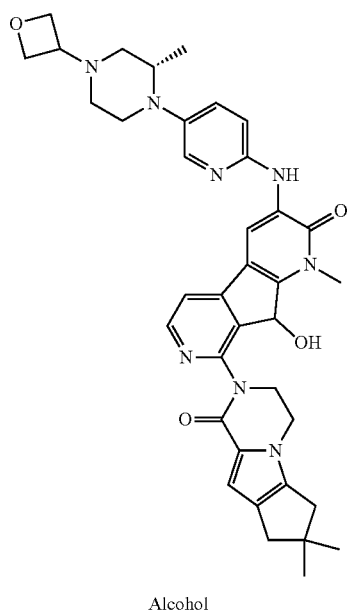

Alcohol

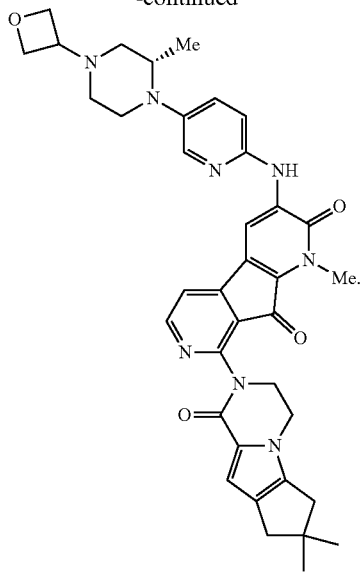

Ketone

13. The method of claim 12, wherein the fragment giving rise to the palladium-carbon bond is an allyl derivative selected from:

(a) a derivative wherein each of $R^6$ to $R^{10}$ is H;
(b) a derivative wherein $R^6$ is —$CH_3$ and each of $R^7$ to $R^{10}$ is H;
(c) a derivative wherein $R^7$ is —$CH_3$ and each of $R^6$ and $R^8$ to $R^{10}$ is H;
(d) a derivative wherein $R^8$ is —$CH_3$ and each of $R^6$, $R^7$, $R^9$ and $R^{10}$ is H;
(e) a derivative wherein $R^6$ is -phenyl and each of $R^7$ to $R^{10}$ is H;
(f) a derivative wherein $R^7$ is -phenyl and each of $R^6$ and $R^8$ to $R^{10}$ is H; and
(g) a derivative of the structure

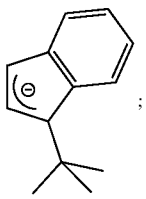

and
the phosphine ligand is of the formula

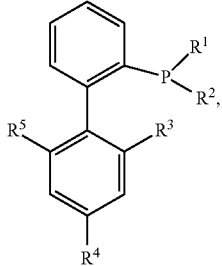

wherein:
R¹ and R² are each independently selected from optionally substituted $C_{1-12}$ alkyl, optionally substituted $C_3$-$C_{20}$ cycloalkyl, and optionally substituted $C_5$ or $C_6$ aryl; and R³ to R⁵ are each independently selected from H, optionally substituted $C_{1-6}$ alkyl, alkoxide of the formula —O—$C_{1-6}$ alkyl, and amine of the formula —N(R¹²)(R¹³) wherein R¹² and R¹³ are independently selected from H and $C_{1-6}$ alkyl.

14. The method of claim 12, wherein:
each of R⁶ to R¹⁰ in the allyl derivative is H; and
the phosphine ligand is SPhos of the following structure:

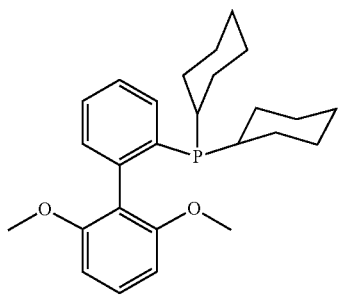

15. The method of claim 14, wherein the palladium catalyst is selected from:
(a) a cationic palladium species comprising an inorganic or organic counterion X; and
(b) a neutral palladium species comprising a coordinated inorganic or organic ligand X;
wherein X is selected from $CH_3C(O)O^-$, $tBuC(O)O^-$, $CF_3SO_3^-$, tosylate, besylate, nosylate, $PF_6^-$, $BF_4^-$, $B(C_6F_5)_4^-$, $NO_3^-$, and $SO_4^{2-}$.

16. The method of claim 15, wherein the palladium catalyst comprises a $CF_3SO_3^-$ organic counterion.

17. The method of claim 12, wherein:
the solvent system predominantly comprises an aprotic low molecular weight ester solvent and water;
the volume ratio of the aprotic low molecular weight ester solvent to water is from about 1:0.1 to about 1:1;
the reaction mixture is heated to from about 60° C. to about 80° C.;
the equivalent ratio of compound 181 to compound 170 is greater than 1:1; and
the equivalent ratio of the palladium catalyst to compound 170 is from about 0.001:1 to about 0.003:1.

18. The method of claim 17, wherein:
(a) the palladium catalyst is [(SPhos)Pd(allyl)] $CF_3SO_3$;
(b) the solvent system predominantly comprises ethyl acetate and water wherein the volume ratio of ethyl acetate to water is from about 1:0.1 to about 1:1; and
(c) the boronate is 4,4,5,5-tetramethyl-1,3,2-dioxaborolane of the structure:

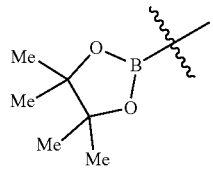

19. The method of claim 12, wherein:
(a) the palladium catalyst is [(SPhos)Pd(allyl)] $CF_3SO_3$;
(b) the solvent system predominantly comprises ethyl acetate and water wherein the volume ratio of ethyl acetate to water is from about 1:0.1 to about 1:1;
(c) the reaction mixture is heated from about 60° ° C. to about 80° ° C.;
(d) the boronate is 4,4,5,5-tetramethyl-1,3,2-dioxaborolane of the structure:

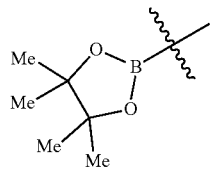

20. The method of claim 19, wherein the purity of compound 190 is at least 99.5 area % by HPLC.

21. The method of claim 9, wherein the yield of compound 190 or salt thereof is at least 90% based on compound 170; and wherein the reaction is a batch reaction, and the batch produces 100 kg or more of compound 190.

22. The method of claim 8, wherein the yield of compound 190 or salt thereof is at least 90% based on compound 170.

23. The method of claim 22, wherein the reaction is a batch reaction, and the batch produces 100 kg or more of compound 190.

* * * * *